US012636348B2

(12) United States Patent
Constable et al.

(10) Patent No.: US 12,636,348 B2
(45) Date of Patent: May 26, 2026

(54) TREATMENT OF OCULAR NEOVASCULARIZATION USING ANTI-VEGF PROTEINS

(71) Applicant: Avalanche Australia Pty Ltd., Southbank (AU)

(72) Inventors: Ian J. Constable, Mosman Park (AU); P. Elizabeth Rakoczy, Scarborough (AU); Chooi-May Lai, Waterford (AU); Thomas W. Chalberg, Jr., Redwood City, CA (US)

(73) Assignee: Avalanche Australia Pty Ltd, Southbank (AU)

( * ) Notice: Subject to any disclaimer, the term of this patent is extended or adjusted under 35 U.S.C. 154(b) by 856 days.

(21) Appl. No.: 17/328,705

(22) Filed: May 24, 2021

(65) Prior Publication Data

US 2022/0111015 A1     Apr. 14, 2022

Related U.S. Application Data

(63) Continuation of application No. 15/961,654, filed on Apr. 24, 2018, now abandoned, which is a continuation of application No. 15/851,650, filed on Dec. 21, 2017, now Pat. No. 10,004,788, which is a continuation of application No. 14/281,749, filed on May 19, 2014, now Pat. No. 9,943,573, which is a continuation of application No. 13/889,275, filed on May 7, 2013, now abandoned.

(60) Provisional application No. 61/775,440, filed on Mar. 8, 2013, provisional application No. 61/691,660, filed on Aug. 21, 2012, provisional application No. 61/678,555, filed on Aug. 1, 2012, provisional application No. 61/670,535, filed on Jul. 11, 2012, provisional application No. 61/647,461, filed on May 15, 2012.

(51) Int. Cl.

| | |
|---|---|
| *A61K 31/7088* | (2006.01) |
| *A61B 3/032* | (2006.01) |
| *A61K 9/00* | (2006.01) |
| *A61K 35/761* | (2015.01) |
| *A61K 38/17* | (2006.01) |
| *A61K 38/45* | (2006.01) |
| *A61K 39/00* | (2006.01) |
| *A61K 45/06* | (2006.01) |
| *A61K 48/00* | (2006.01) |
| *A61K 49/00* | (2006.01) |
| *C07K 14/71* | (2006.01) |
| *C07K 16/081* | (2026.01) |
| *C07K 16/22* | (2006.01) |
| *C12N 7/00* | (2006.01) |
| *C12N 9/12* | (2006.01) |
| *C12N 15/86* | (2006.01) |

(52) U.S. Cl.
CPC .............. *A61K 38/45* (2013.01); *A61B 3/032* (2013.01); *A61K 31/7088* (2013.01); *A61K 35/761* (2013.01); *A61K 38/179* (2013.01); *A61K 45/06* (2013.01); *A61K 48/00* (2013.01); *A61K 48/0075* (2013.01); *A61K 49/0004* (2013.01); *C07K 14/71* (2013.01); *C07K 16/081* (2013.01); *C07K 16/22* (2013.01); *C12N 7/00* (2013.01); *C12N 9/12* (2013.01); *C12N 15/86* (2013.01); *C12Y 207/10001* (2013.01); *C12Y 207/10002* (2013.01); *A61K 9/0048* (2013.01); *A61K 2039/505* (2013.01); *C07K 2317/24* (2013.01); *C07K 2317/55* (2013.01); *C07K 2317/73* (2013.01); *C07K 2319/32* (2013.01); *C12N 2710/14044* (2013.01); *C12N 2750/14141* (2013.01); *C12N 2750/14142* (2013.01); *C12N 2750/14143* (2013.01); *C12N 2750/14171* (2013.01); *C12Y 207/10* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,874,237 A | 10/1989 | Cringle | |
| 5,219,401 A | 6/1993 | Cathignol et al. | |
| 5,383,917 A | 1/1995 | Desai et al. | |
| 5,436,146 A | 7/1995 | Shenk et al. | |

(Continued)

FOREIGN PATENT DOCUMENTS

| | | |
|---|---|---|
| EP | 0407122 A1 | 1/1991 |
| EP | 2292781 A1 | 3/2011 |

(Continued)

OTHER PUBLICATIONS

Batt et al. Prophylactic Antibiotic Use After Intravitreal Injection: Effect on Endophthalmitis Rate. Retina, 2011. 31(10) 2032-2036 ( Author Manuscript, 9 pages).*

(Continued)

*Primary Examiner* — Christopher M Babic
*Assistant Examiner* — Kimberly A Aron
(74) *Attorney, Agent, or Firm* — Wolf, Greenfield & Sacks, P.C.

(57) ABSTRACT

The present disclosure provides compositions and methods for the prevention or treatment of ocular neovascularization, such as AMD, in a human subject, by administering sub-retinally a pharmaceutical composition comprising a pharmaceutically effective amount of a vector comprising a nucleic acid encoding soluble Fms-related tyrosine kinase-1 (sFlt-1) protein to the human subject.

24 Claims, 47 Drawing Sheets

Specification includes a Sequence Listing.

(56)          References Cited

U.S. PATENT DOCUMENTS

| | | |
|---|---|---|
| 5,527,533 A | 6/1996 | Tso et al. |
| 5,641,749 A | 6/1997 | Yan et al. |
| 5,712,380 A | 1/1998 | Kendall et al. |
| 5,753,500 A | 5/1998 | Shenk et al. |
| 5,792,845 A | 8/1998 | O'Reilly et al. |
| 5,814,618 A | 9/1998 | Bujard et al. |
| 5,861,484 A | 1/1999 | Kendall et al. |
| 5,994,136 A | 11/1999 | Naldini et al. |
| 6,013,516 A | 1/2000 | Verma et al. |
| 6,040,183 A | 3/2000 | Ferrari et al. |
| 6,054,485 A | 4/2000 | Schwartz et al. |
| 6,093,570 A | 7/2000 | Ferrari et al. |
| 6,132,732 A | 10/2000 | Young et al. |
| 6,153,436 A | 11/2000 | Hermonat et al. |
| 6,287,815 B1 | 9/2001 | Brown |
| 6,329,181 B1 | 12/2001 | Xiao et al. |
| 6,387,670 B1 | 5/2002 | Leblois-Prehaud et al. |
| 6,458,157 B1 | 10/2002 | Suaning |
| 6,482,634 B1 | 11/2002 | Wilson et al. |
| 6,548,286 B1 | 4/2003 | Samulski et al. |
| 6,723,551 B2 | 4/2004 | Kotin et al. |
| 6,943,153 B1 | 9/2005 | Manning, Jr. et al. |
| 7,070,959 B1 | 7/2006 | Papadopoulos et al. |
| 7,071,159 B2 | 7/2006 | Kendall et al. |
| 7,186,699 B2 | 3/2007 | Harding et al. |
| 7,220,577 B2 | 5/2007 | Zolotukhin |
| 7,585,676 B2 | 9/2009 | Mitrophanous et al. |
| 7,635,474 B2 | 12/2009 | Daly et al. |
| 7,666,405 B2 | 2/2010 | Amalfitano et al. |
| 7,858,367 B2 | 12/2010 | Amalfitano et al. |
| 7,972,278 B2 | 7/2011 | Graham et al. |
| 8,075,137 B2 | 12/2011 | Klistorner et al. |
| 8,118,752 B2 | 2/2012 | Hetling et al. |
| 8,137,274 B2 | 3/2012 | Weng et al. |
| 8,163,543 B2 | 4/2012 | Urabe et al. |
| 8,343,067 B2 | 1/2013 | Jones et al. |
| 8,663,624 B2 | 3/2014 | Schaffer et al. |
| 8,900,858 B2 | 12/2014 | Trono et al. |
| 9,193,956 B2 | 11/2015 | Schaffer et al. |
| 9,198,595 B2 | 12/2015 | Neitz et al. |
| 9,233,131 B2 | 1/2016 | Schaffer et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,943,573 B2 | 4/2018 | Constable et al. |
| 10,000,741 B2 | 6/2018 | Chalberg et al. |
| 10,004,788 B2 | 6/2018 | Constable et al. |
| 11,021,519 B2 | 6/2021 | Chalberg et al. |
| 11,192,925 B2 | 12/2021 | Keravala |
| 11,248,214 B2 | 2/2022 | Thomas et al. |
| 2002/0168342 A1 | 11/2002 | Wang et al. |
| 2002/0194630 A1 | 12/2002 | Manning, Jr. et al. |
| 2003/0087889 A1 | 5/2003 | Strong et al. |
| 2004/0102765 A1 | 5/2004 | Koenig |
| 2004/0234505 A1 | 11/2004 | Naylor et al. |
| 2005/0053922 A1 | 3/2005 | Schaffer et al. |
| 2005/0260203 A1 | 11/2005 | Wiegand et al. |
| 2006/0128020 A1 | 6/2006 | Calos |
| 2006/0166363 A1 | 7/2006 | Zolotukhin et al. |
| 2006/0193830 A1 | 8/2006 | Hauswirth et al. |
| 2006/0234347 A1 | 10/2006 | Harding et al. |
| 2007/0188710 A1 | 8/2007 | Hetling et al. |
| 2007/0190028 A1 | 8/2007 | Qu et al. |
| 2007/0190058 A1 | 8/2007 | Shams |
| 2008/0070855 A1 | 3/2008 | Gills |
| 2008/0152654 A1 | 6/2008 | Reich |
| 2009/0098139 A1 | 4/2009 | Katz et al. |
| 2009/0112201 A1 | 4/2009 | Young |
| 2009/0128776 A1 | 5/2009 | Keating et al. |
| 2009/0191588 A1 | 7/2009 | Hermens et al. |
| 2009/0191597 A1 | 7/2009 | Samulski et al. |
| 2009/0202490 A1 | 8/2009 | Schaffer et al. |
| 2009/0203071 A1 | 8/2009 | Chen |
| 2009/0285826 A1 | 11/2009 | Bonnel et al. |
| 2010/0008170 A1 | 1/2010 | Sato et al. |
| 2010/0081707 A1 | 4/2010 | Ali et al. |
| 2010/0091242 A1 | 4/2010 | Baglini et al. |
| 2010/0272719 A1 | 10/2010 | Yu |
| 2010/0297084 A1 | 11/2010 | Bennett et al. |
| 2011/0001465 A1 | 1/2011 | Liu et al. |
| 2011/0014655 A1 | 1/2011 | Otte et al. |
| 2011/0052678 A1 | 3/2011 | Shantha et al. |
| 2011/0116046 A1 | 5/2011 | Haeri et al. |
| 2011/0136227 A1 | 6/2011 | Bakker et al. |
| 2011/0270256 A1 | 11/2011 | Nelson et al. |
| 2012/0100606 A1 | 4/2012 | Zolotukhin et al. |
| 2012/0141422 A1 | 6/2012 | Barkats |
| 2012/0164106 A1 | 6/2012 | Schaffer et al. |
| 2012/0172419 A1 | 7/2012 | Neitz et al. |
| 2012/0225930 A1 | 9/2012 | Acland et al. |
| 2013/0023034 A1 | 1/2013 | Noordman et al. |
| 2013/0031709 A1 | 2/2013 | Chen |
| 2013/0317091 A1 | 11/2013 | Ye et al. |
| 2013/0323302 A1 | 12/2013 | Constable et al. |
| 2014/0242031 A1 | 8/2014 | Schaffer et al. |
| 2014/0275231 A1 | 9/2014 | Boye et al. |
| 2014/0294771 A1 | 10/2014 | Schaffer et al. |
| 2014/0341977 A1 | 11/2014 | Constable et al. |
| 2014/0364338 A1 | 12/2014 | Schaffer et al. |
| 2014/0371438 A1 | 12/2014 | Constable et al. |
| 2015/0004101 A1 | 1/2015 | Constable et al. |
| 2015/0025939 A1 | 1/2015 | Chatterjee et al. |
| 2015/0079038 A1 | 3/2015 | Deverman et al. |
| 2015/0111275 A1 | 4/2015 | Palanker et al. |
| 2015/0118201 A1 | 4/2015 | Xiao et al. |
| 2015/0132262 A1 | 5/2015 | Schaffer et al. |
| 2015/0225702 A1 | 8/2015 | Schaffer et al. |
| 2015/0232953 A1 | 8/2015 | Schaffer et al. |
| 2015/0259395 A1 | 9/2015 | Chalberg et al. |
| 2016/0015288 A1 | 1/2016 | Neitz et al. |
| 2016/0184394 A1 | 6/2016 | Schaffer et al. |
| 2016/0340393 A1 | 11/2016 | Schaffer et al. |
| 2016/0375151 A1 | 12/2016 | Schaffer et al. |
| 2016/0376323 A1 | 12/2016 | Schaffer et al. |
| 2017/0183647 A1 | 6/2017 | Chavez et al. |
| 2018/0066022 A1 | 3/2018 | Chalberg et al. |
| 2018/0125948 A1 | 5/2018 | Constable et al. |
| 2018/0311319 A1 | 11/2018 | Constable et al. |
| 2018/0320145 A1 | 11/2018 | Thomas et al. |
| 2018/0344197 A1 | 12/2018 | Neitz et al. |
| 2019/0142975 A1 | 5/2019 | Keravala et al. |
| 2019/0154667 A1 | 5/2019 | Keravala et al. |
| 2020/0010851 A1 | 1/2020 | Keravala |
| 2020/0149033 A1 | 5/2020 | Chavez et al. |
| 2021/0040501 A1 | 2/2021 | Keravala |
| 2021/0130413 A1 | 5/2021 | Keravala |

FOREIGN PATENT DOCUMENTS

| | | | |
|---|---|---|---|
| EP | 2298925 | A2 | 3/2011 |
| EP | 2849802 | | 3/2015 |
| JP | H11100327 | A | 4/1999 |
| JP | 2002539176 | A | 11/2002 |
| JP | 2002363107 | A | 12/2002 |
| JP | 6466322 | B2 | 2/2019 |
| WO | WO-9208796 | A1 | 5/1992 |
| WO | WO-9428143 | A1 | 12/1994 |
| WO | WO-9522618 | A1 | 8/1995 |
| WO | WO-9526409 | A1 | 10/1995 |
| WO | WO-9813071 | A1 | 4/1998 |
| WO | WO-9851323 | A1 | 11/1998 |
| WO | WO-9914354 | A1 | 3/1999 |
| WO | WO-9916889 | A1 | 4/1999 |
| WO | WO-9936511 | A2 | 7/1999 |
| WO | WO-9945952 | A2 | 9/1999 |
| WO | WO-9966959 | A2 | 12/1999 |
| WO | WO-2000001815 | A2 | 1/2000 |
| WO | WO-2000015822 | A1 | 3/2000 |
| WO | WO-200212525 | A2 | 2/2002 |
| WO | WO-2002082904 | A2 | 10/2002 |
| WO | WO-2003080648 | A2 | 10/2003 |
| WO | WO-2004079332 | A2 | 9/2004 |
| WO | WO-2005005610 | A2 | 1/2005 |
| WO | 2006031689 | A2 | 3/2006 |

(56)     References Cited

FOREIGN PATENT DOCUMENTS

| | | |
|---|---|---|
| WO | WO-2006110689 A2 | 10/2006 |
| WO | WO-2007084773 A2 | 7/2007 |
| WO | WO-2007148971 A2 | 12/2007 |
| WO | WO-2008142124 A1 | 11/2008 |
| WO | WO-2008150459 A1 | 12/2008 |
| WO | WO-2009073551 A2 | 6/2009 |
| WO | WO-2009104964 A1 | 8/2009 |
| WO | WO-2009105669 A2 | 8/2009 |
| WO | WO-2010099960 A2 | 9/2010 |
| WO | WO-2011020710 A2 | 2/2011 |
| WO | WO-2011034947 A2 | 3/2011 |
| WO | WO-2011088081 A1 | 7/2011 |
| WO | WO-2011112089 A2 | 9/2011 |
| WO | WO-2011122950 A1 | 10/2011 |
| WO | WO-2011126808 A2 | 10/2011 |
| WO | WO-2011137344 A2 | 11/2011 |
| WO | WO-2012068317 A2 | 5/2012 |
| WO | WO-2012145601 A2 | 10/2012 |
| WO | WO-2013173129 A2 | 11/2013 |
| WO | WO-2013188316 A1 | 12/2013 |
| WO | WO-2014186160 A1 | 11/2014 |
| WO | WO-2014207190 A1 | 12/2014 |
| WO | WO-2015048534 A1 | 4/2015 |
| WO | WO-2015134643 A1 | 9/2015 |
| WO | WO-2015142941 A1 | 9/2015 |
| WO | WO-2016141078 A1 | 9/2016 |
| WO | WO-2017112868 A1 | 6/2017 |
| WO | WO-2017190125 A1 | 11/2017 |
| WO | WO-2018075798 A1 | 4/2018 |
| WO | WO-2018160686 A1 | 9/2018 |
| WO | WO-2018170473 A1 | 9/2018 |

OTHER PUBLICATIONS

Acland, et al., "Long-term restoration of rod and cone vision by single dose rAAV mediated gene transfer to the retina in a canine model of childhood blindness." Mol Ther. 2005; 12(6): 1072-1082.

Adamis, et al., "Inhibition of vascular endothelial growth factor prevents retinal ischemia-associated iris neovascularization in a nonhuman primate." Arch Ophthalmol. 1996; 114(1): 66-71.

Adhi, et al., "Optical coherence tomography current and future applications." Curr Opin Ophthalmol. 2013; 24(3): 213-221.

Aflibercept FDA Entry and Label, 2015. 28 pages. downloaded fromhttp://www.accessdata.fda.gov/scripts/cder/drugsatfda/index.cfm?fuseaction=Search.Label-_ApprovalHistory#apphist.

Aiello, et al., "Suppression of retinal neovascularization in vivo by inhibition of vascular endothelial growth factor (VEGF) using soluble VEGF-receptor chimeric proteins." Proc Natl Acad Sci USA. 1995; 92(23):10457-10461.

Akimoto, et al., "Adenovirally expressed basic fibroblast growth factor rescues photoreceptor cells in RCS rats." Invest Ophthalmol Vis Sci. 1999; 40(2): 273-279.

Albert, Henrik, et al. "Site specific integration of DNA into wildtype and mutant lox sites placed in the plant genome." The Plant Journal (1995); 7.4: 649-659.

Alexander, John J., et al. "Restoration of cone vision in a mouse model of achromatopsia." Nature Medicine (2007); 13.6: 685-687.

Ali, et al., "Gene therapy for inherited retinal degeneration." Br J Ophthalmol. 1997; 81(9): 795-801.

Amado, et al., "Safety and efficacy of subretinal readministration of a viral vector in large animals to treat congenital blindness." Sci Transl Med. 2010; 2(21): 21ra16. doi: 10.1126/scitranslmed.3000659.

Anand, et al., "A deviant immune response to viral proteins and transgene product is generated on subretinal administration of adenovirus and Adeno-associated virus." Mol Ther. 2002; 5(2):125-132.

Arnold, et al., "Extracts from "clinical evidence": age related macular degeneration." BMJ. 2000; 321(7263):741-744.

Auricchio, et al., "Exchange of surface proteins impacts on viral vector cellular specificity and transduction characteristics: the retina as a model." Hum Mol Genet. 2001; 10(26): 3075-3081.

Auricchio, et al., "Inhibition of retinal neovascularization by intraocular viral-mediated delivery of anti-angiogenic agents." Mol Ther. 2002; 6(4): 490-494.

[Author Unknown] Aflibercept, Drugs RD (2008); 9(4): 261-269.

Bailey, et al., "Exercise increases soluble vascular endothelial growth factor receptor-1 (sFlt-1) in circulation of healthy volunteers." Med Sci Monit. 2006; 12(2): CR45-50.

Bainbridge, et al., "Effect of gene therapy on visual function in Leber's congenital amaurosis." N Engl J Med. 2008; 358(21): 2231-2239.

Bainbridge, et al., "Inhibition of retinal neovascularisation by gene transfer of soluble VEGF receptor sFlt-1." Gene Ther. 2002; 9(5): 320-326.

Bainbridge, J. W., and Ali, R. R. "The eyes have it! Ocular gene therapy trials for LCA look promising." Gene Ther (2008); 15: 1191-1192.

Barleon, et al., "Mapping of the sites for ligand binding and receptor dimerization at the extracellular domain of the vascular endothelial growth factor receptor FLT-1." J Biol Chem. 1997; 272(16):10382-10388.

Barleon, et al., "Soluble VEGFR-1 secreted by endothelial cells and monocytes is present in human serum and plasma from healthy donors." Angiogenesis. 2001; 4(2):143-154.

Belgore, et al., "Plasma levels of vascular endothelial growth factor (VEGF) and its receptor, Flt-1, in haematological cancers: a comparison with breast cancer." Am J Hematol. 2001; 66(1): 59-61.

Belteki, Gusztav, et al. "Site-specific cassette exchange and germline transmission with mouse ES cells expressing C31 integrase." Nature Biotechnology (2003); 21.3: 321-324.

Bennett, et al., "AAV2 gene therapy readministration in three adults with congenital blindness." Sci Transl Med. 2012; 4(120): 120ra15.

Bennett, et al., "Gene therapy for retinitis pigmentosa." Curr Opin Mol Ther. 2000; 2(4): 420-425.

Bennett, "Immune response following intraocular delivery of recombinant viral vectors." Gene Ther. 2003; 10(11): 977-982.

Bennicelli, et al., "Reversal of blindness in animal models of leber congenital amaurosis using optimized AAV2-mediated gene transfer." Mol Ther. 2008; 16(3): 458-465.

Berge et al., "Pharmaceutical Salts", Journal of Pharmaceutical Sciences, 66(1 ): 1-19 (1977).

Bethke, Bruce, and Sauer, Brian. "Segmental genomic replacement by Cre-mediated recombination: genotoxic stress activation of the p53 promoter in single-copy transformants." Nucleic Acids Research (1997); 25.14: 2828-2834.

Bhisitkul, "Vascular endothelial growth factor biology: clinical implications for ocular treatments." Br J Ophthalmol. 2006; 90(12): 1542-1547.

Bi, Yanzhen, et al. "Pseudo attP sites in favor of transgene integration and expression in cultured porcine cells identified by streptomyces phage phiC31 integrase." BMC Molecular Biology (2013); 14: 20, 12 pages.

Brinkmann, et al., "Selective retina therapy (SRT): a review on methods, techniques, preclinical and first clinical results." Bull Soc Beige Ophtalmol. 2006; 302: 51-69.

Brinkmann, et al., "Origin of retinal pigment epithelium cell damage by pulsed laser irradiance in the nanosecond to microsecond time regimen." Laser Surg Med. 2000; 27: 451-464.

Brown, et al., "Ranibizumab versus verteporfin photodynamic therapy for neovascular age-related macular degeneration: Two-year results of the ANCHOR study." Ophthalmology. 2009; 116(1): 57-65.

Buning, H et al., "Recent developments in adeno associated virus vector technology," J Gene Med 2008; 10: 717-733.

Cai, Xue, et al. "Gene delivery to mitotic and postmitotic photoreceptors via compacted DNA nanoparticles results in improved phenotype in a mouse model of retinitis pigmentosa." The FASEB Journal (2010); 24.4: 1178-1191.

Calcedo, Roberto, et al. "Worldwide epidemiology of neutralizing antibodies to adeno-associated viruses." Journal of Infectious Diseases (2009); 199.3: 381-390.

Calos, Michele P. "The C31 Integrase System for Gene Therapy." Current Gene Therapy (2006); 6.6: 633-645.

(56) References Cited

OTHER PUBLICATIONS

Campochiaro, et al., "Adenoviral vector-delivered pigment epithelium-derived factor for neovascular age-related macular degeneration: results of a phase I clinical trial." Hum Gene Ther. 2006; 17(2): 167-176.

Campochiaro, et al., "Monitoring ocular drug therapy by analysis of aqueous samples." Ophthalmology. 2009; 116(11): 2158-2164.

Campochiaro, "Gene Transfer for Neovascular Age-Related Macular Degeneration." Human Gene Therapy (2011); 22(5): 523-529.

Campochiaro, "Molecular targets for retinal vascular diseases." J Cell Physiol. 2007; 210(3): 575-581.

Cao, et al., "A subretinal matrigel rat choroidal neovascularization (CNV) model and inhibition of CNV and associated inflammation and fibrosis by VEGF trap." Invest Ophthalmol Vis Sci. 2010; 51(11): 6009-6017.

Cayouette, et al., "Adenovirus-mediated gene transfer of ciliary neurotrophic factor can prevent photoreceptor degeneration in the retinal degeneration (rd) mouse." Hum Gene Ther. 1997; 8(4): 423-430.

Chakrabarti, et al., "Normal T-cell turnover in sooty mangabeys harboring active simian immunodeficiency virus infection." J Virol. 2000; 74(3): 1209-1223.

Chalberg, et al., "Integration Specificity of Phage C31 Integrase in the Human Genome", J Mol Biol. (Mar. 17, 2006); 357(1): 28-48. Epub Dec. 22, 2005.

Chalberg, Thomas W., et al. "C31 integrase confers genomic integration and long-term transgene expression in rat retina." Investigative Ophthalmology & Visual Science (2005); 46.6: 2140-2146.

Chen, et al., "Use of nepafenac (Nevanac) in combination with intravitreal anti-VEGF agents in the treatment of recalcitrant exudative macular degeneration requiring monthly injections." Clin Ophthalmol. 2010; 4:1249-1252.

Chiu, M. I., and Nathans, J. "Blue cones and cone bipolar cells share transcriptional specificity as determined by expression of human blue visual pigment-derived transgenes." The Journal of Neuroscience (1994); 14.6: 3426-3436.

Choi, et al., "Production of recombinant Adeno-associated viral vectors." Curr Protoc Hum Genet. 2007; Chapter 12: Unit 12.9.doi: 10.1002/0471142905.hg1209s53.

Chung, et al., "Angiogenesis in myocardial infarction. An acute or chronic process?" Eur Heart J. 2002; 23(20): 1604-1608.

Cideciyan, Artur V., et al. "Human gene therapy for RPE65 isomerase deficiency activates the retinoid cycle of vision but with slow rod kinetics." Proceedings of the National Academy of Sciences (2008); 105.39: 15112-15117.

Cideciyan, et al., "Human RPE65 gene therapy for Leber congenital amaurosis: persistence of early visual improvements and safety at 1 year." Hum Gene Ther. 2009; 20(9): 999-1004.

Clark, et al., "Expression of clusterin/sulfated glycoprotein-2 under conditions of heat stress in rat Sertoli cells and a mouse Sertoli cell line." J Androl. 1997; 18(3): 257-63.

Clinical trial, A Phase I/II Controlled Dose-escalating Trial to Establish the Baseline Safety and Efficacy of a Single Subretinal Injection of rAAV.sFit-1 Into Eyes of Patients With Exudative Age-related Macular Degeneration (AMD). NCT01494805. Updated—Dec. 16, 2011, 4 pages.

Clinical Trial NCT01494805, "Safety and Efficacy Study of rAAV. sFlt-1 in Patients With Exudative Age-Related Macular Degeneration (AMD)." as published first posted on Dec. 19, 2011, 7 pages, Retrieved from: https://clinicaltrials.gov/ct2/show/NCT01494805.

Clinical Trial NCT01494805, History of Changes for "Safety and Efficacy Study of rAAV.sFlt-1 in Patients With Exudative Age-Related Macular Degeneration (AMD)", NCT01494805, Submitted Date: Dec. 15, 2011 (v1), ClinicalTrials.gov, https://clinicaltrials.gov/ct2/history/NCT01494805?V_1=View#StudyPageTop, 9 pages.

Clinical trial, Safety and Tolerability Study of AAV2-sFLT-1 in Patients With Neovascular Age-Related Macular Degeneration (AMD). NCT01024998. Last updated: Jan. 28, 2014.

Comparison of L-opsin promoter to SEQ ID No. 80. Printed Feb. 2, 2017, in U.S. Appl. No. 14/660,657, 4 pages.

Co-pending U.S. Appl. No. 14/444,347, inventor Schaffer; et al., filed Jul. 28, 2014.

Co-pending U.S. Appl. No. 14/444,375, inventor Schaffer; et al., filed Jul. 28, 2014.

Co-pending U.S. Appl. No. 14/606,543, inventor Schaffer; et al., filed Jan. 27, 2015.

Co-pending U.S. Appl. No. 14/938,154, inventor Schaffer; et al., filed Nov. 11, 2015.

Co-pending U.S. Appl. No. 15/229,699, inventor Schaffer; et al., filed Aug. 5, 2016.

Co-pending U.S. Appl. No. 15/244,884, inventor Schaffer; et al., filed Aug. 23, 2016.

Co-pending U.S. Appl. No. 15/244,892, inventor Schaffer; et al., filed Aug. 23, 2016.

Co-pending U.S. Appl. No. 15/939,674, inventor Neitz, et al., filed Mar. 29, 2018.

Csermely, et al., "The 90-kDa molecular chaperone family: structure, function, and clinical applications." A comprehensive review. Pharmacol Ther. 1998; 79(2):129-168.

Curtis, et al., "Risks of mortality, myocardial infarction, bleeding, and stroke associated with therapies for age-related macular degeneration." Arch Ophthalmol. 2010; 128(10): 1273-1279.

Dalkara D., et al., "In Vivo-Directed Evolution of a New Adeno-Associated Virus for Therapeutic Outer Retinal Gene Delivery from the Vitreous," Science Translational Medicine, 2013, vol. 5 (189), 11 pages.

Davidson, et al., "A model system for in vivo gene transfer into the central nervous system using an adenoviral vector." Nat Genet. 1993; 3(3): 219-223.

Davis, et al., "Direct gene transfer into skeletal muscle in vivo: factors affecting efficiency of transfer and stability of expression." Hum Gene Ther. 1993; 4(2): 151-159.

Dawson, et al., "Pigment epithelium-derived factor: a potent inhibitor of angiogenesis." Science. 1999; 285(5425): 245-248.

De Vries, et al., "The fms-like tyrosine kinase, a receptor for vascular endothelial growth factor." Science. 1992; 255(5047): 989-991.

Definition of "plasmid", Biology Dictionary, 2018, 1 page.

Dejneka, et al., "Gene therapy and animal models for retinal disease." Dev Ophthalmol. 2003; 37: 188-198.

Dejneka, et al., "Gene therapy and retinitis pigmentosa: advances and future challenges." Bioessays 2001; 23(7): 662-8.

Deonarain, M.P., "Ligand-targeted receptor-mediated vectors for gene delivery", Expert Opinion on Therapeutic Patents. 1998; 8: 53-69.

Devalois, R.L. and DeValois, K.K. "A multi-stage color model." Vision Research (1993); 33.8: 1053-1065.

Deyle and Russell, "Adeno-associated virus vector integration." Curr. Opin. Mol. Therapy (2009); 11 (4): 442-447.

Diab, et al., "Angiogenic factors for the prediction of pre-eclampsia in women with abnormal midtrimester uterine artery Doppler velocimetry." Int J Gynaecol Obstet. 2008; 102(2):146-151.

Dudus, et al., "Persistent trans gene product in retina, optic nerve and brain after intraocular injection of rAAV." Vision Res. 1999; 39(15): 2545-2553.

Dull, et al., "A third-generation lentivirus vector with a conditional packaging system." Journal of Virology (1998), 72(11):8463-8671.

Easton, et al., "The Hsp110 and Grp170 stress proteins: newly recognized relatives of the Hsp70s." Cell Stress Chaperones. 2000; 5(4): 276-290.

Edelstein et al., "Gene therapy clinical trials worldwide 1989-2004—an overview", Journal Gene Med. (2004); 6: 597-602.

European Patent Application No. 13791695.3, Extended European Search Report dated Dec. 21, 2015, 10 pages.

European Patent Application No. 15765668.7, Extended European Search Report dated Mar. 7, 2018, 18 pages.

European Patent Application No. 15765668.7, Partial Supplemental European Search Report dated Nov. 10, 2017, 8 pages.

European Patent Application No. 18198081.4, Extended European Search Report dated May 24, 2019, 11 pages.

Excoffon et al., "Directed evolution of adeno-associated virus to an infectious respiratory virus," PNAS, Mar. 10, 2009, vol. 106, No. 10, pp. 3865-3870.

(56)     References Cited

OTHER PUBLICATIONS

Ferrara, "Vascular endothelial growth factor: basic science and clinical progress." Endocr Rev. 2004; 25(4): 581-611.

Fong, et al., "The use and development of retroviral vectors to deliver cytokine genes for cancer therapy." Crit Rev Ther Drug Carrier Syst. 2000; 17(1): 1-60.

Fotsis, et al., "The endogenous oestrogen metabolite 2-methoxyoestradiol inhibits angiogenesis and suppresses tumour growth." Nature. 1994; 368(6468): 237-239.

Framme, et al., "Selective targeting of the retinal pigment epithelium in rabbit eyes with a scanning laser beam." Investigative Ophthalmology & Visual Science (2007); 48(4): 1782-1792.

Funk, et al., "Neovascular age-related macular degeneration: intraocular cytokines and growth factors and the influence of therapy with ranibizumab." Ophthalmology. 2009; 116(12): 2393-2399.

Galan, et al., "Association of age-related macular degeneration with polymorphisms in vascular endothelial growth factor and its receptor." Ophthalmology. 2010; 117(9): 1769-1774.

Geller, et al., "An HSV-1 vector expressing tyrosine hydroxylase causes production and release of L-dopa from cultured rat striatal cells." J Neurochem. 1995; 64(2):487-496.

Geller, et al., "Infection of cultured central nervous system neurons with a defective herpes simplex virus 1 vector results in stable expression of *Escherichia coli* beta-galactosidase." Proc Natl Acad Sci USA. 1990; 87(3): 1149-1153.

Geller, et al., "Long-term increases in neurotransmitter release from neuronal cells expressing a constitutively active adenylate cyclase from a herpes simplex virus type 1 vector." Proc Natl Acad Sci USA. 1993; 90(16): 7603-7607.

GenBank [online], Accession No. U47119.2, "Cloning vector pCI, mammalian expression vector." May 10, 2004—uploaded, [retrieved on Apr. 12, 2017], https://www.ncbi.nlm.nih.gov/nuccore/U47119, 2 pages.

Gerdes, et al., "Cell cycle analysis of a cell proliferation-associated human nuclear antigen defined by the monoclonal antibody Ki-67." J Immunol. 1984; 133(4):1710-1715.

Glushakova, Lyudmyla G., et al. "Human blue-opsin promoter preferentially targets reporter gene expression to rat s-cone photoreceptors." Investigative Ophthalmology & Visual Science (2006); 47.8: 3505-3513.

Goldman, et al., "Paracrine expression of a native soluble vascular endothelial growth factor receptor inhibits tumor growth, metastasis, and mortality rate." Proc Natl Acad Sci USA. 1998; 95(15): 8795-8800.

Goverdhana, et al., Regulatable gene expression systems for gene therapy applications: progress and future challenges. Molecular Therapy : The Journal of the American Society of Gene Therapy. 2005; 12(2): 189-211.

Gragoudas, et al., "Pegaptanib for neovascular age-related macular degeneration." N Engl J Med. 2004; 351(27): 2805-2816.

Graubert, et al., "Vascular repair after menstruation involves regulation of vascular endothelial growth factor-receptor phosphorylation by sFLT-1." Am J Pathol. 2001; 158(4): 1399-1410.

Gray and Zolotukhin, "Design and Construction of Functional AAV Vectors." Methods in Molecular Biology. 2011; 807: 25-46.

Groth, Amy C., et al. "A phage integrase directs efficient site-specific integration in human cells." Proc Natl Acad Sci U S A. (2000); 97.11: 5995-6000.

Gunther, Karen L., et al. "A novel mutation in the short-wavelength-sensitive cone pigment gene associated with a tritan color vision defect." Visual Neuroscience (2006); 23.3-4: 403-409.

Hasumi, et al., "Soluble FLT-1 expression suppresses carcinomatous ascites in nude mice bearing ovarian cancer." Cancer Res. 2002; 62(7): 2019-2023.

Hauswirth, et al., "Treatment of leber congenital amaurosis due to RPE65 mutations by ocular subretinal injection of Adeno-associated virus gene vector: short-term results of a phase I trial." Hum Gene Ther. 2008; 19(10): 979-990.

He, et al., "Alternative splicing of vascular endothelial growth factor (VEGF)-R1 (FLT-1) pre-mRNA is important for the regulation of VEGF activity." Mol Endocrinol. 1999; 13(4): 537-545.

Heinis, Christian, and Johnsson, Kai. "Using peptide loop insertion mutagenesis for the evolution of proteins." Methods Mol Biol. (2010); 634: 217-232.

Hoess, R.H. et al. "The role of the loxP spacer region in P1 site-specific recombination." Nucleic Acids Research (1986); 14.5: 2287-2300.

Hoffman, et al., "Cell-mediated immune response and stability of intraocular transgene expression after adenovirus-mediated delivery." Invest Ophthalmol Vis Sci. 1997; 38(11): 2224-2233.

Honda, et al., "Experimental subretinal neovascularization is inhibited by adenovirus-mediated soluble VEGF/flt-1 receptor gene transfection: a role of VEGF and possible treatment for SRN in age-related macular degeneration." Gene Ther. 2000; 7(11): 978-985.

Hu, et al., "Design of retroviral vectors and helper cells for gene therapy." Pharmacol Rev. 2000; 52(4): 493-511.

Huang, et al., "Innate immune recognition of viruses and viral vectors." Hum Gene Ther. 2009; 20(4): 293-301.

Ibrahim, et al., "Heat shock and arsenite induce expression of the nonclassical class I histocompatibility HLA-G gene in tumor cell lines." Cell Stress Chaperones. 2000; 5(3): 207-218.

Ideno, et al., "Prevention of diabetic retinopathy by intraocular soluble flt-1 gene transfer in a spontaneously diabetic rat model". Int J Mol Med. (Jan. 2007); 19(1): 75-79.

International Preliminary Report on Patentability for International Application No. PCT/US2010/048964, mailed Mar. 20, 2012, 14 pages.

International Preliminary Report on Patentability for International Application No. PCT/US2013/040011, mailed Nov. 18, 2014, 48 pages.

International Preliminary Report on Patentability for International Application No. PCT/US2013/045043, mailed Dec. 16, 2014, 9 pages.

International Preliminary Report on Patentability for International Application No. PCT/US2015/021087, mailed Sep. 20, 2016, 8 pages.

International Search Report and Written Opinion for International Application No. PCT/US2010/048964, mailed Jun. 17, 2011, 23 pages.

International Search Report and Written Opinion for International Application No. PCT/US2013/040011, mailed Dec. 17, 2013, 57 pages.

International Search Report and Written Opinion for International Application No. PCT/US2013/045043, mailed Nov. 12, 2013, 11 pages.

International Search Report and Written Opinion for International Application No. PCT/US2015/021087, mailed Aug. 12, 2015, 12 pages.

International Search Report and Written Opinion for International Application No. PCT/US2016/020482, mailed Aug. 8, 2016, 12 pages.

International Search Report and Written Opinion for International Application No. PCT/US2016/068312, mailed May 3, 2017, 22 pages.

Invitation to Pay Additional Fees for International Application No. PCT/US2013/040011, mailed Oct. 11, 2013, 5 pages.

Jacobs, Gerald H. "A perspective on color vision in platyrrhine monkeys." Vision Research (1998); 38.21: 3307-3313.

Jacobs, Gerald H., et al. "Emergence of novel color vision in mice engineered to express a human cone photopigment." Science (2007); 315.5819: 1723-1725.

Jacobson, et al., "Safety in nonhuman primates of ocular AA V2-RPE65, a candidate treatment for blindness in Leber congenital amaurosis." Hum Gene Ther. 2006; 17(8): 845-858.

Jacobson, et al., "Safety of recombinant Adeno-associated virus type 2-RPE65 vector delivered by ocular subretinal injection", Mol Ther. (2006); 13(6):1074-1084.

(56) References Cited

OTHER PUBLICATIONS

Jacobson, et al., "Gene therapy for leber congenital amaurosis caused by RPE65 mutations: safety and efficacy in 15 children and adults followed up to 3 years." Arch Ophthalmol. (2012); 130(1): 9-24.

Johnson-Saliba and Jans, "Gene Therapy: Optimising DNA Delivery to the Nucleus", Curr. Drug. Targets 2001; 2(4): 371-399.

Kaplitt, M.G. et al. (1994). "Long-term gene expression and phenotypic correction using adeno-associated virus vectors in the mammalian brain," Nature Genetics 6:148-154.

Kendall, et al., "Identification of a natural soluble form of the vascular endothelial growth factor receptor, FLT-1, and its heterodimerization with KDR." Biochem Biophys Res Commun. 1996; 226(2): 324-328.

Kendall, et al., "Inhibition of vascular endothelial cell growth factor activity by an endogenously encoded soluble receptor." Proc Natl Acad Sci USA. (1993); 90(22): 10705-10709.

Khaliq, et al., "Increased expression of placenta growth factor in proliferative diabetic retinopathy." Lab Invest. 1998; 78(1): 109-116.

Khani, et al., "AAV-mediated expression targeting of rod and cone photoreceptors with a human rhodopsin kinase promoter." Investigative Ophthalmology & Visual Science. 2007; 48(9): 3954-3961.

Kiang, et al., "Cytoprotection and regulation of heat shock proteins induced by heat shock in human breast cancer T47-D cells: role of [Ca2+]i and protein kinases." FASEB J. 1998; 12(14): 1571-1579.

Klein, et al., "Fifteen-year cumulative incidence of age-related macular degeneration: the Beaver Dam Eye Study." Ophthalmology. 2007; 114(2): 253-262.

Klein, et al., "The relation of cardiovascular disease and its risk factors to the 5-year incidence of age-related maculopathy: the Beaver Dam Eye Study." Ophthalmology. 1997; 104(11): 1804-1812.

Kliffen, et al., "Increased expression of angiogenic growth factors in age-related maculopathy." Br J Ophthalmol. 1997; 81(2): 154-162.

Komaromy, et al., "Targeting gene expression to cones with human cone opsin promoters in recombinant AAV." Gene Ther. 2008; 15(14): 1049-1055.

Komromy, Andrs M., et al. "Gene therapy rescues cone function in congenital achromatopsia." Human Molecular Genetics (Jul. 2010); 19(13): 2581-2593. Epub Apr. 8, 2010.

Kong, et al., "Regional suppression of tumor growth by in vivo transfer of a cDNA encoding a secreted form of the extracellular domain of the fit-1 vascular endothelial growth factor receptor." Hum Gene Ther. 1998; 9(6): 823-833.

Kozak, "Point mutations define a sequence flanking the AUG initiator codon that modulates translation by eukaryotic ribosomes", Cell (1986); 44(2): 283-292 (Abstract Only).

Krysiak, et al., "Soluble vascular endothelial growth factor receptor-1 (sFLT-1) mediates downregulation of FLT-1 and prevents activated neutrophils from women with preeclampsia from additional migration by VEGF." Circ Res. 2005; 97(12): 1253-1261.

Krzystolik, et al., "Prevention of experimental choroidal neovascularization with intravitreal anti-vascular endothelial growth factor antibody fragment." Arch Ophthalmol. 2002; 120(3):338-346.

Kuchenbecker, James A., et al. "Topography of the long-to middle-wavelength sensitive cone ratio in the human retina assessed with a wide-field color multifocal electroretinogram." Visual Neuroscience (2008); 25.03: 301-306.

Kvanta, et al., "Subfoveal fibrovascular membranes in age-related macular degeneration express vascular endothelial growth factor." Invest Ophthalmol Vis Sci. 1996; 37(9): 1929-1934.

Kvaratskhelia, Mamuka, et al. "Molecular mechanisms of retroviral integration site selection." Nucleic Acids Research (2014); 42.16: 10209-10225.

Kwak, et al., "VEGF is major stimulator in model of choroidal neovascularization." Invest Ophthalmol Vis Sci. 2000; 41(10): 3158-3164.

La Salle, "An adenovirus vector for gene transfer into neurons and glia in the brain," Science, Feb. 1993, 259: 988-990.

Lai, et al., "Generation of transgenic mice with mild and severe retinal neovascularisation." Br J Ophthalmol. 2005; 89(7): 911-916.

Lai, et al., "Inhibition of angiogenesis by adenovirus-mediated sFlt-1 expression in a rat model of corneal neovascularization." Hum Gene Ther. 2001; 12(10): 1299-1310.

Lai et al. "Long-Term Evaluation of AAV-Mediated sFlt-1 Gene Therapy for Ocular Neovascularization in Mice and Monkeys." Molecular Therapy (2005); 12:4, p. 659-668.

Lai, et al., "Potential long-term inhibition of ocular neovascularisation by recombinant Adeno-associated virus-mediated secretion gene therapy." Gene Ther. 2002; 9(12): 804-813.

Lai, et al., "Preclinical safety evaluation of subretinal AAV2.sFlt-1 in non-human primates." Gene Ther. 2012; 19(10): 999-1009. Epub Nov. 10, 2011.

Lai, et al., "rAAV.sFlt-1 Gene Therapy Achieves Lasting Reversal of Retinal Neovascularization in the Absence of a Strong Immune Response to the Viral Vector." Invest Ophthalmol Vis Sci. 2009; 50(9): 4279-4287.

Lai, et al., "Recombinant Adeno-associated virus type 2-mediated gene delivery into the Rpe65-/-knockout mouse eye results in limited rescue." Genet Vaccines Ther. 2004; 2:3, 15 pages.

Lai, Timothy YY, et al. "The clinical applications of multifocal electroretinography: a systematic review." Survey of Ophthalmology (2007); 52.1: 61-96.

Lalwani, et al., "A variable-dosing regimen with intravitreal ranibizumab for neovascular age- related macular degeneration: year 2 of the PrONTO Study." Am J Ophthalmol. 2009; 148(1): 43-58.

Langer, Stephen J., et al. "A genetic screen identifies novel noncompatible loxP sites." Nucleic Acids Research (2002); 30.14: 3067-3077.

Lavinksy, D. et al., "Modulation of transgene expression in retinal gene therapy by selective laser treatment." Investigative Ophthalmology & Visual Science. 2013; 54(3): 1873-1880.

Le Meur, et al., "Postsurgical assessment and long-term safety of recombinant adeno-associated virus-mediated gene transfer into the retinas of dogs and primates." Arch Ophthalmol. 2005; 123(4): 500-506.

Le Meur, et al., "Restoration of vision in RPE65-deficient Briard dogs using an AAV serotype 4 vector that specifically targets the retinal pigmented epithelium." Gene Ther. 2007; 14(4): 292-303.

Lebherz, et al., "Novel AAV serotypes for improved ocular gene transfer." J Gene Med. 2008; 10(4): 375-382.

Lee and Saito, "Role of nucleotide sequences of loxP spacer region in Cre-mediated recombination," Gene. Aug. 17, 1998;216(1):55-65.

Levine, et al., "Circulating angiogenic factors and the risk of preeclampsia." N Engl J Med. 2004; 350(7): 672-683.

Li, et al., "Cone-specific expression using a human red opsin promoter in recombinant AAV." Vision Res. 2008; 48(3): 332-338.

Li, et al., "Gene therapy following subretinal AAV5 vector delivery is not affected by a previous intravitreal AAV5 vector administration in the partner eye." Mol Vis. 2009; 15: 267-275.

Li, et al., "Intraocular route of AAV2 vector administration defines humoral immune response and therapeutic potential." Mol Vis. 2008; 14: 1760-1769.

Lieber, et al., "Integrating adenovirus-Adeno-associated virus hybrid vectors devoid of all viral genes." J Virol. 1999; 73(11): 9314-9324.

Lindenberg, Thomas, et al. "Cyclic summation versus m-sequence technique in the multifocal ERG." Graefe's Archive for Clinical and Experimental Ophthalmology (2003); 241.6: 505-510.

Liu, et al., "Gene therapy for ocular diseases." Br J Ophthalmol. 2011; 95(5): 604-612.

Liu, et al., "Soluble Fms-like tyrosine kinase-1 expression inhibits the growth of multiple myeloma in nude mice." Acta Biochim Biophys Sin (Shanghai). 2007; 39(7): 499-506.

Liu, Xiaomei, Han Ping, and Chun Zhang. "Rapid establishment of a HEK 293 cell line expressing FVIII-BDD using AAV site-specific integration plasmids." BMC Research Notes (2014); 7: 626, 6 pages.

Lopez, et al., "Transdifferentiated retinal pigment epithelial cells are immunoreactive for vascular endothelial growth factor in surgically

(56)          References Cited

OTHER PUBLICATIONS excised age-related macular degeneration-related choroidal neovascular membranes." Invest Ophthalmol Vis Sci. 1996; 37(5): 855-868.
Lu, et al., "Complete correction of hemophilia A with adeno-associated viral vectors containing a full-size expression cassette." Hum Gene Ther. (2008); 19(6):648-654. doi: 10.1089/hum.2007.0182.
Lukason, et al., "Inhibition of choroidal neovascularization in a nonhuman primate model by intravitreal administration of an AAV2 vector expressing a novel anti-VEGF molecule." Mol Ther. (Feb. 2011); 19(2): 260-265. Epub Oct. 26, 2010.
Lundstrom, "Alphavirus vectors: applications for DNA vaccine production and gene expression." Intervirology. 2000; 43(4-6): 247-257.
Luo and Saltzman, "Synthetic DNA delivery systems", Nature Biotechnol. 2000; 18(1): 33-37.
Luthert, et al., "Photoreceptor rescue." Eye (Lond). 1998; 12(Pt 3b): 591-596.
MacLachlan, et al., "Preclinical safety evaluation of AAV2-sFLT01—a gene therapy for age-related macular degeneration." Mol Ther. 2011; 19(2): 326-334. Epub Nov. 30, 2010.
Mae, et al., "Gene transfer of the vascular endothelial growth factor receptor flt-1 suppresses pulmonary metastasis associated with lung growth." Am J Respir Cell Mol Biol. 2005; 33(6): 629-635.
Maguire, A.M. et al. (2008). "Safety and efficacy of gene transfer for Leber's congenital amaurosis," N. Engl J Med 358:2240-2248.
Maguire, et al., "Age-dependent effects of RPE65 gene therapy for Leber's congenital amaurosis: a phase 1 dose-escalation trial." Lancet. 2009; 374(9701): 1597-1605.
Mahasreshti, et al., "Adenovirus-mediated soluble FLT-1 gene therapy for ovarian carcinoma." Clin Cancer Res. 2001; 7(7): 2057-2066.
Mahasreshti, et al., "Intravenous delivery of adenovirus-mediated soluble FLT-1 results in liver toxicity." Clin Cancer Res. 2003; 9(7): 2701-2710.
Maheshri, Narendra, et al. "Directed evolution of adeno-associated virus yields enhanced gene delivery vectors." Nature Biotechnology (2006); 24.2: 198-204.
Makous, Walter. "Comment on "emergence of novel color vision in mice engineered to express a human cone photopigment"." Science (2007); 318.5848: 196b-196b.
Malamos, et al., "Correlation of high-definition optical coherence tomography and fluorescein angiography imaging in neovascular macular degeneration." Invest. Ophthalmol Vis Sci. 2009; 50(10): 4926-4933.
Mancuso, et al., "Colorblindness Cure: Gene Therapy Confers a New Sensation", Investigative Opthamology & Visual Science (2008), 49: E-Abstract 3252 (Meeting Abstract).
Mancuso et al. "Gene therapy for red-green colour blindness in adult primates." Nature (2009); 461:7265, p. 784-787.
Mancuso et al., "Gene therapy treatment of color blindness in adult primates." Journal of Vision (2007); 7(15): 15a. (Abstract).
Mancuso, et al., "Recombinant Adeno-associated virus targets passenger gene expression to cones in primate retina", Journal of the Optical Society of America A (2007); 24(5): 1411-1416.
Mancuso, K., et al. "Progress in Developing a Gene Therapy Approach for Treating Color Blindness." Investigative Ophthalmology & Visual Science 46.13 (2005): 4565-4565 & 2005 Annual Meeting of the Association for Research in Vision and Ophthalmology, FL. Lauderdale, FL, 46(Supp S): 4565 (2005).
Mancuso, Katherine, et al. "An adaptation of the Cambridge Colour Test for use with animals." Visual Neuroscience (2006); 23.3-4: 695-701.
Manno, et al., "Successful transduction of liver in hemophilia by AAV-Factor IX and limitations imposed by the host immune response." Nat Med. 2006; 12(3): 342-347.
Mao, Yanxiong, et al. "Persistent Suppression of Ocular Neovascularization with Intravitreal Administration of AAVrh. 10 Coding for Bevacizumab." Human Gene Therapy (2011); 22(12): 1525-1535.
Martin et al., "Gene delivery to the eye using adeno-associated viral vectors", Methods (2002); 28: 267-275.

Mauck, et al., "Longitudinal in vivo Characterization of Expression of Viral Delivered Genes for L-opsin and Green Fluorescent Protein in Cone Photoreceptors of Gerbils." Investigative Ophthalmology & Visual Science (2006); 47.13: 4071-4071.
Mauck, Matthew C., et al. "Longitudinal evaluation of expression of virally delivered transgenes in gerbil cone photoreceptors." Visual Neuroscience (2008); 25(3): 273-282.
Maynard, et al., "Excess placental soluble fms-like tyrosine kinase 1 (sFlt1) may contribute to endothelial dysfunction, hypertension, and proteinuria in preeclampsia." J Clin Invest. 2003; 111(5): 649-658.
McLeod, Maureen, et al. "Identification of the crossover site during FLP-mediated recombination in the *Saccharomyces cerevisiae* plasmid 2 microns circle." Molecular and Cellular Biology (1986); 6.10: 3357-3367.
Merigan, et al., "Tracking Transfection of Macaque Retinal Ganglion Cells With AAV2 Viral Vectors; In vivo Imaging Reveals Differences Between Two Promoters." ARVO Annual Meeting Abstract (May 2008); Investigative Ophthalmology & Visual Science. 2008; vol. 49: 4514.
Michel, et al., "Stress-induced transcription of the clusterin/apoJ gene." Biochem J. 1997; 328 (Pt 1): 45-50.
Miller, et al., "Human effector and memory CD8+ T cell responses to smallpox and yellow fever vaccines." Immunity. 2008; 28(5): 710-722.
Mitchell, et al., "Cost effectiveness of treatments for wet age-related macular degeneration." PharmacoEconomics 2011; 29(2): 107-131.
Mitchell, et al., "Ranibizumab (Lucentis) in neovascular age-related macular degeneration: evidence from clinical trials." Br J Ophthalmol. 2010; 94(1): 2-13.
Miyamoto, et al., "Prevention of leukostasis and vascular leakage in streptozotocin induced diabetic retinopathy via intercellular adhesion molecule-1 inhibition." Proc Natl Acad Sci USA. 1999; 96(19): 10836-10841.
Miyoshi, H. et al. "Development of a self-inactivating lentivirus vector." J Virol. Oct. 1998;72(10):8150-7. doi: 10.1128/JVI.72.10.8150-8157.1998.
Mller et al. "Random peptide libraries displayed on adeno-associated virus to select for targeted gene therapy vectors", Nat Biotechnol, Sep. 2003; 21(9): 1040-6. Epub Aug. 3, 2003.
Nakai, et al., "AAV serotype 2 vectors preferentially integrate into active genes in mice." Nature Genetics (2003); 34 (3): 297-302.
Naldini et al. "Efficient transfer, integration, and sustained long-term expression of the transgene in adult rat brains injected with a lentiviral vector," Proc Natl Acad Sci USA., Oct. 1996;93(21):11382-11388.
Naldini et al., "Lentiviruses as gene transfer agents for delivery to non-dividing cells," Curr Opin Biotechnol., 1998;9(5):457-463.
Naldini, L., et al., "In vivo gene delivery and stable transduction of nondividing cells by a lentiviral vector." Science (1996), 272(5259): 263-267.
Narfstrom, et al., "Assessment of structure and function over a 3-year period after gene transfer in RPE65-/-dogs." Doc Ophthalmol. 2005; 111(1): 39-48.
Narfstrom, et al., "Functional and structural recovery of the retina after gene therapy in the RPE65 null mutation dog." Invest Ophthalmol Vis Sci. 2003; 44(4):1663-1672.
Narfstrom, et al., "In vivo gene therapy in young and adult RPE65-/-dogs produces long-term visual improvement." J Hered. 2003; 94(1): 31-37.
Nathans, et al., "Molecular genetics of human blue cone monochromacy." Science. 1989; 245(4920): 831-838.
Nathans, J., et al. "Molecular genetics of human color vision: the genes encoding blue, green, and red pigments." Science (1986); 232(4747): 193-202.
Nathans, Jeremy, et al. "Molecular genetics of inherited variation in human color vision." Science (1986); 232.4747: 203-210.
Neitz, Maureen, et al. "Spectral tuning of pigments underlying red-green color vision." Science (1991); 252.5008: 971-974.
Nemerow, "A new link between virus cell entry and inflammation: adenovirus interaction with integrins induces specific pro inflammatory responses." Mol Ther. 2009; 17(9): 1490-1491.

(56)  References Cited

OTHER PUBLICATIONS

Neufeld, et al., "Vascular endothelial growth factor (VEGF) and its receptors." FASEB J. 1999; 13(1): 9-22.

Niederkorn, et al., "See no evil, hear no evil, do no evil: the lessons of immune privilege." Nat Immunol. 2006; 7(4): 354-359.

Ohno-Matsui, et al., "Novel mechanism for age-related macular degeneration: an equilibrium shift between the angiogenesis factors VEGF and PEDF." J Cell Physiol. 2001; 189(3): 323-333.

Oikawa, et al., "Three novel synthetic retinoids, Re 80, Am 580 and Am 80, all exhibit anti-angiogenic activity in vivo." Eur J Pharmacol. 1993; 249(1): 113-116.

Palu, G. et al., In pursuit of new developments for gene therapy of human diseases. J Biotechnol. Feb. 5, 1999;68 (1):1-13.

Pang, Ji-jing, et al. "Gene therapy restores vision-dependent behavior as well as retinal structure and function in a mouse model of RPE65 Leber congenital amaurosis." Molecular Therapy (2006); 13.3: 565-572.

Papadakis et al. "Promoters and Control Elements: Designing Expression Cassettes for Gene Therapy." Current Gene Therapy (2004); 4(1): 89-113.

Park, et al., "The fourth immunoglobulin-like loop in the extracellular domain of FLT-1, a VEGF receptor, includes a major heparin-binding site." Biochem Biophys Res. Commun. 1999; 264(3): 730-734.

Paulus, et al., "Selective retinal therapy with microsecond exposures using a continuous line scanning laser." Retina. 2011 ; 31(2): 380-388.

Pechan, et al. "Novel anti-VEGF chimeric molecules delivered by AAV vectors for inhibition of retinal neovascularization." Gene Therapy (2009); 16, p. 10-16.

Perri, et al., "Replicon vectors derived from Sindbis virus and Semliki forest virus that establish persistent replication in host cells." J Virol. 2000; 74(20): 9802-9807.

Pfeifer et al., "Gene therapy: promises and problems." Annu Rev Genomics Hum Genet. (2001); 2: 177-211.

Pieramici, et al., "Age-related macular degeneration and risk factors for the development of choroidal neovascularization in the fellow eye." Curr Opin Ophthalmol. 1998; 9(3): 38-46.

Pitcher, et al., "Development and homeostasis of T cell memory in rhesus macaque." J Immunol. 2002; 168(1): 29-43.

Pollock, et al., "Delivery of a stringent dimerizer-regulated gene expression system in a single retroviral vector." Proceedings of the National Academy of Sciences of the United States of America. 2000; 97(24): 13221-6.

Provost, et al., "Biodistribution of rAAV vectors following intraocular administration: evidence for the presence and persistence of vector DNA in the optic nerve and in the brain." Mol Ther. 2005; 11(2): 275-83.

Pshenichkin, et al., "Heat shock enhances CMV-IE promoter-driven metabotropic glutamate receptor expression and toxicity in transfected cells." Neuropharmacology. 2011; 60: 1292-1300.

Quantin, et al., "Adenovirus as an expression vector in muscle cells in vivo." Proc Natl Acad Sci USA. (1992); 89(7): 2581-2584.

Rapti, Kleopatra, et al. "Neutralizing antibodies against AAV serotypes 1, 2, 6, and 9 in sera of commonly used animal models." Molecular Therapy (2012); 20.1: 73-83.

Recchia, Alessandra, et al. "Site-specific integration of functional transgenes into the human genome by adeno/AAV hybrid vectors." Molecular Therapy (2004); 10.4: 660-670.

Reffin, J. P., et al. "Trials of a computer-controlled colour vision test that preserves the advantages of pseudoisochromatic plates." Colour Vision Deficiencies X. Springer Netherlands (1991); pp. 69-76.

Regan, Benedict C., et al. "Luminance noise and the rapid determination of discrimination ellipses in colour deficiency." Vision Research (1994); 34.10: 1279-1299.

Regeneron press release, Bayer and Regeneron Report Positive Top-Line Results of Two Phase 3 Studies with VEGF Trap-Eye in Wet Age-related Macular Degeneration. Nov. 22, 2010.http://newsroom.regeneron.com/releasedetail.cfm?ReleaseiD=532099 (last accessed Nov. 24, 2010).

Regillo, et al., "Randomized, double-masked, sham-controlled trial of ranibizumab for neovascular age-related macular degeneration: PIER Study year 1." Am J Ophthalmol. 2008; 145(2): 239-248.

Rein, et al., "Forecasting age-related macular degeneration through the year 2050: the potential impact of new treatments." Arch Ophthalmol. 2009; 127(4): 533-540.

Response to request under 27 CFR 1.1 05, dated Apr. 27, 15, in U.S. Appl. No. 10/075,415, pp. 8-10 (3 pages).

Roberts, et al., "Pathogenesis and genetics of pre-eclampsia." Lancet. 2001; 357(9249): 53-56.

Robinson, et al., "The splice variants of vascular endothelial growth factor (VEGF) and their receptors." J Cell Sci. 2001; 114(Pt 5): 853-865.

Rolling, et al., "Long-term real-time monitoring of adeno-associated virus-mediated gene expression in the rat retina." Clin Experiment Ophthalmol. 2000; 28(5): 382-386.

Romano, et al., "Latest developments in gene transfer technology: achievements, perspectives, and controversies over therapeutic applications." Stem Cells. 2000; 18(1): 19-39.

Rome, C., et al., "Spatial and temporal control of expression of therapeutic genes using heat shock protein promoters." Methods (2005); 35.2: 188-198.

Rosenfeld, et al., "In vivo transfer of the human cystic fibrosis transmembrane conductance regulator gene to the airway epithelium." Cell. 1992; 68(1): 143-155.

Rosenfeld, et al., "Ranibizumab for neovascular age-related macular degeneration." N Engl J Med. 2006; 355(14): 1419-1431.

Saishin, et al., "VEGF-TRAP(R1R2) suppresses choroidal neovascularization and VEGF-induced breakdown of the blood-retinal barrier." J Cell Physiol. 2003; 195(2): 241-248.

Salam, et al., "Treatment of proliferative diabetic retinopathy with anti-VEGF agents." Acta Ophthalmol. 2011; 89(5): 405-411.

Samulski, et al., "Helper-Free Stocks of Recombinant Adeno-Associated Viruses: Normal Integration Does Not Require Viral Gene Expression." Journal of Virology (1989); 63.9: 3822-3828.

Sauer, Brian, "Site-specific recombination: developments and applications." Current Opinion in Biotechnology (1994); 5.5: 521-527.

Schlake, Thomas, and Bode, Juergen, "Use of mutated FLP recognition target (FRT) sites for the exchange of expression cassettes at defined chromosomal loci." Biochemistry (1994); 33.43: 12746-12751.

Schmidt, Michael, et al., "Adeno-associated virus type 2 Rep78 induces apoptosis through caspase activation independently of p53." Journal of Virology (2000); 74.20: 9441-9450.

Schmidt-Erfurth, "Clinical safety of ranibizumab in age-related macular degeneration." Expert Opin Drug Saf. 2010; 9(1):149-165.

Schmidt-Erfurth, et al., "Efficacy and safety of monthly versus quarterly ranibizumab treatment in neovascular age-related macular degeneration: the EXCITE study." Ophthalmology. 2011; 118(5): 831-839.

Schuele, et al., "RPE damage thresholds and mechanisms for laser exposure in the microsecond-to-millisecond time regimen." Invest Ophthalmol Vis Sci. 2005; 46: 714-719.

Schwartz, et al., "Embryonic stem cell trials for macular degeneration: a preliminary report." Lancet. 2012; 379(9817): 713-720.

Search Report (English translation) in Chinese Application No. 2013800375773, dated Nov. 24, 2016, 2 pages.

Search result 9, run by the STIC search facility, 2016, 2 pages.

Seddon, et al., "Validation of a prediction algorithm for progression to advanced macular degeneration subtypes." JAMA Ophthalmol. 2013; 131(4): 448-455.

Senecoff, Julie F., et al., "DNA recognition by the FLP recombinase of the yeast 2 plasmid: a mutational analysis of the FLP binding site." Journal of Molecular Biology (1988); 201.2: 405-421.

Shaaban, Salam A., et al. "Transgenic mice expressing a functional human photopigment." Investigative Ophthalmology & Visual Science (1998); 39.6: 1036-1043.

Shah et al., "Outcomes and risk factors associated with endophthalmitis after intravitreal injection of anti-vascular endothelial growth factor agents." Jefferson Digital Commons. 2011; pp. 1-14.

(56)          References Cited

OTHER PUBLICATIONS

Shapley, Robert. "Specificity of cone connections in the retina and color vision. Focus on "specificity of cone inputs to macaque retinal ganglion cells"." Journal of Neurophysiology (2006); 95.2: 587-588.

Sheridan, C., "Gene therapy finds its niche." Nat Biotechnol. 2011; 29(2): 121-128.

Shiose, et al., "Gene transfer of a soluble receptor of VEGF inhibits the growth of experimental eyelid malignant melanoma" Invest Ophthalmol Vis Sci. 2000; 41(9): 2395-2403.

Shoji and Nakashima, "Current Status of Delivery Systems to Improve Target Efficacy of Oligonu-cleotides", Current Pharmaceutical Design. (2004); 10(7): 785-796.

Silva, et al., "Age-related macular degeneration and risk factors for the development of choroidal neovascularisation in the fellow eye: a 3-year follow-up study." Ophthalmologica. 2011; 226(3): 110-118.

Simonelli, et al., "Gene therapy for Leber's congenital amaurosis is safe and effective through 1.5 years after vector administration." Mol Ther. 2010; 18(3): 643-650.

Sramek, C et al., "Non-damaging retinal phototherapy: Dynamic range of heat shock protein expression." Investigative Ophthalmology & Visual Science. 2011; 52(3):1780-1787.

Stefansson, et al., "Metabolic physiology in age related macular degeneration." Prog Retin Eye Res. 2011; 30(1): 72-80.

Stellmach, et al., "Prevention of ischemia-induced retinopathy by the natural ocular antiangiogenic agent pigment epithelium-derived factor." Proc Natl Acad Sci USA. 2001; 98(5): 2593-2597.

Stieger, et al., "AAV-mediated gene therapy for retinal disorders in large animal models." Ilar J. (2009); 50(2): 206-224.

Stieger, et al., "In vivo gene regulation using tetracycline-regulatable systems." Advanced Drug Delivery Reviews. 2009; 61(7-8): 527-41.

Stout, et al., "Surgical approaches to gene and stem cell therapy for retinal disease." Hum Gene Ther. 2011; 22(5): 531-535.

Stratford-Perricaudet, et al., "Widespread long-term gene transfer to mouse skeletal muscles and heart." J Clin Invest. 1992; 90(2): 626-630.

Streilein, et al., "Immunobiology and privilege of neuronal retina and pigment epithelium transplants." Vision Res. 2002; 42(4): 487-495.

Sutter, Erich E. "The fast m-transform: a fast computation of cross-correlations with binary m-sequences." SIAM Journal on Computing (1991); 20.4: 686-694.

Swanson, William H., et al. "Temporal modulation sensitivity and pulse-detection thresholds for chromatic and luminance perturbations." JOSA A (1987); 4.10: 1992-2005.

Szewczenko-Pawlikowski, et al., "Heat shock-regulated expression of calreticulin in retinal pigment epithelium." Mol Cell Biochem. 1997; 177(1-2): 145-52.

Takayama, et al., "Suppression of tumor angiogenesis and growth by gene transfer of a soluble form of vascular endothelial growth factor receptor into a remote organ." Cancer Res. 2000; 60(8): 2169-2177.

Thyagarajan, Bhaskar, et al. "Site-specific genomic integration in mammalian cells mediated by phage C31 integrase." Molecular and Cellular Biology (2001); 21.12: 3926-3934.

Tolentino, et al., "Vascular endothelial growth factor is sufficient to produce iris neovascularization and neovascular glaucoma in a nonhuman primate." Arch Ophthalmol. 1996; 114(8): 964-670.

Ueyama, Hisao, et al. "Analysis of introns and promoters of L/M visual pigment genes in relation to deutan color-vision deficiency with an array of normal gene orders." Journal of Human Genetics (2009); 54.9: 525-530.

Urabe et al. "Insect Cells as a Factory to Produce adeno-Associated Virus Type 2 Vectors" Human Gene Therapy 13:1935-1943 (2002).

US National Health Institute: "Safety and Efficacy Study of rAAV. sFlt-1 in Patients With Exudative Age-Related Macular Degeneration", NCT01494805, Clinical Trials, Updated Dec. 16, 2011;

XP002751808, Retrieved from the Internet: URL:https:jjclinicaltrials. govjarchivejNCT01494805/2011_12_16 [retrieved on—Dec. 4, 2015].

US National Institute of Health: "Safety and Tolerability Study of AAV2-sFLT01 in Patients With Neovascular Age-Related Macular Degeneration (AMD)", NCT01024998, Clinical Trials, Updated Apr. 13, 2012; XP002751809, Retrieved from the Internet: URL:https:jjclinicaltrials.govjarchive/NCT01024998/2012_04_13 [retrieved on–Dec. 4, 2015].

Verma and Somia, "Gene therapy—promises, problems and prospects", Nature 1997; 389: 239-242.

Viard, et al., "Clusterin gene expression mediates resistance to apoptotic cell death induced by heat shock and oxidative stress." J Invest Dermatol. 1999; 112(3): 290-296.

Vigna, et al., "Lentiviral vectors: excellent tools for experimental gene transfer and promising candidates for gene therapy." J Gene Med. 2000; 2(5): 308-316.

Wada, et al., "Expression of vascular endothelial growth factor and its receptor(KDR/flk-1) mRNA in experimental choroidal neovascularization." Curr Eye Res. 1999; 18(3): 203-213.

Wang, et al., "A locus control region adjacent to the human red and green visual pigment genes." Neuron. 1992; 9(3): 429-440.

Wang, et al., "Spatiotemporal control of gene expression by a light-switchable transgene system." Nature Methods. 2012; 9(3): 266-269.

Wells, et al., "Levels of vascular endothelial growth factor are elevated in the vitreous of patients with subretinal neovascularisation." Br J Ophthalmol. 1996; 80(4): 363-366.

Wenkel, et al., "Analysis of immune deviation elicited by antigens injected into the subretinal space." Invest Ophthalmol Vis Sci. 1998; 39(10): 1823-1834.

Wenkel, et al., "Evidence that retinal pigment epithelium functions as an immune-privileged tissue." Invest Ophthalmol Vis Sci. 2000; 41(11): 3467-73.

Wiesel, Torsten N., and Hubel, David H. "Single-cell responses in striate cortex of kittens deprived of vision in one eye." J Neurophysiol (1963); 26.6: 1003-1017.

Wiesmann, et al., "Crystal Structure at 1.7 Resolution of VEGF in Complex with Domain 2 of the Flt-1 Receptor". Cell (Nov. 28, 1997); 91(5): 695-704.

Wolf, et al., "Preeclampsia and future cardiovascular disease: potential role of altered angiogenesis and insulin resistance." J Clin Endocrinol Metab. 2004; 89(12): 6239-6243.

Wong, et al., "Intravitreal VEGF and bFGF produce florid retinal neovascularization and hemorrhage in the rabbit." Curr Eye Res. 2001; 22(2): 140-147.

Wu, et al., "Self-complementary recombinant adeno-associated viral vectors: packaging capacity and the role of rep proteins in vector purity." Hum Gene Ther. 2007; 18(2): 171-182.

Wulff, et al., "Luteal angiogenesis: prevention and intervention by treatment with vascular endothelial growth factor trap(A40)." J Clin Endocrinol Metab. 2001; 86(7): 3377-3386.

Wykoff, et al., "Perioperative management of patients with reported povidone-iodine or penicillin/cephalosporin allergies." Presented at the Annual Meeting for the Association for Research in Vision and Opthalmology. Fort Lauderdale, Fl. May 5, 2011; Abstract No. 6416/D880.

Xiao, et al., "Production of high-titer recombinant adeno-associated virus vectors in the absence of helper adenovirus." J. Virol. 1998; 72(3): 2224-2232.

Xu, Zhengyao, et al. "Accuracy and efficiency define Bxb1 integrase as the best of fifteen candidate serine recombinases for the integration of DNA into the human genome." BMC Biotechnology (2013); 13: 87, 17 pages.

Yang, et al., "Cellular and humoral immune responses to viral antigens create barriers to lung-directed gene therapy with recombinant adenoviruses." J Virol. 1995; 69(4): 2004-2015.

Ye, et al., "sFlt-1 gene therapy of follicular thyroid carcinoma." Endocrinology. 2004; 145(2): 817-822.

Ye, Guo-jie, et al. "Development and Evaluation of Cone-Specific Promoters in Non-human Primates for Gene Therapy of Congenital Cone Diseases Including Achromatopsia." ARVO Annual Meeting Abstract, Investigative Ophthalmology & Visual Science (2014); 55.13: 837-837, 5 pages.

(56) References Cited

OTHER PUBLICATIONS

Yero, et al., "Immunization of mice with Neisseria meningitides serogroup B genomic expression libraries elicits functional antibodies and reduces the level of bacteremia in an infant rat infection model", Vaccine (2005); 23(7): 932-939.

Yin, et al., "Intravitreal injection of AAV2 transduces macaque inner retina." Invest Ophthalmol Vis Sci. 2011; 52(5): 2775-2783.

Zhang, et al., "AAV-mediated Gene Therapy Restores Cone Function in a Rat With an M-cone Opsin Deficiency, A Model For Blue Cone Monochromacy", Investigative Opthamology & Visual Science (2011); ARVO Annual Meeting Abstract, 52:1403.

Zhang, et al., "Suppression of tumor growth by oncolytic adenovirus-mediated delivery of an antiangiogenic gene, soluble Flt-1." Mol Ther. 2005; 11(4): 553-562.

Zheng, et al., "Genomic integration and gene expression by a modified adenoviral vector." Nat Biotechnol. 2000; 18(2): 176-180.

Zufferey, et al., "Multiply attenuated lentiviral vector achieves efficient gene delivery in vivo." Nat Biotechnol. (1997), 15(9): 871-875.

U.S. Appl. No. 16/998,540, filed Aug. 20, 2020, US 2021-0040501 A1, Feb. 11, 2021, Allowed.

U.S. Appl. No. 15/939,674, filed Mar. 29, 2018, US 2018-0344197 A1, Dec. 6, 2018, Pending.

U.S. Appl. No. 16/097,377, filed May 1, 2017, US 2019-0142975 A1, May 16, 2019, Pending.

U.S. Appl. No. 16/098,354, filed May 2, 2017, US 2019-0154667 A1, May 23, 2019, Pending.

U.S. Appl. No. 16/488,689, filed Feb. 28, 2018, US 20210130413 A1, May 6, 2021, Pending.

U.S. Appl. No. 16/494,203, filed Mar. 16, 2018, US 2020-0010851 A1, Jan. 9, 2020, Pending.

U.S. Appl. No. 16/750,736, filed Jan. 23, 2020, US 2020-0149033 A1, May 14, 2020, Pending.

U.S. Appl. No. 17/308,785, filed May 5, 2021, US 2021-0388030 A1, Dec. 16, 2021, Pending.

U.S. Appl. No. 17/514,711, filed Oct. 29, 2021, Pending.

U.S. Appl. No. 17/556,847, filed Dec. 20, 2021, Pending.

U.S. Appl. No. 14/281,749, filed May 19, 2014, US 2015-0004101 A1, Jan. 1, 2015, U.S. Pat. No. 9,943,573, Apr. 17, 2018, Registered.

U.S. Appl. No. 14/660,657, filed Mar. 17, 2015 US 2015-0259395 A1, Sep. 17, 2015, U.S. Pat. No. 10,000,741, Jun. 19, 2018, Registered.

U.S. Appl. No. 15/388,380, filed Dec. 22, 2016, US 2017-0183647 A1, Jun. 29, 2017, U.S. Pat. No. 10,584,328, Mar. 10, 2020, Registered.

U.S. Appl. No. 15/554,664, filed Mar. 2, 2016, US 2018-0066022 A1, Mar. 8, 2018, U.S. Pat. No. 11,021,519, Jun. 1, 2021, Registered.

U.S. Appl. No. 15/788,446, filed Oct. 19, 2017, US 2018-0127471 A1, May 10, 2018, U.S. Pat. No. 11,192,925, Dec. 7, 2021, Registered.

U.S. Appl. No. 15/851,650, filed Dec. 21, 2017, US 2018-0125948 A1, May 10, 2018, U.S. Pat. No. 10,004,788, Jun. 26, 2018, Registered.

U.S. Appl. No. 15/984,085, filed May 18, 2018, US 2018-0320145 A1, Nov. 8, 2018, U.S. Pat. No. 11,248,214, Feb. 15, 2022, Registered.

Applicant's reply to communication from the Examining Division during prosecution of EP3501549, Jun. 16, 2020.

Applicant's reply to communication from the Examining Division during prosecution of EP3501549, Sep. 14, 2020.

Arshad M. Khanani et al., First Interim Results (24 weeks) for the Randomized Phase 2 Dose Expansion Stage of the PRISM Clinical Trial of 4D-150 in High Need Patients with nAMD, presented at Angiogenesis, Exudation, and Degeneration 2024 Conference.

Au, Hau Kiu Edna et al. "Gene Therapy Advances: A Meta-Analysis of AAV Usage in Clinical Settings." Frontiers in medicine vol. 8 809118. Feb. 9, 2022, doi: 10.3389/fmed.2021.809118.

Bastola, Prabhakar et al. "Adeno-Associated Virus Mediated Gene Therapy for Corneal Diseases." Pharmaceutics vol. 12,8 767. Aug. 13, 2020, doi: 10.3390/pharmaceutics12080767.

Bower, Jacquelyn J et al. "Subconjunctival Administration of Adeno-associated Virus Vectors in Small Animal Models." Journal of visualized experiments : JoVE , 181 10.3791/63532. Mar. 16, 2022, doi: 10.3791/63532.

Davis-Smyth, T et al. "The second immunoglobulin-like domain of the VEGF tyrosine kinase receptor Flt-1 determines ligand binding and may initiate a signal transduction cascade." The EMBO journal vol. 15, 18 (1996): 4919-27.

Daya, Shyam, and Kenneth I Berns. "Gene therapy using adeno-associated virus vectors." Clinical microbiology reviews vol. 21,4 (2008): 583-93. doi:10.1128/CMR.00008-08.

FDA approved labelling Sep. 26, 2006 for Lucentis (downloadable at https:// www.accessdata.fda.gov/drugsatfdadocs/nda/2006/ 125156s0000 Lucentis Prntlbl.pdf).

FDA approved labelling Nov. 2011 for Eylea® URL: https://www.accessdata.fda.gov/drugsatfda_docs/labe1/2011/ 1253871b1.pdf [retrieved on Jun. 14, 2024].

Garcia-Quintanilla, Laura et al. "Pharmacokinetics of Intravitreal Anti-VEGF Drugs in Age-Related Macular Degeneration." Pharmaceutics vol. 11,8 365. Jul. 31, 2019, doi: 10.3390/ pharmaceutics11080365.

Irigoyen, Cristina et al. "Subretinal Injection Techniques for Retinal Disease: A Review." Journal of clinical medicine vol. 11,16 4717. Aug. 12, 2022, doi:10.3390/jcm11164717.

Krohne, Tim U et al. "Intraocular pharmacokinetics of ranibizumab following a single intravitreal injection in humans." American journal of ophthalmology vol. 154,4 (2012): 682-686.e2. doi: 10.1016/ j.ajo.2012.03.047.

Lee S, Kang IK, Kim JH, Jung BK, Park K, Chang H, Lee JY, Lee H. Relationship Between Neutralizing Antibodies Against Adeno-Associated Virus in the Vitreous and Serum: Effects on Retinal Gene Therapy. Transl Vis Sci Technol. Apr. 9, 2019;8(2):14. doi: 10.1167/ tvst.8.2.14. PMID: 31016068; PMCID: PMC6467092.

Maynard, S., Venkatesha, S., Thadhani, R et al. Soluble Fms-like Tyrosine Kinase 1 and Endothelial Dysfunction in the Pathogenesis of Preeclampsia. Pediatr Res 57, 1-7 (2005).

Melissa A. Calton, et al. 'Preclinical Characterization of 4D-175, a Novel AAV-Based Investigational Intravitreal Gene Therapy for Geographic Atrophy', Association for Research in Vision and Ophthalmology Annual Meeting (ARVO), May 9, 2024.

Rakoczy, Elizabeth P et al. "Gene therapy with recombinant adeno-associated vectors for neovascular age-related macular degeneration: 1 year follow-up of a phase 1 randomised clinical trial." Lancet (London, England) vol. 386, 10011 (2015): 2395-403. doi:10.1016/ S0140-6736(15)00345-1.

Richard Beckmann et al. (Adverum), ADVM-022 for Neovascular AMD, presented at Gene Therapy for Ophthalmic Disorders Meeting (https://web.archive.org/web/20220910021804/https:/genetherapy-ophthalmology.com/).

Sarra, G M et al. "Kinetics of transgene expression in mouse retina following sub-retinal injection of recombinant adeno-associated virus." Vision research vol. 42,4 (2002): 541-9. doi: 10.1016/s0042-6989(01)00230-9.

Weber, Michel et al. "Recombinant adeno-associated virus serotype 4 mediates unique and exclusive long-term transduction of retinal pigmented epithelium in rat, dog, and nonhuman primate after subretinal delivery." Molecular therapy : the journal of the American Society of Gene.

Zincarelli, Carmela et al. "Analysis of AAV serotypes 1-9 mediated gene expression and tropism in mice after systemic injection." Molecular therapy : the journal of the American Society of Gene Therapy vol. 16,6 (2008): 1073-80. doi:10.1038/mt.2008.76.

* cited by examiner

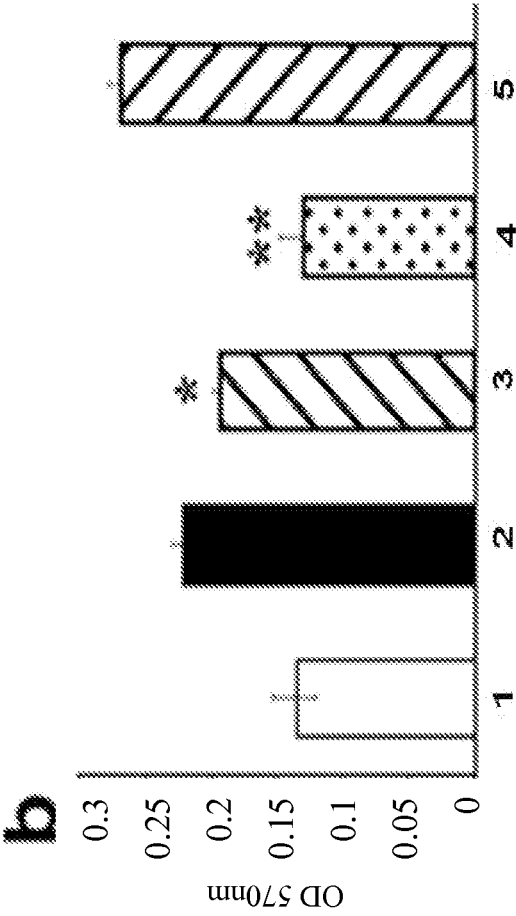
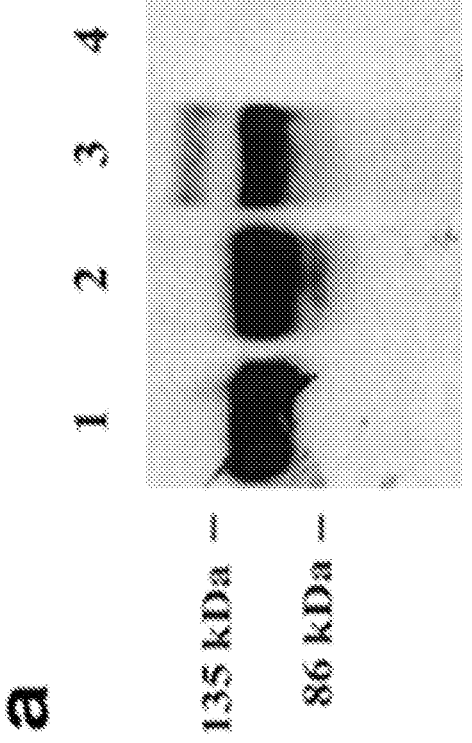
FIG. 2

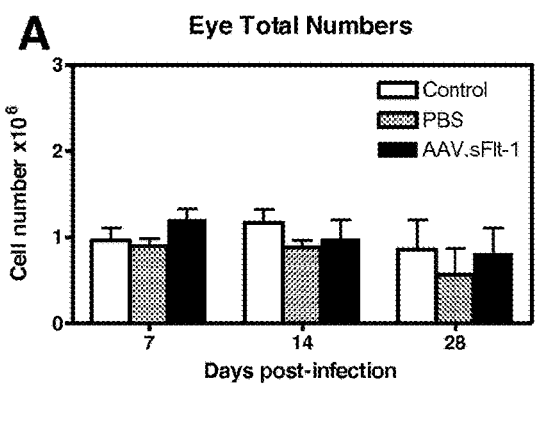
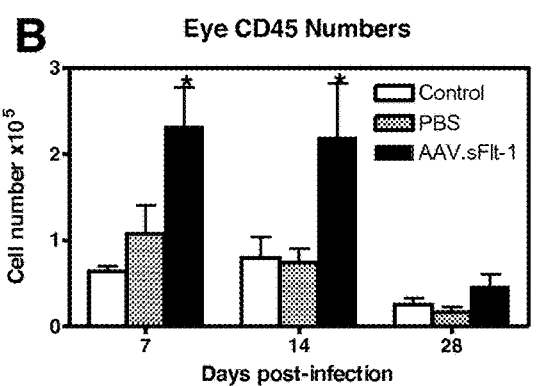
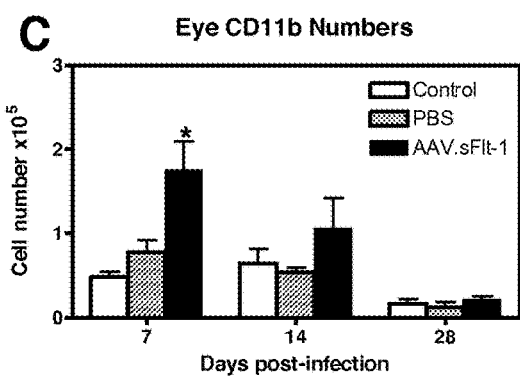
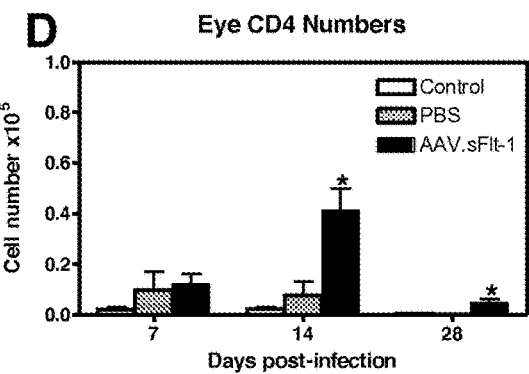
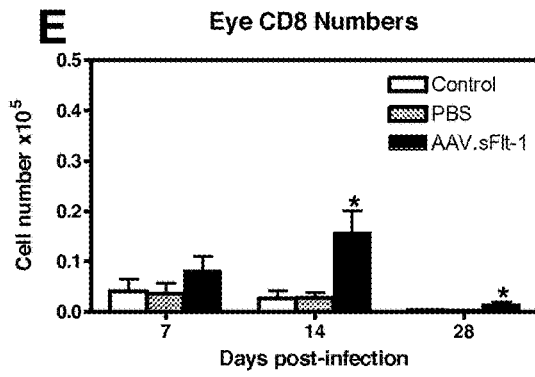
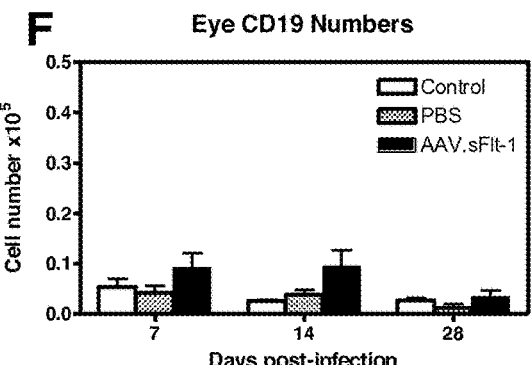
FIG. 4

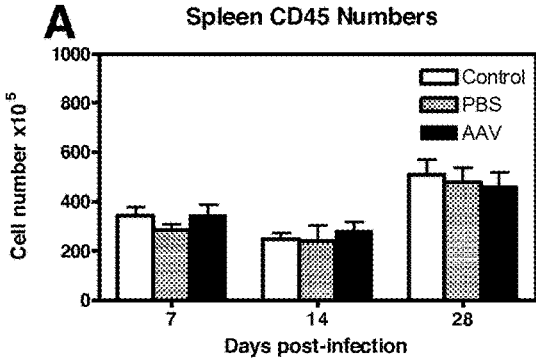
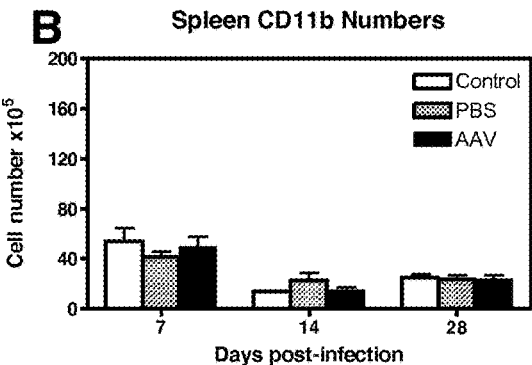
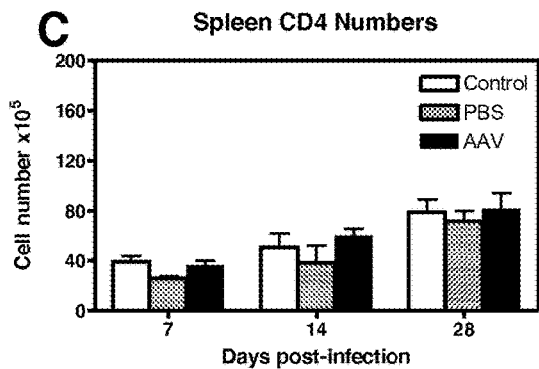
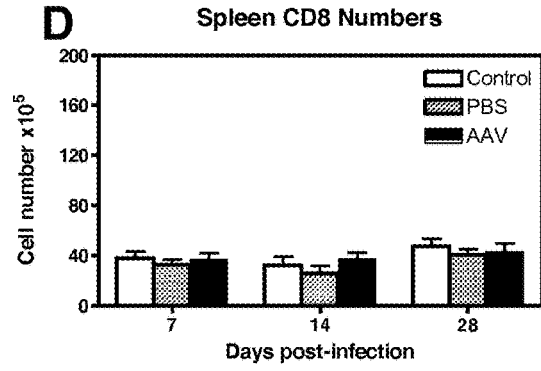
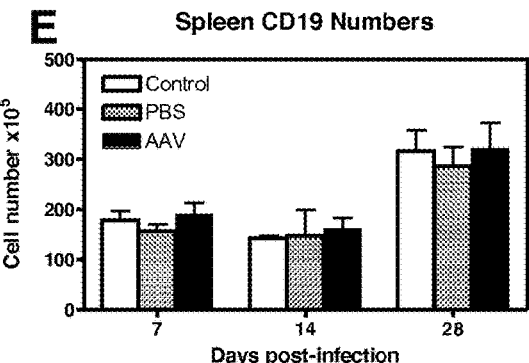
FIG. 5

A
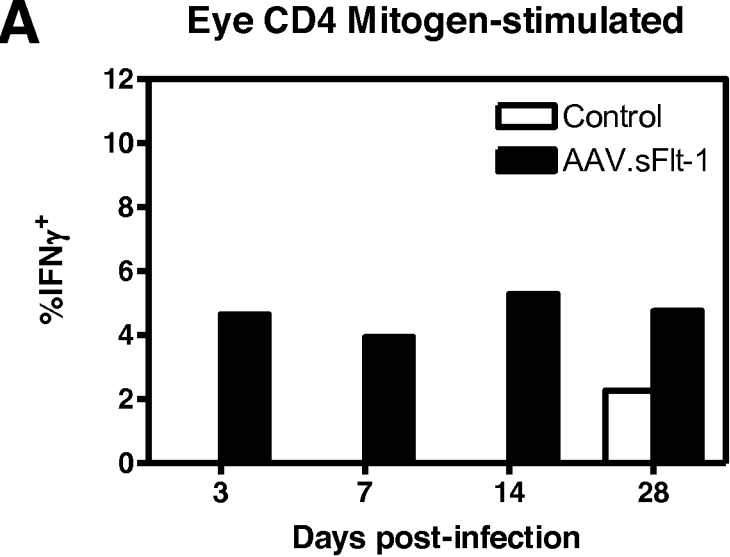
B
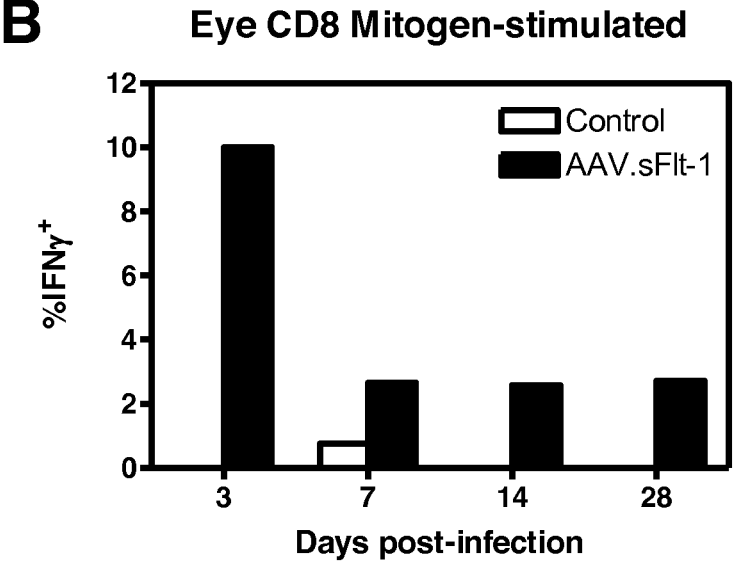
FIG. 6

Origin 1

ATGGAAAAACGCCAGCAACG (SEQ ID NO: 1)

Origin 2

AAAAGGATCTAGGTGAAGATCCTTTTTTGATAATCTCATGACCAAAATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGGGGTTCGTGCACACAGCCCAGCTTGGAGCGAA
CGACCTACACCGAACTGAGATACCTACAGCGTGAGCTATGAGAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACGCCTGGTATCTTTATAGTCCTGTCGGGTTTCGCCACCTCTGAC
TTGAGCGTCGATTTTTGTGATGCTCGTCAGGGGGGCGGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTATTACCGCCTTTGAGTGAGCTGATACCGCTCGCCGCAGC
CGAACGACCGAGCGCAGCGAGTCAGTGAGCGAGGAAGCGGAAGA (SEQ ID NO: 2)

Origin 3

GCGCCACGCTTCCCGAAGGGAGAAAGGCGGACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCTGGCCTTTTGCTCACATGTTCTTTCCTGCGTTATCCCCTGATTCTGT
GGATAACCGTATTACCGCCTTTGAGTGAGCTGATACCGCTCGCCGCAGCCGAACGACCGAGCGCAGCGAGTCAGTGAGCGAGGAA (SEQ ID
NO: 3)

Origin 4

AAAGGATCTTCTTGAGATCCTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCCGTAGTTAGGCCACCA
CTTCAAGAACTCTGTAGCACCGCCTACATACCTCGCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTATAGTCCTGTCGGGTTTCGCCACCTCTGACTTGAGC
GTCGATTTTTGTGATGCTCGTCAGGGGGGCGGAGCCTATGGAAAAACGCCAGCAACGCG (SEQ ID NO: 4)

FIG. 7A

Origin 5

TGTTGTTTGTCGGTTAACGTCGACCTAGAGCTGCCTCGCGCGTTTCGGTGATGACGGTGAAAACCTCTGACACATGCAGCTCCCGGAGACGGT
CACAGCTTGTCTGTAAGCGGATGCCGGGAGCAGACAAGCCCGTCAGGGCGCGTCAGCGGGTGTTGGCGGGTGTCGGGGCGCAGCCATGACC
CAGTCACGTAGCGATAGCGGAGTGTATACTGGCTTAACTATGCGGCATCAGAGCAGATTGTACTGAGAGTGCACCATATGCGGTGTGAAATA
CCGCACAGATGCGTAAGGAGAAAATACCGCATCAGGCGCTCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCAATGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCCGGTAACTATCGTCTTGAGTCCAACCCGGTAAGACACGACT
TATCGCCACTGGCAGCAGCCACTGGTAACAGGATTAGCAGAGCGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGTTACCTTCGGAAAAAGAGTTGGTAGCTCTTGATCCGGCAAACAA
ACCACCGCTGGTAGCGGTGGTTTTTTTTGTTTGCAAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTT (SEQ ID NO: 5)

Origin 6

CCCGTAGAAAAGATCAAAGGATCTTCTTGAGATCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCATTGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACAT (SEQ ID NO: 6)

Origin 7

ATGTGAGCAAAAGGCCAGCAAAAGGCCAGGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAAAAAAGGATCTCAAGAA
GATCCTTTGATCTTTTCTACGGG (SEQ ID NO: 7)

FIG. 7B

Origin 8

TTAATAAGATGATCTTCTTGAGATCGTTTTGGTCTGCGCGTAATCTCTTGCTCTGAAAACGAAAAAACCGCCTTGCAGGGCGGTTTTTCGAAGG
TTCTCTGAGCTACCAACTCTTTGAACCGAGGTAACTGGCTTGGAGGAGCGCAGTCACCAAAACTTGTCCTTTCAGTTTAGCCTTAACCGGCGCA
TGACTTCAAGACTAACTCCTCTAAATCAATTACCAGTGGCTGCTGCCAGTGGTGCTTTTGCATGTCTTTCCGGGTTGGACTCAAGACGATAGTT
ACCGGATAAGGCGCAGCGGTCGGACTGAACGGGGGGTTCGTGCATACAGTCCAGCTTGGAGCGAACTGCCTACCCGGAACTGAGTGTCAGG
CGTGGAATGAGACAAACGCGGCCATAACAGCGGAATGACACCGGTAAACCGAAAGGCAGGAACAGGAGAGCGCACGAGGGAGCCGCCAG
GGGGAAACGCCTGGTATCTTTATAGTCCTGTCGGGTTTCGCCACCACTGATTTGAGCGTCAGATTTCGTGATGCTTGTCAGGGGGGCGGAGCC
TATGGAAAAACGGCTTTGCCGCGGCCCTCTCACTTCCCTGTTAAGTATCTTCCTGGCATCTTCCAGGAAATCTCCGCCCCGTTCGTAAGCCATTT
CCGCTCGCCGCAGTCGAACGACCGAGCGTAGCGAGTCAGTGAGCGAGGAAGCGGAATATATCCTGTATCACATATTCTGCTGACGCACCGGT
GCAGCCTTTTTTCTCCTGCCACATGAAGCACTTCACTGACACCCTCATCAGTGCCAACATAGTAAGCCAGTATACACTCCGCTAGCGC (SEQ ID
NO: 8)

Origin 9

AAACGCCAGCAACGCGGCCTTTTTACGGTTCCTGGCCTTTTGCTGGCCTTTTGCTCACATGTTCTTTCCTGCGTTATCCCCTGATTCTGTGGATA
ACCGTATTACCGCCTTTGAGTGAGCTGATACCGCTCGCCGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATGCAG (SEQ ID NO: 9)

Origin 10

AAATTGTAAACGTTAATATTTTGTTAAAATTCGCGTTAAATATTTGTTAAATCAGCTCATTTTTTAACCAATAGGCCGAAATCGGCAAAATCCCT
TATAAATCAAAAGAATAGACCGCGATAGGGTTGAGTGTTGTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCAAATCAAGTTTTTTGCGGTCGAGGTGCCGTAAAGCTCTAAAT
CGGAACCCTAAAGGGAGCCCCCGATTTAGAGCTTGACGGGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCACACCCGCCGCGCTTAATGCGCCGCTACAGGGCGCGT (SEQ ID
NO: 10)

Origin 11

GGCGCATTAAGCGCGGCGGGTGTGGTGGTTACGCGCAGCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCTCCCTTTAGGGTTCCGATTTAGTGCTTTACGGCACCTCGACCC
CAAAAAACTTGATTAGGGTGATGGTTCACGTAGTGGGCCATCGCCCTGATAGACGGTTTTTCGCCCTTTGACGTTGGAGTCCACGTTCTTTAAT
AGTGGACTCTTGTTCCAAACTGGAA (SEQ ID NO: 11)

Origin 12

ACGCGCCCTGTAGCGGCGCATTAAGCGCGGCGGGTGTGGTGGTTACGCGCAGCGTGACCGCTACACTTGCCAGCGCCCTAGCGCCCGCTCCT
TTCGCTTTCTTCCCTTCCTTTCTCGCCACGTTCGCCGGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGTCTATTCTTTTGATTTATAAGGGATTTTGCCGATT
TCGGCCTATTGGTTAAAAAATGAGCTGATTTAACAAAAATTTAACGCGAATTTTAACAAAATATTAACGCTTACAATTT (SEQ ID NO: 12)

Origin 14

AATTTTTTTTATTTATGCAGAGGCCGAGGCCGCCTCGGCCTCTGAGCTATTCCAGAAGTAGTGAGG (SEQ ID NO: 13)

FIG. 7C

Origin 15

TGGACAGCGAACGCACACTACAACCTTGGATAGAGTTAGGAATTAGTAGACGGACATACTACAGGGATTTAAATGATAATCATTCTCAAAAAT
GACACCAGATAAGCCTAAATCAGATAACAGCCCCAAAAGCGAGCTTTTGGGGTGCCTTTTAGACGGTGCTAGGTTTTTGACAGCAGATAAGCC
TAAATCAGATAACAGCCGAATCGATAAGCCTTAGTTGGTTAAGGGGGCAGGAAATTCATATTGAACAAATGTTTAGTTAAGTGTAGAATAATC
ATACATCCTTATTAAGGGCAAGCATACTCAAGCCCCACAAAGTGTGCTTGAAATCCTTGTAAGGGGAAATCCCCCTTAACCCC (SEQ ID NO:
14)

Origin 16

TTGAGATCCTTTTTTTCTGCGCGTAATCTGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTCCTTCTAGTGTAGCCGTAGTTAGGCCACCACTTCAAGAACT
CTGTAGCACCGCCTACATACCTCGCTCTGCTAATCCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGGTTCGTGCACACAGCCCAGCTTGGAGCGAACGACCTACACCGAACTG
AGATACCTACAGCGTGAGCTATGAGAAAGCGCCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGGGTTTCGCCACCTCTGACTTGAGCGTCGATTTTTG
TGATGCTCGTCAGGGGGGCGGAGCCTATGGAAA (SEQ ID NO: 15)

Origin 17

TTTACGCGCCCTGTAGCGGCGCATTAAGCGCGGCGGGTGTGGTGGTTACGCGCAGCGTGACCGCTACACTTGCCAGCGCCCTAGCGCCCGCT
CCTTTCGCTTTCTTCCCTTCCTTTCTCGCCACGTTCGCCGGCTTTCCCCGTCAAGCTCTAAATCGGGGGCTCCCTTTAGGGTTCCGATTTAGTGCT
TTACGGCACCTCGACCCCAAAAAACTTGATTTGGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTTGAACAACACTCAACCCTATCTCGGGCTATTCTTTTGATTTATAAGGGATTTTGCCG
ATTTCGGCCTATTGGTTAAAAAATGAGCTGATTTAACAAAAATTTAACGCGAATTTTAACAAAATATTAACGTTTACAATTT (SEQ ID NO: 16)

FIG. 7D

Promoter 1

ATGCATTAGTTATTAATAGTAATCAATTACGGGGTCATTAGTTCATAGCCCATATATGGAGTTCCGCGTTACATAACTTACGGTAAATGGCCCG
CCTGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTCTCCACCCCATTGACGTCAATGGGAGTTTGTT
TTGGCACCAAAATCAACGGGACTTTCCAAAATGTCGTAACAACTCCGCCCCATTGACGCAAATGGGCGGTAGGCGTGTACGGTGGGAGGTCT
ATATAAGCAGAGCTGGTTTAGTGAACCGTCAGATCCGCTAGC (SEQ ID NO: 17)

Promoter 2

TCAATATTGGCCATTAGCCATATTATTCATTGGTTATATAGCATAAATCAATATTGGCTATTGGCCATTGCATACGTTGTATCTATATCATAATAT
GTACATTTATATTGGCTCATGTCCAATATGACCGCCATGTTGGCATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGAGTATTTACGGTAAACTGCCCACTTGGCAGTACATCA
AGTGTATCATATGCCAAGTCCGCCCCCTATTGACGTCAATGACGGTAAATGGCCCGCCTGGCATTATGCCCAGTACATGACCTTACGGGACTTT
CCTACTTGGCAGTACATCTACGTATTAGTCATCGCTATTACCATGGTGATGCGGTTTTGGCAGTACACCAATGGGCGTGGATAGCGGTTTGACT
CACGGGGATTTCCAAGTCTCCACCCCATTGACGTCAATGGGAGTTTGTTTTGGCACCAAAATCAACGGGACTTTCCAAAATGTCGTAATAACCC
CGCCCCGTTGACGCAAATGGGCGGTAGGCGTGTACGGTGGGAGGTCTATATAAGCAGAGCTCGTTTAGTGAACCGTCAGAT (SEQ ID NO:
18)

Promoter 3

ACGCGTACTAGTTATTAATAGTAATCAATTACGGGGTCATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTCCCATAGTAACGTCAATAGGGACTTTCCATTGACGTCA
ATGGGTGGAGTATTTACGGTAAACTGCCCACTTGGCAGTACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTCTCCACCCCATTGACGTCAATGGGAGTTTG
TTTTGCACCAAAATCAACGGGACTTTCCAAAATGTCGTAACAACTCCGCCCCATTGACGCAAATGGGCGGTAGGCGTGTACGGTGGGAGGTCT
ATATAAGCAGAGCTCGTTTAGTGAACCGTCAGATCGCCTGGAGACGCCATCCACGCTGTTTTGACCTCCATAGAAGACACCGGGACCGATCCA
GCCTCCGTAC (SEQ ID NO: 19)

Promoter 4

ACGCGTGGAGCTAGTTATTAATAGTAATCAATTACGGGGTCATTAGTTCATAGCCCATATATGGAGTTCCGCGTTACATAACTTACGGTAAATG
GCCCGCCTGGCTGACCGCCCAACGACCCCCGCCCATTGACGTCAATAATGACGTATGTTCCCATAGTAACGTCAATAGGGACTTTCCATTGACG
TCAATGGGTGGAGTATTTACGGTAAACTGCCCACTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCAGTACATCTACGTATTAGTCATCGCTATTACCATGG
TGATGCGGTTTTGGCAGTACATCAATGGGCGTGGATAGCGGTTTGACTCACGGGGATTTCCAAGTCTCCACCCCATTGACGTCAATGGGAGTT
TGTTTTGCACCAAAATCAACGGGACTTTCCAAAATGTCGTAACAACTCCGCCCCATTGACGCAAATGGGCGGTAGGCGTGTACGGTGGGAGG
TCTATATAAGCAGAGCTCGTTTAGTGAACCGTCAGATCGCCTGGAGACGCCATCCACGCTGTTTTGACCTCCATAGAAGACACCGGGACCGAT
CCAGCCTCC (SEQ ID NO: 20)

FIG. 8A

Promoter 5

TAGTTATTAATAGTAATCAATTACGGGGTCATTAGTTCATAGCCCATATATGGAGTTCCGCGTTACATAACTTACGGTAAATGGCCCGCCTGGC
TGACCGCCCAACGACCCCCGCCCATTGACGTCAATAATGACGTATGTTCCCATAGTAACGCCAATAGGGACTTTCCATTGACGTCAATGGGTG
GAGTATTTACGGTAAACTGCCCACTTGGCAGTACATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTACGTATTAGTCATCGCTATTACCATGGTGATGCGGTT
TTGGCAGTACATCAATGGGCGTGGATAGCGGTTTGACTCACGGGGATTTCCAAGTCTCCACCCCATTGACGTCAATGGGAGTTTGTTTTGGCA
CCAAAATCAACGGGACTTTCCAAAATGTCGTAACAACTCCGCCCCATTGACGCAAATGGGCGGTAGGCGTGTACGGTGGGAGGTCTATATAA
GCAGAGCTGGTTTAGTGAACCGTCAGATC (SEQ ID NO: 21)

Promoter 6

GCGGCCGCACGCGTGGAGCTAGTTATTAATAGTAATCAATTACGGGGTCATTAGTTCATAGCCCATATATGGAGTTCCGCGTTACATAACTTAC
GGTAAATGGCCCGCCTGGCTGACCGCCCAACGACCCCCGCCCATTGACGTCAATAATGACGTATGTTCCCATAGTAACGTCAATAGGGACTTT
CCATTGACGTCAATGGGTGGAGTATTTACGGTAAACTGCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTTCCTACTTGGCAGTACATCTACGTATTAGTCATCGCTA
TTACCATGGTGATGCGGTTTTGGCAGTACATCAATGGGCGTGGATAGCGGTTTGACTCACGGGGATTTCCAAGTCTCCACCCCATTGACGTCA
ATGGGAGTTTGTTTTGCACCAAAATCAACGGGACTTTCCAAAATGTCGTAACAACTCCGCCCCATTGACGCAAATGGGCGGTAGGCGTGTACG
GTGGGAGGTCTATATAAGCAGAGCTCGTTTAGTGAACCGTCAGATCGCCTGGAGACGCCATCCACGCTGTTTTGACCTCCATAGAAGACACCG
GGACCGATCCAGCCTC (SEQ ID NO: 22)

Promoter 7

GGCGACCGCCCAGCGACCCCCGCCCGTTGACGTCAATAGTGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTCCGCCCCCTATTGACGTCAATGACGGTAAATGGC
CCGCCTAGCATTATGCCCAGTACATGACCTTACGGGAGTTTCCTACTTGGCAGTACATCTACGTATTAGTCATCGCTATTACCATGGTGATGCG
GTTTTGGCAGTACACCAATGGGCGTGGATAGCGGTTTGACTCACGGGGATTTCCAAGTCTCCACCCCATTGACGTCAATGGGAGTTTGTTTTG
GCACCAAAATCAACGGGACTTTCCAAAATGTCGTAATAACCCCGCCCCGTTGACCCAAATGGGCGGTAGGCGTGTACGGTGGGAGGTCTATA
TAGCAGAGCTCGTTTAGTGAACCGT (SEQ ID NO: 23)

Promoter 8

TTAGTCATATGTTACTTGGCAGAGGCCGCATGGAAAGTCCCTGGACGTGGGACATCTGATTAATACGTGAGGAGGTCAGCCATGTTCTTTTTG
GCAAAGGACTACGGTCATTGGACGTTTGATTGGCATGGGATAGGGTCAGCCAGAGTTAACAGTGTTCTTTTGGCAAAGGGATACGTGGAAAG
CCCCGGGCCATTTACAGTAAACTGATACGGGGACAAAGCACAGCCATATTTAGTCATGTACTGCTTGGCAGAGGGTCTATGGAAAGTCCCTG
GACGTGGGACGTCTGATTAATATGAAAGAAGGTCAGCCAGAGGTAGCTGTGTCCTTTTTGGCAAAGGGATACGGTTATGGGACGTTTGATTG
GACTGGGATAGGGTCAGCCAGAGTTAACAGTGTTCTTTTGGCAAAGGAAACGTGGAAAGTCCCGGGCCATTTACAGTAAACTGATACTGGGA
CAAAGTACACCCATATTTAGTCATGTTCTTTTTGGCAAAGAGCATCTGGAAAGTCCCGGGCAGCATTATAGTCACTTGGCAGAGGGAAAGGGT
CACTCAGAGTTAAGTACATCTTTCCAGGGCCAATATTCCAGTAAATTACACTTAGTTTTATGCAAATCAGCCACAAAGGGGATTTTCCCGGTCA
ATTATGACTTTTTCCTTAGTCATGCGGTATCCAATTACTGCCAAATTGGCAGTACATACTAGGTGATTCACTGACATTTGGCCGTCCTCTGGAAA
GTCCCTGGAAACCGCTCAAGTACTGTATCATGGTGACTTTGCATTTTTGGAGAGCACGCCCCACTCCACCATTGGTCCACGTACCCTATGGGGG
AGTGGTTTATGAGTATATAAGGGGCTCCGGTTTAGAAGCCGGGCAGAGCG (SEQ ID NO: 24)

FIG. 8B

Promoter 9

ATTGACGTCAATAATGACGTATGTTCCCATAGTAACGCCAATAGGGACTTTCCATTGACGTCAATGGGTGGACTATTTACGGTAAACTGCCCAC
TTGGCAGTACATCAAGTGTATCATATGCCAAGTACGCCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCATGGTCGAGGTGAGCCCCACGTTCTGCTTCACTCTCCC
CATCTCCCCCCCCTCCCCACCCCCAATTTTGTATTTATTTATTTTTTAATTATTTTGTGCAGCGATGGGGGCGGGGGGGGGGGGGGGGGGCGCGC
GCCAGGCGGGGCGGGGCGGGGCGAGGGGCGGGGCGGGGCGAGGCGGAGAGGTGCGGCGGCAGCCAATCAGAGCGGCGCGCTCCGAAA
GTTTCCTTTTATGGCGAGGCGGCGGCGGCGGCGGCCCTATAAAAAGCGAAGCGCGCGGCGGGCGGGAGTCGCTGCGACGCTGCCTTCGCCC
CGTGCCCCGCTCCGCCGCCGCCTCGCGCCGCCCGCCCCGGCTCTGACTGACCGCGTTACTCCCACAGGTGAGCGGGCGGGACGGCCCTTCTCC
TCCGGGCTGTAATTAGCGCTTGGTTTAATGACGGCTTGTTTCTTTTCTGTGGCTGCGTGAAAGCCTTGAGGGGCTCCGGGAGGGCCCTTTGTG
CGGGGGGAGCGGCTCGGGGCTGTCCGCGGGGGGACGGCTGCCTTCGGGGGGGGACGGGGCAGGGCGGGGTTCGGCTTCTGGCGTGTGACC
GGCGGCTCTAGAGCCTCTGCTAACCATGTTCATGCCTTCTTCTTTTTCCTACAGCTCCTGGGCAACGTGCTGGTTATTGTGCTGTCTCATCATTTT
GGCAAAGAATT (SEQ ID NO: 25)

Promoter 10

GTCGAGGTGAGCCCCACGTTCTGCTTCACTCTCCCCATCTCCCCCCCCTCCCCACCCCCAATTTTGTATTTATTTATTTTTTAATTATTTTGTGCAG
CGATGGGGGCGGGGGGGGGGGGGGCGCGCGCCAGGCGGGGCGGGGCGGGGCGAGGGGCGGGGCGGGGCGAGGCGGAGAGGTGCGGC
GGCAGCCAATCAGAGCGGCGCGCTCCGAAAGTTTCCTTTTATGGCGAGGCGGCGGCGGCGGCGGCCCTATAAAAAGCGAAGCGCGCGGCG
GGCGGGAGTCGCTGCGTTGCCTTCGCCCCGTGCCCCGCTCCGCGCCGCCTCGCGCCGCCCGCCCCGGCTCTGACTGACCGCGTTACTCCCACA
G (SEQ ID NO: 26)

Promoter 11

TCGAGGTGAGCCCCACGTTCTGCTTCACTCTCCCCATCTCCCCCCCCTCCCCACCCCCAATTTTGTATTTATTTATTTTTTAATTATTTTGTGCAGC
GATGGGGGCGGGGGGGGGGGGGGGGCGCGCGCCAGGCGGGGCGGGGCGGGGCGAGGGGCGGGGCGGGGCGAGGCGGAGAGGTGCGG
CGGCAGCCAATCAGAGCGGCGCGCTCCGAAAGTTTCCTTTTATGGCGAGGCGGCGGCGGCGGCGGCCCTATAAAAAGCGAAGCGCGCGGCG
GGCG (SEQ ID NO: 27)

Promoter 12

CCAGAAAAAGTCAACACACTTGTCATAAAGTCCCGACGAAGTAAAACAAGCGGAATTAATTCAATTTGGCCAAAAAACCTAGTATAAAGACGT
GCATAGTGTCGGGAAT (SEQ ID NO: 28)

Promoter 13

CTTCCTCACGCTGAACCCCTTTAACCGTTTCAGTGGTCGTGAGTCTTCTAATCTGACTGTGTGACGATGTTTTAAGGATTTGGAGGATTGAGGA
GGATCACCTGGTCAGGTAAATCTGAAATATCCGGATTACATCGGAAGTTGAGCACACGGAAAAACAAAAGACTCTTATTGGATTTAGATCCGT
CAGCCACCTGCTGCTGCTCTTCATCATCAGGCGTCTTCATCGCCCTGCAGTGGGCCTGACAACAGCTTGTGTTTATTACACTAAAAACTTTATAA
ACCCATCACAAACCATATCACACAGCAGGGACTTACCTCTTCATCTGTAAGAAGGATTTTTAGAGTTGGCAGCAGAGCAACAGTCAGCTCTGTT
GCCTCACTAAAAGAGATCTTTGTTTGAATCTGTGACCTGTCCAAGTGTACCTCGCTTCTCACCCACTGACCTCTCCACAACAGTGAGCTGGTTG
GCGGGATGCTAATGTTTCTAGTTATTACGTGTAACCAAACTTAAAGAGTACAGATAAATCATTTAGCATAATTAAAGTTTTACTGTCATGTTATT
GGCTGTTAATATGATTGCTGTTGTAAGTATGTGTTGATCACTAACAATTTAATTAATTAAATCAATCATTAAATTAAGTTTGTTTGGAAAAAGAG
GGAAAACTCATCCACTGACCACATGGTTCTAGGTTCAATTCCTTGGAGTTAAAGGGCTAATCCCAGAGCCATTTACCAAAATAATAAATAAATA
TTTAAATAAGACGTGCATGCGACTGCGGTCACCTTTAAAGCACAAAGTTTTTTTTGAGCAGTGAGGTGAACTCGGGTGGATCTGTGTGTTCAC
AGAGAAAACCTTCTGTAAGCAGATTAAGGAGTCAGAAGTTCTTAATCCTGAAAGTTTAGAAAAATCCCAGCAGCATAATCTTTGCTGTAAGTG
GTTTACGAGCGTATATAAGAGGCTGACACAGCGGCAGCGGCAAAGAGCTCAGGGTCACA (SEQ ID NO: 29)

FIG. 8C

Promoter 14

AAATCAAAAGTCCTCAACCTGGTTGGAAGAATATTGGCACTGAATGGTATCAATAAGGTTGCTAGAGAGGGTTAGAGGTGCACAATGTGCTT
CCATAACATTTTATACTTCTCCAATCTTAGCACTAATCAAACATGGTTGAATACTTTGTTTACTATAACTCTTACAGAGTTATAAGATCTGTGAAG
ACAGGGACAGGGACAATACCCATCTCTGTCTGGTTCATAGGTGGTATGTAATAGATATTTTTAAAAATAAGTGAGTTAATGAATGAGGGTGAG
AATGGAGGCACAGAGGTATTAGGGGGAGGTGGGCCCCAGAGAATGGTGCCAAGGTCCAGTGGGGTGACTGGGATCAGCTCAGGCCTGACG
CTGGCCACTCCCACCTAGCTCCTTTCTTTCTAATCTGTTCTCATTCTCCTTGGGAAGGATTGAGGTCTCTGGAAAACAGCCAAACAACTGTTATG
GGAACAGCAAGCCCAAATAAAGCCAAGCATCAGGGGGATCTGAGAGCTGAAAGCAACTTCTGTTCCCCCTCCCTCAGCTGAAGGGGTGGGG
AAGGGCTCCCAAAGCCATAACTCCTTTTAAGGGATTTAGAAGGCATAAAAAGGCCCCTGGCTGAGAACT (SEQ ID NO: 30)

Promoter 15

ACTCACGGGGATTTCCAAGTCTCCACCCCATTGACGTCAATGGGAGTTTGTTTTGGCACCAAAATCAACGGGACTTTCCAAAATGTCGTAATAA
CCCCGCCCCGTTGACGCAAATGGGCGGTAGGCGTGTACGGTGGGAGGTCTATATAAGCAGAGCTCGTTTAGTGAACCGT (SEQ ID NO: 31)

Promoter 16

AAAATCAACGGGACTTTCCAAAATGTCGTAATAACCCCGCCCCGTTGACGCAAATGGGCGGTAGGCGTGTACGGTGGGAGGTCTATATAAGC
AGAGCTCGTTTAGTGAACCGT (SEQ ID NO: 32)

Promoter 17

GTAATACGACTCACTATAGGG (SEQ ID NO: 33)

Promoter 18

TAATACGACTCACTATAGG (SEQ ID NO: 34)

Promoter 19
CCGATTAATCATAAATATGAAAAATAATTGTTGCATCACCCGCCAATGCGTGGCTTAATGCACATCA (SEQ ID NO: 35)

Promoter 20
ATTAACCCTCACTAAAGGG (SEQ ID NO: 36)

Promoter 21

ATTAACCCTCACTAAAGGG (SEQ ID NO: 36)

FIG. 8D

Promoter 22

CTAGACAAGGTCGAACGAGGGGCATGACCCGGTGCGGGGCTTCTTGCACTCGGCATAGGCGAGTGCTAAGAATAACGTTGGCACTCG (SEQ ID NO: 37)

Promoter 23

TATTAGGCGAAGAGGCATCTAGTAGTAGTGGCAGTGGTGAGAACGTGGGCGCTGCTATAGTGAACAATCTCCAGTCGATGGTTAAGAAGAA
GAGTGACAAACCAGCAGTGAATGACTTGTCTGGGTCCGTGAGGAAAAGAAAGAAGCCCGACACAAAGGACAGTAACGTCAAGAAACCCAAG
AAATAGGGGGGACCTGTTTAGATGTATAGGAATAAAAACTCCGAGATGATCTCAATGTGTAATGGAGTTGTAATATTGCAAAGGGGGAAAAT
CAAGACTCAAACGTGTGTATGAGTGAGCGTACGTATATCTCCGAGAGTAGTATGACATAATGATGACTGTGAATCATCGTAATCTCACACAAA
AACCCCATTGTCGGCCATATACCACACCAAGCAACACCACATATCCCCCGGAAAAAAAAACGTGAAAAAAAGAAACAATCAAAACTACAACCT
ACTCCTTGATCACACAGTCATTGATCAAGTTACAGTTCCTGCTAGGGAATGACCAAGGTACAAATCAGCACCTTAATGGTTAGCACGCTCTCTT
ACTCTCTCTCACAGTCTTCCGGCCCCTATTCAAAATTCTGCACTTCCATTTGACCCCAGGGTTGGGAAACAGGGCCACAAAAGAAAAACCCGAC
GTGAATGAAAAAACTAAGAAAAGAAAAAAAATTATCACACCAGAAATTTACCTAATTGGGTAATTCCCATCGGTGTTTTTCCTGGATTGTCGCA
CGCACGCATGCTGAAAAAAGTGTTCGAGTTTTGCTTTTGCCTCGGAGTTTCACGCAAGTTTTTCGATCTCGGAACCGGAGGGCGGTCGCCTTG
TTGTTTGTGATGTCGTGCTTTGGGTGTTCTAATGTGCTGTTATTGTGCTCTTTTTTTTTTCTTCTTTTTTTGGTGATCATATGATATTGCTCGGTAGA
TTACTTTCGTGTGTAGGTATTCTTTTAGACGTTTGGTTATTGGGTAGATATGAGAGAGAGAGAGTGGGTGGGGGAGGAGTTGGTTGTAGGAG
GGACCCCTGGGAGGAAGTGTAGTTGAGTTTTCCCTGACGAATGAAAATACGTTTTTGAGAAGATAATACAGGAAAGGTGTGTCGGTGAATTT
CCATCTATCCGAGGATATGAGTGGAGGAGAGTCGTGTGCGTGTGGTTAATTTAGGATCAGTGGAACACACAAAGTAACTAAGACAGAGAGA
CAGAGAGAAAAATCTGGGGAAGAGACAAAGAGTCAGAGTGTGTGAGTTATTCTGTATTGTGAAATTTTTTTGCCCAACTACATAATATTGCTG
AAACTAATTTTACTTAAAAAGAAAAGCCAACAACGTCCCCAGTAAAACTTTTCTATAAATATCAGCAGTTTTCCCTTTCCTCCATTCCTCTTCTTG
TCTTTTTTCTTACTTTCCCTTTTTTTATACCTTTTCATTATCATCCTTTATAATTGTCTAACCAACAACTATATATCTATCAA (SEQ ID NO: 38)

Promoter 24

CCCACACACCATAGCTTCAAAATGTTTCTACTCCTTTTTTACTCTTCCAGATTTTCTCGGACTCCGCGCATCGCCGTACCACTTCAAAACACCCAA
GCACAGCATACTAAATTTTCCCTCTTTCTTCCTCTAGGGTGTCGTTAATTACCCGTACTAAAGGTTTGGAAAAGAAAAAAGAGACCGCCTCGTT
TCTTTTTCTTCGTCGAAAAAGGCAATAAAAATTTTTATCACGTTTCTTTTTCTTGAAATTTTTTTTTTTAGTTTTTTTCTCTTTCAGTGACCTCCATT
GATATTTAAGTTAATAAACGGTCTTCAATTTCTCAAGTTTCAGTTTCATTTTTCTTGTTCTATTACAACTTTTTTTACTTCTTGTTCATTAGAAAGA
AAGCATAGCAATCTAATCTAAGGGGCG (SEQ ID NO: 39)

Promoter 25

TTGACAATTAATCATCGGCTCGTATAAT (SEQ ID NO: 40)

Promoter 26

TTCAAATATGTATCCGCTCATGAGACA (SEQ ID NO: 41)

Promoter 27

AACTACCCGTAGGTGTAGTTGGCGCAAGCGTCCGATTAGCTCAGGTTTAAGATGTCGAGAGTGAGAGTGGGCGGCTTAACTTTCTCAGTTAG
GCATAAAATTACGTCTTAAATCTCGTAGCGACTAATTTAATAAAAATTGGA (SEQ ID NO: 42)

FIG. 8E

Promoter 28

GCGCAGCACCATGGCCTGAAATAACCTCTGAAAGAGGAACTTGGTTAGGTACCTTCTGAGGCGGAAAGAACCAGCTGTGGAATGTGTGTCAG
TTAGGGTGTGGAAAGTCCCCAGGCTCCCCAGCAGGCAGAAGTATGCAAAGCATGCATCTCAATTAGTCAGCAACCAGGTGTGGAAAGTCCCC
AGGCTCCCCAGCAGGCAGAAGTATGCAAAGCATGCATCTCAATTAGTCAGCAACCATAGTCCCGCCCCTAACTCCGCCCATCCCGCCCCTAACT
CCGCCCAGTTCCGCCCATTCTCCGCCCCATGGCTGACTAATTTTTTTTTATTTATGCAGAGGCCGAGGCCGCCTCGGCCTCTGAGCTATTCCAGAA
GTAGTGAGGAGGCTTTTTTGGAGGCCTAGGCTTTTGCAAAAAGCTT (SEQ ID NO: 43)

Promoter 29

GACGCTTTTTATCGCAACTCTCTACTGT (SEQ ID NO: 44)

Promoter 30
CATGACAAAAACGCGTAACAAAAGTGTCT (SEQ ID NO: 45)

Promoter 31

AGCCGAATTCCTCCTCATTCTTCTCCAAACCTTTATTGAGTACCTACTGTGTGCTGGAATAAGACAGGCAGGGCCATGCCCTCATGAAGCTGAC
AATCCTATTGGTGTGACCATCCCCAGGTGTGTCCCAGGTGTGTTGCAGGTGTGTCCGAGGTATGCCCCAGCTGTCCCAGGTGTGCCCCAGCTG
TCTCAGATGTGCCCCAGCTGTCCCAGGTGTGTCACAGCTGCATTGCAGGTGTGCCCCAGTTGCATTCCATGTGTGCTCCAAGTGTGTACCAGCT
GTCCCAGGTGTGTCTCAGGTGTGCCCCAGCTGTATCCCAGGTGTGCCTCAGCTGTCTTAGGTGTGTCTCAGGTGCATCCCAGGTGTGTCTCAG
ATGTGCCCCAGCTGTCCCAGGTGTGCCCCAGCTGTCCCAGGTGTGCCCCAGCTGTCTCCAGTGTGTCCCAGCTGTGCCCCAGGTGTGTGTCCTA
GGTGTGCCTCAGCTGTCTCAGGTGTGCCCCAGGCATATCCCAGGTGTGCCCCAGCTGTCCCAGGTGTGTCCTACGTGTGCACCAGCTGTATCC
CAGGTGTGCCCCAGGTGTGTCTCAGATGGGTCCCAAGTGTTCCCCAACTGCATTTCAGGTGTCTCAGGTGTGCCCAAGCTGTCCCAGGTGTGT
CCAAGATGTGCCCCAGGTGTGTCTCAGGTGGGTCTCAAGTGCCCCAGCTGCATTTCAGGTGTCTCAGGTGTGCCCCCCAGTGCATCCCAGGTG
TGTCCCAGGTGTGCCCCAGGTGCATCCCAGGTGTGTCCCAGGTGTGCCCCAGCTGTCTCAGGTGTCTCAGGTGTGCCCCAGGCATATCCCAGG
TGTGCCTCAGCTCTCCCAGGTGTGTCCTACATGTGCACCAGCTGTATCTCAGGTGTGTCTCAGGTGTGCCCCAGATGTGCCCCCGGTGTGTCTC
AGGTGGGTCCCAAGTGTTCCCCAGCTGCATTTCAAGTGTCTCAGGTGTGCCCCAGGTGTGCCCCCGCTGTCCCAGGTGTGTCCAAGATGTACC
CCAGGTGTGTCCCAGCTGTCCCAAGTGTGTCTCAGGTGTGCCCCAGGTGTGTTCCAGGTGTTCCCAGCTGTCCCAGCTGTCCCAGGTCTCAG
GTGTGCCCCAGGTGTGTTCCAGGTGTTCACCAGCTGTCCCAGCTGTCCCAGGTCTCAGGTGTGCCCCAGGTATGTTGCAGGTGTTCCCCAGCT
GTCCCAGCTGTCCCAGGTGTGTCCCAGGTGTTCCCCAGGTGTGTCCCAGCTGTCCCAGGTGTGTCCCAGATGTGCCCCAGGTGTACCCCAGGT
GTTTCTCAGGTGGATTCCAGGTGTGTCCCAGGTGAGCCCCAGCTGTATTCCATATGCGTCCCTCTGAGTGGGGCCTTGGTTTGATGTAGCTCCG
GGGATCTTCTGCTCCCTGGTCCTGGTGTCACCAGCAACTGCCTCTTGACAATCCTGCCTTGCCTGCAAACCCCAGGTGAGAAGAAGACAAATG
ACTGGGAACTGACCCCTCAGTAAGCGCTGGTGGTCTCACCTACAGACCCCCAGGAAGCTGGTCACTGTGGGCTTCTTTTCCTCTCTAAATTCCT
ATTATCAGGTGGTTTTCTTTCTCATTTGCTATTTTCTTAAAAATAAAAATAGGGAAAAACAGCCTTTGTAAATTACGGTTTCTTCCGGCTCCATCC
TCTCCGTCAGGCCCACATCCCAAGGAAACAGCAGGCTTGAGCCTGGCTGCTGAAGCCAGGGGCTGGATGGAGCAGCTCAGAACAGAGCTTTG
AGTGCCTCTCCAGCCAGGGGCCCCAGAAGCCTGGTGGTTGTTTGTCCTTCTCAGGGGAAAAGTGAGGCGGCCCCTTGGAGGAAGGGGCCGG
GCAGAATGATCTAATCGGATTCCAAGCAGCTCAGGGGA (SEQ ID NO: 46)

Promoter 32

CTCTGAGCTGCTTCCCTACTCACACTCTGTCCACAACCCCATTTTCCTGATCATGTAGTAGAAAGAAATGGAACACAATCTTTGTAAATAAGCCC
TTGTAAACAAGCAAGAGCTACAGTGCTTCCACAAGCCCTACTGCAAGCCAGGAATGGGAACAGTGGTGTGTGTGCAGCAAATGCCCTGAGCA
CCCCTGTGGATTGGACTCAGAAACATGGAAGTGAGGGTAGGAGGGGATGATCTAAGTCCTGGGCCCAATTAAGAGATCAGATGGTGAAGGG
TTTGGGGGCCTTTAAGGTAAGGAGGCCTGGGCTGATCCTGCAGGCTGATATAAAGTCCTGTAACCCCATAGGCA (SEQ ID NO: 47)

FIG. 8F

Intron 1

GTAAGTATCAAGGTTACAAGACAGGTTTAAGGAGACCAATAGAAACTGGGCTTGTCGAGACAGAGAAGACTCTTGCGTTTCTGATAGGCACC
TATTGGTCTTACTGACATCCACTTTGCCTTTCTCTCCACAG (SEQ ID NO: 48)

Intron 2

GTAAGTTTAGTCTTTTTGTCTTTTATTTCAGGTCCCGGATCCGGTGGTGGTGCAAATCAAAGAACTGCTCCTCAGTGGATGTTGCCTTTACTTCT
AG (SEQ ID NO: 115)

Poly A Region 1

AGACATGATAAGATACATTGATGAGTTTGGACAAACCACAACTAGAATGCAGTGAAAAAAATGCTTTATTTGTGAAATTTGTGATGCTATTGC
TTTATTTGTAACCATTATAAGCTGCAATAAACAAGTTAACAACAACAATTGCATTCATTTTATGTTTCAGGTTCAGGGGGAGATGTGGGAGGTT
TTTTAAAGCAAGTAAAACCTCTACAAATGTGGTA (SEQ ID NO: 49)

Poly A Region 2

CAGACATGATAAGATACATTGATGAGTTTGGACAAACCACAACTAGAATGCAGTGAAAAAAATGCTTTATTTGTGAAATTTGTGATGCTATTG
CTTTATTTGTAACCATTATAAGCTGCAATAAACAAGTTAACAACAACAATTGCATTCATTTTATGTTTCAGGTTCAGGGGGAGATGTGGGAGGT
TTTTTAAAGCAAGTAAAACCTCTACAAATGTGGTA (SEQ ID NO: 50)

Poly A Region 3

GGCCGCTTCGAGCAGACATGATAAGATACATTGATGAGTTTGGACAAACCACAACTAGAATGCAGTGAAAAAAATGCTTTATTTGTGAAATTT
GTGATGCTATTGCTTTATTTGTAACCATTATAAGCTGCAATAAACAAGTTAACAACAACAATTGCATTCATTTTATGTTTCAGGTTCAGGGGGA
GATGTGGGAGGTTTTTTAAAGCAAGTAAAACCTCTACAAATGTGGTAAAATC (SEQ ID NO: 51)

Poly A Region 4

TAATCAGCATACCACATTTGTAGAGGTTTTACTTGCTTTAAAAAACCTCCCACACCTCCCCCTGAACCTGAAACATAAAATGAATGCAATTGTTG
TTGTTAACTTGTTTATTGCAGCTTATAATGGTTACAAATAAAGCAATAGCATCACAAATTTCACAAATAAAGCATTTTTTTCACTGCATTCTAGTT
GTGGTTTGTCCAAACTCATCAATGTATCTTA (SEQ ID NO: 52)

Poly A Region 5

AGACATGATAAGATACATTGATGAGTTTGGACAAACCACAACTAGAATGCAGTGAAAAAAATGCTTTATTTGTGAAATTTGTGATGCTATTGC
TTTATTTGTAACCATTATAAGCTGCAATAAACAAGTTAACAACAACAATTGCATTCATTTTATGTTTCAGGTTCAGGGGGAGATGTGGGAGGTT
TTTTAAAGCAAGTAAAACCTCTACAAATGTGGTA (SEQ ID NO: 49)

Poly A Region 6

CAGACATGATAAGATACATTGATGAGTTTGGACAAACCACAACTAGAATGCAGTGAAAAAAATGCTTTATTTGTGAAATTTGTGATGCTATTG
CTTTATTTGTAACCATTATAAGCTGCAATAAACAAGTTAACAACAACAATTGCATTCATTTTATGTTTCAGGTTCAGGGGGAGATGTGGGAGGT
TTTTTAAAGCAAGTAAAACCTCTACAAATGTGGTA (SEQ ID NO: 50)

FIG. 9A

Poly A Region 7

AACTTGTTTATTGCAGCTTATAATGGTTACAAATAAAGCAATAGCATCACAAATTTCACAAATAAAGCATTTTTTTCACTGCATTCTAGTTGTGG
TTTGTCCAAACTCATCAATGTATCTTATCACGTCTGGTCAGGTGGCA (SEQ ID NO: 53)

Poly A Region 8

AACTTGTTTATTGCAGCTTATAATGGTTACAAATAAAGCAATAGCATCACAAATTTCACAAATAAAGCATTTTTTTCACTGCATTCTAGTTGTGG
TTTGTCCAAACTCATCAATGTATCTTATCACGTCTGG (SEQ ID NO: 54)

Poly A Region 9
CAGACATGATAAGATACATTGATGAGTTTGGACAAACCACAACTAGAATGCAGTGAAAAAAATGCTTTATTTGTGAAATTTGTGATGCTATTG
CTTTATTTGTAACCATTATAAGCTGCAATAAACAAGTTAACAACAACAATTGCATTCATTTTATGTTTCAGGTTCAGGGGGAGATGTGGGAGGT
TTTTTAAAGCAAGTAAAACCTCTACAAATGTGGTA (SEQ ID NO: 50)

Poly A Region 10

AATAAAATATCTTTATTTTCATTACATCTGTGTGTTGGTTTTTTGTGTG (SEQ ID NO: 55)

ITR Region 1 – Interval 1

CTGCGCGCTCGCTCGCTCACTGAGGCCGCCCGGGCAAAGCCCGGGCGTCGGGCGACCTTTGGTCGCCCGGCCTCAGTGAGCGAGCGAGCGC
GCAGAGAGGGAGTGGCCAACTCCATCACTAGGGGTTCCTTGTAGTTAATGATTAACCCGCCATGCTACTTATCTACGCGTAGATAAGTAGCAT
GGCGGGTTAATCATTAACTACAAGGAACCCCTAGTGATGGAGTTGGCCACTCCCTCTCTGCGCGCTCGCTCGCTCACTGAGGCCGGGCGACCA
AAGGTCGCCCGACGCCCGGGCTTTGCCCGGGCGGCCTCAGTGAGCGAGCGAGCGCGCAGCCTTA (SEQ ID NO: 56)

ITR Region 1 – Interval 2

CTGCGCGCTCGCTCGCTCACTGAGGCCGCCCGGGCAAAGCCCGGGCGTCGGGCGACCTTTGGTCGCCCGGCCTCAGTGAGCGAGCGAGCGC
GCAGAGAGGGAGTGGCCAACTCCATCACTAGGGGTTCCTTGTAGTTAATGATTAACCCGCCATGCTACTTATCTACGCGTAGATAAGTAGCAT
GGCGGGTTAATCATTAACTACAAGGAACCCCTAGTGATGGAGTTGGCCACTCCCTCTCTGCGCGCTCGCTCGCTCACTGAGGCCGGGCGACCA
AAGGTCGCCCGACGCCCGGGCTTTGCCCGGGCGGCCTCAGTGAGCGAGCGAGCGCGCAGCCTTA (SEQ ID NO: 56)

ITR Region 2 – Interval 1

AGGCTGCGCGCTCGCTCGCTCACTGAGGCCGCCCGGGCAAAGCCCGGGCGTCGGGCGACCTTTGGTCGCCCGGCCTCAGTGAGCGAGCGAG
CGCGCAGAGAGGGAGTGGCCAACTCCATCACTAGGGGTTCCTTGTAGTTAATGATTAACCCGCCATGCTACTTATCTACGCGTAGATAAGTAG
CATGGCGGGTTAATCATTAACTACAAGGAACCCCTAGTGATGGAGTTGGCCACTCCCTCTCTGCGCGCTCGCTCGCTCACTGAGGCCGGGCGA
CCAAAGGTCGCCCGACGCCCGGGCTTTGCCCGGGCGGCCTCAGTGAGCGAGCGAGCGCGCAGCCTTA (SEQ ID NO: 57)

FIG. 9B

ITR Region 2 – Interval 2

AGGCTGCGCGCTCGCTCGCTCACTGAGGCCGCCCGGGCAAAGCCCGGGCGTCGGGCGACCTTTGGTCGCCCGGCCTCAGTGAGCGAGCGAG
CGCGCAGAGAGGGAGTGGCCAACTCCATCACTAGGGGTTCCTTGTAGTTAATGATTAACCCGCCATGCTACTTATCTACGCGTAGATAAGTAG
CATGGCGGGTTAATCATTAACTACAAGGAACCCCTAGTGATGGAGTTGGCCACTCCCTCTCTGCGCGCTCGCTCGCTCACTGAGGCCGGGCGA
CCAAAGGTCGCCCGACGCCCGGGCTTTGCCCGGGCGGCCTCAGTGAGCGAGCGAGCGCGCAGCCTTA (SEQ ID NO: 57)

ITR Region 3 – Interval 1

AGGAACCCCTAGTGATGGAGTTGGCCACTCCCTCTCTGCGCGCTCGCTCGCTCACTGAGGCCGGGCGACCAAAGGTCGCCCGACGCCCGGGC
TTTGCCCGGGCGGCCTCAGTGAGCGAGCGAGCGCGC (SEQ ID NO: 58)

ITR Region 3 – Interval 2

AGGAACCCCTAGTGATGGAGTTGGCCACTCCCTCTCTGCGCGCTCGCTCGCTCACTGAGGCCGGGCGACCAAAGGTCGCCCGACGCCCGGGC
TTTGCCCGGGCGGCCTCAGTGAGCGAGCGAGCGCGCAG (SEQ ID NO: 59)

Intron 3

TCGAATCCCGGCCGGGAACGGTGCATTGGAACGCGGATTCCCCGTGCCAAGAGTGACGTAAGTACCGCCTATAGAGTCTATAGGCCCACAAA
AAATGCTTTCTTCTTTTAATATACTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAATATTTCTGCATATAAATTGTA
ACTGATGTAAGAGGTTTCATATTGCTAATAGCAGCTACAATCCAGCTACCATTCTGCTTTTATTTTATGGTTGGGATAAGGCTGGATTATTCTGA
GTCCAAGCTAGGCCCTTTTGCTAATCATGTTCATACCTCTTATCTTCCTCCCACAGCTCCTGGGCAACGTGCTGGTCTGTGTGCTGGCCCATCAC
TTTGGCAAAGAATTGGGA (SEQ ID NO: 116)

Intron 4

GTAAGTTTAGTCTTTTTGTCTTTTATTTCAGGTCCCGGATCCGGTGGTGGTGCAAATCAAAGAACTGCTCCTCAGTGGATGTTGCCTTTACTTCT
AG (SEQ ID NO: 117)

Intron 5

GTAAGTTTAGTCTTTTTGTCTTTTATTTCAG (SEQ ID NO: 118)

Intron 6

ACTTACCATACTTTACCCGGAAACTAATCGTCCCACTCTCACATCCTTCATTGCAG (SEQ ID NO: 119)

Intron 7

AAAAGTTCCCCAGCCAGAAGCAGAGAAGATGATGTCAAGAAATCAAGGGGGATAAATGGCCATAGCTGCTGCAAATAGCTTATTGCAGTCTC
TAGAGTGTGGTAAACAGGTTTCCAGTGCCAGCTGTGGAGGTGACAGCGGCAGGGAA (SEQ ID NO: 120)

FIG. 9C

LINKER SEQUENCE 1

TTATGAAGATCCCTCGACCTGCAGCCCAAGCTTGGCGTAATCATG (SEQ ID NO: 60)

LINKER SEQUENCE 2

GATAAGGATCTTCCTAGAGCATGGCTA (SEQ ID NO: 61)

LINKER SEQUENCE 3

ATGTCTGCCCGTATTTCGCGTAAGGAAATCCATTATGTACTATTTAAAAAACACAAACTTTTGGATGTTCGGTTTATTCTTTTTCTTTTACTTTTTT
ATCATGGGAGCCTACTTCCCGTTTTTCCCGATTTGGCTACATGACATCAACCATATCAGCAAAAGTGATACGGGTATTATTTTTGCCGCTATTTC
TCTGTTCTCGCTATTATTCCAACCGCTGTTTGGTCTGCTTTCTGACAAACTCGGCCTCGACTCTAGGCGGCCGCGGGGATC (SEQ ID NO: 62)

LINKER SEQUENCE 4

GGAGGGGTGGAGTCGTGACGTGAATTACGTCATAGGGTTAGGGAGGTCCTGTATTAGAGGTCACGTGAGTGTTTTGCGACATTTTGCGACAC
CATGTGGTCACGCTGGGTATTTAAGCCCGAGTGAGCACGCAGGGTCTCC (SEQ ID NO: 63)

LINKER SEQUENCE 5

GGATCCACTCGAGTGGAGCTCGCGACTAGTCGATTCGAATTCGATATCAAGCTTATCGAT (SEQ ID NO: 64)

LINKER SEQUENCE 6

GCCTGTACGGAAGTGTTACTTCTGCTCTAAAAGCTGCGGAATTGTACCCGCGGCCGCAATTCCCGGGGATCGAAAGAGCCTGCTAAAGCAAA
AAAGAA (SEQ ID NO: 65)

LINKER SEQUENCE 7

CCGAACCCGAATTCTGCAGATATCCAGCACAGTGGCGGCCGCTTCGAG (SEQ ID NO: 66)

LINKER SEQUENCE 8

TAGTTTCCATGGCTACGTAGATAAGTAGCATGGCGGGTTAATCATTAACTACA (SEQ ID NO: 67)

LINKER SEQUENCE 9

TGTAGTTAATGATTAACCCGCCATGCTACTTATCTACGTAGCCATGCTCGATCTGAATTCGGTA (SEQ ID NO: 68)

LINKER SEQUENCE 10

GGCCGCGGGGATCC (SEQ ID NO: 69)

LINKER SEQUENCE 11

GGTTCGAACAG (SEQ ID NO: 70)

FIG. 9D

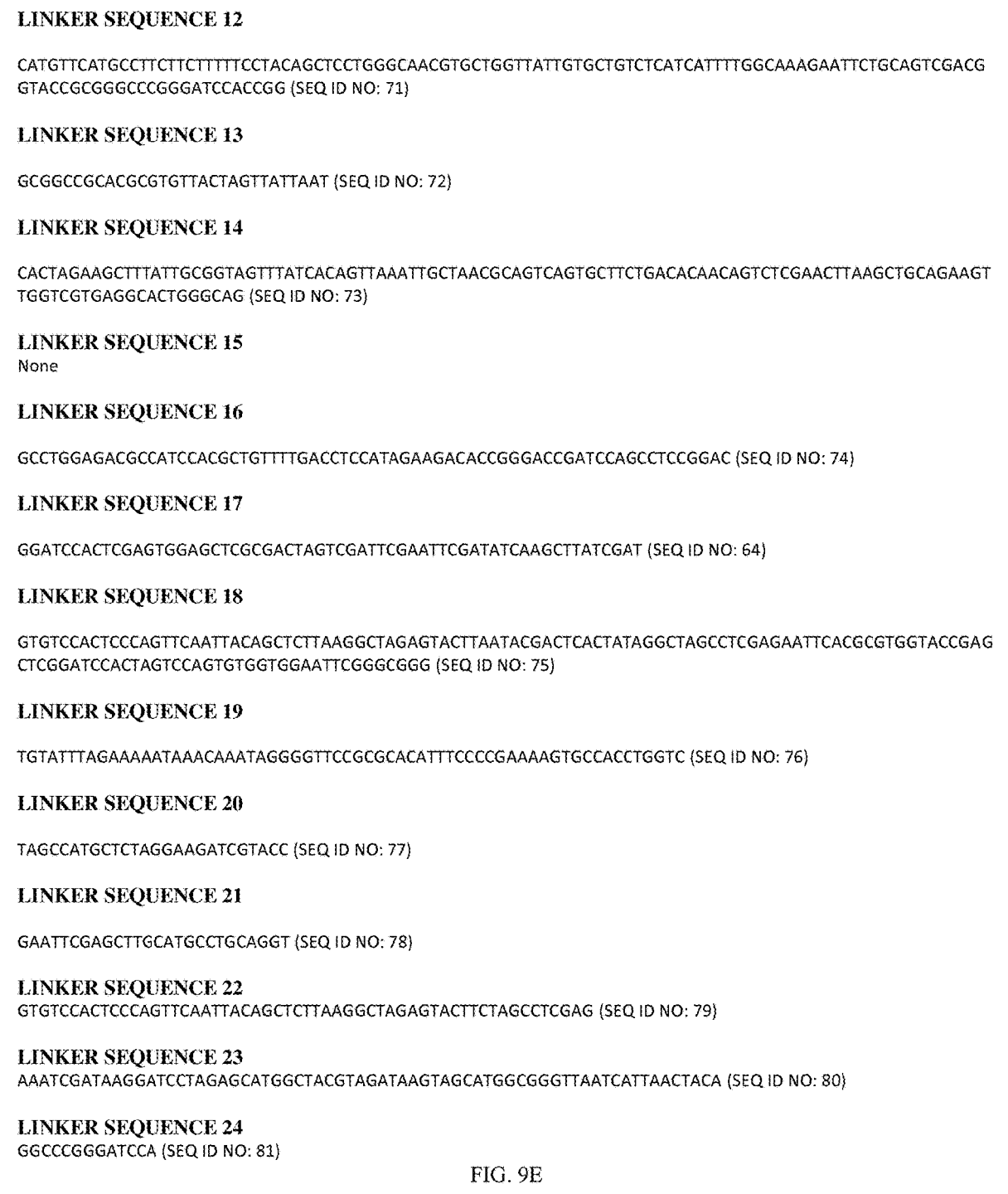

LINKER SEQUENCE 12

CATGTTCATGCCTTCTTCTTTTTCCTACAGCTCCTGGGCAACGTGCTGGTTATTGTGCTGTCTCATCATTTTGGCAAAGAATTCTGCAGTCGACG
GTACCGCGGGCCCGGGATCCACCGG (SEQ ID NO: 71)

LINKER SEQUENCE 13

GCGGCCGCACGCGTGTTACTAGTTATTAAT (SEQ ID NO: 72)

LINKER SEQUENCE 14

CACTAGAAGCTTTATTGCGGTAGTTTATCACAGTTAAATTGCTAACGCAGTCAGTGCTTCTGACACAACAGTCTCGAACTTAAGCTGCAGAAGT
TGGTCGTGAGGCACTGGGCAG (SEQ ID NO: 73)

LINKER SEQUENCE 15
None

LINKER SEQUENCE 16

GCCTGGAGACGCCATCCACGCTGTTTTGACCTCCATAGAAGACACCGGGACCGATCCAGCCTCCGGAC (SEQ ID NO: 74)

LINKER SEQUENCE 17

GGATCCACTCGAGTGGAGCTCGCGACTAGTCGATTCGAATTCGATATCAAGCTTATCGAT (SEQ ID NO: 64)

LINKER SEQUENCE 18

GTGTCCACTCCCAGTTCAATTACAGCTCTTAAGGCTAGAGTACTTAATACGACTCACTATAGGCTAGCCTCGAGAATTCACGCGTGGTACCGAG
CTCGGATCCACTAGTCCAGTGTGGTGGAATTCGGGCGGG (SEQ ID NO: 75)

LINKER SEQUENCE 19

TGTATTTAGAAAAATAAACAAATAGGGGTTCCGCGCACATTTCCCCGAAAAGTGCCACCTGGTC (SEQ ID NO: 76)

LINKER SEQUENCE 20

TAGCCATGCTCTAGGAAGATCGTACC (SEQ ID NO: 77)

LINKER SEQUENCE 21

GAATTCGAGCTTGCATGCCTGCAGGT (SEQ ID NO: 78)

LINKER SEQUENCE 22
GTGTCCACTCCCAGTTCAATTACAGCTCTTAAGGCTAGAGTACTTCTAGCCTCGAG (SEQ ID NO: 79)

LINKER SEQUENCE 23
AAATCGATAAGGATCCTAGAGCATGGCTACGTAGATAAGTAGCATGGCGGGTTAATCATTAACTACA (SEQ ID NO: 80)

LINKER SEQUENCE 24
GGCCCGGGATCCA (SEQ ID NO: 81)

FIG. 9E

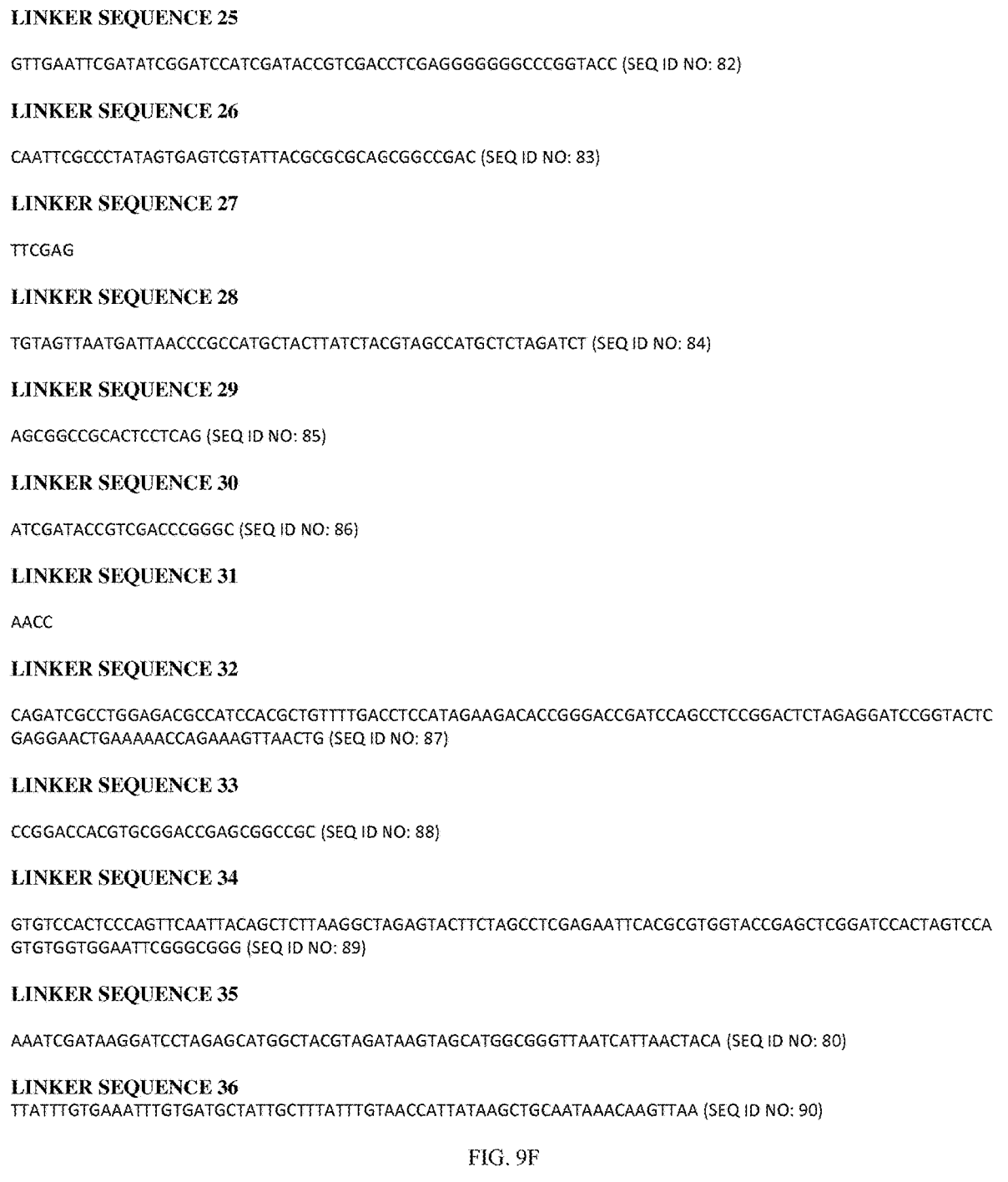

LINKER SEQUENCE 25

GTTGAATTCGATATCGGATCCATCGATACCGTCGACCTCGAGGGGGGGGCCCGGTACC (SEQ ID NO: 82)

LINKER SEQUENCE 26

CAATTCGCCCTATAGTGAGTCGTATTACGCGCGCAGCGGCCGAC (SEQ ID NO: 83)

LINKER SEQUENCE 27

TTCGAG

LINKER SEQUENCE 28

TGTAGTTAATGATTAACCCGCCATGCTACTTATCTACGTAGCCATGCTCTAGATCT (SEQ ID NO: 84)

LINKER SEQUENCE 29

AGCGGCCGCACTCCTCAG (SEQ ID NO: 85)

LINKER SEQUENCE 30

ATCGATACCGTCGACCCGGGC (SEQ ID NO: 86)

LINKER SEQUENCE 31

AACC

LINKER SEQUENCE 32

CAGATCGCCTGGAGACGCCATCCACGCTGTTTTGACCTCCATAGAAGACACCGGGACCGATCCAGCCTCCGGACTCTAGAGGATCCGGTACTC
GAGGAACTGAAAAACCAGAAAGTTAACTG (SEQ ID NO: 87)

LINKER SEQUENCE 33

CCGGACCACGTGCGGACCGAGCGGCCGC (SEQ ID NO: 88)

LINKER SEQUENCE 34

GTGTCCACTCCCAGTTCAATTACAGCTCTTAAGGCTAGAGTACTTCTAGCCTCGAGAATTCACGCGTGGTACCGAGCTCGGATCCACTAGTCCA
GTGTGGTGGAATTCGGGCGGG (SEQ ID NO: 89)

LINKER SEQUENCE 35

AAATCGATAAGGATCCTAGAGCATGGCTACGTAGATAAGTAGCATGGCGGGTTAATCATTAACTACA (SEQ ID NO: 80)

LINKER SEQUENCE 36
TTATTTGTGAAATTTGTGATGCTATTGCTTTATTTGTAACCATTATAAGCTGCAATAAACAAGTTAA (SEQ ID NO: 90)

FIG. 9F

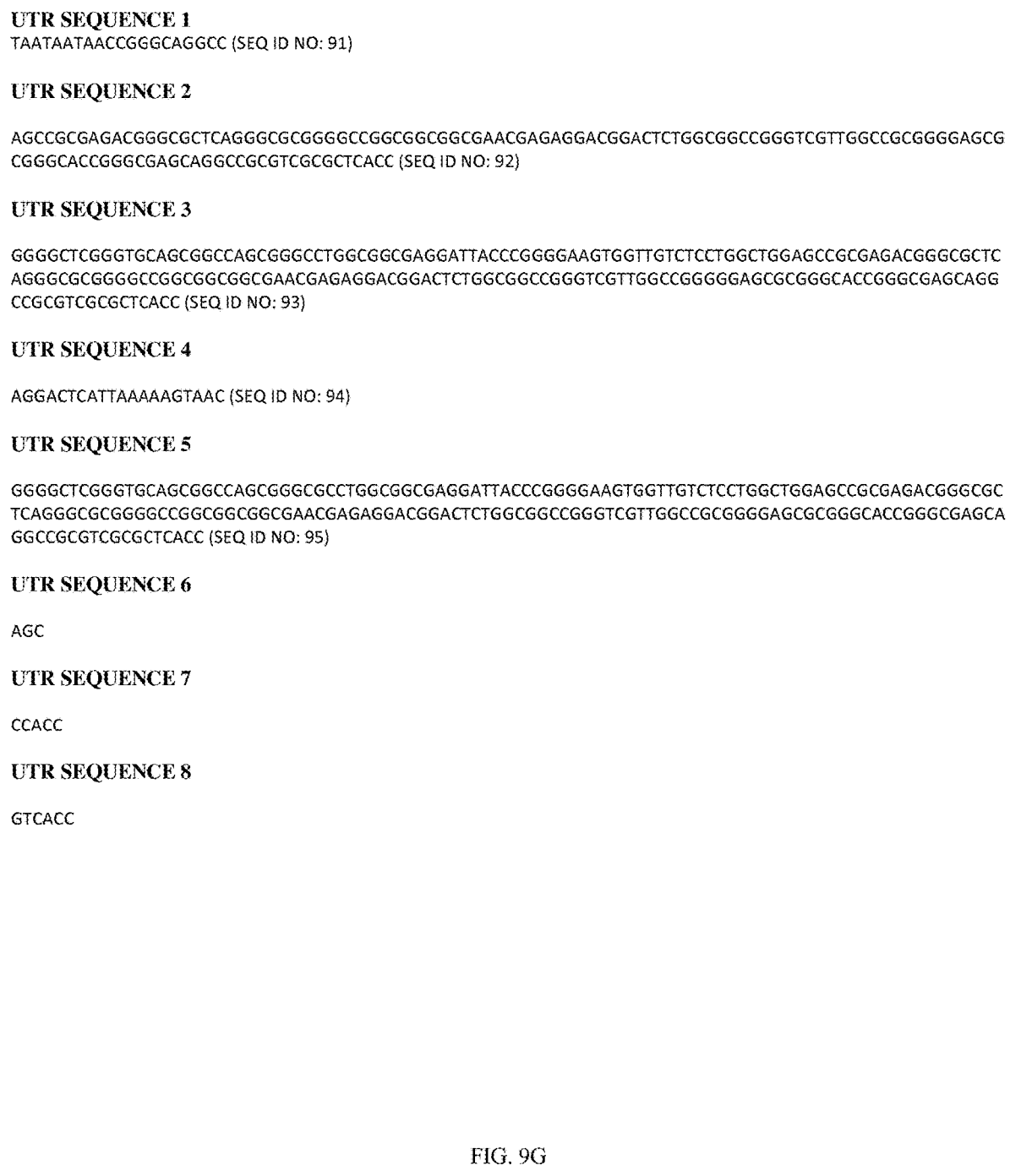

UTR SEQUENCE 1
TAATAATAACCGGGCAGGCC (SEQ ID NO: 91)

UTR SEQUENCE 2

AGCCGCGAGACGGGCGCTCAGGGCGCGGGGCCGGCGGCGGCGAACGAGAGGACGGACTCTGGCGGCCGGGTCGTTGGCCGCGGGGAGCG
CGGGCACCGGGCGAGCAGGCCGCGTCGCGCTCACC (SEQ ID NO: 92)

UTR SEQUENCE 3

GGGGCTCGGGTGCAGCGGCCAGCGGGCCTGGCGGCGAGGATTACCCGGGGAAGTGGTTGTCTCCTGGCTGGAGCCGCGAGACGGGCGCTC
AGGGCGCGGGGCCGGCGGCGGCGAACGAGAGGACGGACTCTGGCGGCCGGGTCGTTGGCCGGGGGAGCGCGGGCACCGGGCGAGCAGG
CCGCGTCGCGCTCACC (SEQ ID NO: 93)

UTR SEQUENCE 4

AGGACTCATTAAAAAGTAAC (SEQ ID NO: 94)

UTR SEQUENCE 5

GGGGCTCGGGTGCAGCGGCCAGCGGGCGCCTGGCGGCGAGGATTACCCGGGGAAGTGGTTGTCTCCTGGCTGGAGCCGCGAGACGGGCGC
TCAGGGCGCGGGGCCGGCGGCGGCGAACGAGAGGACGGACTCTGGCGGCCGGGTCGTTGGCCGCGGGGAGCGCGGGCACCGGGCGAGCA
GGCCGCGTCGCGCTCACC (SEQ ID NO: 95)

UTR SEQUENCE 6

AGC

UTR SEQUENCE 7

CCACC

UTR SEQUENCE 8

GTCACC

FIG. 9G

UTR SEQUENCE 9

GGGCGGGTGCATCAATGCGGCCGAAAAAGACACGGACACGCTCCCCTGGGACCTGAGCTGGTTCGCAGTCTTCCCAAAGGTGCCAAGCAAG
CGTCAGTTCCCCTCAGGCGCTCCAGGTTCAGTGCCTTGTGCCGAGGGTCTCCGGTGCCTTCCTAGACTTCTCGGGACAGTCTGAAGGGGTCAG
GAGCGGCGGGACAGCGCGGGAAGAGCAGGCAAGGGGAGACAGCCGGACTGCGCCTCAGTCCTCCGTGCCAAGAACACCGTCGCGGAGGC
GCGGCCAGCTTCCCTTGGATCGGACTTTCCGCCCCTAGGGCCAGGCGGCGGAGCTTCAGCCTTGTCCCTTCCCCAGTTTCGGGCGGCCCCCAG
AGCTGAGTAAGCCGGGTGGAGGGAGTCTGCAAGGATTTCCTGAGCGCGATGGGCAGGAGGAGGGGCAAGGGCAAGAGGGCGCGGAGCAA
AGACCCTGAACCTGCCGGGGCCGCGCTCCCGGGCCCGCGTCGCCAGCACCTCCCCACGCGCGCTCGGCCCCGGGCCACCCGCCCTCGTCGGC
CCCCGCCCCTCTCCGTAGCCGCAGGGAAGCGAGCCTGGGAGGAAGAAGAGGGTAGGTGGGGAGGCGGATGAGGGGTGGGGGACCCCTTG
ACGTCACCAGAAGGAGGTGCCGGGGTAGGAAGTGGGCTGGGGAAAGGTTATAAATCGCCCCCGCCCTCGGCTGCTCTTCATCGAGGTCCGC
GGGAGGCTCGGAGCGCGCCAGGCGGACACTCCTCTCGGCTCCTCCCCGGCAGCGGCGGCGGCTCGGAGCGGGCTCCGGGGCTCGGGTGCA
GCGGCCAGCGGGCGCCTGGCGGCGAGGATTACCCGGGGAAGTGGTTGTCTCCTGGCTGGAGCCGCGAGACGGGCGCTCAGGGCGCGGGGC
CGGCGGCGGCGAACGAGAGGACGGACTCTGGCGGCCGGGTCGTTGGCCGCGGGGAGCGCGGGCACCGGGCGAGCAGGCCGCGTCGCGCT
CACC (SEQ ID NO: 96)

UTR SEQUENCE 10

TTGCTTGTTAATCAATAAACCGTTTAATTCGTTTCAGTTGAACTTTGGTCTCTGCGTATTTCTTTCTTATC (SEQ ID NO: 97)

UTR SEQUENCE 11

ATTTTGAAGCGGGAGGTTTGAACGCGCAGCCGCC (SEQ ID NO: 98)

UTR SEQUENCE 12

CCGGTCGCCACC (SEQ ID NO: 99)

UTR SEQUENCE 13

GGGGCTCGGGTGCAGCGGCCAGCGGGCGCCTGGCGGCGAGGATTACCCGGGGAAGTGGTTGTCTCCTGGCTGGAGCCGCGAGACGGGCGC
TCAGGGCGCGGGGCCGGCGGCGGCGAACGAGAGGACGGACTCTGGCGGCCGGGTCTTTGGCCGCGGGGAGCGCGGGCACCGGGCGAGCA
GGCCGCGTCGCGCTCACC (SEQ ID NO: 100)

UTR SEQUENCE 14

TCGCCACC

UTR SEQUENCE 15

GGGGTGGGGGACCCCTTGACGTCACCAGAAGGAGGTGCCGGGGTAGGAAGTGGGCTGGGGAAAGGTTATAAATCGCCCCCGCCCTCGGCT
GCTCTTCATCGAGGTCCGCGGGGAGGCTCGGAGCGCGCCAGGCGGACACTCCTCTCGGCTCCTCCCCGGCAGCGGCGGCGGCTCGGAGCGGG
CTCCGGGGCTCGGGTGCAGCGGCCAGCGGGCGCCTGGCGGCGAGGATTACCCGGGGAAGTGGTTGTCTCCTGGCTGGAGCCGCGAGACGG
GCGCTCAGGGCGCGGGGCCGGCGGCGGCGAACGAGAGGACGGACTCTGGCGGCCGGGTCGTTGGCCGCGGGGAGCGCGGGCACCGGGCG
AGCAGGCCGCGTCGCGCTCACC (SEQ ID NO: 101)

UTR SEQUENCE 16

GCGGCCGC

FIG. 9H sFLT-1

ATGGTCAGCTACTGGGACACCGGGGTCCTGCTGTGCGCGCTGCTCAGCTGTCTGCTTCTCACAGGATCTAGTTCAGGTTCAAAATTAAAAGAT
CCTGAACTGAGTTTAAAAGGCACCCAGCACATCATGCAAGCAGGCCAGACACTGCATCTCCAATGCAGGGGGGAAGCAGCCCATAAATGGTC
TTTGCCTGAAATGGTGAGTAAGGAAAGCGAAAGGCTGAGCATAACTAAATCTGCCTGTGGAAGAAATGGCAAACAATTCTGCAGTACTTTAA
CCTTGAACACAGCTCAAGCAAACCACACTGGCTTCTACAGCTGCAAATATCTAGCTGTACCTACTTCAAAGAAGAAGGAAACAGAATCTGCAA
TCTATATATTTATTAGTGATACAGGTAGACCTTTCGTAGAGATGTACAGTGAAATCCCCGAAATTATACACATGACTGAAGGAAGGGAGCTCG
TCATTCCCTGCCGGGTTACGTCACCTAACATCACTGTTACTTTAAAAAAGTTTCCACTTGACACTTTGATCCCTGATGGAAAACGCATAATCTGG
GACAGTAGAAAGGGCTTCATCATATCAAATGCAACGTACAAAGAAATAGGGCTTCTGACCTGTGAAGCAACAGTCAATGGGCATTTGTATAA
GACAAACTATCTCACACATCGACAAACCAATACAATCATAGATGTCCAAATAAGCACACCACGCCCAGTCAAATTACTTAGAGGCCATACTCTT
GTCCTCAATTGTACTGCTACCACTCCCTTGAACACGAGAGTTCAAATGACCTGGAGTTACCCTGATGAAAAAAATAAGAGAGCTTCCGTAAGG
CGACGAATTGACCAAAGCAATTCCCATGCCAACATATTCTACAGTGTTCTTACTATTGACAAAATGCAGAACAAAGACAAAGGACTTTATACTT
GTCGTGTAAGGAGTGGACCATCATTCAAATCTGTTAACACCTCAGTGCATATATATGATAAAGCATTCATCACTGTGAAACATCGAAAACAGC
AGGTGCTTGAAACCGTAGCTGGCAAGCGGTCTTACCGGCTCTCTATGAAAGTGAAGGCATTTCCCTCGCCGGAAGTTGTATGGTTAAAAGATG
GGTTACCTGCGACTGAGAAATCTGCTCGCTATTTGACTCGTGGCTACTCGTTAATTATCAAGGACGTAACTGAAGAGGATGCAGGGAATTATA
CAATCTTGCTGAGCATAAAACAGTCAAATGTGTTTAAAAAACCTCACTGCCACTCTAATTGTCAATGTGAAACCCCAGATTTACGAAAAGGCCGT
GTCATCGTTTCCAGACCCGGCTCTCTACCCACTGGGCAGCAGACAAATCCTGACTTGTACCGCATATGGTATCCCTCAACCTACAATCAAGTGG
TTCTGGCACCCCTGTAACCATAATCATTCCGAAGCAAGGTGTGACTTTTGTTCCAATAATGAAGAGTCCTTTATCCTGGATGCTGACAGCAACA
TGGGAAACAGAATTGAGAGCATCACTCAGCGCATGGCAATAATAGAAGGAAAGAATAAGATGGCTAGCACCTTGGTTGTGGCTGACTCTAGA
ATTTCTGGAATCTACATTTGCATAGCTTCCAATAAAGTTGGGACTGTGGGAAGAAACATAAGCTTTTATATCACAGATGTGCCAAATGGGTTTC
ATGTTAACTTGGAAAAAATGCCGACGGAAGGAGAGGACCTGAAACTGTCTTGCACAGTTAACAAGTTCTTATACAGAGACGTTACTTGGATTT
TACTGCGGACAGTTAATAACAGAACAATGCACTACAGTATTAGCAAGCAAAAAATGGCCATCACTAAGGAGCACTCCATCACTCTTAATCTTAC
CATCATGAATGTTTCCCTGCAAGATTCAGGCACCTATGCCTGCAGAGCCAGGAATGTATACACAGGGGAAGAAATCCTCCAGAAGAAAGAAA
TTACAATCAGAGGTGAGCACTGCAACAAAAAGGCTGTTTTCTCTCGGATCTCCAAATTTAAAAGCACAAGGAATGATTGTACCACACAAAGTA
ATGTAAAACATTAA (SEQ ID NO: 102)

VEGF-Trap

AAGCTTGGGCTGCAGGTCGATCGACTCTAGAGGATCGATCCCCGGGCGAGCTCGAATTCGCAACCACCATGGTCAGCTACTGGGACACCGGG
GTCCTGCTGTGCGCGCTGCTCAGCTGTCTGCTTCTCACAGGATCTAGTTCCGGAGGTAGACCTTTCGTAGAGATGTACAGTGAAATCCCCGAA
ATTATACACATGACTGAAGGAAGGGAGCTCGTCATTCCCTGCCGGGTTACGTCACCTAACATCACTGTTACTTTAAAAAAGTTTCCACTTGACA
CTTTGATCCCTGATGGAAAACGCATAATCTGGGACAGTAGAAAGGGCTTCATCATATCAAATGCAACGTACAAAGAAATAGGGCTTCTGACCT
GTGAAGCAACAGTCAATGGGCATTTGTATAAGACAAACTATCTCACACATCGACAAACCAATACAATCATAGATGTGGTTCTGAGTCCGTCTC
ATGGAATTGAACTATCTGTTGGAGAAAGCTTGTCTTAAATTGTACAGCAAGAACTGAACTAAATGTGGGGATTGACTTCAACTGGGAATACC
CTTCTTCGAAGCATCAGCATAAGAAACTTGTAAACCGAGACCTAAAAACCCAGTCTGGGAGTGAGATGAAGAAATTTTTGAGCACCTTAACTA
TAGATGGTGTAACCCGGAGTGACCAAGGATTGTACACCTGTGCAGCATCCAGTGGGCTGATGACCAAGAAGAACAGCACATTTGTCAGGGTC
CATGAAAAGGGCCCGGGCGACAAAACTCACACATGCCCACCGTGCCCAGCACCTGAACTCCTGGGGGGACCGTCAGTCTTCCTCTTCCCCCCA
AAACCCAAGGACACCCTCATGATCTCCCGGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGATGAGCTGACCAAGAACCAGGTCAGCCTGACCTGCCT
GGTCAAAGGCTTCTATCCCAGCGACATCGCCGTGGAGTGGGAGAGCAATGGGCAGCCGGAGAACAACTACAAGACCACGCCTCCCGTGCTG
GACTCCGACGGCTCCTTCTTCCTCTATAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGAGCGGCCGC (SEQ ID NO: 103)

FIG. 10A

VEGF-Trap

ATGGTCAGCTACTGGGACACCGGGGTCCTGCTGTGCGCGCTGCTCAGCTGTCTGCTTCTCACAGGATCTAGTTCCGGAAGTGATACCGGTAGA
CCTTTCGTAGAGATGTACAGTGAAATCCCCGAAATTATACACATGACTGAAGGAAGGGAGCTCGTCATTCCCTGCCGGGTTACGTCACCTAAC
ATCACTGTTACTTTAAAAAAGTTTCCACTTGACACTTTGATCCCTGATGGAAAACGCATAATCTGGGACAGTAGAAAGGGCTTCATCATATCAA
ATGCAACGTACAAAGAAATAGGGCTTCTGACCTGTGAAGCAACAGTCAATGGGCATTTGTATAAGACAAACTATCTCACACATCGACAAACCA
ATACAATCATAGATGTGGTTCTGAGTCCGTCTCATGGAATTGAACTATCTGTTGGAGAAAAGCTTGTCTTAAATTGTACAGCAAGAACTGAACT
AAATGTGGGGATTGACTTCAACTGGGAATACCCTTCTTCGAAGCATCAGCATAAGAAACTTGTAAACCGAGACCTAAAAACCCAGTCTGGGAG
TGAGATGAAGAAATTTTTTGAGCACCTTAACTATAGATGGTGTAACCCGGAGTGACCAAGGATTGTACACCTGTGCAGCATCCAGTGGGCTGAT
GACCAAGAAGAACAGCACATTTGTCAGGGTCCATGAAAAGGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCACAGGTGTACACCCTGCCCCCATCCCGGGATGAGCTGACCAAG
AACCAGGTCAGCCTGACCTGCCTGGTCAAAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTCTCCCTGTCTCCGGGTAAATGA (SEQ ID NO: 104)

VEGF-Trap

AAGCTTGGGCTGCAGGTCGATCGACTCTAGAGGATCGATCCCCGGGCGAGCTCGAATTCGCAACCACCATGGTCAGCTACTGGGACACCGGG
GTCCTGCTGTGCGCGCTGCTCAGCTGTCTGCTTCTCACAGGATCTAGTTCCGGAGGTAGACCTTTCGTAGAGATGTACAGTGAAATCCCCGAA
ATTATACACATGACTGAAGGAAGGGAGCTCGTCATTCCCTGCCGGGTTACGTCACCTAACATCACTGTTACTTTAAAAAAGTTTCCACTTGACA
CTTTGATCCCTGATGGAAAACGCATAATCTGGGACAGTAGAAAGGGCTTCATCATATCAAATGCAACGTACAAAGAAATAGGGCTTCTGACCT
GTGAAGCAACAGTCAATGGGCATTTGTATAAGACAAACTATCTCACACATCGACAAACCAATACAATCATAGATATCCAGCTGTTGCCCAGGA
AGTCGCTGGAGCTGCTGGTAGGGGAGAAGCTGGTCCTCAACTGCACCGTGTGGGCTGAGTTTAACTCAGGTGTCACCTTTGACTGGGACTAC
CCAGGGAAGCAGGCAGAGCGGGGTAAGTGGGTGCCCGAGCGACGCTCCCAACAGACCCACACAGAACTCTCCAGCATCCTGACCATCCACA
ACGTCAGCCAGCACGACCTGGGCTCGTATGTGTGCAAGGCCAACAACGGCATCCAGCGATTTCGGGAGAGCACCGAGGTCATTGTGCATGAA
AATGGCCCGGGCGACAAAACTCACACATGCCCACCGTGCCCAGCACCTGAACTCCTGGGGGGACCGTCAGTCTTCCTCTTCCCCCCAAAACCC
AAGGACACCCTCATGATCTCCCGGACCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTACCGTGTGGTCAGCGTCCTCACCGTC
CTGCACCAGGACTGGCTGAATGGCAAGGAGTACAAGTGCAAGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGCTGACCAAGAACCAGGTCAGCCTGACCTGCCTGGTCA
AAGGCTTCTATCCCAGCGACATCGCCGTGGAGTGGGAGAGCAATGGGCAGCCGGAGAACAACTACAAGACCACGCCTCCCGTGCTGGACTCC
GACGGCTCCTTCTTCCTCTATAGCAAGCTCACCGTGGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAATGAGCGGCCGC (SEQ ID NO: 105)

Lucentis/ ranibizumab Protein Sequence (hVEGF humanized antibody)

DIQLTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 106)

FIG. 10B

DNA sequence 1 coding for lucentis/ ranibizumab (generated from protein sequence)

GATATTCAGCTGACCCAGAGCCCGAGCAGCCTGAGCGCGAGCGTGGGCGATCGCGTGACCATTACCTGCAGCGCGAGCCAGGATATTAGCA
ACTATCTGAACTGGTATCAGCAGAAACCG
GGCAAAGCGCCGAAAGTGCTGATTTATTTTACCAGCAGCCTGCATAGCGGCGTGCCGAGC
CGCTTTAGCGGCAGCGGCAGCGGCACCGATTTTACCCTGACCATTAGCAGCCTGCAGCCG
GAAGATTTTGCGACCTATTATTGCCAGCAGTATAGCACCGTGCCGTGGACCTTTGGCCAG
GGCACCAAAGTGGAAATTAAACGCACCGTGGCGGCGCCGAGCGTGTTTATTTTTCCGCCG
AGCGATGAACAGCTGAAAAGCGGCACCGCGAGCGTGGTGTGCCTGCTGAACAACTTTTAT
CCGCGCGAAGCGAAAGTGCAGTGGAAAGTGGATAACGCGCTGCAGAGCGGCAACAGCCAG
GAAAGCGTGACCGAACAGGATAGCAAAGATAGCACCTATAGCCTGAGCAGCACCCTGACC
CTGAGCAAAGCGGATTATGAAAAACATAAAGTGTATGCGTGCGAAGTGACCCATCAGGGC
CTGAGCAGCCCGGTGACCAAAAGCTTTAACCGCGGCGAATGC (SEQ ID NO: 107)

DNA sequence 2 coding for lucentis/ ranibizumab (generated from protein sequence)

GATATTCAATTGACTCAATCTCCTTCTTCTTTGTCTGCTTCTGTTGGTGATCGTGTTACTATTACTTGTTCTGCTTCTCAAGATATTTCTAATTATTT
GAATTGGTATCAACAAAAACCTGGTAAAGCTCCTAAAGTTTTGATTTATTTTACTTCTTCTTTGCATTCTGGTGTTCCTTCTCGTTTTTCTGGTTCT
GGTTCTGGTACTGATTTTACTTTGACTATTTCTTCTTTGCAACCTGAAGATTTTGCTACTTATTATTGTCAACAATATTCTACTGTTCCTTGGACTT
TTGGTCAAGGTACTAAAGTTGAAATTAAACGTACTGTTGCTGCTCCTTCTGTTTTTATTTTTCCTCCTTCTGATGAACAATTGAAATCTGGTACTG
CTTCTGTTGTTTGTTTGTTGAATAATTTTTATCCTCGTGAAGCTAAAGTTCAATGGAAAGTTGATAATGCTTTGCAATCTGGTAATTCTCAAGAA
TCTGTTACTGAACAAGATTCTAAAGATTCTACTTATTCTTTGTCTTCTACTTTGACTTTGTCTAAAGCTGATTATGAAAAACATAAAGTTTATGCT
TGTGAAGTTACTCATCAAGGTTTGTCTTCTCCTGTTACTAAATCTTTTAATCGTGGTGAATGT (SEQ ID NO: 108)

FIG. 10C

MVSYWDTGVLLCALLSCLLLTGSSSGSKLKDPELSLKGTQHIAGQTLHLQCRGEAAMQHKWSLPEMVSKESERLSITKSAC
GRNGKQFCSTLTLNTAQANHTGFYSCKYLAVPTSKKKETESAIYIFISDTGRPFVEMYSEIPEIIHMTEGRELVIPCRVTSPNIT
VTLKKFPLDTLIPDGKRIIWDSRKGFIISNATYKEIGLLTCEATVNGHLYKTNYLTHRQTNTIIDVQISTPRPVKLLRGHTLVLNC
TATTPLNTRVQMTWSYPDEKNKRASVRRRIDQSNSHANIFYSVLTIDKMQNKDKGLYTCRVRSGPSFKSVNTSVHIYDKAF
ITVKHRKQQVLETVAGKRSYRLSMKVKAFPSPEVVWLKDGLPATEKSARYLTRGYSLIIKDVTEEDAGNYTILLSIKQSNVFK
NLTATLIVNVKPQIYEKAVSSFPDPALYPLGSRQ (SEQ ID NO: 109)

FIG. 11A

IYIFISDTGRPFVEMYSEIPEIIHMTEGRELVIPCRVTSPNITVTLKKFPLDTLIPDGKRIIWDSRKGFIISNATYKEIGLLTCEATV
NGHLYKTNYLTHRQTNTI (SEQ ID NO: 121)

FIG. 11B

AATCTATATATTTATTAGTGATACAGGTAGACCTTTCGTAGAGATGTACAGTGAAATCCCCGAA
ATTATACACATGACTGAAGGAAGGGAGCTCGTCATTCCCTGCCGGGTTACGTCACCTAACATC
ACTGTTACTTTAAAAAAGTTTCCACTTGACACTTTGATCCCTGATGGAAAACGCATAATCTGGG
ACAGTAGAAAGGGCTTCATCATATCAAATGCAACGTACAAAGAAATAGGGCTTCTGACCTGTG
AAGCAACAGTCAATGGGCATTTGTATAAGACAAACTATCTCACACATCGACAAACCAATACAA
TCA (SEQ ID NO: 122)

FIG. 11C

Zeocin resistance

ATGGCCAAGTTGACCAGTGCCGTTCCGGTGCTCACCGCGCGCGACGTCGCCGGAGCGGTCGAGTTCTGGACCGACCGGCTCGGGTTCTCCCG
GGACTTCGTGGAGGACGACTTCGCCGGTGTGGTCCGGGACGACGTGACCCTGTTCATCAGCGCGGTCCAGGACCAGGTGGTGCCGGACAAC
ACCCTGGCCTGGGTGTGGGTGCGCGGCCTGGACGAGCTGTACGCCGAGTGGTCGGAGGTCGTGTCCACGAACTTCCGGGACGCCTCCGGGC
CGGCCATGACCGAGATCGGCGAGCAGCCGTGGGGGCGGGAGTTCGCCCTGCGCGACCCGGCCGGCAACTGCGTGCACTTCGTGGCCGAGG
AGCAGGACTGA (SEQ ID NO: 110)

Zeocin resistance

ATGTCTAAATTAACCTCTGCTGTTCCAGTGTTAACCGCCCGTGATGTTGCCGGTGCAGTGGAATTTTGGACTGACCGTTTGGGTTTCTCACGTG
ACTTTGTCGAAGATGATTTTGCTGGCGTTGTGCGTGATGACGTCACTTTGTTCATCTCTGCTGTTCAGGATCAGGTCGTCCCAGACAACACTTT
GGCCTGGGTCTGGGTTCGTGGTTTGGACGAATTGTACGCTGAGTGGAGTGAAGTTGTGTCTACAAACTTTCGTGATGCATCAGGTCCAGCTAT
GACCGAAATTGGCGAACAACCTTGGGGCCGTGAGTTCGCTTTACGTGATCCAGCCGGTAATTGCGTGCACTTCGTTGCTGAGGAGCAAGATT
AG (SEQ ID NO: 111)

Amp

ATGAGTATTCAACATTTCCGTGTCGCCCTTATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAGCTAACCGCTTTTTTGCACAACATGGGGGATCAT
GTAACTCGCCTTGATCGTTGGGAACCGGAGCTGAATGAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGGATGAACGAAATAGACAGATCGCTGAGATAGGTG
CCTCACTGATTAAGCATTGGTAA (SEQ ID NO: 112)

Amp

ATGAGTATTCAACATTTCCGTGTCGCCCTTATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAGCTAACCGCTTTTTTGCACAACATGGGGGATCAT
GTAACTCGCCTTGATCGTTGGGAACCGGAGCTGAATGAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGGATGAACGAAATAGACAGATCGCTGAGATAGGTG
CCTCACTGATTAAGCATTGGTAA (SEQ ID NO: 112)

FIG. 12A

Neomycin

ATGATTGAACAAGATGGATTGCACGCAGGTTCTCCGGCCGCTTGGGTGGAGAGGCTATTCGGCTATGACTGGGCACAACAGACAATCGGCTG
CTCTGATGCCGCCGTGTTCCGGCTGTCAGCGCAGGGGCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCTCGACGTTGTCACTGAAGCGGGAAGGGACTGGCTG
CTATTGGGCGAAGTGCCGGGGCAGGATCTCCTGTCATCTCACCTTGCTCCTGCCGAGAAAGTATCCATCATGGCTGATGCAATGCGGCGGCTG
CATACGCTTGATCCGGCTACCTGCCCATTCGACCACCAAGCGAAACATCGCATCGAGCGAGCACGTACTCGGATGGAAGCCGGTCTTGTCGAT
CAGGATGATCTGGACGAAGAGCATCAGGGGCTCGCGCCAGCCGAACTGTTCGCCAGGCTCAAGGCGCGCATGCCCGACGGCGAGGATCTCG
TCGTGACCCATGGCGATGCCTGCTTGCCGAATATCATGGTGGAAAATGGCCGCTTTTCTGGATTCATCGACTGTGGCCGGCTGGGTGTGGCG
GACCGCTATCAGGACATAGCGTTGGCTACCCGTGATATTGCTGAAGAGCTTGGCGGCGAATGGGCTGACCGCTTCCTCGTGCTTTACGGTATC
GCCGCTCCCGATTCGCAGCGCATCGCCTTCTATCGCCTTCTTGACGAGTTCTTCTGA (SEQ ID NO: 113)

Ampicillin Resistance

AGGTGGCACTTTTCGGGGAAATGTGCGCGGAACCCCTATTTGTTTATTTTTCTAAATACATTCAAATATGTATCCGCTCATGAGACAATAACCCT
GATAAATGCTTCAATAATATTGAAAAAGGAAGAGTATGAGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGCACTTTTAAAGTTCTGCTATGTGGCGCGGTATTATCCCGTGTT
GACGCCGGGCAAGAGCAACTCGGTCGCCGCATACACTATTCTCAGAATGACTTGGTTGAGTACTCACCAGTCACAGAAAAGCATCTTACGGAT
GGCATGACAGTAAGAGAATTATGCAGTGCTGCCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAACCGGAGCTGAATGAAGCCATACCAAACGACG
AGCGTGACACCACGATGCCTGCAGCAATGGCAACAACGTTGCGCAAACTATTAACTGGCGAACTACTTACTCTAGCTTCCCGGCAACAATTAA
TAGACTGGATGGAGGCGGATAAAGTTGCAGGACCACTTCTGCGCTCGGCCCTTCCGGCTGGCTGGTTTATTGCTGATAAATCTGGAGCCGGT
GAGCGTGGGTCTCGCGGTATCATTGCAGCACTGGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAGGGAGCTTCCAGGGGGAAACGCCTGGTATCTTTATAG
TCCTGTCGGGTTTCGCCACCTCTGACTTGAGCGTCGATTTTTGTGATGCTCGTCAGGGGGGCGGAGCCTATGGAAAAACGCCAGCAACGCGG
CCTTTTTACGGTTCCTGGCCTTTTGCTGGCCTTTTGCTCACATGTTCTTTCCTGCGTTATCCCCTGATTCTGTGGATAACCGTATTACCGCCTTTGA
GTGAGCTGATACCGCTCGCCGCAGCCGAACGACCGAGCGCAGCGAGTCAGTGAGCGAGGAAGCGGAAGAGCGCCTGATGCGGTATTTTCTC
CTTACGCATCTGTGCGGTATTTCACACCGCATATGGTGCACTCTCAGTACAATCTGCTCTGATGCCGCATAGTTAAGCCAGTAT (SEQ ID NO:
114)

FIG. 12B

AAV expression kinetics inform dosing schedule for clinical study

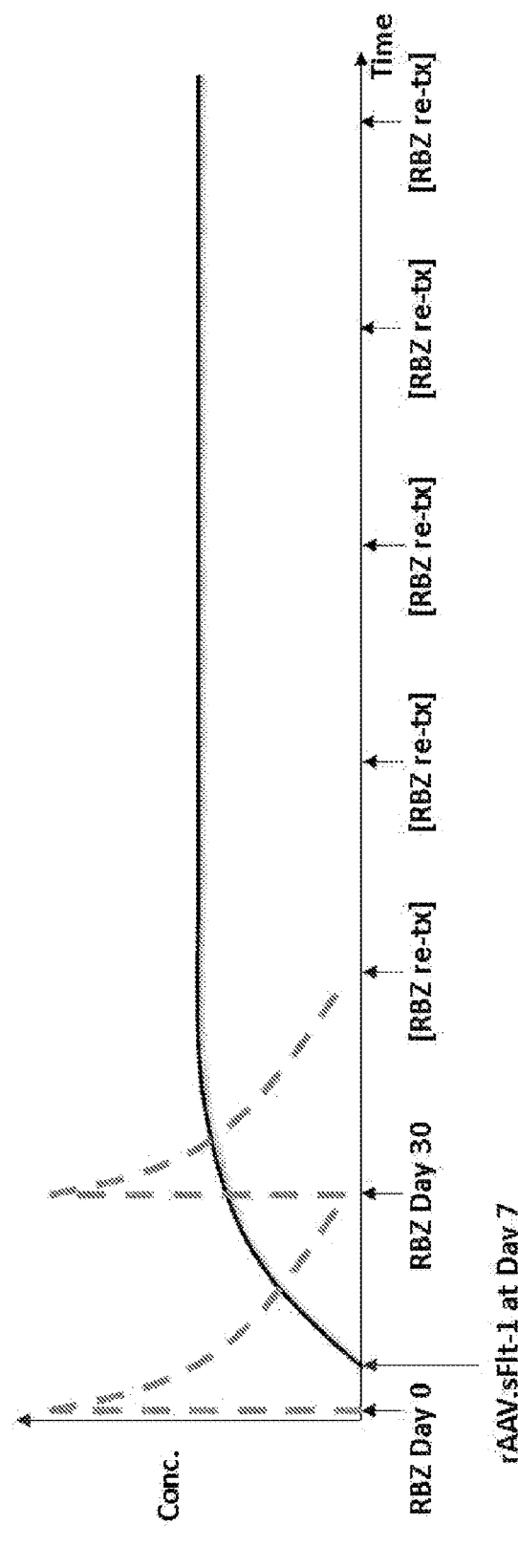

rAAV.sFlt-1 at Day 7

- Protocol for study of safety and efficacy of rAAV.sFlt-1 in humans with wet AMD is informed by expression kinetics
- rAAV.sFlt-1 reaches optimal expression of anti-VEGF protein sFLT-1 at 6-8 weeks
- Subjects in all arms receive two mandatory injections of 0.5 mg ranibizumab on day 0 and day 30
- Expect greater need for re-treatment or rescue treatment in control arm

FIG. 13

| Subject | Visit | Study Eye | | | | Fellow Eye | | | |
|---|---|---|---|---|---|---|---|---|---|
| | | AC-cells | AC-flare | VC-BE | VC-IOE | AC-cells | AC-flare | VC-BE | VC-IOE |
| R1001 | SCR | 0 | 0 | Unrem. | Unrem. | 0 | 0 | Unrem. | Unrem. |
| | Baseline | 0 | 0 | Unrem. | Unrem. | 0 | 0 | Unrem. | Unrem. |
| | Day 8 | 0 | 0 | Trace | Trace | 0 | 0 | Unrem. | Unrem. |
| | Day 11 | 0 | 0 | Unrem. | Trace | 0 | 0 | Unrem. | Unrem. |
| | Day 21 | 0 | 0 | Unrem. | Unrem. | 0 | 0 | Unrem. | Unrem. |
| | Day 30 | 0 | 0 | Unrem. | Unrem. | 0 | 0 | Unrem. | Unrem. |
| | Day 60 | 0 | 0 | Unrem. | Unrem. | 0 | 0 | Unrem. | Unrem. |
| R1002 | SCR | 0 | 0 | Unrem. | Unrem. | 0 | 0 | Unrem. | Unrem. |
| | Baseline | 0 | 0 | Unrem. | Unrem. | 0 | 0 | Unrem. | Unrem. |
| | Day 8 | 0 | 0 | Unrem. | Unrem. | 0 | 0 | Unrem. | |
| | Day 11 | 0 | 0 | Trace | Trace | | | | |
| | Day 21 | 0 | 0 | Unrem. | Unrem. | 0 | 0 | Unrem. | Unrem. |
| | Day 30 | 0 | 0 | Unrem. | Unrem. | 0 | 0 | Unrem. | Unrem. |
| | Day 60 | 0 | 0 | Unrem. | Unrem. | 0 | 0 | Unrem. | Unrem. |
| R1003 | SCR | 0 | 0 | Unrem. | Unrem. | 0 | 0 | Unrem. | Unrem. |
| | Baseline | 0 | 0 | Unrem. | Unrem. | 0 | 0 | Unrem. | Unrem. |
| | Day 7 | 0 | 0 | Unrem. | Unrem. | 0 | 0 | Unrem. | Unrem. |
| | Day 30 | 0 | 0 | Unrem. | Unrem. | 0 | 0 | Unrem. | Unrem. |
| | Day 60 | 0 | 0 | Unrem. | Unrem. | 0 | 0 | Unrem. | Unrem. |
| R1004 | SCR | 0 | 0 | Unrem. | Unrem. | 0 | 0 | Unrem. | Unrem. |
| | Day 8 | 0 | 0 | Unrem. | Trace | 0 | 0 | Unrem. | |
| | Day 11 | 0 | 0 | Unrem. | Unrem. | | | | |
| | Day 21 | 0 | 0 | Unrem. | Unrem. | 0 | 0 | Unrem. | Unrem. |
| | Day 30 | 0 | 0 | Unrem. | Unrem. | 0 | 0 | Unrem. | Unrem. |
| | Day 60 | 0 | 0 | Unrem. | Unrem. | 0 | 0 | Unrem. | Unrem. |

FIG. 14

| Date | OCT CPT | BCVA Snellen Eq |
|---|---|---|
| December 2011 | 704 μm | 20/320 |
| Baseline | 642 μm | 20/250 |
| Day 21 | 472 μm | 20/400 |
| Day 30 | 498 μm | 20/400 |
| Day 60 | 393 μm | 20/200 |
| Day 90 | 361 μm | 20/400 |

| Subject | Visit Day | Blood | Tear (Study) | Tear (Fellow) | Saliva | Urine |
|---|---|---|---|---|---|---|
| R1005 | SCR | 0 | 0 | 0 | 0 | 0 |
| | Day 8 | 0 | 35,000* | 0 | 0 | 0 |
| | Day 30 | 0 | 0 | 0 | 0 | 0 |
| R1006 | SCR | 0 | 0 | 0 | 0 | 0 |
| | Day 8 | 0 | 0 | 0 | 0 | 0 |
| | Day 30 | 0 | 0 | 0 | 0 | 0 |
| R1007 | SCR | 0 | 0 | 0 | 0 | 0 |
| | Day 8 | 0 | 0 | 0 | 0 | 0 |
| | Day 30 | 0 | 0 | 0 | 0 | 0 |
| R1008 | SCR | 0 | 0 | 0 | 0 | 0 |
| | Day 8 | 0 | 0 | 0 | 0 | 0 |
| | Day 30 | 0 | 0 | 0 | 0 | 0 |

FIG. 17

| Subject | Visit Day | Serum | Tear (Study) | Tear (Fellow) | Saliva | Urine |
|---|---|---|---|---|---|---|
| R1001 | SCR | 0 | ND | ND | ND | 0 |
|  | Day 8 | 0 | ND | ND | ND | 0 |
|  | Day 21 | 0 | ND | ND | 0 | 0 |
|  | Day 30 | 0 | ND | ND | 0 | 0 |
|  | Day 60 | 0 | ND | ND | 0 | 0 |
| R1002 | SCR | 0 | ND | ND | ND | ND |
|  | Day 8 | 0 | ND | ND | 0 | 0 |
|  | Day 21 | 0 | ND | ND | 0 | 0 |
|  | Day 30 | 0 | ND | ND | 0 | 0 |
|  | Day 60 | 0 | ND | ND | 0 | 0 |
| R1003 | SCR | 0 | ND | ND | 0 | 0 |
|  | Day 30 | 0 | ND | ND | 0 | 0 |
| R1004 | SCR | 0 | ND | ND | 0 | 0 |
|  | Day 8 | 0 | ND | ND | ND | 0 |
|  | Day 21 | 0 | ND | ND | ND | 0 |
|  | Day 30 | 0 | ND | ND | 0 | 0 |
|  | Day 60 | 0 | ND | ND | 0 | 0 |

FIG. 18

| Subject | Visit Day | Serum | Tear (Study) | Tear (Fellow) | Saliva | Urine |
|---------|-----------|-------|--------------|---------------|--------|-------|
| R1001 | SCR | 85.51±9.28 | ND | ND | ND | 0 |
| | Day 8 | 76.67±24.46 | ND | ND | 0 | 0 |
| | Day 21 | 46.19±11.65 | ND | ND | 875.27±99.44 | 0 |
| | Day 30 | 60.19±10.61 | ND | ND | 0 | 0 |
| | Day 60 | 14.89±20.97 | ND | ND | 0 | 0 |
| | Day 90 | 9.24±1.13 | ND | ND | 438.58±210.88 | 0 |
| R1002 | SCR | 35.82±37.12 | ND | ND | ND | ND |
| | Day 8 | 46.19±6.99 | ND | ND | 1680.55±104.84 | 149.16±3.49 |
| | Day 21 | 12.42±5.82 | ND | ND | 407.93±17.47 | 102.03±26.79 |
| | Day 30 | 79.88±21.21 | ND | ND | 2337.78±123.30 | 0 |
| | Day 60 | 9.95±9.32 | ND | ND | 1607.72±314.52 | 0 |
| | Day 90 | 58.15+11.33 | ND | ND | 571.66+36.28 | 0 |
| R1003 | SCR | 55.51±22.54 | ND | ND | 1105.90±83.53 | 0 |
| | Day 30 | 79.88±14.58 | ND | ND | 1915.90±83.53 | 0 |
| | Day 90 | 34.90+15.31 | ND | ND | 892.35+54.42 | 0 |
| R1004 | SCR | 331.13±216.11 | ND | ND | 17.46±7.95 | 60.20±3.49 |
| | Day 8 | 62.67±4.66 | ND | ND | ND | 140.92±45.43 |
| | Day 21 | 4.19±5.82 | ND | ND | ND | 134.33±15.14 |
| | Day 30 | 62.07±7.95 | ND | ND | 1834.44±198.87 | 37.13±47.66 |
| | Day 60 | 9.13±15.14 | ND | ND | 92.77±50.67 | 25.60±15.14 |
| | Day 90 | 20.47+5.55 | ND | ND | ND | 0 |

FIG. 19

Anti-VEGF reinjections for patients in rAAV.sFlt-1 clinical study

| Week | 8 | 12 | 16 | 20 | 24 | 28 | 32 | 36 | 40 | 44 | 48 | 52 | (Month) 15 |
|---|---|---|---|---|---|---|---|---|---|---|---|---|---|
| R1003 Control | O | X | X | O | O | X | O | X | O | O | X | O | |
| R1007 Control | O | O | O | X | O | O | O | O | O | O | O | O | |
| R1001 | O | O | O | O | O | O* | O* | O | O | O | O | O | O |
| R1002 | O | O | O | O | O | O | O | O* | O | O | O | O | |
| R1004 | O | O | O | O | O | O* | O | O | O | O | O | X | |
| R1005 | O | O | O* | O | O | O* | O | O | O | O | O | O | |
| R1006 | O | X | O* | O | O | O | O | O | O | O | O | O | |
| R1008 | O | O | O | O | O* | O | O | O | O | O | O | O | |

- \* Missed visit (no injection)The table above shows partial results from a clinical study of the safety and efficacy of rAAV.sFlt-1 in patients with wet AMD.
- According to study protocol, patients initially received intravitreal injections of anti-VEGF at 0 and 30 days vision after which were monitored for disease activity every 4 weeks.
- Additional intravitreal injections of anti-VEGF therapy were administered to patients if exhibited other signs of disease activity as defined in the study protocol.
- "X" indicates patient received an intravitreal injection of anti-VEGF therapy (Lucentis) during a monitoring visit in the listed week.

FIG 23

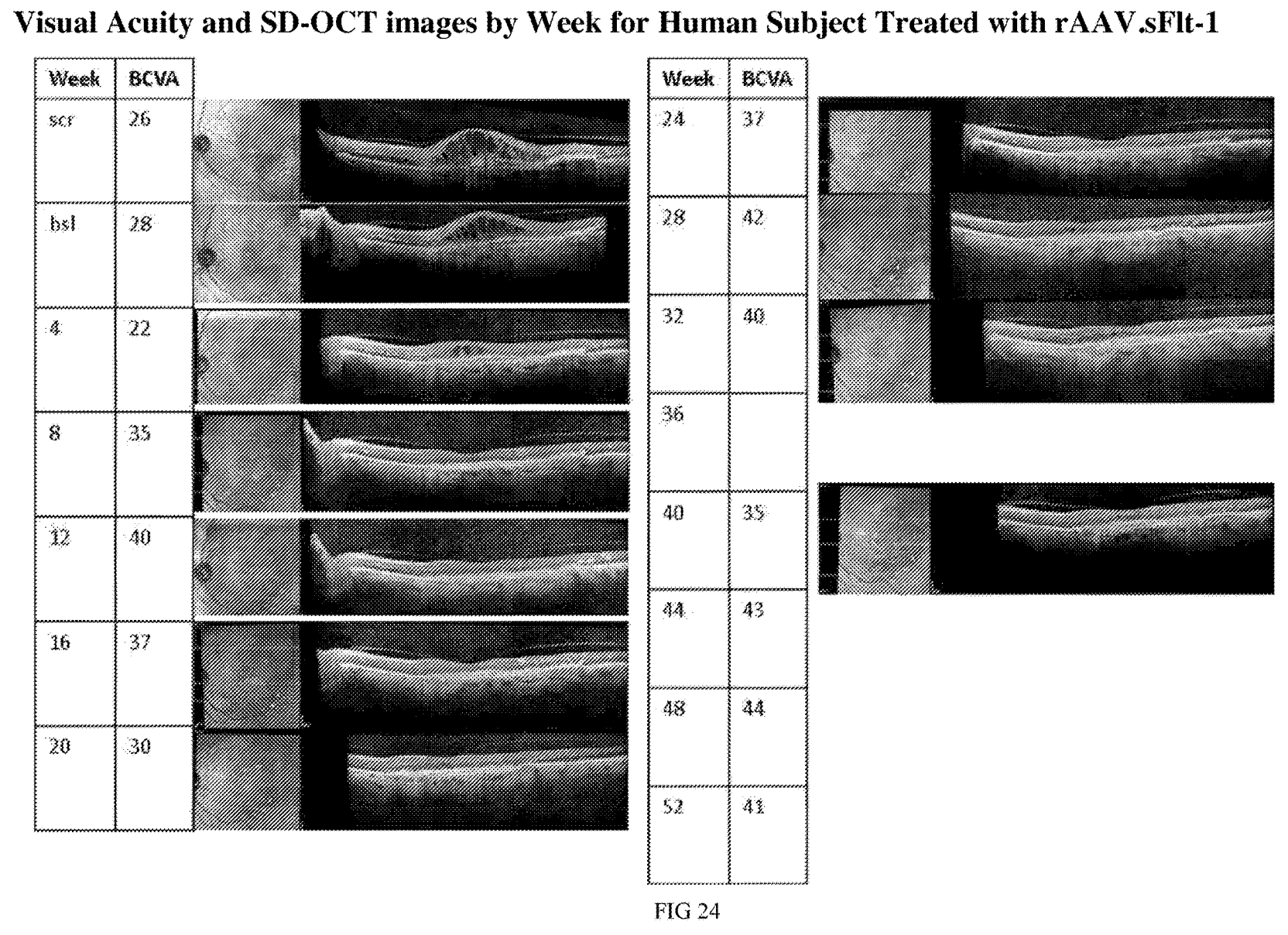

Visual Acuity and SD-OCT images by Week for Human Subject Treated with rAAV.sFlt-1

| Week | BCVA |
|------|------|
| 24 | 37 |
| 28 | 42 |
| 32 | 40 |
| 36 | |
| 40 | 35 |
| 44 | 43 |
| 48 | 44 |
| 52 | 41 |

| Week | BCVA |
|------|------|
| scr | 26 |
| bsl | 28 |
| 4 | 22 |
| 8 | 35 |
| 12 | 40 |
| 16 | 37 |
| 20 | 30 |

FIG 24

FIG. 25A: HEK293 Tranduction by AAV.sFlt-1 at 72hours
MOI range: 1e4-1e5 (8e4 cell seed/24 well)

FIG 25A

FIG 25B: HEK293 Transduction by AAV.sFlt-1 at 72hours
MOI range: 1e5-1e6 (>1.5e5 cells seed/ 24 well)

SEQUENCE LISTING

<160> NUMBER OF SEQ ID NOS: 124

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
atggaaaaac gccagcaacg                                                        20

<210> SEQ ID NO 2
<211> LENGTH: 881
<212> TYPE: DNA
<213> ORGANISM: Artificial Sequence
<220> FEATURE:
<223> OTHER INFORMATION: Synthetic polynucleotide

<400> SEQUENCE: 2
aaaaggatct aggtgaagat ccttttttgat aatctcatga ccaaaatccc ttaacgtgag     60
ttttcgttcc actgagcgtc agaccccgta gaaaagatca aaggatcttc ttgagatcct    120
ttttttctgc gcgtaatctg ctgcttgcaa acaaaaaaac caccgctacc agcggtggtt    180
tgtttgccgg atcaagagct accaactctt tttccgaagg taactggctt cagcagagcg    240
cagataccaa atactgtcct tctagtgtag ccgtagttag gccaccactt caagaactct    300
gtagcaccgc ctacatacct cgctctgcta tcctgttac cagtggctgc tgccagtggc     360
gataagtcgt gtcttaccgg gttggactca agacgatagt taccggataa ggcgcagcgg    420
tcgggctgaa cggggggttc gtgcacacag cccagcttgg agcgaacgac ctacaccgaa    480
ctgagatacc tacagcgtga gctatgagaa agcgccacgc ttcccgaagg gagaaaggcg    540
gacaggtatc cggtaagcgg cagggtcgga acaggagagc gcacgaggga gcttccaggg    600
ggaaacgcct ggtatcttta tagtcctgtc gggtttcgcc acctctgact tgagcgtcga    660
tttttgtgat gctcgtcagg ggggcggagc ctatggaaaa acgccagcaa cgcggccttt    720
ttacggttcc tggccttttg ctggcctttt gctcacatgt tctttcctgc gttatcccct    780
gattctgtgg ataaccgtat taccgccttt gagtgagctg ataccgctcg ccgcagccga    840
acgaccgagc gcagcgagtc agtgagcgag gaagcggaag a                         881

<210> SEQ ID NO 3
<211> LENGTH: 362
<212> TYPE: DNA
<213> ORGANISM: Artificial Sequence
<220> FEATURE:
<223> OTHER INFORMATION: Synthetic polynucleotide

<400> SEQUENCE: 3
gcgccacgct tcccgaaggg agaaaggcgg acaggtatcc ggtaagcggc agggtcggaa      60
caggagagcg cacgagggag cttccagggg gaaacgcctg gtatctttat agtcctgtcg    120
ggtttcgcca cctctgactt gagcgtcgat ttttgtgatg ctcgtcaggg gggcggagcc    180
tatggaaaaa cgccagcaac gcggcctttt tacggttcct ggccttttgc tggccttttg    240
ctcacatgtt ctttcctgcg ttatcccctg attctgtgga taaccgtatt accgcctttg    300
agtgagctga taccgctcgc cgcagccgaa cgaccgagcg cagcgagtca gtgagcgagg    360
aa                                                                   362

```
<210> SEQ ID NO 4
<211> LENGTH: 615
<212> TYPE: DNA
<213> ORGANISM: Artificial Sequence
<220> FEATURE:
<223> OTHER INFORMATION: Synthetic polynucleotide

<400> SEQUENCE: 4
aaaggatctt cttgagatcc tttttttctg cgcgtaatct gctgcttgca aacaaaaaa       60 ccaccgctac cagcggtggt ttgtttgccg gatcaagagc taccaactct ttttccgaag      120
gtaactggct tcagcagagc gcagatacca aatactgttc ttctagtgta gccgtagtta      180
ggccaccact tcaagaactc tgtagcaccg cctacatacc tcgctctgct aatcctgtta      240
ccagtggctg ctgccagtgg cgataagtcg tgtcttaccg ggttggactc aagacgatag      300
ttaccggata aggcgcagcg gtcgggctga acggggggtt cgtgcacaca gcccagcttg      360
gagcgaacga cctacaccga actgagatac ctacagcgtg agctatgaga aagcgccacg      420
cttcccgaag ggagaaaggc ggacaggtat ccggtaagcg gcagggtcgg aacaggagag      480
cgcacgaggg agcttccagg gggaaacgcc tggtatcttt atagtcctgt cgggtttcgc      540
cacctctgac ttgagcgtcg attttttgtga tgctcgtcag ggggcggag cctatggaaa      600 aacgccagca acgcg                                                       615

<210> SEQ ID NO 5
<211> LENGTH: 1258
<212> TYPE: DNA
<213> ORGANISM: Artificial Sequence
<220> FEATURE:
<223> OTHER INFORMATION: Synthetic polynucleotide

<400> SEQUENCE: 5
tgttgtttgt cggttaacgt cgacctagag ctgcctcgcg cgtttcggtg atgacggtga       60
aaacctctga cacatgcagc tcccggagac ggtcacagct tgtctgtaag cggatgccgg      120
gagcagacaa gcccgtcagg gcgcgtcagc gggtgttggc gggtgtcggg gcgcagccat      180
gacccagtca cgtagcgata gcggagtgta tactggctta actatgcggc atcagagcag      240
attgtactga gagtgcacca tatgcggtgt gaaataccgc acagatgcgt aaggagaaaa      300
taccgcatca ggcgctcttc cgcttcctcg ctcactgact cgctgcgctc ggtcgttcgg      360
ctgcggcgag cggtatcagc tcactcaaag gcggtaatac ggttatccac agaatcaggg      420
gataacgcag gaaagaacat gtgagcaaaa ggccagcaaa aggccaggaa ccgtaaaaag      480
gccgcgttgc tggcgttttt ccataggctc cgcccccctg acgagcatca caaaaatcga      540
cgctcaagtc agaggtggcg aaacccgaca ggactataaa gataccaggc gtttccccct      600
ggaagctccc tcgtgcgctc tcctgttccg accctgccgc ttaccggata cctgtccgcc      660
tttctccctt cgggaagcgt ggcgctttct caatgctcac gctgtaggta tctcagttcg      720
gtgtaggtcg ttcgctccaa gctgggctgt gtgcacgaac ccccgttca gcccgaccgc      780 tgcgccttat ccggtaacta tcgtcttgag tccaacccgg taagacacga cttatcgcca      840
ctggcagcag ccactggtaa caggattagc agagcgaggt atgtaggcgg tgctacagag      900
ttcttgaagt ggtggcctaa ctacggctac actagaagga cagtatttgg tatctgcgct      960
ctgctgaagc cagttacctt cggaaaaaga gttggtagct cttgatccgg caaacaaacc     1020
accgctggta gcggtggttt ttttgtttgc aagcagcaga ttacgcgcag aaaaaaagga     1080
tctcaagaag atcctttgat cttttctacg gggtctgacg ctcagtggaa cgaaaactca     1140
```
cgttaaggga ttttggtcat gagattatca aaaaggatct tcacctagat ccttttaaat    1200
taaaaatgaa gttttaaatc aatctaaagt atatatgagt aaacttggtc tgacagtt      1258

<210> SEQ ID NO 6
<211> LENGTH: 674
<212> TYPE: DNA
<213> ORGANISM: Artificial Sequence
<220> FEATURE:
<223> OTHER INFORMATION: Synthetic polynucleotide

<400> SEQUENCE: 6
cccgtagaaa agatcaaagg atcttcttga gatccttttt ttctgcgcgt aatctgctgc      60
ttgcaaacaa aaaaaccacc gctaccagcg gtggtttgtt tgccggatca agagctacca     120
actctttttc cgaaggtaac tggcttcagc agagcgcaga taccaaatac tgtccttcta     180
gtgtagccgt agttaggcca ccacttcaag aactctgtag caccgcctac atacctcgct     240
ctgctaatcc tgttaccagt ggctgctgcc agtggcgata agtcgtgtct taccgggttg     300
gactcaagac gatagttacc ggataaggcg cagcggtcgg gctgaacggg gggttcgtgc     360
acacagccca gcttggagcg aacgacctac accgaactga gatacctaca gcgtgagcat     420
tgagaaagcg ccacgcttcc cgaagggaga aaggcggaca ggtatccggt aagcggcagg     480
gtcggaacag gagagcgcac gagggagctt ccagggggaa acgcctggta tctttatagt     540
cctgtcgggt ttcgccacct ctgacttgag cgtcgatttt tgtgatgctc gtcaggggggg     600 cggagcctat ggaaaaacgc cagcaacgcg gcctttttac ggttcctggc cttttgctgg     660
ccttttgctc acat                                                       674

<210> SEQ ID NO 7
<211> LENGTH: 674
<212> TYPE: DNA
<213> ORGANISM: Artificial Sequence
<220> FEATURE:
<223> OTHER INFORMATION: Synthetic polynucleotide

<400> SEQUENCE: 7
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata aagataccag gcgtttcccc ctggaagctc cctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag gacagtattt ggtatctgcg ctctgctgaa gccagttacc     540
ttcggaaaaa gagttggtag ctcttgatcc ggcaaacaaa ccaccgctgg tagcggtggt     600 tttttttgttt gcaagcagca gattacgcgc agaaaaaaag gatctcaaga agatcctttg     660 atctttttcta cggg                                                      674

<210> SEQ ID NO 8
<211> LENGTH: 830
<212> TYPE: DNA
<213> ORGANISM: Artificial Sequence
<220> FEATURE:
<223> OTHER INFORMATION: Synthetic polynucleotide -continued

```
<400> SEQUENCE: 8
ttaataagat gatcttcttg agatcgtttt ggtctgcgcg taatctcttg ctctgaaaac    60
gaaaaaaccg ccttgcaggg cggttttttcg aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtctttccg ggttggactc aagacgatag ttaccggata aggcgcagcg   300
gtcggactga acggggggtt cgtgcataca gtccagcttg gagcgaactg cctacccgga   360
actgagtgtc aggcgtggaa tgagacaaac gcggccataa cagcggaatg acaccggtaa   420
accgaaaggc aggaacagga gagcgcacga gggagccgcc aggggggaaac gcctggtatc   480 tttatagtcc tgtcgggttt cgccaccact gatttgagcg tcagatttcg tgatgcttgt   540
caggggggcg gagcctatgg aaaaacggct ttgccgcggc cctctcactt ccctgttaag   600
tatcttcctg gcatcttcca ggaaatctcc gccccgttcg taagccattt ccgctcgccg   660
cagtcgaacg accgagcgta gcgagtcagt gagcgaggaa gcggaatata tcctgtatca   720
catattctgc tgacgcaccg gtgcagcctt ttttctcctg ccacatgaag cacttcactg   780
acaccctcat cagtgccaac atagtaagcc agtatacact ccgctagcgc                830

<210> SEQ ID NO 9
<211> LENGTH: 237
<212> TYPE: DNA
<213> ORGANISM: Artificial Sequence
<220> FEATURE:
<223> OTHER INFORMATION: Synthetic polynucleotide

<400> SEQUENCE: 9
aaacgccagc aacgcggcct ttttacggtt cctggccttt tgctggcctt ttgctcacat    60
gttctttcct gcgttatccc ctgattctgt ggataaccgt attaccgcct ttgagtgagc   120
tgataccgct cgccgcagcc gaacgaccga gcgcagcgag tcagtgagcg aggaagcgga   180
agagcgccca atacgcaaac cgcctctccc cgcgcgttgg ccgattcatt aatgcag      237

<210> SEQ ID NO 10
<211> LENGTH: 456
<212> TYPE: DNA
<213> ORGANISM: Artificial Sequence
<220> FEATURE:
<223> OTHER INFORMATION: Synthetic polynucleotide

<400> SEQUENCE: 10
aaattgtaaa cgttaatatt ttgttaaaat tcgcgttaaa tatttgttaa atcagctcat    60
tttttaacca ataggccgaa atcggcaaaa tcccttataa atcaaaagaa tagaccgcga   120
tagggttgag tgttgttcca gtttggaaca agagtccact attaaagaac gtggactcca   180
acgtcaaagg gcgaaaaacc gtctatcagg gcgatggccc actacgtgaa ccatcaccca   240
aatcaagttt tttgcggtcg aggtgccgta aagctctaaa tcggaaccct aaagggagcc   300
cccgatttag agcttgacgg ggaaagccgg cgaacgtggc gagaaaggaa gggaagaaag   360
cgaaaggagc gggcgctagg gcgctggcaa gtgtagcggt cacgctgcgc gtaaccacca   420
cacccgccgc gcttaatgcg ccgctacagg gcgcgt                             456

<210> SEQ ID NO 11
<211> LENGTH: 307
<212> TYPE: DNA
```

-continued

```
<213> ORGANISM: Artificial Sequence
<220> FEATURE:
<223> OTHER INFORMATION: Synthetic polynucleotide

<400> SEQUENCE: 11
ggcgcattaa gcgcggcggg tgtggtggtt acgcgcagcg tgaccgctac acttgccagc      60
gccctagcgc ccgctccttt cgctttcttc ccttcctttc tcgccacgtt cgccggcttt     120
ccccgtcaag ctctaaatcg ggggctccct ttagggttcc gatttagtgc tttacggcac     180
ctcgacccca aaaaacttga ttagggtgat ggttcacgta gtgggccatc gccctgatag     240
acggtttttc gccctttgac gttggagtcc acgttcttta atagtggact cttgttccaa     300
actggaa                                                               307

<210> SEQ ID NO 12
<211> LENGTH: 456
<212> TYPE: DNA
<213> ORGANISM: Artificial Sequence
<220> FEATURE:
<223> OTHER INFORMATION: Synthetic polynucleotide

<400> SEQUENCE: 12
acgcgccctg tagcggcgca ttaagcgcgg cgggtgtggt ggttacgcgc agcgtgaccg      60
ctacacttgc cagcgcccta gcgcccgctc ctttcgcttt cttcccttcc tttctcgcca     120
cgttcgccgg ctttccccgt caagctctaa atcggggggct ccctttaggg ttccgattta     180
gtgctttacg gcacctcgac cccaaaaaac ttgattaggg tgatggttca cgtagtgggc     240
catcgccctg atagacggtt tttcgcccctt tgacgttgga gtccacgttc tttaatagtg     300
gactcttgtt ccaaactgga acaacactca accctatctc ggtctattct tttgatttat     360
aagggatttt gccgatttcg gcctattggt taaaaaatga gctgatttaa caaaaattta     420
acgcgaattt taacaaaata ttaacgctta caattt                               456

<210> SEQ ID NO 13
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 13 aattttttttt atttatgcag aggccgaggc cgcctcggcc tctgagctat ccagaagta      60 gtgagg                                                                 66

<210> SEQ ID NO 14
<211> LENGTH: 362
<212> TYPE: DNA
<213> ORGANISM: Artificial Sequence
<220> FEATURE:
<223> OTHER INFORMATION: Synthetic polynucleotide

<400> SEQUENCE: 14
tggacagcga acgcacacta caaccttgga tagagttagg aattagtaga cggacatact      60
acagggattt aaatgataat cattctcaaa aatgacacca gataagccta aatcagataa     120
cagccccaaa agcgagcttt tggggtgcct tttagacggt gctaggtttt tgacagcaga     180
taagcctaaa tcagataaca gccgaatcga taagccttag ttggttaagg gggcaggaaa     240
ttcatattga acaaatgttt agttaagtgt agaataatca tacatcctta ttaagggcaa     300
gcatactcaa gccccacaaa gtgtgcttga aatccttgta aggggaaatc cccttaacc     360
```

-continued

```
cc                                                                 362

<210> SEQ ID NO 15
<211> LENGTH: 589
<212> TYPE: DNA
<213> ORGANISM: Artificial Sequence
<220> FEATURE:
<223> OTHER INFORMATION: Synthetic polynucleotide

<400> SEQUENCE: 15
ttgagatcct tttttctgc gcgtaatctg ctgcttgcaa acaaaaaaac caccgctacc      60
agcggtggtt tgtttgccgg atcaagagct accaactctt tttccgaagg taactggctt     120
cagcagagcg cagataccaa atactgtcct tctagtgtag ccgtagttag gccaccactt     180
caagaactct gtagcaccgc ctacatacct cgctctgcta tcctgttac cagtggctgc      240 tgccagtggc gataagtcgt gtcttaccgg gttggactca agacgatagt taccggataa     300
ggcgcagcgg tcgggctgaa cggggggttc gtgcacacag cccagcttgg agcgaacgac     360
ctacaccgaa ctgagatacc tacagcgtga gctatgagaa agcgccacgc ttcccgaagg     420
gagaaaggcg gacaggtatc cggtaagcgg caggtcgga acaggagagc gcacgaggga      480
gcttccaggg ggaaacgcct ggtatcttta tagtcctgtc gggtttcgcc acctctgact     540
tgagcgtcga ttttgtgat gctcgtcagg ggggcggagc ctatggaaa                  589

<210> SEQ ID NO 16
<211> LENGTH: 459
<212> TYPE: DNA
<213> ORGANISM: Artificial Sequence
<220> FEATURE:
<223> OTHER INFORMATION: Synthetic polynucleotide

<400> SEQUENCE: 16
tttacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgattt gggtgatggt tcacgtagtg     240
ggccatcgcc ctgatagacg gtttttcgcc ctttgacgtt ggagtccacg ttctttaata     300
gtggactctt gttccaaact tgaacaacac tcaaccctat ctcgggctat tcttttgatt     360
tataagggat tttgccgatt tcggcctatt ggttaaaaaa tgagctgatt aacaaaaat      420 ttaacgcgaa ttttaacaaa atattaacgt ttacaattt                            459

<210> SEQ ID NO 17
<211> LENGTH: 602
<212> TYPE: DNA
<213> ORGANISM: Artificial Sequence
<220> FEATURE:
<223> OTHER INFORMATION: Synthetic polynucleotide

<400> SEQUENCE: 17
atgcattagt tattaatagt aatcaattac ggggtcatta gttcatagcc catatatgga      60
gttccgcgtt acataactta cggtaaatgg cccgcctggc tgaccgccca acgacccccg     120
cccattgacg tcaataatga cgtatgttcc catagtaacg ccaatanggga ctttccattg     180 acgtcaatgg gtggagtatt tacggtaaac tgcccacttg gcagtacatc aagtgtatca     240
tatgccaagt acgccccta ttgacgtcaa tgacggtaaa tggcccgcct ggcattatgc      300
```

-continued

```
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gc                                                                   602

<210> SEQ ID NO 18
<211> LENGTH: 741
<212> TYPE: DNA
<213> ORGANISM: Artificial Sequence
<220> FEATURE:
<223> OTHER INFORMATION: Synthetic polynucleotide

<400> SEQUENCE: 18
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
agtaacgcca tagggactt tccattgacg tcaatgggtg gagtatttac ggtaaactgc    360
ccacttggca gtacatcaag tgtatcatat gccaagtccg cccctattg acgtcaatga    420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt    600 caatgggagt ttgttttggc accaaaatca cgggactttc caaaatgtc gtaataaccc    660 cgccccgttg acgcaaatgg gcggtaggcg tgtacggtgg gaggtctata taagcagagc    720
tcgtttagtg aaccgtcaga t                                             741

<210> SEQ ID NO 19
<211> LENGTH: 664
<212> TYPE: DNA
<213> ORGANISM: Artificial Sequence
<220> FEATURE:
<223> OTHER INFORMATION: Synthetic polynucleotide

<400> SEQUENCE: 19
acgcgtacta gttattaata gtaatcaatt acggggtcat tagttcatag cccatatatg     60
gagttccgcg ttacataact tacggtaaat ggcccgcctg gctgaccgcc caacgacccc    120
cgcccattga cgtcaataat gacgtatgtt cccatagtaa cgtcaatagg actttccat    180 tgacgtcaat gggtggagta tttacggtaa actgcccact tggcagtaca tcaagtgtat    240
catatgccaa gtacgccccc tattgacgtc aatgacggta aatggcccgc ctggcattat    300
gcccagtaca tgaccttatg ggactttcct acttggcagt acatctacgt attagtcatc    360
gctattacca tggtgatgcg gttttggcag tacatcaatg ggcgtggata gcggtttgac    420
tcacggggat ttccaagtct ccaccccatt gacgtcaatg ggagtttgtt ttgcaccaaa    480
atcaacggga ctttccaaaa tgtcgtaaca actccgcccc attgacgcaa atgggcggta    540
ggcgtgtacg gtgggaggtc tatataagca gagctcgttt agtgaaccgt cagatcgcct    600
ggagacgcca tccacgctgt tttgacctcc atagaagaca ccgggaccga tccagcctcc    660
```

-continued

```
gtac                                                                   664

<210> SEQ ID NO 20
<211> LENGTH: 663
<212> TYPE: DNA
<213> ORGANISM: Artificial Sequence
<220> FEATURE:
<223> OTHER INFORMATION: Synthetic polynucleotide

<400> SEQUENCE: 20
acgcgtggag ctagttatta atagtaatca attacggggt cattagttca tagcccatat     60
atggagttcc gcgttacata acttacggta aatggcccgc ctggctgacc gcccaacgac    120
ccccgcccat tgacgtcaat aatgacgtat gttcccatag taacgtcaat agggactttc    180
cattgacgtc aatgggtgga gtatttacgg taaactgccc acttggcagt acatcaagtg    240
tatcatatgc caagtacgcc ccctattgac gtcaatgacg gtaaatggcc cgcctggcat    300
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta acaactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tcc                                                                   663

<210> SEQ ID NO 21
<211> LENGTH: 589
<212> TYPE: DNA
<213> ORGANISM: Artificial Sequence
<220> FEATURE:
<223> OTHER INFORMATION: Synthetic polynucleotide

<400> SEQUENCE: 21
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatc                589

<210> SEQ ID NO 22
<211> LENGTH: 670
<212> TYPE: DNA
<213> ORGANISM: Artificial Sequence
<220> FEATURE:
<223> OTHER INFORMATION: Synthetic polynucleotide

<400> SEQUENCE: 22
gcggccgcac gcgtggagct agttattaat agtaatcaat tacggggtca ttagttcata     60
```

```
gcccatatat ggagttccgc gttacataac ttacggtaaa tggcccgcct ggctgaccgc      120
ccaacgaccc ccgcccattg acgtcaataa tgacgtatgt tcccatagta acgtcaatag      180
ggactttcca ttgacgtcaa tgggtggagt atttacggta aactgcccac ttggcagtac      240
atcaagtgta tcatatgcca agtacgcccc ctattgacgt caatgacggt aaatggcccg      300
cctggcatta tgcccagtac atgaccttat gggactttcc tacttggcag tacatctacg      360
tattagtcat cgctattacc atggtgatgc ggttttggca gtacatcaat gggcgtggat      420
agcggtttga ctcacgggga tttccaagtc tccaccccat tgacgtcaat gggagtttgt      480
tttgcaccaa aatcaacggg actttccaaa atgtcgtaac aactccgccc cattgacgca      540
aatgggcggt aggcgtgtac ggtgggaggt ctatataagc agagctcgtt tagtgaaccg      600
tcagatcgcc tggagacgcc atccacgctg ttttgacctc catagaagac accgggaccg      660
atccagcctc                                                              670

<210> SEQ ID NO 23
<211> LENGTH: 490
<212> TYPE: DNA
<213> ORGANISM: Artificial Sequence
<220> FEATURE:
<223> OTHER INFORMATION: Synthetic polynucleotide

<400> SEQUENCE: 23
ggcgaccgcc cagcgacccc cgcccgttga cgtcaatagt gacgtatgtt cccatagtaa       60
cgccaatagg gactttccat tgacgtcaat gggtggagta tttacggtaa actgcccact      120
tggcagtaca tcaagtgtat catatgccaa gtccgccccc tattgacgtc aatgacggta      180
aatggcccgc ctagcattat gcccagtaca tgaccttacg ggagtttcct acttggcagt      240
acatctacgt attagtcatc gctattacca tggtgatgcg gttttggcag tacaccaatg      300
ggcgtggata gcggtttgac tcacggggat ttccaagtct ccaccccatt gacgtcaatg      360
ggagtttgtt ttggcaccaa aatcaacggg actttccaaa atgtcgtaat aaccccgccc      420
cgttgaccca aatgggcggt aggcgtgtac ggtgggaggt ctatatagca gagctcgttt      480
agtgaaccgt                                                              490

<210> SEQ ID NO 24
<211> LENGTH: 887
<212> TYPE: DNA
<213> ORGANISM: Artificial Sequence
<220> FEATURE:
<223> OTHER INFORMATION: Synthetic polynucleotide

<400> SEQUENCE: 24
ttagtcatat gttacttggc agaggccgca tggaaagtcc ctggacgtgg gacatctgat       60
taatacgtga ggaggtcagc catgttcttt ttggcaaagg actacggtca ttggacgttt      120
gattggcatg ggatagggtc agccagagtt aacagtgttc ttttggcaaa gggatacgtg      180
gaaagccccg ggccatttac agtaaactga tacggggaca aagcacagcc atatttagtc      240
atgtactgct tggcagaggg tctatggaaa gtccctggac gtgggacgtc tgattaatat      300
gaaagaaggt cagccagagg tagctgtgtc cttttttggca aagggatacg gttatgggac      360
gtttgattgg actgggatag ggtcagccag agttaacagt gttctttggg caaaggaaac      420
gtggaaagtc ccgggccatt tacagtaaac tgatactggg acaaagtaca cccatattta      480
gtcatgttct ttttgcaaa gagcatctgg aaagtcccgg gcagcattat agtcacttgg      540
cagagggaaa gggtcactca gagttaagta catctttcca gggccaatat tccagtaaat      600
```

-continued tacacttagt tttatgcaaa tcagccacaa aggggatttt cccggtcaat tatgactttt          660
tccttagtca tgcggtatcc aattactgcc aaattggcag tacatactag gtgattcact          720
gacatttggc cgtcctctgg aaagtccctg gaaaccgctc aagtactgta tcatggtgac          780
tttgcatttt tggagagcac gccccactcc accattggtc cacgtaccct atgggggagt          840
ggtttatgag tatataaggg gctccggttt agaagccggg cagagcg          887

<210> SEQ ID NO 25
<211> LENGTH: 935
<212> TYPE: DNA
<213> ORGANISM: Artificial Sequence
<220> FEATURE:
<223> OTHER INFORMATION: Synthetic polynucleotide

<400> SEQUENCE: 25
attgacgtca ataatgacgt atgttcccat agtaacgcca atagggactt tccattgacg          60
tcaatgggtg gactatttac ggtaaactgc ccacttggca gtacatcaag tgtatcatat          120
gccaagtacg ccccctattg acgtcaatga cggtaaatgg cccgcctggc attatgccca          180
gtacatgacc ttatgggact ttcctacttg gcagtacatc tacgtattag tcatcgctat          240
taccatggtc gaggtgagcc ccacgttctg cttcactctc cccatctccc cccctcccc          300 accccaatt ttgtatttat ttattttta attattttgt gcagcgatgg gggcgggggg          360
gggggggggg cgcgcgccag gcggggcggg gcggggcgag gggcggggcg gggcgaggcg          420
gagaggtgcg gcggcagcca atcagagcgg cgcgctccga aagtttcctt ttatggcgag          480
gcggcggcgg cggcggccct ataaaaagcg aagcgcgcgg cgggcgggag tcgctgcgac          540
gctgccttcg ccccgtgccc cgctccgccg ccgcctcgcg ccgcccgccc cggctctgac          600
tgaccgcgtt actcccacag gtgagcgggc gggacggccc ttctcctccg ggctgtaatt          660
agcgcttggt ttaatgacgg cttgtttctt ttctgtggct gcgtgaaagc cttgaggggc          720
tccgggaggg ccctttgtgc gggggagcg gctcggggct gtccgcgggg ggacggctgc          780 cttcggggg gacggggcag ggcgggggttc ggcttctggc gtgtgaccgg cggctctaga          840
gcctctgcta accatgttca tgccttcttc tttttcctac agctcctggg caacgtgctg          900
gttattgtgc tgtctcatca ttttggcaaa gaatt          935

<210> SEQ ID NO 26
<211> LENGTH: 367
<212> TYPE: DNA
<213> ORGANISM: Artificial Sequence
<220> FEATURE:
<223> OTHER INFORMATION: Synthetic polynucleotide

<400> SEQUENCE: 26
gtcgaggtga gccccacgtt ctgcttcact ctccccatct ccccccctc cccacccca          60 attttgtatt tatttatttt ttaattattt tgtgcagcga tggggcggg gggggggggg          120 gcgcgcgcca ggcggggcgg ggcggggcga ggggcggggc ggggcgaggc ggagaggtgc          180
ggcggcagcc aatcagagcg gcgcgctccg aaagtttcct tttatggcga ggcggcggcg          240
gcggcggccc tataaaaagc gaagcgcgcg gcgggcggga tcgctgcgt tgccttcgcc          300 ccgtgccccg ctccgcgccg cctcgcgccg cccgccccgg ctctgactga ccgcgttact          360
cccacag          367

<210> SEQ ID NO 27

-continued

```
<211> LENGTH: 278
<212> TYPE: DNA
<213> ORGANISM: Artificial Sequence
<220> FEATURE:
<223> OTHER INFORMATION: Synthetic polynucleotide

<400> SEQUENCE: 27
tcgaggtgag ccccacgttc tgcttcactc tccccatctc ccccccctcc ccaccccaa      60 ttttgtattt atttattttt taattatttt gtgcagcgat gggggcgggg ggggggggg     120 ggcgcgcgcc aggcggggcg gggcggggcg aggggcgggg cggggcgagg cggagaggtg     180
cggcggcagc caatcagagc ggcgcgctcc gaaagtttcc ttttatggcg aggcggcggc     240
ggcggcggcc ctataaaaag cgaagcgcgc ggcgggcg                             278

<210> SEQ ID NO 28
<211> LENGTH: 109
<212> TYPE: DNA
<213> ORGANISM: Artificial Sequence
<220> FEATURE:
<223> OTHER INFORMATION: Synthetic polynucleotide

<400> SEQUENCE: 28
ccagaaaaag tcaacacact tgtcataaag tcccgacgaa gtaaaacaag cggaattaat      60
tcaatttggc caaaaaacct agtataaaga cgtgcatagt gtcgggaat                 109

<210> SEQ ID NO 29
<211> LENGTH: 999
<212> TYPE: DNA
<213> ORGANISM: Artificial Sequence
<220> FEATURE:
<223> OTHER INFORMATION: Synthetic polynucleotide

<400> SEQUENCE: 29
cttcctcacg ctgaacccct ttaaccgttt cagtggtcgt gagtcttcta atctgactgt      60
gtgacgatgt tttaaggatt tggaggattg aggaggatca cctggtcagg taaatctgaa     120
atatccggat tacatcggaa gttgagcaca cggaaaaaca aaagactctt attggattta     180
gatccgtcag ccacctgctg ctgctcttca tcatcaggcg tcttcatcgc cctgcagtgg     240
gcctgacaac agcttgtgtt tattacacta aaaactttat aaacccatca caaaccatat     300
cacacagcag ggacttacct cttcatctgt aagaaggatt tttagagttg gcagcagagc     360
aacagtcagc tctgttgcct cactaaaaga gatctttgtt tgaatctgtg acctgtccaa     420
gtgtacctcg cttctcaccc actgacctct ccacaacagt gagctggttg gcgggatgct     480
aatgtttcta gttattacgt gtaaccaaac ttaaagagta cagataaatc atttagcata     540
attaaagttt tactgtcatg ttattggctg ttaatatgat tgctgttgta agtatgtgtt     600
gatcactaac aatttaatta attaaatcaa tcattaaatt aagtttgttt ggaaaaagag     660
ggaaaactca tccactgacc acatggttct aggttcaatt ccttggagtt aaagggctaa     720
tcccagagcc atttaccaaa ataataaata aatatttaaa taagacgtgc atgcgactgc     780
ggtcaccttt aaagcacaaa gttttttttg agcagtgagg tgaactcggg tggatctgtg     840
tgttcacaga gaaaaccttc tgtaagcaga ttaaggagtc agaagttctt aatcctgaaa     900
gtttagaaaa atcccagcag cataatcttt gctgtaagtg gtttacgagc gtatataaga     960
ggctgacaca gcggcagcgg caaagagctc agggtcaca                            999

<210> SEQ ID NO 30
<211> LENGTH: 626
```

```
<212> TYPE: DNA
<213> ORGANISM: Artificial Sequence
<220> FEATURE:
<223> OTHER INFORMATION: Synthetic polynucleotide

<400> SEQUENCE: 30
aaatcaaaag tcctcaacct ggttggaaga atattggcac tgaatggtat caataaggtt      60
gctagagagg gttagaggtg cacaatgtgc ttccataaca ttttatactt ctccaatctt     120
agcactaatc aaacatggtt gaatactttg tttactataa ctcttacaga gttataagat     180
ctgtgaagac agggacaggg acaataccca tctctgtctg gttcataggt ggtatgtaat     240 agatatttt aaaaataagt gagttaatga atgagggtga gaatggaggc acagaggtat     300 taggggagg tgggccccag agaatggtgc caaggtccag tggggtgact gggatcagct     360
caggcctgac gctggccact cccacctagc tcctttcttt ctaatctgtt ctcattctcc     420
ttgggaagga ttgaggtctc tggaaaacag ccaaacaact gttatgggaa cagcaagccc     480
aaataaagcc aagcatcagg gggatctgag agctgaaagc aacttctgtt cccctcccct     540
cagctgaagg ggtgggaag ggctcccaaa gccataactc cttttaaggg atttagaagg     600
cataaaaagg cccctggctg agaact                                         626

<210> SEQ ID NO 31
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 31
actcacgggg atttccaagt ctccaccca ttgacgtcaa tgggagtttg ttttggcacc      60
aaaatcaacg ggactttcca aaatgtcgta ataaccccgc cccgttgacg caaatgggcg     120
gtaggcgtgt acggtgggag gtctatataa gcagagctcg tttagtgaac cgt           173

<210> SEQ ID NO 32
<211> LENGTH: 113
<212> TYPE: DNA
<213> ORGANISM: Artificial Sequence
<220> FEATURE:
<223> OTHER INFORMATION: Synthetic polynucleotide

<400> SEQUENCE: 32
aaaatcaacg ggactttcca aaatgtcgta ataaccccgc cccgttgacg caaatgggcg      60
gtaggcgtgt acggtgggag gtctatataa gcagagctcg tttagtgaac cgt           113

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
gtaatacgac tcactatagg g                                               21

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide
```

-continued

<400> SEQUENCE: 34
taatacgact cactatagg                                                                    19

<210> SEQ ID NO 35
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 35
ccgattaatc ataaatatga aaaataattg ttgcatcacc cgccaatgcg tggcttaatg     60
cacatca                                                                                 67

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 36 attaccctc actaaaggg                                                                     19

<210> SEQ ID NO 37
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 37
ctagacaagg tcgaacgagg ggcatgaccc ggtgcggggc ttcttgcact cggcataggc     60
gagtgctaag aataacgttg gcactcg                                                            87

<210> SEQ ID NO 38
<211> LENGTH: 1478
<212> TYPE: DNA
<213> ORGANISM: Artificial Sequence
<220> FEATURE:
<223> OTHER INFORMATION: Synthetic polynucleotide

<400> SEQUENCE: 38
tattaggcga agaggcatct agtagtagtg gcagtggtga gaacgtgggc gctgctatag     60
tgaacaatct ccagtcgatg gttaagaaga agagtgacaa accagcagtg aatgacttgt    120
ctgggtccgt gaggaaaaga aagaagcccg acacaaagga cagtaacgtc aagaaaccca    180
agaaatAGGG gggacctgtt tagatgtata ggaataaaaa ctccgagatg atctcaatgt    240
gtaatggagt tgtaatattg caaagggggga aaatcaagac tcaaacgtgt gtatgagtga    300
gcgtacgtat atctccgaga gtagtatgac ataatgatga ctgtgaatca tcgtaatctc    360
acacaaaaac cccattgtcg gccatatacc acaccaagca acaccacata tcccccggaa    420
aaaaaaacgt gaaaaaaga aacaatcaaa actacaacct actccttgat cacacagtca    480
ttgatcaagt tacagttcct gctagggaat gaccaaggta caaatcagca ccttaatggt    540
tagcacgctc tcttactctc tctcacagtc ttccggcccc tattcaaaat tctgcacttc    600
catttgaccc cagggttggg aaacagggcc acaaaagaaa aacccgacgt gaatgaaaaa    660
actaagaaaa gaaaaaaat tatcacacca gaaatttacc taattgggta attcccatcg    720
gtgtttttcc tggattgtcg cacgcacgca tgctgaaaaa agtgttcgag ttttgctttt    780

-continued

```
gcctcggagt ttcacgcaag tttttcgatc tcggaaccgg agggcggtcg ccttgttgtt      840
tgtgatgtcg tgctttgggt gttctaatgt gctgttattg tgctcttttt tttttcttctt     900 tttttggtga tcatatgata ttgctcggta gattactttc gtgtgtaggt attctttttag     960 acgtttggtt attgggtaga tatgagagag agagagtggg tgggggagga gttggttgta     1020
ggagggaccc ctgggaggaa gtgtagttga gttttccctg acgaatgaaa atacgttttt     1080
gagaagataa tacaggaaag gtgtgtcggt gaatttccat ctatccgagg atatgagtgg     1140
aggagagtcg tgtgcgtgtg gttaatttag gatcagtgga acacacaaag taactaagac     1200
agagagacag agagaaaaat ctggggaaga gacaaagagt cagagtgtgt gagttattct     1260
gtattgtgaa attttttttgc ccaactacat aatattgctg aaactaattt tacttaaaaa     1320
gaaaagccaa caacgtcccc agtaaaactt ttctataaat atcagcagtt ttcccttttcc     1380 tccattcctc ttcttgtctt ttttcttact ttcccttttt tatacctttt cattatcatc     1440
ctttataatt gtctaaccaa caactatata tctatcaa                             1478
```

<210> SEQ ID NO 39
<211> LENGTH: 412
<212> TYPE: DNA
<213> ORGANISM: Artificial Sequence
<220> FEATURE:
<223> OTHER INFORMATION: Synthetic polynucleotide

<400> SEQUENCE: 39

```
cccacacacc atagcttcaa aatgtttcta ctcctttttt actcttccag attttctcgg       60
actccgcgca tcgccgtacc acttcaaaac acccaagcac agcatactaa attttccctc      120
tttcttcctc tagggtgtcg ttaattaccc gtactaaagg tttggaaaag aaaaaagaga     180
ccgcctcgtt tcttttttctt cgtcgaaaaa ggcaataaaa atttttatca cgtttctttt     240
tcttgaaatt tttttttttta gtttttttct ctttcagtga cctccattga tatttaagtt     300
aataaacggt cttcaatttc tcaagtttca gtttcatttt tcttgttcta ttacaacttt     360
ttttacttct tgttcattag aaagaaagca tagcaatcta atctaagggg cg             412
```

<210> SEQ ID NO 40
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 40

```
ttgacaatta atcatcggct cgtataat                                          28
```

<210> SEQ ID NO 41
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 41

```
ttcaaatatg tatccgctca tgagaca                                           27
```

<210> SEQ ID NO 42
<211> LENGTH: 143
<212> TYPE: DNA
<213> ORGANISM: Artificial Sequence
<220> FEATURE:

-continued

<223> OTHER INFORMATION: Synthetic polynucleotide

<400> SEQUENCE: 42
aactacccgt aggtgtagtt ggcgcaagcg tccgattagc tcaggtttaa gatgtcgaga      60
gtgagagtgg gcggcttaac tttctcagtt aggcataaaa ttacgtctta aatctcgtag     120
cgactaattt aataaaaatt gga                                             143

<210> SEQ ID NO 43
<211> LENGTH: 419
<212> TYPE: DNA
<213> ORGANISM: Artificial Sequence
<220> FEATURE:
<223> OTHER INFORMATION: Synthetic polynucleotide

<400> SEQUENCE: 43
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc ccctaactcc gcccagttcc gcccattctc     300
cgccccatgg ctgactaatt tttttattt atgcagaggc cgaggccgcc tcggcctctg     360
agctattcca gaagtagtga ggaggctttt ttggaggcct aggcttttgc aaaaagctt     419

<210> SEQ ID NO 44
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 44 gacgctttt atcgcaactc tctactgt                                          28

<210> SEQ ID NO 45
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 45
catgacaaaa acgcgtaaca aaagtgtct                                        29

<210> SEQ ID NO 46
<211> LENGTH: 1904
<212> TYPE: DNA
<213> ORGANISM: Artificial Sequence
<220> FEATURE:
<223> OTHER INFORMATION: Synthetic polynucleotide

<400> SEQUENCE: 46
agccgaattc ctcctcattc ttctccaaac ctttattgag tacctactgt gtgctggaat      60
aagacaggca gggccatgcc ctcatgaagc tgacaatcct attggtgtga ccatccccag     120
gtgtgtccca ggtgtgttgc aggtgtgtcc gaggtatgcc ccagctgtcc caggtgtgcc     180
ccagctgtct cagatgtgcc ccagctgtcc caggtgtgtc acagctgcat tgcaggtgtg     240
ccccagttgc attccatgtg tgctccaagt gtgtaccagc tgtcccaggt gtgtctcagg     300
tgtgccccag ctgtatccca ggtgtgcctc agctgtctta ggtgtgtctc aggtgcatcc     360

```
caggtgtgtc tcagatgtgc cccagctgtc ccaggtgtgc cccagctgtc ccaggtgtgc    420
cccagctgtc tccagtgtgt cccagctgtg ccccaggtgt gtgtcctagg tgtgcctcag    480
ctgtctcagg tgtgccccag gcatatccca ggtgtgcccc agctgtccca ggtgtgtcct    540
acgtgtgcac cagctgtatc ccaggtgtgc cccaggtgtg tctcagatgg gtcccaagtg    600
ttccccaact gcatttcagg tgtctcaggt gtgcccaagc tgtcccaggt gtgtccaaga    660
tgtgccccag gtgtgtctca ggtgggtctc aagtgcccca gctgcatttc aggtgtctca    720
ggtgtgcccc ccagtgcatc ccaggtgtgt cccaggtgtg ccccaggtgc atcccaggtg    780
tgtcccaggt gtgcccagc tgtctcaggt gtctcaggtg tgcccaggc atatcccagg     840 tgtgcctcag ctctcccagg tgtgtcctac atgtgcacca gctgtatctc aggtgtgtct    900
caggtgtgcc ccagatgtgc ccccggtgtg tctcaggtgg gtcccaagtg ttccccagct    960
gcatttcaag tgtctcaggt gtgcccagg tgtgcccccg ctgtcccagg tgtgtccaag   1020
atgtacccca ggtgtgtccc agctgtccca agtgtgtctc aggtgtgccc caggtgtgtt   1080
ccaggtgttc cccagctgtc ccagctgtcc caggtctcag gtgtgcccca ggtgtgttcc   1140
aggtgttcac cagctgtccc agctgtccca ggtctcaggt gtgccccagg tatgttgcag   1200
gtgttcccca gctgtcccag ctgtcccagg tgtgtcccag gtgttcccca ggtgtgtccc   1260
agctgtccca ggtgtgtccc agatgtgccc caggtgtacc ccaggtgttt ctcaggtgga   1320
ttccaggtgt gtcccaggtg agcccagct gtattccata tgcgtccctc tgagtggggc   1380
cttggtttga tgtagctccg gggatcttct gctccctggt cctggtgtca ccagcaactg   1440
cctcttgaca atcctgcctt gctgcaaac cccaggtgag aagaagacaa atgactggga   1500 actgaccccct cagtaagcgc tggtggtctc acctacagac ccccaggaag ctggtcactg   1560
tgggcttctt ttcctctcta aattcctatt atcaggtggt tttctttctc atttgctatt   1620
ttcttaaaaa taaaaatagg gaaaaacagc ctttgtaaat tacggtttct tccggctcca   1680
tcctctccgt caggcccaca tcccaaggaa acagcaggct tgagcctggc tgctgaagcc   1740
aggggctgga tggagcagct cagaacagag ctttgagtgc ctctccagcc aggggcccca   1800
gaagcctggt ggttgtttgt ccttctcagg ggaaaagtga ggcggcccct tggaggaagg   1860
ggccgggcag aatgatctaa tcggattcca agcagctcag ggga             1904
```

<210> SEQ ID NO 47
<211> LENGTH: 352
<212> TYPE: DNA
<213> ORGANISM: Artificial Sequence
<220> FEATURE:
<223> OTHER INFORMATION: Synthetic polynucleotide
<400> SEQUENCE: 47

```
ctctgagctg cttccctact cacactctgt ccacaacccc attttcctga tcatgtagta     60
gaaagaaatg gaacacaatc tttgtaaata agcccttgta aacaagcaag agctacagtg    120
cttccacaag ccctactgca agccaggaat gggaacagtg gtgtgtgtgc agcaaatgcc    180
ctgagcaccc ctgtggattg gactcagaaa catggaagtg agggtaggag gggatgatct    240
aagtcctggg cccaattaag agatcagatg gtgaagggtt tgggggcctt taaggtaagg    300
aggcctgggc tgatcctgca ggctgatata aagtcctgta accccatagg ca            352
```

<210> SEQ ID NO 48
<211> LENGTH: 133
<212> TYPE: DNA

-continued

```
<213> ORGANISM: Artificial Sequence
<220> FEATURE:
<223> OTHER INFORMATION: Synthetic polynucleotide

<400> SEQUENCE: 48
gtaagtatca aggttacaag acaggtttaa ggagaccaat agaaactggg cttgtcgaga      60
cagagaagac tcttgcgttt ctgataggca cctattggtc ttactgacat ccactttgcc     120
tttctctcca cag                                                       133

<210> SEQ ID NO 49
<211> LENGTH: 221
<212> TYPE: DNA
<213> ORGANISM: Artificial Sequence
<220> FEATURE:
<223> OTHER INFORMATION: Synthetic polynucleotide

<400> SEQUENCE: 49
agacatgata agatacattg atgagtttgg acaaaccaca actagaatgc agtgaaaaaa      60
atgctttatt tgtgaaattt gtgatgctat tgctttattt gtaaccatta taagctgcaa     120
taaacaagtt aacaacaaca attgcattca ttttatgttt caggttcagg gggagatgtg     180
ggaggttttt taaagcaagt aaaacctcta caaatgtggt a                         221

<210> SEQ ID NO 50
<211> LENGTH: 222
<212> TYPE: DNA
<213> ORGANISM: Artificial Sequence
<220> FEATURE:
<223> OTHER INFORMATION: Synthetic polynucleotide

<400> SEQUENCE: 50
cagacatgat aagatacatt gatgagtttg gacaaaccac aactagaatg cagtgaaaaa      60
aatgctttat ttgtgaaatt tgtgatgcta ttgctttatt tgtaaccatt ataagctgca     120
ataaacaagt taacaacaac aattgcattc attttatgtt tcaggttcag ggggagatgt     180
gggaggtttt ttaaagcaag taaaacctct acaaatgtgg ta                        222

<210> SEQ ID NO 51
<211> LENGTH: 239
<212> TYPE: DNA
<213> ORGANISM: Artificial Sequence
<220> FEATURE:
<223> OTHER INFORMATION: Synthetic polynucleotide

<400> SEQUENCE: 51
ggccgcttcg agcagacatg ataagataca ttgatgagtt tggacaaacc acaactagaa      60
tgcagtgaaa aaaatgcttt atttgtgaaa tttgtgatgc tattgcttta tttgtaacca     120
ttataagctg caataaacaa gttaacaaca caattgcat tcattttatg tttcaggttc      180 aggggagat gtgggaggtt ttttaaagca agtaaaacct ctacaaatgt ggtaaaatc       239

<210> SEQ ID NO 52
<211> LENGTH: 222
<212> TYPE: DNA
<213> ORGANISM: Artificial Sequence
<220> FEATURE:
<223> OTHER INFORMATION: Synthetic polynucleotide

<400> SEQUENCE: 52
taatcagcat accacatttg tagaggtttt acttgcttta aaaaacctcc cacacctccc      60
cctgaacctg aaacataaaa tgaatgcaat tgttgttgtt aacttgttta ttgcagctta     120
```

-continued

```
taatggttac aaataaagca atagcatcac aaatttcaca aataaagcat tttttttcact      180 gcattctagt tgtggtttgt ccaaactcat caatgtatct ta                          222

<210> SEQ ID NO 53
<211> LENGTH: 142
<212> TYPE: DNA
<213> ORGANISM: Artificial Sequence
<220> FEATURE:
<223> OTHER INFORMATION: Synthetic polynucleotide

<400> SEQUENCE: 53
aacttgttta ttgcagctta taatggttac aaataaagca atagcatcac aaatttcaca       60
aataaagcat tttttttcact gcattctagt tgtggtttgt ccaaactcat caatgtatct      120
tatcacgtct ggtcaggtgg ca                                                 142

<210> SEQ ID NO 54
<211> LENGTH: 132
<212> TYPE: DNA
<213> ORGANISM: Artificial Sequence
<220> FEATURE:
<223> OTHER INFORMATION: Synthetic polynucleotide

<400> SEQUENCE: 54
aacttgttta ttgcagctta taatggttac aaataaagca atagcatcac aaatttcaca       60
aataaagcat tttttttcact gcattctagt tgtggtttgt ccaaactcat caatgtatct      120
tatcacgtct gg                                                            132

<210> SEQ ID NO 55
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 55
aataaaatat ctttattttc attacatctg tgtgttggtt ttttgtgtg                    49

<210> SEQ ID NO 56
<211> LENGTH: 341
<212> TYPE: DNA
<213> ORGANISM: Artificial Sequence
<220> FEATURE:
<223> OTHER INFORMATION: Synthetic polynucleotide

<400> SEQUENCE: 56
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctacgcg tagataagta       180
gcatggcggg ttaatcatta actacaagga acccctagtg atggagttgg ccactccctc       240
tctgcgcgct cgctcgctca ctgaggccgg gcgaccaaag gtcgcccgac gcccgggctt       300
tgcccgggcg gcctcagtga gcgagcgagc gcgcagcctt a                           341

<210> SEQ ID NO 57
<211> LENGTH: 344
<212> TYPE: DNA
<213> ORGANISM: Artificial Sequence
<220> FEATURE:
<223> OTHER INFORMATION: Synthetic polynucleotide
```

-continued

<400> SEQUENCE: 57
aggctgcgcg ctcgctcgct cactgaggcc gcccgggcaa agcccgggcg tcgggcgacc          60
tttggtcgcc cggcctcagt gagcgagcga gcgcgcagag agggagtggc caactccatc         120
actaggggtt ccttgtagtt aatgattaac ccgccatgct acttatctac gcgtagataa         180
gtagcatggc gggttaatca ttaactacaa ggaacccta gtgatggagt tggccactcc          240
ctctctgcgc gctcgctcgc tcactgaggc cgggcgacca aaggtcgccc gacgcccggg         300
ctttgcccgg gcggcctcag tgagcgagcg agcgcgcagc ctta                          344

<210> SEQ ID NO 58
<211> LENGTH: 128
<212> TYPE: DNA
<213> ORGANISM: Artificial Sequence
<220> FEATURE:
<223> OTHER INFORMATION: Synthetic polynucleotide

<400> SEQUENCE: 58
aggaacccct agtgatggag ttggccactc cctctctgcg cgctcgctcg ctcactgagg          60
ccgggcgacc aaaggtcgcc cgacgcccgg gctttgcccg ggcggcctca gtgagcgagc         120
gagcgcgc                                                                   128

<210> SEQ ID NO 59
<211> LENGTH: 130
<212> TYPE: DNA
<213> ORGANISM: Artificial Sequence
<220> FEATURE:
<223> OTHER INFORMATION: Synthetic polynucleotide

<400> SEQUENCE: 59
aggaacccct agtgatggag ttggccactc cctctctgcg cgctcgctcg ctcactgagg          60
ccgggcgacc aaaggtcgcc cgacgcccgg gctttgcccg ggcggcctca gtgagcgagc         120
gagcgcgcag                                                                 130

<210> SEQ ID NO 60
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 60
ttatgaagat ccctcgacct gcagcccaag cttggcgtaa tcatg                          45

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 61
gataaggatc ttcctagagc atggcta                                              27

<210> SEQ ID NO 62
<211> LENGTH: 273
<212> TYPE: DNA
<213> ORGANISM: Artificial Sequence
<220> FEATURE:
<223> OTHER INFORMATION: Synthetic polynucleotide

<400> SEQUENCE: 62

```
atgtctgccc gtatttcgcg taaggaaatc cattatgtac tatttaaaaa acacaaactt      60
ttggatgttc ggtttattct ttttcttta cttttttatc atgggagcct acttcccgtt      120
tttcccgatt tggctacatg acatcaacca tatcagcaaa agtgatacgg gtattatttt     180
tgccgctatt tctctgttct cgctattatt ccaaccgctg tttggtctgc tttctgacaa     240
actcggcctc gactctaggc ggccgcgggg atc                                  273

<210> SEQ ID NO 63
<211> LENGTH: 141
<212> TYPE: DNA
<213> ORGANISM: Artificial Sequence
<220> FEATURE:
<223> OTHER INFORMATION: Synthetic polynucleotide

<400> SEQUENCE: 63
ggaggggtgg agtcgtgacg tgaattacgt cataggggtta gggaggtcct gtattagagg     60
tcacgtgagt gttttgcgac attttgcgac accatgtggt cacgctgggt atttaagccc     120
gagtgagcac gcagggtctc c                                                141

<210> SEQ ID NO 64
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 64
ggatccactc gagtggagct cgcgactagt cgattcgaat tcgatatcaa gcttatcgat     60

<210> SEQ ID NO 65
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 65
gcctgtacgg aagtgttact tctgctctaa aagctgcgga attgtacccg cggccgcaat     60
tcccggggat cgaaagagcc tgctaaagca aaaaagaa                              98

<210> SEQ ID NO 66
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 66
ccgaacccga attctgcaga tatccagcac agtggcggcc gcttcgag                   48

<210> SEQ ID NO 67
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 67
tagtttccat ggctacgtag ataagtagca tggcgggtta atcattaact aca            53

<210> SEQ ID NO 68
```

<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 68
tgtagttaat gattaacccg ccatgctact tatctacgta gccatgctcg atctgaattc      60
ggta                                                                   64

<210> SEQ ID NO 69
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 69
ggccgcgggg atcc                                                        14

<210> SEQ ID NO 70
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 70
ggttcgaaca g                                                           11

<210> SEQ ID NO 71
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 71
catgttcatg ccttcttctt tttcctacag ctcctgggca acgtgctggt tattgtgctg      60
tctcatcatt ttggcaaaga attctgcagt cgacggtacc gcgggcccgg gatccaccgg     120

<210> SEQ ID NO 72
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 72
gcggccgcac gcgtgttact agttattaat                                       30

<210> SEQ ID NO 73
<211> LENGTH: 115
<212> TYPE: DNA
<213> ORGANISM: Artificial Sequence
<220> FEATURE:
<223> OTHER INFORMATION: Synthetic polynucleotide

<400> SEQUENCE: 73
cactagaagc tttattgcgg tagtttatca cagttaaatt gctaacgcag tcagtgcttc      60
tgacacaaca gtctcgaact taagctgcag aagttggtcg tgaggcactg ggcag          115

<210> SEQ ID NO 74
<211> LENGTH: 68

-continued

```
<212> TYPE: DNA
<213> ORGANISM: Artificial Sequence
<220> FEATURE:
<223> OTHER INFORMATION: Synthetic oligonucleotide

<400> SEQUENCE: 74
gcctggagac gccatccacg ctgttttgac ctccatagaa gacaccggga ccgatccagc      60
ctccggac                                                               68

<210> SEQ ID NO 75
<211> LENGTH: 133
<212> TYPE: DNA
<213> ORGANISM: Artificial Sequence
<220> FEATURE:
<223> OTHER INFORMATION: Synthetic polynucleotide

<400> SEQUENCE: 75
gtgtccactc ccagttcaat tacagctctt aaggctagag tacttaatac gactcactat     60
aggctagcct cgagaattca cgcgtggtac cgagctcgga tccactagtc cagtgtggtg    120
gaattcgggc ggg                                                       133

<210> SEQ ID NO 76
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 76
tgtatttaga aaaataaaca aatagggggtt ccgcgcacat ttccccgaaa agtgccacct     60
ggtc                                                                  64

<210> SEQ ID NO 77
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 77
tagccatgct ctaggaagat cgtacc                                          26

<210> SEQ ID NO 78
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 78
gaattcgagc ttgcatgcct gcaggt                                          26

<210> SEQ ID NO 79
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 79
gtgtccactc ccagttcaat tacagctctt aaggctagag tacttctagc ctcgag         56

<210> SEQ ID NO 80
```

-continued

```
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 80
aaatcgataa ggatcctaga gcatggctac gtagataagt agcatggcgg gttaatcatt       60
aactaca                                                                 67

<210> SEQ ID NO 81
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 81
ggcccgggat cca                                                          13

<210> SEQ ID NO 82
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 82
gttgaattcg atatcggatc catcgatacc gtcgacctcg aggggggggcc cggtacc        57

<210> SEQ ID NO 83
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 83
caattcgccc tatagtgagt cgtattacgc gcgcagcggc cgac                       44

<210> SEQ ID NO 84
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 84
tgtagttaat gattaacccg ccatgctact tatctacgta gccatgctct agatct         56

<210> SEQ ID NO 85
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 85
agcggccgca ctcctcag                                                    18

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide
```

-continued

<400> SEQUENCE: 86
atcgataccg tcgacccggg c                                                              21

<210> SEQ ID NO 87
<211> LENGTH: 122
<212> TYPE: DNA
<213> ORGANISM: Artificial Sequence
<220> FEATURE:
<223> OTHER INFORMATION: Synthetic polynucleotide

<400> SEQUENCE: 87
cagatcgcct ggagacgcca tccacgctgt tttgacctcc atagaagaca ccgggaccga    60
tccagcctcc ggactctaga ggatccggta ctcgaggaac tgaaaaacca gaaagttaac   120
tg                                                                                  122

<210> SEQ ID NO 88
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 88
ccggaccacg tgcggaccga gcggccgc                                                       28

<210> SEQ ID NO 89
<211> LENGTH: 115
<212> TYPE: DNA
<213> ORGANISM: Artificial Sequence
<220> FEATURE:
<223> OTHER INFORMATION: Synthetic polynucleotide

<400> SEQUENCE: 89
gtgtccactc ccagttcaat tacagctctt aaggctagag tacttctagc ctcgagaatt    60
cacgcgtggt accgagctcg gatccactag tccagtgtgg tggaattcgg gcggg         115

<210> SEQ ID NO 90
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 90
ttatttgtga aatttgtgat gctattgctt tatttgtaac cattataagc tgcaataaac    60
aagttaa                                                                             67

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
taataataac cgggcaggcc                                                               20

<210> SEQ ID NO 92
<211> LENGTH: 124
<212> TYPE: DNA
<213> ORGANISM: Artificial Sequence
<220> FEATURE:

<223> OTHER INFORMATION: Synthetic polynucleotide

<400> SEQUENCE: 92
agccgcgaga cgggcgctca gggcgcgggg ccggcggcgg cgaacgagag gacggactct          60
ggcggccggg tcgttggccg cggggagcgc gggcaccggg cgagcaggcc gcgtcgcgct         120
cacc                                                                     124

<210> SEQ ID NO 93
<211> LENGTH: 194
<212> TYPE: DNA
<213> ORGANISM: Artificial Sequence
<220> FEATURE:
<223> OTHER INFORMATION: Synthetic polynucleotide

<400> SEQUENCE: 93
ggggctcggg tgcagcggcc agcgggcctg gcggcgagga ttacccgggg aagtggttgt          60
ctcctggctg gagccgcgag acgggcgctc agggcgcggg gccggcggcg gcgaacgaga         120
ggacggactc tggcggccgg gtcgttggcc ggggagcgc gggcaccggg cgagcaggcc         180
gcgtcgcgct cacc                                                          194

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
aggactcatt aaaaagtaac                                                     20

<210> SEQ ID NO 95
<211> LENGTH: 197
<212> TYPE: DNA
<213> ORGANISM: Artificial Sequence
<220> FEATURE:
<223> OTHER INFORMATION: Synthetic polynucleotide

<400> SEQUENCE: 95
ggggctcggg tgcagcggcc agcgggcgcc tggcggcgag gattacccgg ggaagtggtt          60
gtctcctggc tggagccgcg agacgggcgc tcagggcgcg gggccggcgg cggcgaacga         120
gaggacggac tctggcggcc gggtcgttgg ccgcggggag cgcgggcacc gggcgagcag         180
gccgcgtcgc gctcacc                                                       197

<210> SEQ ID NO 96
<211> LENGTH: 1000
<212> TYPE: DNA
<213> ORGANISM: Artificial Sequence
<220> FEATURE:
<223> OTHER INFORMATION: Synthetic polynucleotide

<400> SEQUENCE: 96
gggcgggtgc atcaatgcgg ccgaaaaaga cacggacacg ctcccctggg acctgagctg          60
gttcgcagtc ttcccaaagg tgccaagcaa gcgtcagttc ccctcaggcg ctccaggttc         120
agtgccttgt gccgagggtc tccggtgcct tcctagactt ctcgggacag tctgaagggg         180
tcaggagcgg cgggacagcg cgggaagagc aggcaagggg agacagccgg actgcgcctc         240
agtcctccgt gccaagaaca ccgtcgcgga ggcgcggcca gcttcccttg gatcggactt         300
tccgccccta gggccaggcg gcggagcttc agccttgtcc cttccccagt ttcgggcggc         360

```
ccccagagct gagtaagccg ggtggaggga gtctgcaagg atttcctgag cgcgatgggc    420
aggaggaggg gcaagggcaa gagggcgcgg agcaaagacc ctgaacctgc cggggccgcg    480
ctcccgggcc cgcgtcgcca gcacctcccc acgcgcgctc ggccccgggc cacccgccct    540
cgtcggcccc cgcccctctc cgtagccgca gggaagcgag cctgggagga agaagagggt    600
aggtggggag gcggatgagg ggtgggggac cccttgacgt caccagaagg aggtgccggg    660
gtaggaagtg ggctggggaa aggttataaa tcgcccccgc cctcggctgc tcttcatcga    720
ggtccgcggg aggctcggag cgcgccaggc ggacactcct ctcggctcct ccccggcagc    780
ggcggcggct cggagcgggc tccggggctc gggtgcagcg gccagcgggc gcctggcggc    840
gaggattacc cggggaagtg gttgtctcct ggctggagcc gcgagacggg cgctcagggc    900
gcggggccgg cggcggcgaa cgagaggacg gactctggcg gccgggtcgt tggccgcggg    960
gagcgcgggc accgggcgag caggccgcgt cgcgctcacc                          1000
```

```
<210> SEQ ID NO 97
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 97
ttgcttgtta atcaataaac cgtttaattc gtttcagttg aactttggtc tctgcgtatt    60
tctttcttat c                                                          71
```

```
<210> SEQ ID NO 98
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 98
attttgaagc gggaggtttg aacgcgcagc cgcc                                 34
```

```
<210> SEQ ID NO 99
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 99
ccggtcgcca cc                                                         12
```

```
<210> SEQ ID NO 100
<211> LENGTH: 197
<212> TYPE: DNA
<213> ORGANISM: Artificial Sequence
<220> FEATURE:
<223> OTHER INFORMATION: Synthetic polynucleotide

<400> SEQUENCE: 100
ggggctcggg tgcagcggcc agcgggcgcc tggcggcgag gattacccgg ggaagtggtt    60
gtctcctggc tggagccgcg agacgggcgc tcagggcgcg gggccggcgg cggcgaacga    120
gaggacggac tctggcggcc gggtctttgg ccgcggggag cgcgggcacc gggcgagcag    180
gccgcgtcgc gctcacc                                                    197
```

```
<210> SEQ ID NO 101
<211> LENGTH: 382
<212> TYPE: DNA
<213> ORGANISM: Artificial Sequence
<220> FEATURE:
<223> OTHER INFORMATION: Synthetic polynucleotide

<400> SEQUENCE: 101
ggggtggggg accccttgac gtcaccagaa ggaggtgccg gggtaggaag tgggctgggg      60
aaaggttata aatcgccccc gccctcggct gctcttcatc gaggtccgcg ggaggctcgg     120
agcgcgccag gcggacactc ctctcggctc ctccccggca gcggcggcgg ctcggagcgg     180
gctccggggc tcgggtgcag cggccagcgg gcgcctggcg gcgaggatta cccggggaag     240
tggttgtctc ctggctggag ccgcgagacg ggcgctcagg gcgcggggcc ggcggcggcg     300
aacgagagga cggactctgg cggccgggtc gttggccgcg gggagcgcgg gcaccgggcg     360
agcaggccgc gtcgcgctca cc                                              382

<210> SEQ ID NO 102
<211> LENGTH: 2064
<212> TYPE: DNA
<213> ORGANISM: Homo sapiens

<400> SEQUENCE: 102
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggggaagc agcccataaa     180 tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc ctgccgggtt     480
acgtcaccta acatcactgt tactttaaaa aagtttccac ttgacacttt gatccctgat     540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata agagagcttc cgtaaggcga     840
cgaattgacc aaagcaattc ccatgccaac atattctaca gtgttcttac tattgacaaa     900
atgcagaaca agacaaagg actttatact tgtcgtgtaa ggagtggacc atcattcaaa     960
tctgttaaca cctcagtgca tatatatgat aaagcattca tcactgtgaa acatcgaaaa    1020
cagcaggtgc ttgaaaccgt agctggcaag cggtcttacc ggctctctat gaaagtgaag    1080
gcatttccct cgccggaagt tgtatggtta aaagatgggt tacctgcgac tgagaaatct    1140
gctcgctatt tgactcgtgg ctactcgtta attatcaagg acgtaactga agaggatgca    1200
gggaattata caatcttgct gagcataaaa cagtcaaatg tgtttaaaaa cctcactgcc    1260
actctaattg tcaatgtgaa accccagatt tacgaaaagg ccgtgtcatc gtttccagac    1320
ccggctctct acccactggg cagcagacaa atcctgactt gtaccgcata tggtatccct    1380
caacctacaa tcaagtggtt ctggcacccc tgtaaccata atcattccga agcaaggtgt    1440
```

-continued

```
gacttttgtt ccaataatga agagtccttt atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga aactgtcttg cacagttaac    1740
aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagagg tgagcactgc    1980
aacaaaaagg ctgttttctc tcggatctcc aaatttaaaa gcacaaggaa tgattgtacc    2040
acacaaagta atgtaaaaca ttaa                                           2064
```

```
<210> SEQ ID NO 103
<211> LENGTH: 1453
<212> TYPE: DNA
<213> ORGANISM: Artificial Sequence
<220> FEATURE:
<223> OTHER INFORMATION: Synthetic polynucleotide
```

```
<400> SEQUENCE: 103
```

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttactttta aaaagtttc cacttgacac tttgatccct gatggaaaac     300
gcataatctg ggacagtaga aagggcttca tcatatcaaa tgcaacgtac aaagaaatag     360
ggcttctgac ctgtgaagca acagtcaatg gcatttgta taagacaaac tatctcacac     420
atcgacaaac caatacaatc atagatgtgg ttctgagtcc gtctcatgga attgaactat     480
ctgttggaga aaagcttgtc ttaaattgta gcagcaagaac tgaactaaat gtggggattg     540
acttcaactg ggaatacct tcttcgaagc atcagcataa gaaacttgta aaccgagacc     600
taaaaaccca gtctgggagt gagatgaaga aattttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc ccccaaaac     840 ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgcccca tcccgggatg agctgaccaa gaaccaggtc agcctgacct    1200
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
```

```
tgatgcatga ggctctgcac aaccactaca cgcagaagag cctctccctg tctccgggta   1440
aatgagcggc cgc                                                       1453

<210> SEQ ID NO 104
<211> LENGTH: 1377
<212> TYPE: DNA
<213> ORGANISM: Artificial Sequence
<220> FEATURE:
<223> OTHER INFORMATION: Synthetic polynucleotide

<400> SEQUENCE: 104
atggtcagct actgggacac cggggtcctg ctgtgcgcgc tgctcagctg tctgcttctc     60
acaggatcta gttccggaag tgataccggt agacctttcg tagagatgta cagtgaaatc    120
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaaggggcttc atcatatcaa atgcaacgta caaagaaata    300
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagac tgaactaaa tgtggggatt    480 gacttcaact gggaataccc ttcttcgaag catcagcata agaaacttgt aaaccgagac    540
ctaaaaaccc agtctgggag tgagatgaag aaattttttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377

<210> SEQ ID NO 105
<211> LENGTH: 1444
<212> TYPE: DNA
<213> ORGANISM: Artificial Sequence
<220> FEATURE:
<223> OTHER INFORMATION: Synthetic polynucleotide

<400> SEQUENCE: 105
aagcttgggc tgcaggtcga tcgactctag aggatcgatc cccgggcgag ctcgaattcg     60
caaccaccat ggtcagctac tgggacaccg gggtcctgct gtgcgcgctg ctcagctgtc    120
tgcttctcac aggatctagt tccggaggta gacctttcgt agagatgtac agtgaaatcc    180
ccgaaattat acacatgact gaaggaaggg agctcgtcat tccctgccgg gttacgtcac    240
ctaacatcac tgttacttta aaaaagtttc cacttgacac tttgatccct gatggaaaac    300
```

-continued

```
gcataatctg ggacagtaga aagggcttca tcatatcaaa tgcaacgtac aaagaaatag    360
ggcttctgac ctgtgaagca acagtcaatg ggcatttgta taagacaaac tatctcacac    420
atcgacaaac caatacaatc atagatatcc agctgttgcc caggaagtcg ctggagctgc    480
tggtagggga gaagctggtc ctcaactgca ccgtgtgggc tgagtttaac tcaggtgtca    540
cctttgactg ggactaccca gggaagcagg cagagcgggg taagtgggtg cccgagcgac    600
gctcccaaca gacccacaca gaactctcca gcatcctgac catccacaac gtcagccagc    660
acgacctggg ctcgtatgtg tgcaaggcca caacggcat ccagcgattt cgggagagca     720
ccgaggtcat tgtgcatgaa aatggcccgg gcgacaaaac tcacacatgc ccaccgtgcc    780
cagcacctga actcctgggg ggaccgtcag tcttcctctt ccccccaaaa cccaaggaca    840
ccctcatgat ctcccggacc cctgaggtca catgcgtggt ggtggacgtg agccacgaag    900
accctgaggt caagttcaac tggtacgtgg acggcgtgga ggtgcataat gccaagacaa    960
agccgcggga ggagcagtac aacagcacgt accgtgtggt cagcgtcctc accgtcctgc   1020
accaggactg gctgaatggc aaggagtaca gtgcaaggt ctccaacaaa gccctcccag    1080
cccccatcga gaaaaccatc tccaaagcca aagggcagcc ccgagaacca caggtgtaca   1140 ccctgcccc atcccgggat gagctgacca agaaccaggt cagcctgacc tgcctggtca    1200
aaggcttcta tcccagcgac atcgccgtgg agtgggagag caatgggcag ccggagaaca   1260
actacaagac cacgcctccc gtgctggact ccgacggctc cttcttcctc tatagcaagc   1320
tcaccgtgga caagagcagg tggcagcagg ggaacgtctt ctcatgctcc gtgatgcatg   1380
aggctctgca caaccactac acgcagaaga gcctctccct gtctccgggt aaatgagcgg   1440
ccgc                                                                1444
```

```
<210> SEQ ID NO 106
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 106

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

-continued

```
145            150            155            160

Glu Ser Val Thr Glu Gln Asp Ser Lys Asp Ser Thr Tyr Ser Leu Ser
            165            170            175

Ser Thr Leu Thr Leu Ser Lys Ala Asp Tyr Glu Lys His Lys Val Tyr
            180            185            190

Ala Cys Glu Val Thr His Gln Gly Leu Ser Ser Pro Val Thr Lys Ser
        195            200            205

Phe Asn Arg Gly Glu Cys
    210

<210> SEQ ID NO 107
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 107
gatattcagc tgacccagag cccgagcagc ctgagcgcga gcgtgggcga tcgcgtgacc      60
attacctgca gcgcgagcca ggatattagc aactatctga actggtatca gcagaaaccg     120
ggcaaagcgc cgaaagtgct gatttatttt accagcagcc tgcatagcgg cgtgccgagc     180
cgctttagcg gcagcggcag cggcaccgat tttaccctga ccattagcag cctgcagccg     240
gaagattttg cgacctatta ttgccagcag tatagcaccg tgccgtggac ctttggccag     300
ggcaccaaag tggaaattaa acgcaccgtg gcggcgccga gcgtgtttat ttttccgccg     360
agcgatgaac agctgaaaag cggcaccgcg agcgtggtgt gcctgctgaa caacttttat     420
ccgcgcgaag cgaaagtgca gtggaaagtg dataacgcgc tgcagagcgg caacagccag     480
gaaagcgtga ccaacagga tagcaaagat agcacctata gcctgagcag caccctgacc     540
ctgagcaaag cggattatga aaaacataaa gtgtatgcgt gcgaagtgac ccatcagggc     600
ctgagcagcc cggtgaccaa aagctttaac cgcggcgaat gc                       642

<210> SEQ ID NO 108
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 108
gatattcaat tgactcaatc tccttcttct ttgtctgctt ctgttggtga tcgtgttact      60
attacttgtt ctgcttctca agatatttct aattatttga attggtatca acaaaaacct     120
ggtaaagctc ctaaagtttt gatttatttt acttcttctt tgcattctgg tgttccttct     180
cgtttttctg gttctggttc tggtactgat tttactttga ctatttcttc tttgcaacct     240
gaagattttg ctacttatta ttgtcaacaa tattctactg ttccttggac ttttggtcaa     300
ggtactaaag ttgaaattaa acgtactgtt gctgctcctt ctgtttttat ttttcctcct     360
tctgatgaac aattgaaatc tggtactgct tctgttgttt gtttgttgaa taatttttat     420
cctcgtgaag ctaaagttca atggaaagtt gataatgctt tgcaatctgg taattctcaa     480
gaatctgtta ctgaacaaga ttctaaagat tctacttatt ctttgtcttc tactttgact     540
ttgtctaaag ctgattatga aaaacataaa gtttatgctt gtgaagttac tcatcaaggt     600
ttgtcttctc ctgttactaa atctttaat cgtggtgaat gt                       642
```

```
<210> SEQ ID NO 109
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 109

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Ala Gly Gln Thr Leu His
        35                  40                  45

Leu Gln Cys Arg Gly Glu Ala Ala Met Gln His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
            325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
```

```
            370              375              380
Thr Arg Gly Tyr Ser Leu Ile Ile Lys Asp Val Thr Glu Glu Asp Ala
385              390              395              400

Gly Asn Tyr Thr Ile Leu Leu Ser Ile Lys Gln Ser Asn Val Phe Lys
            405              410              415

Asn Leu Thr Ala Thr Leu Ile Val Asn Val Lys Pro Gln Ile Tyr Glu
            420              425              430

Lys Ala Val Ser Ser Phe Pro Asp Pro Ala Leu Tyr Pro Leu Gly Ser
        435              440              445

Arg Gln
    450
```

<210> SEQ ID NO 110
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 110

```
atggccaagt tgaccagtgc cgttccggtg ctcaccgcgc gcgacgtcgc cggagcggtc    60
gagttctgga ccgaccggct cgggttctcc cgggacttcg tggaggacga cttcgccggt   120
gtggtccggg acgacgtgac cctgttcatc agcgcggtcc aggaccaggt ggtgccggac   180
aacaccctgg cctgggtgtg ggtgcgcggc ctggacgagc tgtacgccga gtggtcggag   240
gtcgtgtcca cgaacttccg ggacgcctcc gggccggcca tgaccgagat cggcgagcag   300
ccgtgggggc gggagttcgc cctgcgcgac ccggccggca actgcgtgca cttcgtggcc   360
gaggagcagg actga                                                    375
```

<210> SEQ ID NO 111
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 111

```
atgtctaaat taacctctgc tgttccagtg ttaaccgccc gtgatgttgc cggtgcagtg    60
gaattttgga ctgaccgttt gggtttctca cgtgactttg tcgaagatga ttttgctggc   120
gttgtgcgtg atgacgtcac tttgttcatc tctgctgttc aggatcaggt cgtcccagac   180
aacactttgg cctgggtctg ggttcgtggt ttggacgaat gtacgctga gtggagtgaa   240 gttgtgtcta caaactttcg tgatgcatca ggtccagcta tgaccgaaat tggcgaacaa   300
ccttggggcc gtgagttcgc tttacgtgat ccagccggta attgcgtgca cttcgttgct   360
gaggagcaag attag                                                    375
```

<210> SEQ ID NO 112
<211> LENGTH: 861
<212> TYPE: DNA
<213> ORGANISM: Artificial Sequence
<220> FEATURE:
<223> OTHER INFORMATION: Synthetic polynucleotide

<400> SEQUENCE: 112

```
atgagtattc aacatttccg tgtcgccctt attccctttt ttgcggcatt ttgccttcct    60
gtttttgctc acccagaaac gctggtgaaa gtaaaagatg ctgaagatca gttgggtgca   120
```

-continued

```
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861
```

```
<210> SEQ ID NO 113
<211> LENGTH: 795
<212> TYPE: DNA
<213> ORGANISM: Artificial Sequence
<220> FEATURE:
<223> OTHER INFORMATION: Synthetic polynucleotide

<400> SEQUENCE: 113
```

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

```
<210> SEQ ID NO 114
<211> LENGTH: 2038
<212> TYPE: DNA
<213> ORGANISM: Artificial Sequence
<220> FEATURE:
<223> OTHER INFORMATION: Synthetic polynucleotide

<400> SEQUENCE: 114
```

```
aggtggcact tttcggggaa atgtgcgcgg aacccctatt tgtttatttt tctaaataca     60
ttcaaatatg tatccgctca tgagacaata accctgataa atgcttcaat aatattgaaa    120
aaggaagagt atgagtattc aacatttccg tgtcgccctt attccctttt ttgcggcatt    180
```

```
ttgccttcct gtttttgctc acccagaaac gctggtgaaa gtaaaagatg ctgaagatca      240
gttgggtgca cgagtgggtt acatcgaact ggatctcaac agcggtaaga tccttgagag      300
ttttcgcccc gaagaacgtt ttccaatgat gagcactttt aaagttctgc tatgtggcgc      360
ggtattatcc cgtgttgacg ccgggcaaga gcaactcggt cgccgcatac actattctca      420
gaatgacttg gttgagtact caccagtcac agaaaagcat cttacggatg gcatgacagt      480
aagagaatta tgcagtgctg ccataaccat gagtgataac actgcggcca acttacttct      540
gacaacgatc ggaggaccga aggagctaac cgcttttttg cacaacatgg gggatcatgt      600
aactcgcctt gatcgttggg aaccggagct gaatgaagcc ataccaaacg acgagcgtga      660
caccacgatg cctgcagcaa tggcaacaac gttgcgcaaa ctattaactg gcgaactact      720
tactctagct tcccggcaac aattaataga ctggatggag gcggtaaag ttgcaggacc      780 acttctgcgc tcggcccttc cggctggctg gtttattgct gataaatctg gagccggtga      840
gcgtgggtct cgcggtatca ttgcagcact ggggccagat ggtaagccct cccgtatcgt      900
agttatctac acgacgggga gtcaggcaac tatggatgaa cgaaatagac agatcgctga      960
gataggtgcc tcactgatta agcattggta actgtcagac caagtttact catatatact     1020
ttagattgat ttaaaacttc attttaatt aaaaggatc taggtgaaga tcctttttga     1080
taatctcatg accaaaatcc cttaacgtga gttttcgttc cactgagcgt cagacccgt     1140 agaaaagatc aaaggatctt cttgagatcc ttttttttctg cgcgtaatct gctgcttgca     1200
aacaaaaaaa ccaccgctac cagcggtggt ttgtttgccg gatcaagagc taccaactct     1260
ttttccgaag gtaactggct tcagcagagc gcagatacca aatactgtcc ttctagtgta     1320
gccgtagtta ggccaccact tcaagaactc tgtagcaccg cctacatacc tcgctctgct     1380
aatcctgtta ccagtggctg ctgccagtgg cgataagtcg tgtcttaccg ggttggactc     1440
aagacgatag ttaccggata aggcgcagcg gtcgggctga acggggggtt cgtgcacaca     1500
gcccagcttg gagcgaacga cctacaccga actgagatac ctacagcgtg agctatgaga     1560
aagcgccacg cttcccgaag ggagaaaggc ggacaggtat ccggtaagcg gcagggtcgg     1620
aacaggagag cgcacgaggg agcttccagg gggaaacgcc tggtatcttt atagtcctgt     1680
cgggtttcgc cacctctgac ttgagcgtcg attttttgtga tgctcgtcag gggggcggag     1740
cctatggaaa aacgccagca acgcggcctt tttacggttc ctggcctttt gctggccttt     1800
tgctcacatg ttctttcctg cgttatcccc tgattctgtg gataaccgta ttaccgcctt     1860
tgagtgagct gataccgctc gccgcagccg aacgaccgag cgcagcgagt cagtgagcga     1920
ggaagcggaa gagcgcctga tgcggtattt tctccttacg catctgtgcg gtatttcaca     1980
ccgcatatgg tgcactctca gtacaatctg ctctgatgcc gcatagttaa gccagtat      2038
```

```
<210> SEQ ID NO 115
<211> LENGTH: 97
<212> TYPE: DNA
<213> ORGANISM: Artificial Sequence
<220> FEATURE:
<223> OTHER INFORMATION: Synthetic oligonucleotide

<400> SEQUENCE: 115
gtaagtttag tcttttttgtc ttttatttca ggtcccggat ccggtggtgg tgcaaatcaa       60
agaactgctc ctcagtggat gttgccttta cttctag                                97

<210> SEQ ID NO 116
```

-continued

```
<211> LENGTH: 493
<212> TYPE: DNA
<213> ORGANISM: Artificial Sequence
<220> FEATURE:
<223> OTHER INFORMATION: Synthetic polynucleotide

<400> SEQUENCE: 116
tcgaatcccg gccgggaacg gtgcattgga acgcggattc cccgtgccaa gagtgacgta      60
agtaccgcct atagagtcta taggcccaca aaaaatgctt tcttctttta atatactttt     120
ttgtttatct tatttctaat actttcccta atctctttct ttcagggcaa taatgataca     180
atgtatcatg cctctttgca ccattctaaa gaataacagt gataatttct gggttaaggc     240
aatagcaata tttctgcata taaatatttc tgcatataaa ttgtaactga tgtaagaggt     300
ttcatattgc taatagcagc tacaatccag ctaccattct gcttttattt tatggttggg     360
ataaggctgg attattctga gtccaagcta ggcccttttg ctaatcatgt tcatacctct     420
tatcttcctc ccacagctcc tgggcaacgt gctggtctgt gtgctggccc atcactttgg     480
caaagaattg gga                                                         493

<210> SEQ ID NO 117
<211> LENGTH: 97
<212> TYPE: DNA
<213> ORGANISM: Artificial Sequence
<220> FEATURE:
<223> OTHER INFORMATION: Synthetic oligonucleotide

<400> SEQUENCE: 117
gtaagtttag tcttttgtc ttttatttca ggtcccggat ccggtggtgg tgcaaatcaa       60
agaactgctc ctcagtggat gttgccttta cttctag                                97

<210> SEQ ID NO 118
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 118
gtaagtttag tcttttgtc ttttatttca g                                       31

<210> SEQ ID NO 119
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 119
acttaccata ctttacccgg aaactaatcg tcccactctc acatccttca ttgcag          56

<210> SEQ ID NO 120
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 120
aaaagttccc cagccagaag cagagaagat gatgtcaaga aatcaagggg gataaatggc       60
catagctgct gcaaatagct tattgcagtc tctagagtgt ggtaaacagg tttccagtgc      120
cagctgtgga ggtgacagcg gcagggaa                                          148
```

```
<210> SEQ ID NO 121
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 121

Ile Tyr Ile Phe Ile Ser Asp Thr Gly Arg Pro Phe Val Glu Met Tyr
1               5                   10                  15

Ser Glu Ile Pro Glu Ile Ile His Met Thr Glu Gly Arg Glu Leu Val
            20                  25                  30

Ile Pro Cys Arg Val Thr Ser Pro Asn Ile Thr Val Thr Leu Lys Lys
        35                  40                  45

Phe Pro Leu Asp Thr Leu Ile Pro Asp Gly Lys Arg Ile Ile Trp Asp
    50                  55                  60

Ser Arg Lys Gly Phe Ile Ile Ser Asn Ala Thr Tyr Lys Glu Ile Gly
65                  70                  75                  80

Leu Leu Thr Cys Glu Ala Thr Val Asn Gly His Leu Tyr Lys Thr Asn
                85                  90                  95

Tyr Leu Thr His Arg Gln Thr Asn Thr Ile
            100                 105

<210> SEQ ID NO 122
<211> LENGTH: 320
<212> TYPE: DNA
<213> ORGANISM: Artificial Sequence
<220> FEATURE:
<223> OTHER INFORMATION: Synthetic polynucleotide

<400> SEQUENCE: 122
aatctatata tttattagtg atacaggtag acctttcgta gagatgtaca gtgaaatccc        60
cgaaattata cacatgactg aaggaaggga gctcgtcatt ccctgccggg ttacgtcacc       120
taacatcact gttactttaa aaaagtttcc acttgacact ttgatccctg atggaaaacg       180
cataatctgg gacagtagaa agggcttcat catatcaaat gcaacgtaca aagaaatagg       240
gcttctgacc tgtgaagcaa cagtcaatgg gcatttgtat aagacaaact atctcacaca       300
tcgacaaacc aatacaatca                                                    320

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
cactagtcca gtgtggtgga                                                     20

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
agccaggaga caaccacttc                                                     20
```

TREATMENT OF OCULAR NEOVASCULARIZATION USING ANTI-VEGF PROTEINS

This application is a continuation of U.S. application Ser. No. 15/961,654, filed Apr. 24, 2018, which is a continuation of U.S. application Ser. No. 15/851,650, filed Dec. 21, 2017, now U.S. Pat. No. 10,004,788, issued Jun. 26, 2018, which is a continuation of U.S. application Ser. No. 14/281,749, filed May 19, 2014, now U.S. Pat. No. 9,943,573, issued Apr. 17, 2018, which is a continuation of U.S. application Ser. No. 13/889,275, filed May 7, 2013, now abandoned, which claims priority under 35 USC § 119(e) to U.S. Provisional Application No. 61/647,461, filed May 15, 2012, U.S. Provisional Application No. 61/670,535, filed Jul. 11, 2012, U.S. Provisional Application No. 61/678,555, filed Aug. 1, 2012, U.S. Provisional Application No. 61/691,660, filed Aug. 21, 2012, and U.S. Provisional Application No. 61/775,440, filed Mar. 8, 2013, each of which is incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is AVBI_001_11US_ST25.txt. The text file is about 80 KB, was created on May 24, 2021, and is being submitted electronically via EFS-Web.

BACKGROUND OF THE DISCLOSURE

Age-related macular degeneration (AMD) is one of the leading causes of vision irreversible damage in people over the age of 50 years. AMD is clinically divided into two types as "dry" and "wet". The wet form of AMD may develop rapidly and often results in blindness. The pathological changes of the disease may cause severe visual impairment. The manifestations of AMD may include, but is not limited to retinal pigment epithelial cells (RPE) dysfunction and choroidal neovascularization (CNV) in the macular area. Fluid leakage, RPE or neural epithelial detachment and bleeding from ruptured blood vessels can occur in severe cases. It has been found that many cellular factors play important roles in regulation in CNV generation, among which may include but are not limited to vascular endothelial growth factor (VEGF), VEGF receptor (VEGFR), platelet-derived growth factor (PDGF), hypoxia inducible factor (HIF), angiopoietin (Ang) and other cytokines, mitogen-activated protein kinases (MAPK) and others.

One currently approved treatment for wet AMD is Lucentis®. Lucentis® is an anti-angiogenesis agent and targets all isoforms of Vascular Endothelial Growth Factor (VEGF). Clinical studies have shown improved or stable vision in approximately 95% of patients administered Lucentis®, compared to approximately 60% of the patients who received sham treatment. Although Lucentis® is the first approved agent to improve vision it requires intravitreal administrations every 4 weeks for optimal visual benefit. Eylea® is another VEGF inhibitor that has been approved to treat wet AMD. Eylea® also requires frequent intravitreal injections every 4-8 weeks for optimal visual benefit. Intravitreal routes of administration may increase risks for serious complications such as infectious endophthalmitis and retinal detachment, for which cumulative risk increases with repeated administrations. Increased intraocular pressure, traumatic cataract, and retinal tears have also been reported. Finally, with a treatment that is delivered by an ophthalmologist, treatment frequency determines the burden to the patient, physician, and health system in general and to the extent possible should be reduced. The limitations of currently available therapy for CNV secondary to AMD have created a need in the art for alternative approaches which address the high frequency of treatments required and the invasiveness of the treatment procedure. Neovascularization involving VEGF elevation can also lead to other ocular pathologies, such as diabetic retinopathy, diabetic macular edema (DME), and retinal vein occlusions (RVO). These diseases lead to retinal neovascularization and vision loss. VEGF inhibitors such as Lucentis® have demonstrated efficacy in DME and RVO, and, like with wet AMD, require frequent intravitreal administration in order to maintain benefit.

SUMMARY OF THE DISCLOSURE

The present disclosure provides compositions and methods for treating CNV, such as found in the wet form of AMD, in a human subject.

In one aspect, the present disclosure provides compositions and methods for treating AMD in a human subject, comprising: administering subretinally a pharmaceutical composition comprising a pharmaceutically effective amount of a VEGF inhibitor to a human subject in need of treatment for AMD. In one aspect, the pharmaceutical composition comprises a recombinant virus. In another aspect, the VEGF inhibitor comprises a nucleic acid encoding soluble Fms-related tyrosine kinase-1 (sFLT-1) protein.

In one aspect, the present disclosure provides compositions and methods for the prevention of CNV in human subjects with AMD, comprising: administering subretinally a pharmaceutical composition comprising a pharmaceutically effective amount of a recombinant virus comprising a nucleic acid encoding soluble Fms-related tyrosine kinase-1 (sFLT-1) protein to a human subject in need of a treatment for AMD.

In some aspects, the virus is selected from adeno-associated virus (AAV), helper-dependent adenovirus, retrovirus, herpes simplex virus, lentivirus, poxvirus, hemagglutinatin virus of Japan-liposome (HVJ) complex, Moloney murine leukemia virus, and HIV-based virus. In some aspects, the AAV capsid or inverted terminal repeats (ITRs) is selected from the group consisting of: AAV1, AAV2, AAV3, AAV4, AAV5, AAV6, AAV7, AAV8, AAV9, AAV10, AAV11, AAV12, rh10, and hybrids thereof.

In some aspects, the recombinant virus comprises a promoter selected from cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter and opsin promoter.

In some aspects, the recombinant virus comprises an enhancer.

In some aspects, the recombinant virus comprises an intron or chimeric intron.

In some aspects, the recombinant virus comprises a SV40 poly A sequence.

In some aspects, the recombinant virus comprises a human sFlt-1 protein or a functional fragment thereof.

In some aspects, the recombinant virus is generated from a plasmid comprising either an ampicillin resistance marker or a non-ampicillin resistance marker.

In some aspects, the recombinant virus comprises bacterial regulatory sequences such as a T7 RNA polymerase promoter.

In some aspects, the recombinant virus lacks bacterial regulatory sequences such as a T7 RNA polymerase promoter.

In some aspects, the recombinant virus comprises a regulatory nucleic acid fragment that is capable of directing selective expression of the sFlt-1 protein or a functional fragment thereof in an eye cell.

In some aspects, the pharmaceutical composition comprises about $1\times10^6$ to about $1\times10^{15}$ recombinant viral vector genomes, about $1\times10^7$ to about $1\times10^{14}$ recombinant viral vector genomes, about $1\times10^8$ to about $1\times10^{13}$ recombinant viral vector genomes, about $1\times10^9$ to about $3\times10^{12}$ recombinant viral vector genomes, or about $1\times10^{10}$ to about $3\times10^{12}$ recombinant viral vector genomes.

In some aspects, the pharmaceutical composition is administered via subretinal injection.

In some aspects, the method further comprises administering to the human subject a pharmaceutically effective amount of a VEGF inhibitor. In some aspects, the VEGF inhibitor comprises an antibody against VEGF or a functional fragment thereof. In some aspects, the VEGF inhibitor comprises ranibizumab. In some aspects, the pharmaceutical composition is administered at least 5, 6, 7, or 8 days after the administering the VEGF inhibitor. In some aspects, the pharmaceutical composition is administered within 30, 60, or 90 days of administering the VEGF inhibitor.

In some aspects, the VEGF inhibitor is administered for 1 time prior to administering the pharmaceutical composition comprising the recombinant virus and 1 to 2 times following administration. In some aspects, the VEGF inhibitor is administered for at least 2 times prior to administering the pharmaceutical composition and 1 to 2 times following administration. In some aspects, the VEGF inhibitor is administered over a period of 6 to 7 weeks.

In some aspects the VEGF inhibitor is an anti-VEGF antibody, such as bevacizumab or ranibizumab. In other aspects the VEGF inhibitor is a soluble receptor, fusion protein, or fragment thereof, such as aflibercept or sFLT01.

In some aspects, the AMD is wet AMD.

In some aspects, AMD is dry AMD.

In some aspects, the human subject is at risk for wet AMD.

In some aspects, the human subject presents symptoms of early stage wet AMD.

In some aspects, at least 3, 5, 10, 15, or 20 treatments of a different VEGF inhibitor for the treatment of AMD have been previously administered to said human subject In some aspects, best corrected visual acuity (BCVA) did not improve after said treatment with ranibizumab.

In some aspects, best corrected visual acuity (BCVA), as measured by ETDRS (Early Treatment Diabetic Retinopathy Study) letters, improves by more than 1 line after said treatment with ranibizumab.

In some aspects, human subject presents symptoms of early stage dry AMD.

In some aspects, treatment is administered at a frequency of at least biannually.

In some aspects, administering step is carried out in said human subject where the subject is age 20, 40, 50, 55, or 65 years or older.

In some aspects, administration is to a site outside the fovea.

In some aspects, administration is to one or more cells of the subretinal space of the central retina.

In some aspects, administration is to one or more cells of the outer macula.

In some aspects, administration is to one or more cells of the inner macula.

In some aspects, administration is to retinal pigment epithelial cells.

In some aspects, administration does not adversely affect central retinal function or central retinal structure.

In some aspects, administration does not increase systemic levels of VEGF inhibitor in the human subject.

In some aspects, administration does not increase systemic levels of sFlt-1 in the human subject.

In some aspects, administering step is carried out simultaneously, or sequentially in both eyes In some aspects, administering step is carried out in one eye.

In some aspects, administering step is carried out in one eye when fellow eye presents symptoms of AMD.

In some aspects, administering step is carried out in a human subject resistant to penicillin.

In some aspects, administering step is carried out in a human subject sensitive to penicillin.

In some aspects, administering step is carried out in a human subject allergic to penicillin.

In some aspects, administering step is carried out in a human subject not allergic to penicillin.

In some aspects, administering step causes no inflammation of the vitreous is observed by biomicroscopy (BE) and indirect ophthalmoscopy (IOE) following the administering step.

In some aspects, administering step does not cause a cytotoxic T cell.

In some aspects, administering step does not cause a cytotoxic T cell response a measure by in increase in cytotoxic T cells of less than 10% greater than the baseline range.

In some aspects, T cells do not display an activated effector phenotype following the administering step.

In some aspects, best corrected visual acuity (BCVA) improves by 1, 2, 3, 4 or 5 lines or more. as measured by ETDRS (Early Treatment Diabetic Retinopathy Study) letters, following the administering step.

In some aspects, reduction in neovascularization is observed using Fluorescein Angiography (FA) following the administering step In some aspects, frequency of administration of ranibizumab is reduced to less than 12 doses per year. In some aspects, frequency of administration of aflibercept is reduced to less than 6 doses per year.

In some aspects, ranibizumab or aflibercept or other VEGF inhibitor is administered with reduced frequency or no longer administered.

In some aspects, the virus comprises a sFLT-1 gene or a functional fragment thereof with ≥90% sequence homology to the human sFLT-1 gene sequence.

In some aspects, the virus administered comprises a sFLT-1 gene, gene variant or gene fragment.

In some aspects, no vector is detected in the human subject's tear, blood, saliva or urine samples 7, 14, 21 or 30 days after administering the pharmaceutical composition.

In some aspects, the presence of the viral vector is detected by qPCR or ELISA.

In some aspects, the sFLT-1 protein levels in the vitreous of the human subject is about 500-5,000 pg/ml, about 600-4,000 pg/ml, about 800-3,000 pg/ml about 900-2,000 pg/ml, or about 1,000-1,800 pg/ml 7, 14, 21 or 30 days after administering the pharmaceutical composition. In some aspects, the sFlt-1 protein level, which may also be called the sFlt-1 protein concentration, in the vitreous of the human subject is elevated at 7, 14, 31, 30, 60, 90, 180, 270 and 365 days after administering the pharmaceutical composition.

In some aspects, the human subject shows no clinically significant retinal toxicity as assessed by serial ophthalmic examinations over least a two months period.

In some aspects, no superficial, anterior segment or vitreous inflammatory signs are present in the human subject over least a two months period.

In some aspects, the human subject does not require rescue treatment with a VEGF inhibitor at least 120 days post administering the recombinant viruses. In some aspects, the human subject does not require rescue treatment with a VEGF inhibitor at least 180 days or at least 210 days post administering the recombinant viruses. In some aspects, the human subject does not require rescue treatment with a VEGF inhibitor for at least 270 days after administering the recombinant viruses. In some aspects, the human subject does not require rescue treatment with a VEGF inhibitor for at least 365 days after administering the recombinant viruses.

In some aspects, there is no evidence of visual acuity loss, IOP elevation, retinal detachment, or any intraocular or systemic immune response in said human subject at least 180 days or at least 210 days post said administering the recombinant viruses. In some aspects, there is no evidence of visual acuity loss, IOP elevation, retinal detachment, or any intraocular or systemic immune response in said human subject at least 365 days after administering the recombinant viruses.

In another aspect, the present disclosure provides a pharmaceutical composition comprising about $1\times10^6$ to about $1\times10^{15}$ recombinant viruses, wherein each of the recombinant virus comprises a nucleic acid encoding soluble Fms-related tyrosine kinase-1 (sFlt-1) protein.

In some aspects, the disclosure provides for a method for the treatment or prophylaxis of ocular neovascularization in a human subject comprising: administering to one or more subretinal sites a pharmaceutically effective amount of a pharmaceutical composition comprising a nucleic acid encoding sFLT-1 to a human subject in need of treatment.

In some aspects, the disclosure provides for a human subject that has or is suspected of having one or more conditions selected from the group consisting of: age-related macular degeneration (AMD), wet-AMD, dry-AMD, retinal neovascularization, choroidal neovascularization and diabetic retinopathy. In some cases the human subject has or is suspected of having one or more conditions selected from the group consisting of: proliferative diabetic retinopathy, retinal vein occlusion, central retinal vein occlusion, branched retinal vein occlusion, diabetic macular edema, diabetic retinal ischemia, ischemic retinopathy and diabetic retinal edema.

In some aspects, the disclosure provides for a pharmaceutical composition comprising a recombinant virus, the virus selected from the group consisting of: adeno-associated virus (AAV), adenovirus, helper-dependent adenovirus, retrovirus, herpes simplex virus, lentivirus, poxvirus, hemagglutinatin virus of Japan-liposome (HVJ) complex, Moloney murine leukemia virus, and HIV-based virus.

In some aspects, the disclosure provides for a nucleic acid encoding the sFLT-1 which is operatively linked to a promoter selected from the group consisting of: cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter and opsin promoter.

In some aspects, the disclosure provides sFLT-1 nucleic acid, wherein the sFLT-1 encodes at least 1 dimerization domain. In some cases the sFLT-1 nucleic acid does not contain a prokaryotic regulatory sequence. In some cases the sFLT-1 nucleic acid does contain a prokaryotic regulatory sequence.

In some aspects, the disclosure provides for a pharmaceutical composition comprising a virus or a plasmid.

In some aspects, the disclosure provides for administration of one or more treatments of a VEGF inhibitor to the human subject. In some cases the VEGF inhibitor is administered within 30, 90, or 180 days of administration of the pharmaceutical composition. In some cases the pharmaceutical composition of the disclosure and VEGF inhibitor are administered at least 24 hours apart.

In some aspects, the disclosure provides for a pharmaceutical composition administered to a human subject at least 55 years old.

In some aspects, the disclosure provides for administering the pharmaceutical composition outside the fovea.

In some aspects, the disclosure provides for the best corrected visual acuity (BCVA) of the human subject, to improve by at least 1, 2, 3, 4 or 5 lines as measured by ETDRS (Early Treatment Diabetic Retinopathy Study) letters following the administering of the pharmaceutical composition.

In some aspects, the disclosure provides for the best corrected visual acuity (BCVA) to decrease by fewer than 15 letters as measured by ETDRS (Early Treatment Diabetic Retinopathy Study) following the administering of the pharmaceutical composition.

In some aspects, the disclosure provides for administering the pharmaceutical composition under conditions selected from the group consisting of: administering the pharmaceutical composition in one eye, administering the pharmaceutical composition sequentially in two eyes, and administering the pharmaceutical composition simultaneously in two eyes.

In some aspects, the disclosure provides for a reduction in neovascularization as observed by a Fluorescein Angiography (FA) follows the administering of the pharmaceutical composition.

In some aspects, the disclosure provides for no superficial, anterior segment or vitreous inflammatory signs are present in the human subject at least 1 week after injection.

In some aspects, the disclosure provides for no superficial, anterior segment or vitreous inflammatory signs are present in the human subject at 1 week or at 3, 6, 9 or 12 months after administration of the pharmaceutical composition.

In some aspects, the disclosure provides for the human subject not to require rescue treatment for at least 30, 60, 90, 120, 180, 270 or 365 days after the administering of the pharmaceutical composition.

In some aspects, the disclosure provides for the human subject to experience no visual acuity loss, IOP elevation, retinal detachment, intraocular or systemic immune response after administering the pharmaceutical composition.

In some aspects, the disclosure provides for no increased anti-AAV cytotoxic T cell response is measured following the administering step.

In some aspects, the disclosure provides for no virus detected in the human subject's blood, saliva or urine samples, 3, 7, 14, 21 or 30 days after administering the pharmaceutical composition.

In some aspects, the disclosure provides for sFLT-1 protein levels in the vitreous of the human subject to be about 500-5,000 pg/ml, 7, 14, 21, 30, 60, 90, 120, 150, 180, 270 or 365 days after administering the pharmaceutical composition in the human subject.

In some aspects, the disclosure provides for the human subject to receive one or more treatments with VEGF inhibitors prior to the administering of the pharmaceutical composition.

In some aspects, the disclosure provides for the human subject as resistant to treatment with VEGF inhibitors.

In some aspects, the disclosure provides for a human subject who has not previously received a VEGF inhibitor before administering the pharmaceutical composition.

In some aspects, the disclosure provides for administering of the pharmaceutical composition at a frequency less than 3 times a year in the human subject.

In some aspects, the disclosure provides for administering of the pharmaceutical composition to reduce the frequency of administration of additional VEGF inhibitor treatments in the human subject.

In some aspects, the disclosure provides for the concentration of sFLT-1 protein in the vitreous of the human subject to be elevated when measured at 7, 14, 21, 30, 60, 90, 120, 150, 180, 270 or 365 days after administering of the pharmaceutical composition.

In some aspects, the disclosure provides for a human subject who has the vitreous gel removed prior to or within one day or one week of the administration of the pharmaceutical composition.

In some aspects, the disclosure provides for a pharmaceutical composition administered using a vitrectomy system that is smaller than 20 gauge.

In some aspects, the disclosure provides for a pharmaceutical composition administered using a vitrectomy system that does not require sutures.

In some aspects, the disclosure provides for a pharmaceutical composition administered using a cannula tip that is smaller than 39 gauge.

In some aspects, the disclosure provides for a pharmaceutical composition followed by gas/fluid exchange in the vitreous chamber.

In some aspects, the disclosure provides for the central retinal thickness of the subject not to increase by more than 50 microns, 100 microns, or 250 microns within 12 months following treatment with said pharmacological agent.

In some aspects, the disclosure provides for geographic atrophy not to progress in the diseased eye of the human subject as compared to the diseased eyes of untreated human subjects.

In some aspects, the disclosure provides for a pharmaceutical composition comprising recombinant viruses or plasmids comprising a nucleic acid comprising at least 1 promoter sequence operatively linked to a sFLT-1 transgene sequence. In some cases the pharmaceutical composition of the disclosure comprises a promoter sequence and the sFLT-1 transgene sequence separated by a sequence greater than 300 base pairs. In some cases the pharmaceutical composition of the disclosure comprises a promoter sequence and the sFLT-1 transgene sequence separated by a UTR sequence. In some cases the UTR sequence comprises at least 10 base pairs. In some cases, the pharmaceutical composition comprises at least 3 linker sequences each comprising at least 50 base pairs.

In some aspects, the disclosure provides for a pharmaceutical composition, wherein the sFLT-1 nucleic acid encodes at least 1 dimerization domain.

In some aspects, the disclosure provides for a pharmaceutical composition comprising a promoter sequence selected from the group consisting of SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 340, SEQ ID No. 41, SEQ ID No. 42, SEQ ID No. 43, SEQ ID No. 44, SEQ ID No. 45, SEQ ID No. 46, and SEQ ID No. 47; a sequence encoding a VEGF inhibitor selected from the group consisting of SEQ ID No. 102, SEQ ID No. 103, SEQ ID No. 104, SEQ ID No. 105, SEQ ID No. 106, SEQ ID No. 107 and SEQ ID No. 108; an intron sequence consisting of SEQ ID No. 48, SEQ ID No. 115, SEQ ID No. 116, SEQ ID No. 117, SEQ ID No. 118, and SEQ ID No. 119; a UTR sequence selected from the group consisting of SEQ ID No. 91, SEQ ID No. 2, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, and SEQ ID No. 101; and a termination sequence selected from the group consisting of SEQ ID No. 49, SEQ ID No. 50, SEQ ID No. 51, SEQ ID No. 52, SEQ ID No. 53, SEQ ID No. 54, and SEQ ID No. 55.

In some aspects, the disclosure provides for a unit dose of a pharmaceutical composition comprising recombinant viruses of $1 \times 10^6$ to $1 \times 10^{15}$ vector genomes, wherein the recombinant viruses comprise a nucleic acid encoding sFLT-1 operatively linked to a promoter. In some cases the unit dose of the pharmaceutical composition comprises $1 \times 10^{10}$ to $3 \times 10^{12}$ vector genomes.

In some aspects, the disclosure provides for a method of generating a recombinant virus in a cell, the method comprising: introducing into a cell, a nucleic acid comprising at least 1 promoter sequence operatively linked to an sFLT-1 transgene sequence, an ITR sequence, and UTR sequence; and purifying the recombinant virus. In some cases the UTR sequence is a human UTR sequence. In some cases, the nucleic acid sequence does not contain a beta-lactam antibiotic resistance sequence. In some cases the recombinant virus produces sFLT-1 protein in the range of 100-10,000 pg/mL when measured at 72 hours following transduction of HEK293 cells at a multiplicity of infection (MOI) of $1 \times 10^6$. In some cases, the recombinant virus inhibits proliferation of human umbilical vascular endothelial (HUVEC) cells.

In some aspects, the disclosure provides for a cell for generating recombinant viral vector, the cell comprising at least 1 promoter polynucleotide sequence operatively linked to a sFLT-1 transgene sequence, an ITR polynucleotide sequence, and a UTR polynucleotide sequence.

In some aspects, the disclosure provides for a nucleic acid comprising a sequence encoding sFLT-1 for use in treatment or prophylaxis of ocular neovascularization in a human; wherein said use comprises administering directly to a human subject in need thereof, to one or more sub retinal sites in said human subject, an effective amount of a pharmaceutical composition; wherein said pharmaceutical composition comprises said nucleic acid.

In some aspects, the disclosure provides the nucleic acid for use, wherein said sFLT-1 is an inhibitor of VEGF and wherein said treating or reducing the likelihood of ocular neovascularization occurs as a result of VEGF inhibition.

In some aspects, the disclosure provides for the nucleic acid for use, wherein the pharmaceutical composition is capable of elevating levels of sFLT-1 protein in the vitreous of the human subject after at least 72 hours after administration of said pharmaceutical composition to said human subject, compared to levels of sFLT-1 protein in the vitreous of said human prior to said administration.

In some aspects, the disclosure provides for the nucleic acid for use, wherein the nucleic acid comprising said sFLT-1 comprises a recombinant virus, the virus selected from the group consisting of: adeno-associated virus (AAV), adenovirus, helper-dependent adenovirus, retrovirus, herpes simplex virus, lentivirus, poxvirus, hemagglutinatin virus of Japan-liposome (HVJ) complex, Moloney murine leukemia virus, and HIV-based virus.

In some aspects, the disclosure provides for the nucleic acid for use, wherein the nucleic acid encoding the sFLT-1 is operatively linked to a promoter selected from the group consisting of: cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter and opsin promoter.

In some aspects, the disclosure provides for the nucleic acid for use, wherein the nucleic acid is packaged by a virus or is plasmid DNA.

In some aspects, the disclosure provides for the nucleic acid for use, said use further comprising administration of one or more additional VEGF inhibitors to the human subject in need of treatment or reduction, optionally wherein said additional VEGF inhibitor is ranibizumab or bevacizumab.

In some aspects, the disclosure provides for the nucleic acid for use, said use comprising administering said pharmaceutical composition to a human subject at least 50, 55, or 65 years old.

In some aspects, the disclosure provides for the nucleic acid for use, said use comprising administering said pharmaceutical composition outside the fovea.

In some aspects, the disclosure provides for the nucleic acid for use, wherein the best corrected visual acuity (BCVA) of the human subject in need of treatment, improves by at least 1, 2, 3, 4 or 5 lines as measured by ETDRS (Early Treatment Diabetic Retinopathy Study) letters following the administering of an effective amount of the pharmaceutical composition.

In some aspects, the disclosure provides for the nucleic acid for use, wherein the administering of the pharmaceutical composition is performed at a frequency at least once per 3, 6, 9, 12, 18, or 24 months in a human subject in need of treatment.

In some aspects, the disclosure provides for the nucleic acid for use, wherein the administering of the pharmaceutical composition is performed at a frequency less than 3 times a year in the human subject or is performed at a frequency reducing the frequency of administration of additional VEGF inhibitor treatments in the human subject.

In some aspects, the disclosure provides for a unit dose of pharmaceutical composition comprising about $1 \times 10^6$ to $1 \times 10^{15}$ or $1 \times 10^{10}$ to $3 \times 10^{12}$ vector genomes. In some aspects, the recombinant viruses comprise a nucleic acid encoding sFLT-1, or a functional fragment thereof, operatively linked to a promoter.

In some aspects, the disclosure provides for a method for the treatment or prophylaxis of ocular neovascularization in a human subject comprising: administering to one or more subretinal sites a pharmaceutically effective amount of a pharmaceutical composition comprising a nucleic acid encoding a VEGF inhibitor to a human subject in need of treatment. In some aspects, the VEGF inhibitor is an anti-VEGF antibody or a functional fragment thereof. In some aspects, the VEGF inhibitor is a soluble receptor, fusion protein, or a functional fragment thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings of which:

FIG. 2 depicts expression, secretion and biological activity of sFLT-1 from rAAV.sflt-1-transduced cells. (a) Western blot analysis of conditioned media from Ad.sFlt-1-transduced 293 cells (lane 1), rAAV.sFlt-1-transduced D407 cells (lane 2), rAAV.sFlt-1-transduced 293 cells (lane 3), and AAV.gfp-transduced D407 cells (lane 4). (b) Inhibition of VEGF-induced HUVEC proliferation by conditioned media from rAAV.sFlt-1-transduced cells. HUVECs were cultured in starvation medium (column 1), in medium containing recombinant VEGF (column 2), in medium containing VEGF and 40 µL conditioned medium from rAAV.sFlt-1-transduced 293 cells (column 3), in medium containing VEGF and 80 µL conditioned medium from rAAV.sFlt-1-transduced 293 cells (column 4), and in medium containing VEGF and 80 µL conditioned medium from rAAV.gfp-transduced 293 cells (column 5). (*P<0.02, **P<0.005 for differences between rAAV.sFlt-1 plus VEGF, and VEGF only.

FIG. 4: Immune Cell Subset Population in mouse eyes. Graphs showing immune cell subset population at the different times post injection.

FIG. 5: Immune Cell Subset Population in mouse spleens. Graphs showing immune cell subset population at the different times post injection.

FIG. 6 depicts diagrams comparing Ki67 responses in CD4+ T cells in different mice at different times post injection.

FIGS. 7A to 7D depict various exemplary replication origin sequences.

FIGS. 8A to 8F depict the sequences of various exemplary promoters.

FIGS. 9A to 9C depict the sequence of various exemplary introns, poly A sequences, and ITR regions.

FIGS. 9D to 9F depict the sequence of various exemplary linker sequences.

FIGS. 9G to 9H depict the sequence of various exemplary UTR sequences.

FIGS. 10A to 10C depict the sequence encoding various exemplary anti-VEGF proteins.

FIG. 11A depicts the amino acid sequence of sFLT-1. FIG. 11B depicts the amino acid sequence of sFLT-1 domain 2, a functional fragment of sFLT-1. FIG. 11C depicts a nucleic acid sequence coding for sFLT-1 domain 2.

FIGS. 12A to 12B depict the sequences of various exemplary antibiotic resistance genes.

FIG. 13 depicts the PK of one exemplary composition (rAAV.sFlt-1), wherein it reaches optimal anti-VEGF expression at 6-8 weeks. RBZ is a standard care of anti-VEGF, such as ranibizumab. "RBZ rescue" means rescue treatment.

FIG. 14 depicts ophthalmologic assessment of the patients. Inflammation was evaluated by biomicroscopy (BE) and indirect ophthalmoscopy (IOE). Unrem: unremarkable.

FIG. 17 depicts biodistribution: qPCR for sFLT-1 sequence (copy number detected).

FIG. 18 depicts biodistribution: AAV capsid measured by ELISA, AAV titer in capsids/mL.

FIG. 19 depicts biodistribution of sFLT-1 measured by ELISA. Shown are human sFLT-1 concentration (pg/mL).

FIG. 23 depicts a table of human subjects who received Lucentis rescue injections (VEGF inhibitor readministration) by week in a clinical study of rAAV.sFlt-1.

FIG. 24 depicts visual acuity and SD-OCT images by week for a human subject treated with rAAV.sFlt-1 in a clinical study of rAAV.sFlt-1.

FIGS. 25A and 25B depicts data on production of human sFlt-1 protein in human embryonic kidney 293 (HEK293) cells as detected by ELISA. rAAV.sFlt-1 was produced using plasmid transfection in HEK293 cells. A second construct, rAAV(bv).sFlt-1, was produced using recombinant baculovirus in Sf9 insect cells. sFlt-1 protein concentration was measured via ELISA after 72 at various MOI.

DETAILED DESCRIPTION OF THE DISCLOSURE

Figure 1:
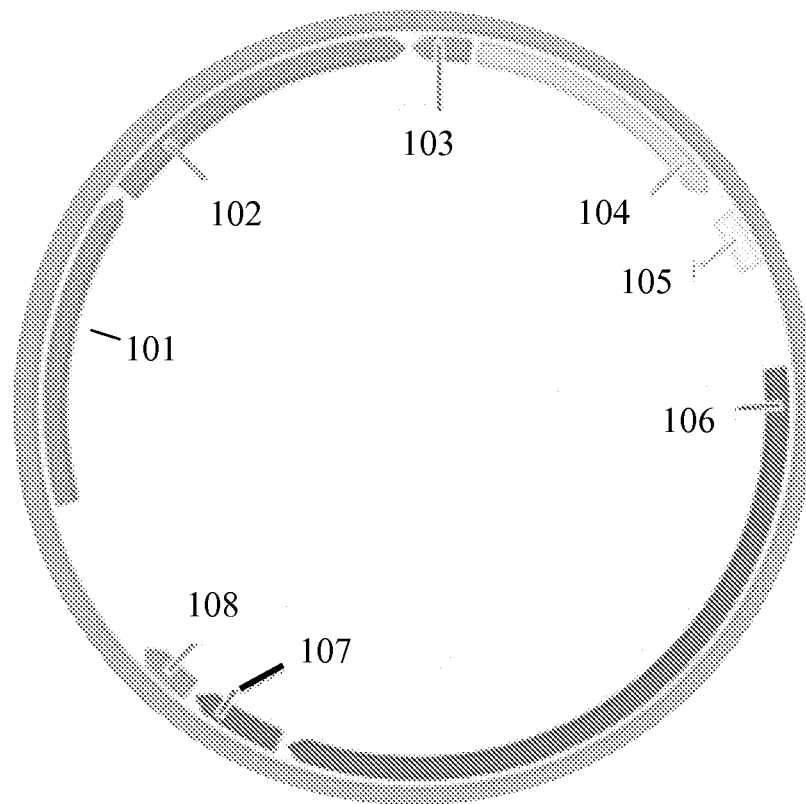
FIG. 1 depicts the schematic representation of an exemplary plasmid.

The present disclosure provides compositions and methods for the prevention or treatment of ocular neovascularization, such as AMD, in a human subject, by administering subretinally a pharmaceutical composition comprising a pharmaceutically effective amount of a vector comprising a nucleic acid encoding soluble Fms-related tyrosine kinase-1 (sFlt-1) protein to the human subject.

Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details or with other methods. The present disclosure is not limited by the illustrated ordering of acts or events, as some acts may occur in different orders and/or concurrently with other acts or events. Furthermore, not all illustrated acts or events are required to implement a methodology in accordance with the present disclosure.

The terminology of the present disclosure is for the purpose of describing particular cases only and is not intended to be limiting of compositions, methods and compositions of this disclosure.

The compositions and methods of this disclosure as described herein may employ, unless otherwise indicated, conventional techniques and descriptions of molecular biology (including recombinant techniques), cell biology, biochemistry, immunochemistry and ophthalmic techniques, which are within the skill of those who practice in the art. Such conventional techniques include methods for observing and analyzing the retina, or vision in a subject, cloning and propagation of recombinant virus, formulation of a pharmaceutical composition, and biochemical purification and immunochemistry. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes. Before the present compositions, research tools and methods are described, it is to be understood that this disclosure is not limited to the specific methods, compositions, targets and uses described, as such may, of course, vary. It is also to be understood that the terminology used herein is for the purpose of describing particular aspects only and is not intended to limit the scope of the present disclosure, which will be limited only by appended claims.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Ranges can be expressed herein as from "about" one particular value, and/or to "about" another particular value. When such a range is expressed, another case includes from the one particular value and/or to the other particular value. Similarly, when values are expressed as approximations, by use of the antecedent "about," it will be understood that the particular value forms another case. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

I. AMD

AMD is the leading cause of blindness in patients over the age of 50 and it is characterized by progressive degeneration of the photoreceptors, outer retina, and retinal pigment epithelium at the macula. The advanced "wet" form (neovascular or exudative) of AMD is less common, but may frequently cause a rapid and often substantial loss of central vision in patients. In the wet form of AMD, choroidal neovascularization forms and develops into a network of vessels that may grow under and through the retinal pigment epithelium. As this is accompanied by leakage of plasma and/or hemorrhage into the subretinal space, there could be severe sudden loss of central vision if this occurs in the macula.

The term "AMD" if not otherwise specified, can be either dry AMD or wet AMD. The present disclosure contemplates treatment or prevention of AMD, wet AMD and/or dry AMD.

As is previously known in the art, AMD has been shown to have no single cause. This highly complex disease may result from variable contributions including but not limited to age, genetic predisposition, and environment or combination thereof. In humans, for example, established epidemiologic risk factors may include but are not limited to cigarette smoking, diet, female sex, Caucasian race, and a family history of AMD. Because AMD is rare in individuals younger than 50 years, the only required risk factor is age, which implicates the multitude of cellular changes that accompany normal aging in the pathogenesis of AMD.

The etiologic complexity of AMD is reflected by the relative paucity of effective therapies, preventive strategies, and good animal models with which to study it. Due to the complexity and incomplete characterization of the disease, AMD is incompletely modeled in animals. This is in part due to anatomical differences in animal and primate retinas, as well as the protracted time needed for the disease to develop. Evidence from human molecular genetic and animal studies support the notion that altered homeostasis of a multitude of mechanisms responsible for normal photoreceptor-RPE physiology can precipitate the disease. At least on the molecular level, the disease can be explored in animal models and, in some cases, even in those whose gene defects are not the primary causes of AMD in humans.

Previous genetic studies as well as in depth pathological analysis, reveals that no simple inheritance pattern for AMD, and no one pathology is common to various AMD animal models. While nonhuman primate models are known in the art to better approximate CNV in humans, than mice or rat models, fundamental differences in retinal anatomy, histology and even genetics of nonhuman primates yield different species specific pathologies.

Further, and as describe herein, laser photocoagulation may be used to induce CNV, one AMD like symptom in animal models. In some cases, laser treatment ruptures the Bruch's membrane and evokes a fibrovascular proliferative response that originates in the choroid. This response is the basis for modeling choroidal neovascularization in late-stage AMD and was developed in rhesus and cynomolgus macaques.

Using an argon laser, spots are kept small and induced with sufficient power to rupture the Bruch's membrane. This is funduscopically visible as a bubble at the time of photocoagulation. Photocoagulation induces thrombosis of choroidal vessels followed by re-endothelialization 48 hours later and growth of new vessels into the subretinal space by a week. Because newly formed vessels are more permeable, neovascular development can be monitored with fluorescein angiography to assess vessel leakage.

Spontaneous neovascular involution (indicated by decreased fluorescein leakage) commences at approximately 3 to 7 weeks and then gradually progresses (over a period of approximately 2 to 13 months) until leakage is no longer apparent at the site.

The extent of new vessel growth compared to poorly vascularized scarring can be variable in all models and is influenced by species, location of injury in the retina, and intensity of the laser beam. The inherent variability in differences of treatment from species to species further supports the idea that no one animal model fully recapitulates AMD in humans.

Therapies for AMD have changed during the past few years, with the availability of aptamers, antibodies, and soluble receptor decoys that bind the protein VEGF. The VEGF protein or VEGF ligand, has been shown to stimulate the formation of new blood vessels (i.e. angiogenesis) through binding to cellular receptors, including the VEGF receptor. As known in the art, anti-VEGF agents may prevent, to some extent, the neovascularization and angiogenesis that occurs in wet AMD. Intraocular injection of Macugen® or Lucentis® or Eylea® (anti-VEGF agents) is costly, and in most cases the treatment must be repeated every four to six weeks or every eight weeks in the case of Eylea®. For example, Lucentis is a VEGF antibody fragment which costs about $1950/inj. Monthly. Avastin (VEGF Antibody) is used off label, and Eylea (VEGF trap) costs about, $1850/inj and is administered every second month. All of these medicines share common problems of decreasing pharmacokinetic profile and thus require repeat ocular injections.

There is a need in the art for a practical, economically viable, longer lasting treatment strategy. The disclosure provides for a novel therapeutic to address some of these needs.

The present disclosure provides an anti-VEGF molecule, such as sFLT-1, delivered by any suitable vector, (e.g. recombinant viral system) to the retina of a human subject having or suspected of having AMD or related neovascular retinal diseases. In some cases, sFLT-1 may be potent direct binding protein of VEGF. In some cases, sFLT-1 may also block or inhibit VEGF activity.

For example, as known in the art, sFLT-1 (as described further herein) has been observed to bind to the VEGF protein dimer with a Kd=10 pM.

The present invention also provides compositions and methods related to rAAV mediated gene delivery into the eye. Long term gene expression in dog eyes (>8 years) has been observed with AAV based system. sFLT-1 mRNA expression in the retina is maintained at least for 18 months. Three human trials for Leber's congenital amarousis have been conducted that demonstrated the safety of an AAV based delivery system in the context of a retinal degenerative disease such as LCA.

II. VEGF and Fms-Related Tyrosine Kinase-1 (sFLT-1) Protein

A. VEGF

Vascular endothelial growth factor (herein referred to as "VEGF" or "VEGF ligand") is a potent endothelial cell-specific mitogen that plays a key role in physiological blood vessel formation. In some cases, VEGF activity results from the binding of VEGF ligand to one or more VEGF receptors in a cell. The binding of VEGF ligand to VEGF receptor may have numerous downstream cellular and biochemical effects, including but not limited to angiogenesis in tissues. VEGF has been implicated in virtually every type of angiogenic or neovascular disorder, including those associated with cancer, ischemia, and inflammation. Additionally, VEGF has been implicated in eye diseases, including but not limited to ischemic retinopathy, intraocular neovascularization, age-related macular degeneration (AMD), wet-AMD, dry-AMD, retinal neovascularization, diabetic macular edema, diabetic retina ischemia, diabetic retinal edema, proliferative diabetic retinopathy, retinal vein occlusion, central retinal vein occlusion, branched retinal vein occlusion. Further, anti-VEGF treatments, including the compositions and methods of this disclosure as described herein, may be used in the treatment of one or more of these diseases described herein.

Recent data suggests that VEGF is the principal angiogenic growth factor in the pathogenesis of the wet form of AMD.

VEGF, a 46-kDa homodimeric glycopeptide, is expressed by several different ocular cell types including but not limited to pigment epithelial cells, pericytes, vascular endothelial cells, neuroglia and ganglion cells. In some cases, VEGF is express in specific spatial and temporal patterns during retinal development. In some cases, the human isoforms of VEGF may include proteins of 206, 189, 183, 165, 148, 145, and 121 amino acids per monomer, however the predominant human VEGF isoforms include but are not limited to VEGF121, VEGF165, VEGF189 and VEGF206. These proteins are produced by alternative splicing of the VEGF mRNA and differ in their ability to bind to heparin and to the specific VEGF receptors or coreceptors (neuropilins). The domain encoded by exons 1-5 of the VEGF gene contains information required for the recognition of the known VEGF receptors KDR/FLK-1 and FLT-1. This domain is present in all of the VEGF isoforms. VEGF acts via these receptors, which are high-affinity receptor tyrosine kinases, leading to endothelial cell proliferation, migration, and increased vasopermeability.

VEGF is one of the several factors involved in the complex process of angiogenesis and has a very high specificity for vascular endothelial cells. VEGF is a regulator of physiological angiogenesis during processes such as embryogenesis, skeletal growth and reproductive function, but it has also been implicated in pathological angiogenesis associated with disease such as in cancer, placental disorders and other conditions. The potential biological effects of VEGF may be mediated by specific fins-like membrane spanning receptors, FLT-1 and FLK-1/KDR. In some cases, these naturally occurring binding partners of VEGF may effect binding of VEGF to VEGF receptors, thus modulating activation of the VEGF receptor and subsequent downstream pathways.

As related to cancer, several VEGF inhibitors, including a humanized monoclonal antibody to VEGF (rhuMab VEGF), an anti-VEGFR-2 antibody, small molecules inhibiting VEGFR-2 signal transduction and a soluble VEGF receptor have shown some therapeutic properties.

As related to intraocular neovascular diseases, such as diabetic retinopathy, retinal vein occlusions, or age related macular degeneration, some VEGF antagonists have shown therapeutic effects, despite the need for frequent administration.

B. Anti-VEGF

The recombinant virus of the present disclosure comprises the sequence encoding an anti-VEGF protein, including, but not limited to the VEGF-binding proteins or functional fragments thereof disclosed in U.S. Pat. Nos. 5,712,380, 5,861,484 and 7,071,159 and VEGF-binding fusion proteins disclosed in U.S. Pat. No. 7,635,474. An anti-VEGF protein may also include the sFLT-1 protein as described herein.

The recombinant viruses or plasmids of the present disclosure may comprise the sequence encoding an anti-VEGF protein, including the naturally occurring protein sFlt-1, as described in U.S. Pat. No. 5,861,484 and that sequence described by SEQ ID NO: 109. It also includes, but is not limited to functional fragments thereof, including sequences of sFlt-1 domain 2 or those set forth in SEQ ID NO: 121, as well as related constructs, such as the VEGF-binding fusion proteins disclosed in U.S. Pat. No. 7,635,474. An anti-VEGF protein may also include the sFLT-1 protein as described herein. These sequences can be expressed from DNA encoding such sequences using the genetic code, a standard technique that is understood by those skilled in the art. As can be appreciated by those with skill in the art, due to the degeneracy of the genetic code, anti-VEGF protein sequences can be readily expressed from a number of different DNA sequences.

"sFlt-1 protein" herein refers to a polypeptide sequence, or functional fragment thereof, with at least 90%, or more, homology to the naturally occurring human sFLT-1 sequence, such that the sFlt-1 protein or polypeptide binds to VEGF and/or the VEGF receptor. Homology refers to the % conservation of residues of an alignment between two sequences (e.g. as Naturally occurring human sFLT-1 protein may include any suitable variants of sFLT-1, including, but not limited to functional fragments, sequences comprising insertions, deletions, substitutions, pseudofragments, pseudogenes, splice variants or artificially optimized sequences. In some cases, "sFLT-1 protein" may be at least about 90%, 91%, 92%, 93%, 94%, 95%, 96%, 97%, 98%, 99%, 99.9%, 99.99% or 100% homologous to the naturally occurring human sFLT-1 protein sequence. In some cases, "sFLT-1 protein" may be at most about 90%, 91%, 92%, 93%, 94%, 95%, 96%, 97%, 98%, 99%, 99.9%, 99.99% or 100% homologous to the naturally occurring human sFLT-1 protein sequence. In some cases, "sFLT-1 protein" may be at least about 90%, 91%, 92%, 93%, 94%, 95%, 96%, 97%, 98%, 99%, 99.9%, 99.99% or 100% spatially homologous to the naturally occurring human sFLT-1 protein conformation. In some cases, "sFLT-1 protein" may be at most about 90%, 91%, 92%, 93%, 94%, 95%, 96%, 97%, 98%, 99%, 99.9%, 99.99% or 100% spatially homologous to the naturally occurring human sFLT-1 protein conformation.

Further, the soluble truncated form of the VEGF receptor FLT-1, sFLT-1, is the only known endogenous specific inhibitor of VEGF. In nature, it is generated by alternative mRNA splicing and lacks the membrane-proximal immunoglobulin-like domain, the transmembrane spanning region and the intracellular tyrosine-kinase domain. Structurally, FLT-1 and sFLT-1 protein may both comprise multiple functional domains. In some variants, FLT and sFLT proteins commonly share 6 interlinked domain; 3 domains involved in dimerization of the protein and 3 domains involved in the binding of a ligand, such as VEGF.

sFLT-1 is a soluble truncated form of the FLT-1 and it is expressed endogenously. As described herein, "soluble" FLT-1, or sFLT-1 refers to FLT-1 that is not restricted to the cellular membrane. Unbound sFLT-1 may diffuse freely in extracellular space or solution.

sFLT-1 is the only known endogenous specific inhibitor of VEGF. This interaction is specific and can be competed away with 100-fold excess unlabeled VEGF. In some cases, the angiostatic activity of sFLT-1 may result from inhibition of VEGF by two mechanisms: i) sequestration of VEGF, to which it binds with high affinity, and ii) formation of inactive heterodimers with membrane-spanning isoforms of the VEGF receptors FLTt-1 and FLK-1/KDR. As known in the art, in vitro binding assays have indicate that sFLT-1 binds VEGF with high affinity and may also inhibit VEGF driven proliferation of human umbilical vein endothelial cells. In animal models for cancer, sFLT-1 inhibits tumor growth. In some cases, sFLT-1 may function in a substoichiometric or dominant negative manner, as excess VEGF in the extracellular space may be prevented from binding and subsequently activating the VEGF receptor. These properties of sFLT-1 have been described in Kendall and Thomas, 1993; *Proc Natl Acad Sci.* 90: 10705-10709, which is incorporated herein by reference in its entirety. As is known in the art, functional fragments of sFLT-1 can be used in place of the full-length protein. More specifically, the VEGF binding domain (domain 2), or alternatively domain 2 of sFLT-1 plus domain 3 from sFLT1, KDR, or another family member, can be used to bind and inactivate VEGF. Such functional fragments are described in Wiesmann et al., 1997; *Cell*, 91: 695-704, which is incorporated herein by reference in its entirety. The terms "sFLT-1" and "a functional fragment of sFLT-1" are equivalent and used here interchangeably.

III. Vectors and Recombinant Viruses

The compositions and methods of the disclosure provide for the delivery of a nucleic acid encoding an anti-VEGF (e.g. sFLT-1 proteins) to cells in a human subject or patient in need thereof. In some cases, delivery of the nucleic acid may be referred to as gene therapy.

The composition and methods of the disclosure provide for any suitable method for delivery of the anti-VEGF nucleic acid (e.g. sFLT-1). In some cases, delivery of the nucleic acid may be performed using any suitable "vector" (sometimes also referred to as "gene delivery" or "gene transfer vehicle). Vector, delivery vehicle, gene delivery vehicle or gene transfer vehicle, may refer to any suitable macromolecule or complex of molecules comprising a polynucleotide to be delivered to a target cell. In some cases, a target cell may be any cell to which the nucleic acid or gene is delivered. The polynucleotide to be delivered may comprise a coding sequence of interest in gene therapy, such as the sFLT-1 gene.

For example, suitable vectors may include but are not limited to, viral vectors such as adenoviruses, adeno-associated viruses (AAV), and retroviruses, liposomes, other lipid-containing complexes, and other macromolecular complexes capable of mediating delivery of a polynucleotide to a target cell.

In some cases, a vector may be an organic or inorganic molecule. In some cases, a vector may be small molecule (i.e. <5 kD), or a macromolecule (i.e. >5 kD). For example a vector may include but is not limited to inert, non-biologically active molecules such as metal particles. In some cases, a vector may be gold particles.

In some cases a vector may comprise a biologically active molecule. For example, vectors may comprise polymerized macromolecules such as dendrimers.

In some cases, a vector may comprise a recombinant viral vector that incorporates one or more nucleic acids. As described herein, nucleic acids may refer to polynucleotides. Nucleic acid and polynucleotide may be used interchangeably. In some cases nucleic acids may comprise DNA or RNA. In some cases, nucleic acids may include DNA or RNA for the expression of sFLT-1. In some cases RNA nucleic acids may include but are not limited to a transcript of a gene of interest (e.g. sFLT-1), introns, untranslated regions, termination sequences and the like. In other cases, DNA nucleic acids may include but are not limited to sequences such as hybrid promoter gene sequences, strong constitutive promoter sequences, the gene of interest (e.g. sFLT-1), untranslated regions, termination sequences and the like. In some cases, a combination of DNA and RNA may be used.

As described in the disclosure herein, the term "expression construct" is meant to include any type of genetic construct containing a nucleic acid or polynucleotide coding for gene products in which part or all of the nucleic acid encoding sequence is capable of being transcribed. The transcript may be translated into a protein. In some cases it may be partially translated or not translated. In certain aspects, expression includes both transcription of a gene and translation of mRNA into a gene product. In other aspects, expression only includes transcription of the nucleic acid encoding genes of interest.

In one aspect, the present disclosure provides a recombinant virus, such as adeno-associated virus (rAAV) as a vector to mediate the expression of sFLT-1.

In some cases, the viral vector of the disclosure may be measured as pfu (plaque forming units). In some cases, the pfu of recombinant virus, or viral vector of the compositions and methods of the disclosure may be about $10^8$ to about $5 \times 10^{10}$ pfu. In some cases, recombinant viruses of this disclosure are at least about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu. In some cases, recombinant viruses of this disclosure are at most about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu.

In some cases, the viral vector of the disclosure may be measured as vector genomes. In some cases, recombinant viruses of this disclosure are $1 \times 10^{10}$ to $3 \times 10^{12}$ vector genomes. In some cases, recombinant viruses of this disclosure are $1 \times 10^9$ to $3 \times 10^{13}$ vector genomes. In some cases, recombinant viruses of this disclosure are $1 \times 10^8$ to $3 \times 10^{14}$ vector genomes. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ vector genomes. In some cases, recombinant viruses of this disclosure are $1 \times 10^8$ to $3 \times 10^{14}$ vector genomes. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ vector genomes.

In some cases, the viral vector of the disclosure may be measured using multiplicity of infection (MOI). In some cases, MOI may refer to the ratio, or multiple of vector or viral genomes to the cells to which the nucleic may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI. In some cases, recombinant viruses of the disclosure are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects the nucleic acid may be delivered without the use of a virus (i.e. with a non-viral vector), and may be measured as the quantity of nucleic acid. Generally, any suitable amount of nucleic acid may be used with the compositions and methods of this disclosure. In some cases, nucleic acid may be at least about 1 pg, 10 pg, 100 pg, 1 pg, 10 pg, 100 pg, 200 pg, 300 pg, 400 pg, 500 pg, 600 pg, 700 pg, 800 pg, 900 pg, 1 µg, 10 µg, 100 µg, 200 µg, 300 µg, 400 µg, 500 µg, 600 µg, 700 µg, 800 µg, 900 µg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg 1 g, 2 g, 3 g, 4 g, or 5 g. In some cases, nucleic acid may be at most about 1 pg, 10 pg, 100 pg, 1 pg, 10 pg, 100 pg, 200 pg, 300 pg, 400 pg, 500 pg, 600 pg, 700 pg, 800 pg, 900 pg, 1 µg, 10 µg, 100 µg, 200 µg, 300 µg, 400 µg, 500 µg, 600 µg, 700 µg, 800 µg, 900 µg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g.

In some aspects, a self-complementary vector (sc) may be used. The use of self-complementary AAV vectors may bypass the requirement for viral second-strand DNA synthesis and may lead to greater rate of expression of the transgene protein, as provided by Wu, Hum Gene Ther. 2007, 18(2):171-82, incorporated by reference herein.

In some aspects, several AAV vectors may be generated to enable selection of the most optimal serotype, promoter, and transgene.

In some cases, the vector can be a targeted vector, especially a targeted vector that selectively binds to a specific cell, such as cancer cells or tumor cells or eye cells. Viral vectors for use in the disclosure can include those that exhibit low toxicity to a target cell and induce production of therapeutically useful quantities of the anti-VEGF protein in a cell specific manner.

The compositions and methods of the disclosure provide for any suitable viral nucleic acid delivery systems including but not limited to use of at least one of an adeno-associated virus (AAV), adenovirus, helper-dependent adenovirus, retrovirus, herpes simplex virus, lentivirus, poxvirus, hemagglutinatin virus of Japan-liposome (HVJ) complex, Moloney murine leukemia virus, and HIV-based virus. Preferably, the viral vector comprises a strong eukaryotic promoter operably linked to the polynucleotide e.g., a cytomegalovirus (CMV) promoter.

Generally, any suitable viral vectors may be engineered to be optimized for use with the compositions and methods of the disclosure. For example, viral vectors derived from adenovirus (Ad) or adeno-associated virus (AAV) may be used. Both human and non-human viral vectors can be used and the recombinant viral vector can be altered such that it may be replication-defective in humans. Where the vector is an adenovirus, the vector can comprise a polynucleotide having a promoter operably linked to a gene encoding the anti-VEGF protein and is replication-defective in humans.

To combine advantageous properties of two viral vector systems, hybrid viral vectors may be used to deliver a nucleic acid encoding a sFLT-1 protein to a target cell or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000.

Retroviral genomes contained within an adenovirus may integrate within the target cell genome and effect stable gene expression.

Replication-defective recombinant adenoviral vectors can be produced in accordance with known techniques. See, Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

Additionally preferred vectors may include but are not limited to viral vectors, fusion proteins and chemical conjugates. Retroviral vectors include Moloney murine leukemia viruses and HIV-based viruses. In some cases a HIV-based viral vector may be used, wherein the HIV-based viral vector comprises at least two vectors wherein the gag and pol genes are from an HIV genome and the env gene is from another virus. DNA viral vectors may be used. These vectors include pox vectors such as orthopox or avipox vectors, herpesvirus vectors such as a herpes simplex I virus (HSV) vector [Geller, A. I. et al., J. Neurochem, 64: 487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A.: 90 7603 (1993); Geller, A. I., et al., Proc Natl. Acad. Sci USA: 87:1149 (1990)], Adenovirus Vectors [LeGal LaSalle et al., Science, 259:988 (1993); Davidson, et al., Nat. Genet. 3: 219 (1993); Yang, et al., J. Virol. 69: 2004 (1995)] and Adeno-associated Virus Vectors [Kaplitt, M. G., et al., Nat. Genet. 8:148 (1994)], incorporated by reference herein.

Other viral vectors that can be used in accordance with the present disclosure include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, may also be used in the disclosure. For example, retroviral vectors may be based on murine leukemia virus (MLV), as provided by Hu and Pathak, Pharmacol. Rev. 52:493511, 2000 and Fong et al., Crit. Rev. Ther. Drug Carrier Syst. 17:1-60, 2000, incorporated by reference herein. MLV-based vectors may contain up to 8 kb of heterologous (therapeutic) DNA in place of the viral genes. The heterologous DNA may include a tissue-specific promoter and a anti-VEGF protein nucleic acid. In methods of delivery to neoplastic cells, it may also encode a ligand to a tissue specific receptor.

Additional retroviral vectors may be used including but not limited to replication-defective lentivirus-based vectors, including human immunodeficiency (HIV)-based vectors, as provided by Vigna and Naldini, J. Gene Med. 5:308-316, 2000 and Miyoshi et al., J. Virol. 72:8150-8157, 1998, incorporated by reference herein. Lentiviral vectors may be advantageous in that they are capable of infecting both actively dividing and non-dividing cells. They may also be highly efficient at transducing human epithelial cells.

Lentiviral vectors for use in the disclosure may be derived from human and non-human (including SIV) lentiviruses. Examples of lentiviral vectors include nucleic acid sequences required for vector propagation as well as a tissue-specific promoter operably linked to an anti-VEGF protein gene. Nucleic acid sequences may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), may also be used in the disclosure. Use of alphaviruses is described in Lundstrom, K., Intervirology 43:247-257, 2000 and Perri et al., Journal of Virology 74:9802-9807, 2000, incorporated by reference herein.

Recombinant, replication-defective alphavirus vectors may be advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

Pox viral vectors may introduce a gene into the cell's cytoplasm. Avipox virus vectors may result in only a short term expression of the gene or nucleic acid. Adenovirus vectors, adeno-associated virus vectors and herpes simplex virus (HSV) vectors may be used with the compositions and methods of the disclosure. The adenovirus vector may result in a shorter term expression (e.g., less than about a month) than adeno-associated virus, in some aspects, and may exhibit much longer expression. The particular vector chosen may depend upon the target cell and the condition being treated.

Adeno-associated viruses (AAV) are small non-enveloped single-stranded DNA viruses. They are non-pathogenic human parvoviruses and may be dependent on helper viruses, including adenovirus, herpes simplex virus, vaccinia virus and CMV, for replication. Exposure to wild-type (wt) AAV is not associated or known to cause any human pathologies and is common in the general population, usually occurring in the first decade of life in association with an adenoviral infection.

As described herein, "AAV" refers to Adeno-associated virus "rAAV" refers to a recombinant adeno-associated virus.

In some cases, the wild-type AAV encodes rep and cap genes. The rep gene is required for viral replication and the cap gene is required for synthesis of capsid proteins. Through a combination of alternative translation start and splicing sites, the small genome may be able to express four rep and three cap gene products. The rep gene products and sequences in the inverted terminal repeats (145 bp ITRs, which flank the genome) may be critical in this process. To date, 11 serotypes of AAV have been isolated. AAV2 may be used with composition and methods of the disclosure. The compositions and methods of the disclosure provide for use of any suitable AAV serotype. In some aspects, the AAV is selected from the group consisting of: AAV1, AAV2, AAV2.5, AAV3, AAV4, AAV5, AAV6, AAV7, AAV8, AAV9, AAV10, AAV11, AAV12, rh10, and hybrids thereof.

In some aspects, the present disclosure provides a recombinant virus comprising a nucleic acid further comprising a human form of the truncated, soluble VEGF receptor 1 (sFLT-1) and is named rAAV.sFlt-1. The vector is a recombinant, replicative-deficient adeno-associated viral (rAAV) vector, of serotype 2. In another aspect, the vector is a recombinant, replicative-deficient adeno-associated viral (rAAV) vector, of serotype 2 named rAAV.sFlt-1.

AAV2 is the most characterized. rAAV2 has been shown to be able to mediate long-term transgene expression in the eyes of many species of animals. In rats, rAAV mediated reporter gene (green fluorescent protein) was still present at 18 months post injection. In monkeys, the same reported gene was present at 17 months post injection. Similarly, high sFLT-1 protein levels were present in the vitreous of rAAV.sFlt-1 injected monkey eyes at 15 months post injection.

rAAV.sFlt-1 has been tested in animal models for intraocular neovascular disorders. rAAV.sFlt-1 appeared to slow the progression of neovascularization in animal models of corneal neovascularization and retinal neovascularization. Interestingly rAAV-mediated sFlt-1 indicated some inhibition of neovascularization in a monkey model of choroidal neovascularization (model for the wet form of age related macular degeneration or AMD). In this study, the presence of the rAAV.sFlt-1 construct showed low levels of expression of sFLT-1 in the eyes of monkeys and, did not affect the well-being or retinal function of the monkeys. There is no evidence to suggest any safety issues associated with systemic exposure to rAAV.sFlt-1. The overall positive findings and lack of toxicity of rAAV vectors in these studies, as well as the findings with rAAV.sFlt-1 in mammalian models of choroidal neovascularization/AMD provide extensive supporting data that the vector has a favorable safety profile when administered to the eye.

Despite the ability of rAAV.sFlt-1 to ameliorate certain symptoms of AMD in the monkey model, sFLT-1 proteins levels are unexpectedly low in the retina. Expression levels of sFLT-1 driven by a constitutively active mammalian promoter have been shown in the art to provide high levels of protein expression in numerous cell types. While not being bound to theory, multiple possibilities may exist for this lower than expected expression level. As a large multi-domain protein, sFLT-1 may be susceptible to premature proteolyitic degradation, poor kinetics of expression, or non optimal sorting. With respect to the latter, as a secreted protein, sFLT-1, as expressed recombinantly in cell, enters the secretory pathway. In retinal cells, including RPE cells, sFLT-1 may be secreted either apically or basolaterally, depending on either ER or Golgi apparatus sorting of the protein. In some cases, non-optimal sorting may secrete the molecule to the undesired basolatteral membrane, thus decreasing the concentration of sFLT-1 molecules available to inhibit VEGF signaling and neovascular angiogenesis on the apical surface of the RPE cell layer.

Additionally, it was unknown in the art how this unexpectedly lower level of sFLT-1 may affect efficacy of the drug towards treatment of the actual AMD disease in humans. While barely elevated levels in the monkey model showed promising signs of ameliorating symptoms of AMD, the monkey animal model for AMD merely serves a surrogate for AMD disease. As described herein, AMD symptoms are artificially induced (via laser) in the retina. While this model is suitable for various analyses, the actual efficacy of the drug in the treatment of symptoms in the monkey model is difficult to extrapolate to treatment of disease in humans. Unexpectedly lower protein levels as generated by the rAAV.sFlt-1 further increases difficulty in this assessment without experiments in humans.

In addition, 3 clinical trials on Lebers Congenital Amaurosis (LCA) are being conducted in the UK and USA using the rAAV2 backbone. LCA is a rare inherited eye disease that appears at birth or in the first few months of life and it is characterized by nystagmus, sluggish or no pupillary responses, and severe vision loss or blindness. To date, no safety issues have been reported following injection of the rAAV2 construct into the subretinal space of 6 participants in these two trials. Both teams involved in the clinical trials concluded that their findings have supported further gene therapy studies In LCA patients.

Given the apparent technical difficulties in generating substantially or sustained elevated levels of sFLT-1 in monkeys, various optimization strategies may be taken to address one or more of the technical issues underlying lower protein levels of sFlt-1 in the retina after introduction of rAAV.sFlt-1. In some cases, optimization strategies, including ones as provided by the composition and methods of this disclosure may include increasing optimizing the sFlt-1 protein sequence, or domains, introducing control elements to direct correct sorting after expression in retinal cells, or elevating levels of sFlt-1 protein to compensate for any of these possible factors. In some cases, the composition and methods of the disclosure provide for specific strategies directed toward the latter, involving the incorporation of specific nucleic acid sequences directed towards improving the elevating protein levels in human retinans over sFlt-1 levels as observed previously in monkey studies. As described herein, various sequences, linkers, UTRs, introns, sFLT-1 variants or combination thereof may be used to elevate protein levels of sFlt-1 protein in the retina after exposure to rAAV.sFlt-1.

Vectors can comprise components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Examples of negative selectable markers may include the inclusion of resistance genes to antibiotics, such as ampicillin or kanamycin. Such marker genes can provide an added measure of control that can be advantageous in gene therapy contexts. A large variety of such vectors are known in the art and are generally available.

In some cases, nucleic acids encoding antibiotic resistances markers may include but are not limited to sequences such as SEQ ID No. 110, SEQ ID No. 111, SEQ ID No. 112, SEQ ID No. 113 or SEQ ID No. 114.

In many of the viral vectors compatible with methods of the disclosure, one or more promoters can be included in the vector to allow more than one heterologous gene to be expressed by the vector. Further, the vector can comprise a sequence which encodes a signal peptide or other moiety which facilitates expression of the anti-VEGF protein from the target cell.

The nucleic acid encoding a gene product may be under transcriptional control by a promoter. A "promoter", as provided herein, refers to a suitable DNA sequence required to initiate transcription of a gene. The phrase "under transcriptional control" means that the promoter is in the correct location and orientation in relation to the nucleic acid to control RNA polymerase initiation and expression of the gene. In some cases, promoter may include a "strong" or constitutively active promoter. For example, the CMV promoter may be used as known in the art a constitutively active promoter. In some cases, the CMV promoter may comprise additional regulatory elements for promoting expression. In some cases, the CMV promoter may comprise the initial-early CMV promoter.

In some cases a promoter may refer to a "weak" promoter, or sequence that yields lower levels of sFLT-1 protein than a strong promoter. In some cases a promoter may be used such that the promoter drives selective expression of sFLT-1. In some cases a promoter or other regulatory elements used in combination with other sequences as described herein may be used to drive selective expression of sFLT-1 in an eye cell, or eye tissue.

Additionally, "promoter", 104 may also be used herein interchangeably to refer to any additional suitable transcriptional control modules that may be present around the initiation site for RNA polymerases. The compositions and methods of this disclosure may use any suitable promoters and transcriptional control modules for expression of a transgene, 106. Additional transcriptional control modules may include but are not limited to elements such as HSV thymidine kinase (tk) and SV40 early transcription units. Generally, promoters may be composed of discrete functional modules, each consisting of approximately 7-20 bp of DNA, or 20-5000 bp of DNA, and contain one or more recognition sites for transcriptional activator or repressor proteins. The composition and methods of the disclosure provide for any suitable regulatory sequences or combination thereof. In some cases, these transcriptional control module sequences may be referred to or identified as enhancer or repressor sequences.

At least one module in each promoter functions to position the start site for RNA synthesis. One example is the TATA box. Other example may include some promoters that lack a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Generally, these are located in a region 30-110 bp upstream of the start site, although a number of promoters may contain functional elements downstream of the start site as well. The spacing between promoter elements frequently may be flexible, so that promoter function is preserved when elements are inverted or moved relative to one another. In the tk promoter for example, the spacing between promoter elements can be increased to 50 bp apart before activity begins to decline. Depending on the promoter, individual elements may position to function either co-operatively or independently to activate transcription.

The compositions and methods of the disclosure provide for any suitable sequences for the control of expression of a nucleic acid sequence of interest in the targeted cell. Thus, where a human cell is targeted, sequences may the nucleic acid coding region may be engineered to be adjacent to and under the control of a promoter that is capable of being expressed in a human cell. Generally, such a promoter might include either a human or viral promoter.

In various aspects of the disclosure, the human cytomegalovirus (CMV) immediate early gene promoter (ie—CMV), the SV40 early promoter, the Rous sarcoma virus long terminal repeat, β-actin, rat insulin promoter and glyceraldehyde-3-phosphate dehydrogenase can be used to obtain a high level of expression of the coding sequence of interest (e.g. sFLT-1). The use of other viral or mammalian cellular or bacterial phage promoters which are well-known in the art to achieve expression of a coding sequence of interest is contemplated as well, provided that the levels of expression are sufficient for a given purpose. In some aspects, prokaryotic regulatory sequences may be present in the vector, such as the T7 RNA polymerase promoter sequence. In other aspects, the vector is free from such regulatory sequences. By employing a promoter with known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic. The composition and methods of the disclosure provide for any suitable combination of promoter sequence, regulatory sequences and transgene. In some cases, a combination of sequences may result in no toxicity to the cell. In some cases, a combination of sequences may result in high toxicity to the cell. In some cases, a combination of sequences may result in moderate levels of toxicity in the cell.

The ecdysone system (Invitrogen, Carlsbad, Calif.) is one such system for transgene expression. This system is designed to allow regulated expression of a gene of interest in mammalian cells. It consists of a tightly regulated expression mechanism that allows little basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest may be used in the compositions and methods of this disclosure. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

In some circumstances, it may be desirable to regulate expression of a transgene in a gene therapy vector. For example, different viral promoters with varying strengths of activity may be utilized depending on the level of expression desired. In mammalian cells, the CMV immediate early promoter may be used to provide strong transcriptional activation. Modified versions of the CMV promoter that are less potent have also been used when reduced levels of expression of the transgene are desired. When expression of a transgene in hematopoietic cells is desired, retroviral promoters such as the LTRs (Long Terminal Repeat) from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic Virus, HSV-TK, and avian sarcoma virus.

In some aspects, tissue-specific promoters are used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate.

In some cases, promoters or regulatory sequence elements may be used to direct selective expression in eye cells or eye tissue. For example, promoter, sequence elements or regulatory sequences found in specific eye cell types, such as retinal pigment epithelial cells, may be used in a suitable expression construct (e.g., the RPE65 or VMD2 promoter).

The selection of appropriate promoters can be readily accomplished. In some cases a high expression, or strong promoter may be used. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). Promoters are discussed infra. The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618, incorporated by reference herein. Generally promoter sequences and/or any associated regulatory sequences may comprise about at least 150 bp, 200 bp, 300 bp, 400 bp, 500 bp, 600 bp, 700 bp, 800 bp, 900 bp, 1000 bp, 2000 bp, 3000 bp, 4000 bp, 5000 bp or 10000 bp. Promoter sequences and any associated regulatory sequences, may comprise about at most 150 bp, 200 bp, 300 bp, 400 bp, 500 bp, 600 bp, 700 bp, 800 bp, 900 bp, 1000 bp, 2000 bp, 3000 bp, 4000 bp, 5000 bp or 10000 bp.

In some aspects, the recombinant virus or plasmid comprises a promoter selected from cytomegalovirus (CMV) promoter, Rous sarcoma virus (RSV) promoter, and MMT promoter, EF-1 alpha promoter, UB6 promoter, chicken beta-actin promoter, CAG promoter, RPE65 promoter and opsin promoter. Generally, promoter sequences and promoter/enhancer sequences as provided by the present disclosure may include but are not limited to any sequences selected from SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 340, SEQ ID No. 41, SEQ ID No. 42, SEQ ID No. 43, SEQ ID No. 44, SEQ ID No. 45, SEQ ID No. 46, and SEQ ID No. 47.

In some aspects, an antibiotic marker is used in the process for production of the recombinant virus. Antibiotic resistance markers may be used to identify positive transgenic cells in the generation of recombinant virus. In some aspects, the antibiotic marker comprises a sequence encoding an antibiotic resistance gene, such as those provided herein including but not limited to sequences shown in FIG. 8A and FIG. 8B. For example markers conferring resistance may include but are not limited to kanamycin, gentamicin, ampicillin, chloramphenicol, tetracycline, doxycycline, or hygromycin. In some aspects, the antibiotic resistance gene is a non-beta-lactam antibiotic resistance gene such as kanamycin.

In some aspects, the recombinant virus and/or plasmid used to generate recombinant virus, comprise a sequence encoding a replication origin sequence, such as those provided herein. Origin of replication sequences, generally provide sequence useful for propagating a plasmid. Generally, origin of replication sequences as provided by the present disclosure may include but are not limited to any sequences selected from sequences as provided in FIG. 7A, FIG. 7B, FIG. 7C and FIG. 7D.

In some aspects, an origin or origin of replication sequences may include but is not limited to sequences such as SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, or SEQ ID No. 17.

In some aspects, the recombinant virus and/or plasmid used to generate recombinant virus, comprise an enhancer, such as those provided herein.

In some aspects, the recombinant virus and/or plasmid used to generate recombinant virus, comprise a chimeric intron or an intron, 105, such as those provided herein and disclosed in U.S. Pat. No. 7,635,474, incorporated by reference herein. Intron or chimeric intron may be used interchangeably herein. In some cases, an intron may refer to any sequence that may be transcribed but is not translated. In some cases, an intron may refer to any sequence that be transcribed and is removed from a mature RNA transcript in a cell. In some cases, an intron may comprise about at least 1 bp, 50 bp, 100 bp, 150 bp, 200 bp, 300 bp, 400 bp, 500 bp, 600 bp, 700 bp, 800 bp, 900 bp, 1000 bp, 2000 bp, 3000 bp, 4000 bp or 5000 bp. In some cases, an intron may comprise may comprise about at least 1 bp, 50 bp, 100 bp, 150 bp, 200 bp, 300 bp, 400 bp, 500 bp, 600 bp, 700 bp, 800 bp, 900 bp, 1000 bp, 2000 bp, 3000 bp, 4000 bp or 5000 bp. In some cases, an intron may be about 300 bp. In some cases, an intron may be about 200-400 bp. In some cases, a chimeric intron may be about 100-500 bp. In some cases, an intron may be about 50-200 bp. In some cases, an intron may be either an intact naturally occurring intron or a chimeric intron.

In some aspects, an intron may include but is not limited to sequences such as SEQ ID No. 48, SEQ ID No. 115, SEQ ID No. 116, SEQ ID No. 117, SEQ ID No. 118, SEQ ID No. 119 or SEQ ID No. 120.

In some aspects, the recombinant virus and/or plasmid used to generate recombinant virus, comprise a poly A (polyadenylation) sequence, 107, such as those provided herein (e.g. SV40 poly A sequence). Generally, any suitable polyA sequence may be used for the desired expression of the transgene (i.e. sFLT-1). For example, in some cases, the present disclosure provides for a sequence comprising SV40 polyA sequence, or portion of SV40 polyA sequence. In some cases, native polyA sequences as found downstream (3'UTR) of the human sFLT-1 gene as found in human genomic sequence may be used. In other cases, polyA sequences as found downstream of genes other than sFLT-1 may be used. In other cases, the present disclosure provides for polyA sequences comprising a combination of one or more polyA sequences or sequence elements. In some cases, no polyA sequence is used. In some cases one or more polyA sequences may be referred to as untranslated regions (UTRs), 3' UTRs, or termination sequences.

In certain aspects of the disclosure, the use of internal ribosome entry site (IRES) or foot-mouth disease virus (FMDV) elements may be used to create multigene, or polycistronic, messages. IRES elements are able to bypass the ribosome scanning model of 5' methylated Cap dependent translation and begin translation at internal sites. IRES elements from two members of the picornavirus family (poliovirus and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame may be accessible to ribosomes for efficient translation. Multiple genes can be efficiently expressed using a single promoter/enhancer to transcribe a single message. An alternative system for co-expression of two proteins in gene therapy delivery vectors is the FMDV 2A system. The FMDV 2A system employs a retroviral plasmid vector in which two genes may be linked to a nucleotide sequence encoding the 2A sequence from the picornavirus foot-and-mouth disease virus. Transcription and translation gives rise to a bicistronic mRNA and two independent protein products.

Any heterologous open reading frame can be linked to IRES elements. This may include genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

A polyA sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A polyA sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A polyA sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

In some cases, a polyA or termination sequence may include but is not limited to sequences such as SEQ ID No. 49, SEQ ID No. 50, SEQ ID No. 51, SEQ ID No. 52, SEQ ID No. 53, SEQ ID No. 54, and SEQ ID No. 55.

Generally, polyA sequences, as provided by the present disclosure, may include but are not limited to any sequences selected from PolyA Regions 1-10 as provided in FIG. 9A and FIG. 9B.

In some cases, polyA sequences may be optimized for various parameters affecting protein expression, including but not limited to mRNA half-life of the transgene in the cell, stability of the mRNA of the transgene or transcriptional regulation. For example, polyA sequences maybe altered to increase mRNA transcript of the transgene, which may result in increased protein expression. In some cases, the polyA sequences maybe altered to decrease the half-life of the mRNA transcript of the transgene, which may result in decreased protein expression.

In some aspects, the recombinant virus and/or plasmid used to generate recombinant virus, comprise a polynucleotide encoding a human sFLT-1 protein or a functional fragment thereof. In some cases, the recombinant virus and/or plasmid used to generate recombinant virus, comprises a nucleic acid encoding another anti-VEGF protein or VEGF inhibitor.

In some cases, a VEGF inhibitor may include but is not limited to sequences such as SEQ ID No. 102, SEQ ID No. 103, SEQ ID No. 104, SEQ ID No. 105, SEQ ID No. 106, SEQ ID No. 107, SEQ ID No. 108, or SEQ ID No. 122

In some cases, nucleic acids of a VEGF inhibitor may encode for polypeptide sequences which may include but are not limited to polypeptide sequences such as SEQ ID No. 109 or SEQ ID No. 121.

In some aspects, the recombinant virus and/or plasmid used to generate recombinant virus, comprise a regulatory nucleic acid fragment that is capable of directing selective expression of the sFLT-1 protein in an eye cell. In some cases, eye cells may comprise retinal pigment epithelial cells (RPE).

In some aspects, the recombinant virus and/or plasmid used to generate recombinant virus, may comprise one or more untranslated regions (UTR) or sequences. Generally, any suitable UTR sequence may be used for the desired optimal expression of the transgene (i.e. sFLT-1). For example, in some cases, UTR regions or sequences may comprise native sequences. In some cases, UTR sequences may be sequences as found upstream (5' UTR) or downstream (3'UTR) of the human sFLT-1 gene as found in human genomic sequence or portions thereof. In other cases, UTR sequences may comprise non-native sequences, such as found upstream or downstream of genes other than sFLT-1 or comprise sequences further comprising a combination of one or more UTR sequence elements as further described herein. In some cases, only a 5' UTR sequence is used. In some cases, only a 3' UTR sequence is used. In some cases, no UTR sequences are used.

A UTR sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A UTR sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A UTR sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

Generally, UTR sequences as provided by the present disclosure may include but are not limited to any sequences including but to limited to SEQ ID No. 91, SEQ ID No. 2, SEQ ID No. 92, SEQ ID No. 93, SEQ ID No. 94, SEQ ID No. 95, SEQ ID No. 96, SEQ ID No. 97, SEQ ID No. 98, SEQ ID No. 99, SEQ ID No. 100, and SEQ ID No. 101.

In some cases, variations of either the 5'UTR and/or 3'UTR may be optimized for a desired level of protein expression. In some cases, 3'UTR sequences may be optimized for various parameters affecting protein expression, including but not limited to mRNA half-life of the transgene in the cell, stability or secondary structure of the mRNA of the transgene or conditional regulation (e.g. binding of various factors to modulate translation). For example, the 3'UTR sequence maybe altered to increase the half-life of the mRNA transcript of the transgene, which may result in increased protein expression. In some cases, the 3'UTR sequence maybe altered to decrease the half-life of the mRNA transcript of the transgene, which may result in decreased protein expression.

Generally, 3' UTRs sequences may comprise various sequence elements. The present disclosure provides for 3' UTR sequences that may include but are not limited to sequence elements such as one or more polyadenylation signals, linker sequences, spacer sequences, SECIS elements, AU-rich or ARE sequences or miRNA or RNAi binding sequences, transcription terminator sequences, 3' termination sequences or variants and/or combinations thereof.

In some cases, 5'UTR sequences may be optimized for various parameters affecting protein expression, including but not limited to mRNA half-life of the transgene in the cell, stability or secondary structure of the mRNA of the transgene or transcriptional regulation. For example, the 5'UTR sequences maybe altered to increase translation efficiency of mRNA transcript of the transgene, which may result in increased protein expression. In some cases, the 5'UTR sequences maybe altered to decrease translation efficiency of mRNA transcript of the transgene, which may result in decreased protein expression.

Generally, 5' UTRs sequences may comprise various sequence elements. The present disclosure provides for 5' UTR sequences that may include but are not limited to sequence elements such as one or more ribosome binding sites (RBS), linker sequences, spacer sequences, regulatory sequences, regulatory response elements, riboswitches, sequences that promote or inhibit translation initiation, regulatory sequences for mRNA transport or variants and/or combinations thereof.

In some aspects, the recombinant virus and/or plasmid used to generate recombinant virus, may comprise one or more linker or spacer sequences. As described herein, linker sequence or spacer sequence may be used interchangeably. Generally, a linker sequence or spacer sequence may be any suitable sequence used to create a non-contiguous sequence between at least two sequence elements. For example, in one aspect of the disclosure, a linker sequence may be found inserted between an ITR-1, 108 sequence, or ITR-2, 103, and an antibiotic resistance gene sequence, 106 as reflected in FIG. 1A. In another example, linker sequences may be inserted adjacent to any sequence element of the recombinant virus or the plasmid encoding the recombinant virus including the ITR sequences, the promoter or promoter/enhancer sequences, the intron sequence, the transgene sequence and the poly A region sequence. Generally, any suitable linker or spacer sequence may be used to create non-contiguous sequences. For example, in some cases, linker sequences may be randomly generated sequence. In some cases, linker sequence may be non-specific sequence optimized to prevent formation of secondary structure or intramolecular interactions that may adversely affect protein expression. In some cases, linker sequences may comprise any additional functional sequence elements, including but not limited to introns, regulatory sequences, enhancers or the like. Functional elements in linker sequences may be used for the desired optimal production of virus and/or expression of transgene expression. In some cases, linker sequences are cloning sites, remnants of prior cloning sites or other non-significant sequences and the insertion of such linkers between any two sequence elements is optional.

Generally, linker sequence, as provided by the present disclosure, may include but are not limited to any sequences selected from sequences as provided in FIG. 9D, FIG. 9E and FIG. 9F.

In some cases, the length of the linker sequence may be optimized for the desired optimal production of virus and/or expression of transgene expression. In some cases, the length of one or more linker sequences located at one or more sites in the virus genome or plasmid may be varied to produce the desired optimal protein expression. For example, a linker sequence may be found between the intron, as described herein and the transgene (i.e. sFLT-1). The length of the linker sequence may be varied to produce varying effects on the transcription and subsequent translation of the transgene in the cell.

A linker sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A linker sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A linker sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

In some cases, a linker or spacer sequence may include but is not limited to SEQ ID No. 60, SEQ ID No. 61, SEQ ID No. 62, SEQ ID No. 63, SEQ ID No. 64, SEQ ID No. 65, SEQ ID No. 66, SEQ ID No. 67, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No. 79, SEQ ID No. 80, SEQ ID No. 81, SEQ ID No. 82, SEQ ID No. 83, SEQ ID No. 84, SEQ ID No. 85, SEQ ID No. 86, SEQ ID No. 87, SEQ ID No. 88, SEQ ID No. 89, and SEQ ID No. 90.

In some aspects, the recombinant virus comprises inverted terminal repeat (ITR) sequences used for packaging the recombinant gene expression cassette into the virion of the viral vector. In some cases, the ITR is from adeno-associated virus (AAV). In some cases, the ITR is from AAV serotype 2. In some cases, an ITR may include but is not limited to SEQ ID No. 56, SEQ ID No. 57, SEQ ID No. 58, or SEQ ID No. 59.

In some aspects, the recombinant virus and/or plasmid used to generate recombinant virus comprises nucleic acid elements in the following order: a) a first ITR sequence; b) a promoter sequence; c) an intron sequence; d) a first UTR sequence; e) a sequence encoding a VEGF inhibitor; f) a second UTR sequence; g) a poly A sequence; and h) a second ITR sequence. In some aspects of the recombinant virus and/or plasmid used to generate the recombinant virus, the promoter sequence comprises a promoter/enhancer sequence. In some aspects, the sequence encoding a VEGF inhibitor comprises a sequence encoding human sFLT-1 protein or a functional fragment thereof. In other aspects, the plasmid used to generate the recombinant virus further comprises an origin of replication sequence, 102. In some aspects, the plasmid further comprises a sequence for an antibiotic resistance gene as provided herein.

In some aspects, the recombinant virus and/or plasmid used to generate recombinant virus comprises nucleic acid elements in the following order: a) a first ITR sequence; b) a first linker sequence; c) a promoter sequence; d) a second linker sequence; e) an intron sequence; f) a third linker sequence; g) a first UTR sequence; h) a sequence encoding a VEGF inhibitor; i) a second UTR sequence; j) a fourth linker sequence; k) a poly A sequence; l) a fifth linker sequence; and m) a second ITR sequence. In some aspects of the recombinant virus and/or plasmid used to generate recombinant virus, the promoter sequence comprises a promoter/enhancer sequence. In some aspects, the sequence encoding a VEGF inhibitor comprises a sequence encoding human sFLT-1 protein or a functional fragment thereof. In other aspects, the plasmid used to generate the recombinant virus further comprises an origin of replication sequence. In some aspects, the plasmid further comprises a sequence for an antibiotic resistance gene as provided herein.

IV. Pharmaceutical Compositions

A pharmaceutical composition is a formulation containing one or more active ingredients as well as one or more excipients, carriers, stabilizers or bulking agents, which is suitable for administration to a human patient to achieve a desired diagnostic result or therapeutic or prophylactic effect. For storage stability and convenience of handling, a pharmaceutical composition can be formulated as a lyophilized (i.e. freeze dried) or vacuum dried powder which can be reconstituted with saline or water prior to administration to a patient. Alternately, the pharmaceutical composition can be formulated as an aqueous solution. A pharmaceutical composition can contain a proteinaceous active ingredient. Unfortunately, proteins can be very difficult to stabilize, resulting in loss of protein and/or loss of protein activity during the formulation, reconstitution (if required) and during the storage prior to use of a protein containing pharmaceutical composition. Stability problems can occur because of protein denaturation, degradation, dimerization, and/or polymerization. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Pharmaceutical compositions suitable for internal use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants such as polysorbates (Tween™), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol (Triton X100™), N, N-dimethyldodecylamine-N-oxide, hexadecyltrimethylammonium bromide (HTAB), polyoxyl 10 lauryl ether, Brij 721™, bile salts (sodium deoxycholate, sodium cholate), pluronic acids (F-68, F-127), polyoxyl castor oil (Cremophor™), nonylphenol ethoxylate (Tergitol™), cyclodextrins and, ethylbenzethonium chloride (Hyamine™). Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof In one aspect, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated by reference herein.

It is especially advantageous to formulate oral or parenteral compositions in dosage unit form for ease of administration and uniformity of dosage. Dosage unit form as used herein refers to physically discrete units suited as unitary dosages for the human subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The pharmaceutical compositions of the disclosure encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the disclosure: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. Pharma Sci.,* 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present disclosure.

As used herein, a "pharmaceutical addition salt" comprises a pharmaceutically acceptable salt of an acid form of one of the components of the compositions of the disclosure. These comprise organic or inorganic acid salts of the amines. Preferred acid salts are the hydrochlorides, acetates, salicylates, nitrates and phosphates. Other suitable pharmaceutically acceptable salts are well known to those skilled in the art and comprise basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in *Nature*, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and comprise alkaline, alkaline earth, ammonium and quaternary ammonium cations. Carbonates or hydrogen carbonates are also possible. For oligonucleotides, preferred examples of pharmaceutically acceptable salts comprise but are not limited to: (I) salts formed with cations such as sodium, potassium, ammonium, magnesium, calcium, polyamides such as spermine and spermidine, and the like; (II) acid addition salts formed with inorganic acids, for example hydrochloric acid, hydrobromic acid, sulfuric acid, phosphoric acid, nitric acid and the like; (III) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, naphthalenedisulfonic acid, polygalacturonic acid, and the like; and (IV) salts formed from elemental anions such as chlorine, bromine, and iodine.

Pharmaceutical compositions of the present disclosure comprise, but are not limited to, solutions, emulsions, and liposome-containing formulations. These compositions may be generated from a variety of components that comprise, but are not limited to, preformed liquids, self-emulsifying solids and self-emulsifying semisolids.

Certain compositions of the present disclosure also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, generally with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., *Antisense Res. Dev.*, 1995, 5, 115-121; Takakura et al., *Antisense & Nucl. Acid Drug Dev.*, 1996, 6, 177-183).

The vector or recombinant viruses (virions) can be incorporated into pharmaceutical compositions for administration to mammalian patients, particularly humans. The vector or virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some aspects, the pharmaceutical composition provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some aspects, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the anti-VEGF contained in the adenoviral vector delivery system, may be in the range of 6.5 to 7.75, 7 to 7.5, or 7.2 to 7.4. The pH of the formulation may range from about 3.0 to about 12.0. The pH of the immunogenic composition may be at least about 3, 4, 5, 6, 7, 8, 9, 10, 11 or 12 pH units. The pH of the immunogenic composition may be at most about 3, 4, 5, 6, 7, 8, 9, 10, 11 or 12 pH units.

In some aspects, the pharmaceutical composition provided herein comprises substances which increase the viscosity of the suspension, such as sodium carboxymethyl cellulose, sorbitol, or dextran, in the amount about 1-10 percent, such as 1, 2, 3, 4, 5, 6, 7, 8, 9, or 10 percent.

Certain aspects of the disclosure provide pharmaceutical compositions containing one or more recombinant virus and one or more other chemotherapeutic agents.

Examples of such chemotherapeutic agents comprise, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MIX), colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J., pages 1206-1228).

Anti-inflammatory drugs, comprising but not limited to nonsteroidal anti-inflammatory drugs and corticosteroids, and antiviral drugs, comprising but not limited to ribivirin, vidarabine, acyclovir and ganciclovir, may also be combined in compositions of the disclosure (Me Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this disclosure. Two or more combined compounds may be used together or sequentially.

In another related aspect, compositions of the disclosure may contain one or more recombinant viruses, particularly sFLT-1 with different sequences. Two or more combined viruses may be used together or sequentially.

In another aspect, the present disclosure provides a unit dose of a pharmaceutical composition comprising about $1 \times 10^6$ about $1 \times 10^{15}$ viral genomes, wherein the viruses comprises a nucleic acid encoding sFLT-1.

In some cases, the unit dose of the pharmaceutical composition of the disclosure may be measured as pfu (plaque forming units). In some cases, the pfu of the unit dose of the pharmaceutical composition of the disclosure may be about $1 \times 10^8$ to about $5 \times 10^{10}$ pfu. In some cases, the pfu of the unit dose of the pharmaceutical composition of the disclosure is at least about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu. In some cases, the pfu of the unit dose of the pharmaceutical composition of the disclosure is at most about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu.

In some cases, the viral vector of the disclosure may be measured as vector genomes. In some cases, the unit dose of the pharmaceutical composition of the disclosure is $1 \times 10^{10}$ to $3 \times 10^{12}$ vector genomes. In some cases, the unit dose of the pharmaceutical composition of the disclosure is $1 \times 10^9$ to $3 \times 10^{13}$ vector genomes. In some cases, the unit dose of the pharmaceutical composition of the disclosure is $1 \times 10^{10}$ to $1 \times 10^{11}$ vector genomes. In some cases, the unit dose of the pharmaceutical composition of the disclosure is $1 \times 10^8$ to $3 \times 10^{14}$ vector genomes. In some cases, the unit dose of the pharmaceutical composition of the disclosure is at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ vector genomes. In some cases, the unit dose of the pharmaceutical composition of the disclosure is $1 \times 10^8$ to $3 \times 10^{14}$ vector genomes. In some cases, the unit dose of the pharmaceutical composition of the disclosure is at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ vector genomes.

In some cases, the unit dose of the pharmaceutical composition of the disclosure may be measured using multiplicity of infection (MOI). In some cases, MOI may refer to the ratio, or multiple of vector or viral genomes to the cells to which the nucleic may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI.

In some aspects the nucleic acid may be delivered without the use of a virus (i.e. with a non-viral vector), and may be measured as the quantity of nucleic acid. Generally, any suitable amount of nucleic acid may be used with the compositions and methods of this disclosure. In some cases, the amount of nucleic acid may be at least about 1 pg, 10 pg, 100 pg, 1 pg, 10 pg, 100 pg, 200 pg, 300 pg, 400 pg, 500 pg, 600 pg, 700 pg, 800 pg, 900 pg, 1 ng, 10 ng, 100 ng, 200 ng, 300 ng, 400 ng, 500 ng, 600 ng, 700 ng, 800 ng, 900 ng, 1 μg, 10 μg, 100 μg, 200 μg, 300 μg, 400 μg, 500 μg, 600 μg, 700 μg, 800 μg, 900 μg, 1 mg, 10 mg, 100 mg, 200 mg, 300 mg, 400 mg, 500 mg, 600 mg, 700 mg, 800 mg, 900 mg 1 g, 2 g, 3 g, 4 g, or 5 g. In some cases, nucleic acid may be at most about 1 pg, 10 pg, 100 pg, 1 pg, 10 pg, 100 pg, 200 pg, 300 pg, 400 pg, 500 pg, 600 pg, 700 pg, 800 pg, 900 pg, 1 ng, 10 ng, 100 ng, 200 ng, 300 ng, 400 ng, 500 ng, 600 ng, 700 ng, 800 ng, 900 ng, 1 μg, 10 μg, 100 μg, 200 μg, 300 μg, 400 μg, 500 μg, 600 μg, 700 μg, 800 μg, 900 μg, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g.

In some aspects, the pharmaceutical composition comprises about $1 \times 10^6$ to about $1 \times 10^{15}$ recombinant viruses, about $1 \times 10^7$ to about $1 \times 10^{14}$ recombinant viruses, about $1 \times 10^8$ to about $1 \times 10^{13}$ recombinant viruses, about $1 \times 10^9$ to about $3 \times 10^{12}$ recombinant viruses, or about $1 \times 10^{10}$ to about $3 \times 10^{12}$ recombinant viruses.

Kits

Compositions and reagents useful for the present disclosure may be packaged in kits to facilitate application of the present disclosure. In some aspects, the present method provides for a kit comprising a recombinant nucleic acid of the disclosure. In some aspects, the present method provides for a kit comprising a recombinant virus of the disclosure. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose.

In another aspect, the present disclosure provides a kit comprising the pharmaceutical compositions provided herein. In yet another aspect, the disclosure provides kits in the treatment of diseases such as, for example: AMD, DME, RVO, angiogenesis related diseases, cancer, autoimmune diseases, infectious disease organisms, and the like.

In one aspect, a kit comprises: (a) a recombinant virus provided herein, and (b) instructions to administer to cells or an individual a therapeutically effective amount of the recombinant virus. In some aspects, the kit may comprise pharmaceutically acceptable salts or solutions for administering the recombinant virus. Optionally, the kit can further comprise instructions for suitable operational parameters in the form of a label or a separate insert. For example, the kit may have standard instructions informing a physician or laboratory technician to prepare a dose of recombinant virus.

Optionally, the kit may further comprise a standard or control information so that a patient sample can be compared with the control information standard to determine if the test amount of recombinant virus is a therapeutic amount consistent with for example, a shrinking of a tumor. Optionally, the kit could further comprise devices for administration, such as a syringe, filter needle, extension tubing, cannula, and subretinal injector.

Recombinant viruses may be generated by any suitable means. The methods and compositions and of the disclosure provide for generation of recombinant virus through various means, including the use of transgenic cells, which may include mammalian cells, insect cells, animal cells or fungal cells.

For example, in some aspects, recombinant viruses may be generated through transfection of insect cells via recombinant baculovirus. In some cases, recombinant baculovirus may be generated as an intermediate, whereby the baculovirus may contain sequences necessary for the generation of other viruses such as AAV or rAAV2 viruses. In some cases one or more baculoviruses may be used in the generation of recombinant viruses used for the composition and methods of treatment of this disclosure. In some cases insect cells such as Sf9, High-Five or Sf21 cell lines may be used. In some cases, cell lines may be generated using transient methods (i.e. infection with not stably integrated transgenes.) In other cases, cell lines may be generated through the generation of stable cell lines ((i.e. infection with transgenes stably integrated into the host cell genome.) In other aspects, the pharmaceutical composition provided herein is manufactured using adherent human embryonic kidney 293 (HEK293) cells. In an alternative aspect, the pharmaceutical composition provided herein is manufactured using suspension-adapted HEK293 cells. In another aspect, the pharmaceutical composition provided herein is manufactured using the baculovirus expression system (BVES) in insect cells. In some aspects, the vector is produced using herpes-helper virus. In some aspects, the vector is produced using producer-clone methods. In some aspects, the vector is produced using Ad-AAV.

Generally, any suitable method may be used in the biochemical purification of recombinant viruses for use in a pharmaceutical composition as described herein. Recombinant viruses may be harvested directly from cells, or from the culture media surrounding host cells. Virus may be purified using various biochemical means, such as gel filtration, filtration, chromatography, affinity purification, gradient ultracentrifugation, or size exclusion methods. Recombinant virus may be tested for content (i.e., identity), purity, or potency (i.e., activity) using any suitable means, before formulation into a pharmaceutical composition. Method may include but are not limited to immunoassays, ELISA, SDS-PAGE, western blot, Northern blot, Southern blot or PCR, HUVEC assays and the like.

V. Method of Treatment

In another aspect, the present disclosure provided a method for treating a pathological angiogenesis related disease, comprising administering a pharmaceutically effective amount of the pharmaceutical compositions provided herein to a human subject in need of such treatment. In some aspects, the disease is selected from the group of ocular neovascular diseases consisting of: age-related macular degeneration (AMD), wet-AMD, dry-AMD, retinal neovascularization, choroidal neovascularization diabetic retinopathy, proliferative diabetic retinopathy, retinal vein occlusion, central retinal vein occlusion, branched retinal vein occlusion, diabetic macular edema, diabetic retinal ischemia, ischemic retinopathy and diabetic retinal edema.

In some cases, dry AMD may be treated. In some cases, dry AMD may be referred to as central geographic atrophy, characterized by atrophy of the retinal pigment epithelial later below the retina and subsequent loss of photoreceptors in the central part of the eye. The composition and methods of this disclosure provide for the treatment of any and all forms of AMD.

In another aspect, the present disclosure provides a method for prophylactic treatment of AMD or ocular neovascular diseases as described herein, comprising administering a pharmaceutically effective amount of the pharmaceutical compositions provided herein to a human subject in need of such treatment. The present disclosure may be used to treat patients at risk of developing AMD, or presenting early symptoms of the disease. This may include treatment of eyes either simultaneously or sequentially. Simultaneous treatment may mean that the treatment is administered to each eye at the same time or that both eyes are treated during the same visit to a treating physician or other healthcare provider. It has been documented that patients have a higher risk of developing AMD in a healthy fellow eye of an eye that presents symptoms of AMD, or in patients who have a genetic predisposition toward developing AMD. The present disclosure can be used as a prophylactic treatment in prevention of AMD in the fellow eye.

While the mechanism underlying the increased risk for the progression of ocular neovascular disease in a fellow eye is unknown, there are multiple studies in the art detailing this elevated risk. For example, in one such large scale study, of 110 fellow eyes observed that progressed to advanced AMD, choroidal neovascularization (CNV) developed in 98 eyes and foveal geographic atrophy (GA) in 15 eyes. *Ophthalmologica.* 2011; 226(3):110-8. doi: 10.1159/000329473. Curr Opin Ophthalmol. 1998 June; 9(3):38-46. No nonocular characteristic (age, gender, history of hypertension or smoking) or ocular feature of the study eye at baseline (lesion composition, lesion size, or visual acuity) was predictive of progression to advanced AMD in this cohort. However, statistical analysis indicates that AMD symptoms of the first eye, including drusen size, focal hyperpigmentation, and nonfoveal geographic atrophy had significant independent relationships in assessing risk of developing of AMD in the fellow eye. Recent studies have indicated that of ocular characteristics, genetic factors and certain environmental factors may play a role in the increased risk of developing AMD in the fellow eye. JAMA Ophthalmol. 2013 Apr. 1; 131(4):448-55. doi: 10.1001/jamaophthalmol.2013.2578. Given the well characterized elevated risk of AMD development in untreated fellow eyes, there is need in the art of methods for preventing onset and subsequent vision loss due to the disease.

The term "subject," or "individual" or "patient" as used herein in reference to individuals having a disease or disorder or are suspected of having a disease or disorder, and the like. Subject, individual or patent may be used interchangeably in the disclosure and encompass mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some aspects of the methods and compositions provided herein, the mammal is a human.

The term "subject" or "individual" also includes humans suffering from the disorder or disease, age 20 and older. Unexpectedly, the present disclosure can be used in a range of patient ages. This includes younger patients not generally associated with AMD disease, which presents more frequently in patients over the age of 65. Human subjects, or patients of the disclosure may include ages at least about 20, 25, 30, 35, 40, 45, 50, 55, 60, 65, 70, 75, 80, 85, 90, 95 or 100. Human subjects, or patients of the disclosure may include ages at most about 20, 25, 30, 35, 40, 45, 50, 55, 60, 65, 70, 75, 80, 85, 90, 95 or 100.

In some aspects, the term "subject," or "individual" includes patients with varying responses to penicillin, such as resistance or sensitivity to its effects or patients who show or lack symptoms of allergic response to the drug.

A. Method of Delivery

In some aspects, the pharmaceutical composition is administered to subretinal sites using any direction method. In some cases, the delivery method may be by injection, such as those described in US Pat Pub. No. 2010008170, which is incorporated by reference in its entirety. In some cases, direct administration to subretinal sites includes injection of a liquid pharmaceutical composition via syringe. In another example, direct administration may involve injection via a cannula or other suitable instrument for delivery for a vector or recombinant virus. In other examples, direct administration may comprise an implant further comprising a suitable vector for delivery of transgenes such as sFLT-1. In some cases the implant may be either directly implanted in or near the retina.

The central retina, macula, and fovea regions of the retina are unique amongst mammals to primates. Furthermore, there are distinct differences in the anatomy and subsequent pathogenesis of AMD between primate and humans. The central retina is the area of the retina surrounding the posterior pole between the vascular arcades of a primate eye, which includes the fovea, macula, and surrounding area. The macula is near the center of the retina and has a diameter of approximately 1.5 mm. This area contains the highest concentration of both rod and cone photoreceptors. At the center of the macula is the fovea, a small pit that contains the largest concentration of cone photoreceptors. The macula and fovea regions of the retina also contain underlying RPE cells. These regions of the retina are responsible for perception of fine detail (acuity) and color. As this region is responsible for the most important part of human vision (fine vision), safe and effective targeting of the vector to the subretinal space of the macula and fovea is desired. In some cases, a pharmaceutical composition of the disclosure is administered in the central retina. In some cases, it is administered in the central retina outside the fovea.

Briefly, the general method for delivering a vector to the subretinal space of the macula and fovea may be illustrated by the following brief outline. This example is merely meant to illustrate certain features of the method, and is in no way meant to be limiting.

Generally, the vector can be delivered in the form of a suspension injected intraocularly (subretinally) under direct observation using an operating microscope. This procedure may involve vitrectomy followed by injection of vector suspension using a fine cannula through one or more small retinotomies into the subretinal space.

Briefly, an infusion cannula can be sutured in place to maintain a normal globe volume by infusion (of e.g. saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g. saline) creates space to accommodate the intraocular injection of vector, and (3) its controlled removal reduces the possibility of retinal tears and unplanned retinal detachment.

In some aspects, the vector is directly injected into the subretinal space within the central retina, by utilizing a cannula of the appropriate bore size (e.g. 27-45 gauge), thus creating a bleb in the subretinal space. In other aspects, the subretinal injection of vector suspension is preceded by subretinal injection of a small volume (e.g. about 0.1 to about 0.5 ml) of an appropriate fluid (such as saline or Ringer's solution) into the subretinal space within the central retina. This initial injection into the subretinal space establishes an initial fluid bleb within the subretinal space, causing localized retinal detachment at the location of the initial bleb. This initial fluid bleb can facilitate targeted delivery of vector suspension to the subretinal space (by defining the plane of injection prior to vector delivery), and minimize possible vector administration into the choroid and the possibility of vector injection or reflux into the vitreous cavity. In some aspects, this initial fluid bleb can be further injected with fluids comprising one or more vector suspensions and/or one or more additional therapeutic agents by administration of these fluids directly to the initial fluid bleb with either the same or additional fine bore cannulas.

Intraocular administration of the vector suspension and/or the initial small volume of fluid can be performed using a fine bore cannula (e.g. 27-45 gauge) attached to a syringe. In some aspects, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (within the central retina). In one aspect, administration is performed to a site outside the fovea. Under direct visualization the vector suspension is injected mechanically under the neurosensory retina causing a localized retinal detachment with a self-sealing non-expanding retinotomy. As noted above, the vector can be either directly injected into the subretinal space creating a bleb within the central retina or the vector can be injected into an initial bleb within the central retina, causing it to expand (and expanding the area of retinal detachment). In some aspects, the injection of vector suspension is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. In some aspects, the vector is injected over about 15-17 minutes. In some aspects, the vector is injected over about 17-20 minutes. In some aspects, the vector is injected over about 20-22 minutes. In some aspects, the vector is injected over about 1 minute or over about 1-3 minutes or in less than one minute. In some aspects, the vector is injected at a rate of about 35 to about 65 µl/min or 65 µl/min to about 150 µl/min. In some aspects, the vector is injected at a rate of about 35 µl/min. In some aspects, the vector is injected at a rate of about 40 µl/min. In some aspects, the vector is injected at a rate of about 45 µl/min. In some aspects, the vector is injected at a rate of about 50 μl/ml. In some aspects, the vector is injected at a rate of about 55 μl/min. In some aspects, the vector is injected at a rate of about 60 μl/ml. In some aspects, the vector is injected at a rate of about 65 μl/min. In some aspects, the vector is injected at a rate of about 100 μl/min. One of ordinary skill in the art would recognize that the rate and time of injection of the bleb may be directed by, for example, the volume of the vector or size of the bleb necessary to create sufficient retinal detachment to access the cells of central retina, the size of the cannula used to deliver the vector, and the ability to safely maintain the position of the cannula of the disclosure.

One or multiple (e.g. 2, 3, or more) blebs can be created. Generally, the total volume of bleb or blebs created by the methods and systems of the disclosure cannot exceed the fluid volume of the eye, for example about 4 ml in a typical human subject. The total volume of each individual bleb is preferably at about 0.1-0.2 ml. One of ordinary skill in the art will appreciate that in creating the bleb according to the methods and systems of the disclosure that the appropriate intraocular pressure must be maintained in order to avoid damage to the ocular structures. The size of each individual bleb may be, for example, about 50 μl to about 100 μl, about 50 μl to about 200 μl, about 0.1 to about 0.2 ml, about 0.1 to about 0.3 ml, or >0.3 ml.

In order to safely and efficiently transduce areas of target retina (e.g. the central retina) outside the edge of the original location of the bleb, in some cases it may be desirable to manipulate the bleb to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area generally resists detachment by subretinal injection.

In some aspects fluid-air exchange is utilized following subretinal injection; fluid from the infusion cannula is temporarily replaced by air, e.g. from blowing air onto the surface of the retina. As the volume of the air displaces saline fluid from the vitreous cavity, the bleb is kept in place without efflux into the vitreous cavity. By positioning the eye globe appropriately, the bleb of subretinal vector in some cases can be manipulated to involve adjacent areas (e.g. the macula and/or fovea). In some cases, the mass of the bleb is sufficient to cause it to gravitate, even without use of the fluid-air exchange. Movement of the bleb may be further be facilitated by altering the position of the human subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal vector may be left in situ without retinopexy to the retinotomy and without intraocular tamponade, and the retina will spontaneously reattach within about 48 hours.

Subretinal administration of AAV-2 for treatment of an ocular disease has been demonstrated in treatment of the rare genetic disease, Leber's Congenital Amaurosis ("LCA"). The pathology of LCA and the LCA patient population are different from those of wet-AMD and therefore it was not expected that treatment of wet AMD with gene therapy, and in particular, with AAV-2, would be safe and effective prior to the rAAV.sFLT clinical study. Specifically, LCA is a degenerative genetic disease caused by insufficient expression of the retinal protein RPE-65. It causes slow deterioration of vision in babies and young children that leads to total blindness by young adulthood, generally prior to age 25 to 30. By contrast, as described here previously, wet AMD is caused by growth of new blood vessels in the retina late in life, generally beginning between age 65-75. The presence of new vessels raises the concern that AAV particles, the transgene or the transgene product, would be transported outside the eye in greater amounts than was shown in the LCA study. Additionally, the immune system and immune response to foreign substances changes as patients age creating uncertainly prior to study results disclosed in Example 12 that treatment of wet AMD with a viral vector such as rAAV.sFLT-1 would be safe and effective.

B. Effect of Treatment

In some aspects, a single injection of the pharmaceutical composition of the present disclosure into the affected eye not only has the benefits of the Lucentis® treatment, but may also require only one single injection.

The pharmaceutical composition of the present disclosure can stop leakage in existing blood vessels and can inhibit further new vessel formation in the subretinal space of patients suffering from CNV secondary to AMD for at least 18 months, and in some aspects the activity continues for 3-5 years. Inhibition of leakage and new vessel formation prevents the development of blindness in affected patients.

In some aspects, the sFLT-1 protein levels in the vitreous of said human subject is about 500-5,000 pg/ml, about 600-4,000 pg/ml, about 800-3,000 pg/ml about 900-2,000 pg/ml, or about 1,000-1,800 pg/ml, 500-700 pg/ml, 700-1,000 pg/ml, 1,000-1200 pg/ml, 1200-1,500 pg/ml, 1,800-2000 pg/ml. In some cases, protein levels in the vitreous of the human subject is at least about 100, 200, 300, 400, 500, 600, 700. 800, 900, 1000, 1100, 1200, 1300, 1400, 1500, 1600, 1700, 1800, 1900, 2000, 2100, 2200, 2300 or 2400 pg/ml. In some cases, protein levels in the vitreous of the human subject is at most about 100, 200, 300, 400, 500, 600, 700, 800, 900, 1000, 1100, 1200, 1300, 1400, 1500, 1600, 1700, 1800, 1900, 2000, 2100, 2200, 2300 or 2400 pg/ml.

In some cases, protein "levels" may refer to any quantity or relative quantity of protein. In some cases, level may be measured as a concentration (e.g. pM, nM, uM etc.), a molality (e.g. m), as a mass (e.g. pg, ug, ng etc.) or any suitable measurement. In some cases, a unitless measurement may indicate a level.

In some cases, protein levels may be measured at least about 0.1, 0.2, 0.3, 0.4, 0.5, 0.6, 0.7 0.8, 0.9, 1.0, 2, 3, 4, 5, 6, 7, 14, 21 or 30, 50, 75, 100, 125, 150, 175, 200, 225, 250, 275, 300, 325, 350 or 365 days after administering said pharmaceutical composition. In some cases, protein levels may be measured at most about 0.1, 0.2, 0.3, 0.4, 0.5, 0.6, 0.7 0.8, 0.9, 1.0, 2, 3, 4, 5, 6, 7, 14, 21 or 30, 50, 75, 100, 125, 150, 175, 200, 225, 250, 275, 300, 325, 350 or 365 days after administering said pharmaceutical composition. In some cases, protein levels are measured at least 72 hours after administering said pharmaceutical composition.

Administration of the pharmaceutical composition of the present disclosure general leads to no side effects or adverse events.

In some aspects, no vector is detected in the human subject's tear, blood, saliva or urine samples 7, 14, 21 or 30 days after administering said pharmaceutical composition. In some aspects, the presence of the viral vector is detected by qPCR or ELISA as known in the art.

In some cases, no vector is detected in the human subject's tear, blood, saliva or urine samples at least about 0.1, 0.2, 0.3, 0.4, 0.5, 0.6, 0.7 0.8, 0.9, 1.0, 2, 3, 4, 5, 6, 7, 14, 21 or 30, 50, 75, 100, 125, 150, 175, 200, 225, 250, 275, 300, 325, 350 or 365 days after administering said pharmaceutical composition. In some cases, no vector is detected in the human subject's tear, blood, saliva or urine samples at most about 0.1, 0.2, 0.3, 0.4, 0.5, 0.6, 0.7 0.8, 0.9, 1.0, 2, 3, 4, 5, 6, 7, 14, 21 or 30, 50, 75, 100, 125, 150, 175, 200, 225, 250, 275, 300, 325, 350 or 365 days after administering said pharmaceutical composition. In some cases, no vector is detected in the human subject's tear, blood, saliva or urine samples are measured at least 72 hours after administering said pharmaceutical composition.

In some aspects, the human subject shows no clinically significant retinal toxicity as assessed by serial ophthalmic examinations over at least about a 2, 3, 4, 5, 6, 7, 8, 9, 10, 11 or 12 month months period. In some aspects, the human subject shows no clinically significant retinal toxicity as assessed by serial ophthalmic examinations over at most about a 2, 3, 4, 5, 6, 7, 8, 9, 10, 11 or 12 month months period.

In some aspects, no superficial, anterior segment or vitreous inflammatory signs are present in the human subject over least a two months period. In some cases, no superficial, anterior segment or vitreous inflammatory signs are present in the human subject at 1 week or at 3, 6, 9 or 12 months after administration of the pharmaceutical composition.

In some aspects, no inflammatory signs are seen including a cytotoxic T cell response within about a 10% of normal range following administering step. In some aspects, there is no increase in T-cell response as measured by ELISpot. In some aspects, T cells do not express HLA-DR or Ki67, and do not develop an activated effector phenotype, as described in Lai et al. 2011; *Gene Therapy*, which is herein incorporated by reference in its entirety. In some aspects, no inflammation of the vitreous is observed by biomicroscopy (BE) and indirect ophthalmoscopy (IOE) following the administering step. In some aspects, trace inflammation of the vitreous that resolved within 10 days is observed by biomicroscopy (BE) and indirect ophthalmoscopy (IOE) following the administering step. In some aspects, the human subject does not require rescue treatment at least 120 days post administration. In some aspects, the human subject does not require rescue treatment for at least 30 days, at least 60 days, at least 90 days, at least 120 days at least 180 days, at least 270 days or at least 365 days after administration.

As used herein, rescue treatment refers to an administration of a dose of a VEGF inhibitor after the initial administration of the pharmaceutical composition described in the present disclosure. A rescue treatment is administered to boost the amount of VEGF inhibition in the eye patient in order to arrest or reverse signs and symptoms of disease progression. The decision to administer a rescue treatment may be based on predetermined diagnostic criteria, as in the clinical study described in Example 12, or on a physician's clinical judgment that signs of active disease are present in a patient.

In some aspects, there is no evidence of visual acuity loss, IOP elevation, retinal detachment, or any intraocular or systemic immune response in said human subject at least 120 days post administration. In some aspects, there is no evidence of visual acuity loss, IOP elevation, retinal detachment, or any intraocular or systemic immune response in said human subject at least 30 days, at least 60 days, at least 90 days, at least 120 days at least 180 days, at least 270 days or at least 365 days after administration. In some aspects, there is no evidence of visual acuity loss, IOP elevation, retinal detachment, or any intraocular or systemic immune response in said human subject at most 30 days, at least 60 days, at least 90 days, at least 120 days at least 180 days, at least 270 days or at least 365 days after administration.

In some aspects, a patient's best corrected visual acuity (BCVA) improves by 1, 2 3, 4, 5 or more lines.

In some aspects, a reduction in neovascularization as assessed by Fluorescein Angiography (FA) follows the administering step.

In some cases, retinal thickness may be measured to examine the effects of treatment. In some cases, the central retinal thickness of the human subject does not increase by more than 50 microns, 100 microns, or 250 microns within 12 months following treatment with the pharmaceutical composition of the disclosure. In some cases, the central retinal thickness of the human subject decreases by at least 50 microns, 100 microns, 200 microns, 250 microns, 300 microns, 400 microns, 500 microns, 600 microns within 3 months, 6 months or 9 months 12 months following treatment with the pharmaceutical composition of the disclosure. The decrease in the central retinal thickness of the human subject may be measured comparing the central retinal thickness at point in time to a baseline measurement taken at or within 1, 3, 7 or 10 days of the administration of the pharmaceutical composition of the disclosure.

C. Combination Treatment with VEGF Inhibitors

In some aspects, the method further comprises administering to the human subject a pharmaceutically effective amount of a VEGF inhibitor.

In some aspects, the VEGF inhibitor comprises an antibody against VEGF or a functional fragment thereof. In some aspects, the VEGF inhibitor comprises ranibizumab. In other aspects the VEGF inhibitor is a soluble receptor, fusion protein, or fragment thereof, such as aflibercept or sFLT01. In some aspects, the pharmaceutical composition is administered at least 1, 2, 3, 4, 5, 6, 7, or 8 days after the administering of said VEGF inhibitor. In some aspects, the pharmaceutical composition is administered at most 1, 2, 3, 4, 5, 6, 7, or 8 days after the administering of said VEGF inhibitor. In some aspects, the pharmaceutical composition is administered within 90 days after the administering of said VEGF inhibitor.

In some aspects, the patient is treated under a protocol such as outlined in FIG. 13. After the protein expressed by the recombinant virus is expressed at a suitable level, (or "on"), the patients are followed with criteria-based re-treatment:

If disease recurs, ranibizumab re-treatment is allowed

Expect 5-8 re-treatments per year with control group

In treatment group, expect equivalent vision with substantial decrease in number of re-treatments.

The patient is eligible for re-treatment if signs of active CNV are present:

Based upon objective criteria as evaluated by masked personnel (technician and ophthalmologist)

Re-treatment criteria are based upon substantial experience with "as needed" (PRN) treatment in previous trials with anti-VEGF agents.

Re-treatment is warranted based on signs of active disease; such as:

>10 Early Treatment Diabetic Retinopathy Study (ETDRS) letter loss from human subject's previous visit (attributable to retinal causes), OR a decrease of >5 ETDRS letters from previous visit in conjunction with patient perception of functional loss;

Any increased, new, or persistent subsensory, sub-Retinal Pigment Epithelial (RPE), or intraretinal fluid on OCT; Signs of increased CNV leakage via FA.

In some aspects, the VEGF inhibitor is administered for at least 1 time prior to administering the said pharmaceutical composition and an additional 1 or 2 times at about 30 day intervals following said administration to prevent disease progression while protein expression increase to suitable levels. In some aspects, the VEGF inhibitor is administered for at least 2 times prior to administering said pharmaceutical composition. In some aspects, the VEGF inhibitor is administered over a period of 6 to 7 weeks following administration of said pharmaceutical composition.

In some aspects, the frequency of administration of VEGF inhibitor is reduced by less than a year or stopped altogether.

In some aspects, the present disclosure is used after 3 or more treatments of VEGF inhibitors. In some aspects, the present disclosure is used after observation that AMD patients show no improvement in BCVA after use of other VEGF inhibitors.

D. Other Combination Treatments

In another preferred aspect, treatment of a patient comprises administration one or more of the pharmaceutical compositions provided herein, in conjunction with other therapies, for example, chemotherapy, radiation, surgery, anti-inflammatory agents, selected vitamins and the like. The other agents can be administered, prior to, after or co-administered with the pharmaceutical compositions.

Aspects of the disclosure may be practiced without the theoretical aspects presented. Moreover, the theoretical aspects are presented with the understanding that Applicants do not seek to be bound by the theory presented.

While preferred aspects of the present disclosure have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein may be employed in practicing the disclosure. It is intended that the following claims define the scope of the disclosure and that methods and structures within the scope of these claims and their equivalents be covered thereby.

The effective dose of the nucleic acid will be a function of the particular expressed protein, the particular disease to be targeted, the patient and his or her clinical condition, weight, age, sex, etc.

EXAMPLES

It will be understood by those of skill in the art that numerous and various modifications can be made to yield essentially similar results without departing from the spirit of the present disclosure. All of the references referred to herein are incorporated by reference in their entirety for the subject matter discussed. The following examples are included for illustrative purposes only and are not intended to limit the scope of the disclosure.

It must be explained, if not specified, that the percentage of following examples are all weight percent content wt %.

Example 1 rAAV.sFlt-1

One example recombinant virus is rAAV.sFlt-1. It encodes a vector and a human form of the truncated, soluble VEGF receptor 1 (sFLT-1). The vector is a recombinant, replicative-deficient adeno-associated viral (rAAV) vector, of serotype 2.

The rAAV.sFlt-1 was manufactured under Good Manufacturing Practices (cGMP). At the manufacture site, the final product was aliquoted into sterile, low-virus-binding microcentrifuge tubes (individually wrapped, low-retention, sterilised flat cap vials) according to the protocol requirements (i.e. 200 µl of $1\times10^{10}$ or $1\times10^{11}$ viral genomes) and stored at $-80°$ C. to await final product release. Each vial contained enough vector for use in a single patient (100 µl to be administered).

The recombinant virus, rAAV.sFlt-1, is a recombinant adeno-associated virus 2 (rAAV2) vector carrying the soluble VEGFR receptor 1 (VEGFR1) or sFLT-1 driven by the human cytomegalovirus (CMV) promoter. The rAAV.sFlt-1 vector and intact AAV2 genome used as the backbone was prepared as described in Lai et. al. Gene Therapy 2002 vol. 9 (12) 804-813). The rAAV2 vector is devoid of viral coding sequences, i.e., rep and cap have been replaced with an expression cassette for the therapeutic gene. The active moiety of rAAV.sFlt-1 is sFlt-1. sFLT-1 is the soluble truncated form of the vascular endothelial growth factor receptor 1 (VEGFR1 or Flt-1) which occurs naturally. sFLT-1 is the only known endogenous specific inhibitor of VEGF. sFLT-1 is generated by alternative splicing and it lacks the membrane-proximal immunoglobulin-like domain, the transmembrane spanning region and the intracellular tyrosine-kinase domain. Hence, it contains only the first six extracellular immunoglobulin-like loops followed by 31 unique amino acid residues. sFLT-1 was first identified in human umbilical vein endothelial cells (HU-VEC), but it has since been found to occur naturally in the placenta and circulating systematically in pregnant women. The sFLT-1 used in generating rAAV.sFlt-1 contains an open reading frame encoding only the first six extracellular immunoglobulin-like domains of the full length membrane-spanning FLT-1, followed by a unique 31-amino acid long C-terminal extension, representing the alternatively splices, secreted soluble FLT-1 isoform described earlier.

While the ITR has been shown to possess mild promoter activity, for maximum levels of transgene expression, the cassette generally includes a promoter/enhancer combination, a small intron sequence, the cDNA of the therapeutic gene, and a polyadenylation signal. In rAAV.sFlt-1, the human CMV major immediate early gene enhancer/promoter and a chimeric intron were placed upstream of the sFLT-1 cDNA. A simian virus 40 polyadenylation (SV40 poly A) signal was placed downstream of the sFLT-1 cDNA.

Binding of sFLT-1 to VEGF in vitro has been widely demonstrated. The ability of sFLT-1 to inhibit VEGF-driven angiogenesis has attracted considerable attention for its potential clinical application, but no evidence of efficacy or suitability in humans was shown prior to the clinical study of rAAV.sFlt-1 described in Example 12. The angiostatic activity of sFLT-1 results from inhibition of VEGF by two mechanisms: i) sequestration of VEGF, to which it binds with high affinity, and ii) formation of inactive heterodimers with membrane-spanning isoforms of the VEGF receptors Flt-1 and KDR/Flk-1.

Nucleotide Sequence and Diagram of Plasmid Vector Used to Generate rAAV.sFlt-1 rAAV.sFlt-1 was generated by triple transfection of human embryonic kidney 293 cells with DNA from the pSSV.CI.hsFlt-1 plasmid vector and helper plasmids, as is known in the art (Xiao et al., 1998. J Virology, 72(3): 2224-2232). rAAV.sFlt-1 was purified using a sequential process of nuclei isolation, density gradient centrifugation and heparin sulfate affinity column chromatography. A diagrammatic representation of the sFLT-1 plasmid vector is given in FIG. 1.

Formulation rAAV.sFlt-1 was formulated in sterile phosphate buffered saline (pH7) at 2 concentrations: 1×1010 vector genome/100 μL (low dose) and 1×1011 vector genome/100 μL (high dose) in sterile low-virus-binding microcentrifuge tubes. The formulation is preservative-free and is for one-thaw, single use by subretinal injection only.

rAAV(bv).sFlt-1

A second example recombinant virus is rAAV(bv).sFlt-1. rAAV(bv).sFlt-1 is a recombinant, replicative-deficient adeno-associated viral (rAAV) vector, of serotype 2 that is produced using a baculovirus expression system (BEVS) in Sf9 insect cells, and encodes a human form of the truncated, soluble VEGF receptor 1 (sFLT-1). The vector was produced using infection in Sf9 cells with two recombinant baculoviruses, Bac-inRep-inCap and Bac-sFlt-1. Bac-sFlt-1 was derived from bacmid DNA that was generated from transformation of electrocompetent cells with an 8.7 kb plasmid, AVA01-pFB-CMV-sFlt, which was cloned from the Frag001m-BHKan and the plasmid backbone V109-pFB-AAV-CMV-SV40 pA-Kan using standard molecular biology techniques, as described in Maniatis et al., and as further described below. Frag001m was formed from the following sequential nucleic acide elements which were chemically synthesized by Blue Heron Biotech, LLC (Bothell, Wash.) and cloned into a BHKan backbone: an ITR (AAV serotype 2), CMV-IE promoter, chimeric intron, 5' untranslated region (UTR), sFlt-1 coding sequence, SV40 polyA region, ITR (AAV serotype 2). The plasmid V109-pFB-AAV-CMV-SV40pA-Kan was obtained from Virovek, Inc. (Hayward, Calif.). The plasmid contained a kanamycin antibiotic resistance gene, a ColE1 origin and a recombinant AAV cassette, which contained a CMV-IE promoter, an intron, multiple cloning sequences and a SV40 polyA region, flanked by inverted terminal repeats (ITRs) from AAV serotype 2. This rAAV cassette was flanked by a gentamicin resistance gene and Tn7L attachment sites. AVA01-pFB-CMV-sFlt did not contain a T7 RNA polymerase promoter or other prokaryotic regulatory sequence. Bac-inRep-inCap is a recombinant baculovirus containing expression cassettes for rep and cap genes from AAV serotype 2.

rAAV(bv).sFlt-1 Production in Baculovirus rAAV(bv).sFlt-1 was produced in baculovirus according to the methods described in U.S. patent application Ser. No. 12/297,958 and more specifically as follows: Sf9 cells were grown at 28° C. to about 107 cells/ml in SF900 II SFM media containing 100 units/ml of penicillin and 100 μg/ml streptomycin, and diluted to about 5×106 cells/ml prior to infection. Bac-inRep-inCap and Bac-sFlt-1, each at m.o.i. of one were used to infect the cells at 28° C. for 3 days to produce AAV type 2 vectors. After 3 days of infection, cell pellets were collected by centrifugation at 2,000 rpm for 15 min in a tabletop centrifuge. The cell pellets were lysed in lysis buffer as described by Urabe et al., Hum Gene Ther. 1; 13(16):1935-43 (2002) and cellular nucleic acids (DNA and RNA) were digested by benzonase (Sigma, St. Louis, Mo.). The cell lysates were cleared by centrifugation at 8,000 rpm for 30 min in an Avanti J-25 centrifuge (Beckman, Fullerton, Calif.) and then loaded onto an SW28 centrifuge tube containing 5 ml of 1.55 g/cc, and 10 ml of 1.32 g/cc of CsCl solutions. After centrifugation at 28,000 rpm for about 16 hours at 15° C., the rAAV-containing fraction was collected by puncturing the centrifuge tube using a syringe needle and subjected to a second round of CsCl ultracentrifugation. The rAAV-containing fraction was collected again by puncturing the centrifuge tube using a syringe needle and dialyzed in PBS buffer to remove the salts and detergents. Vector titers were determined by quantitative real-time PCR assay according to manufacturer's protocol (Applied Biosystems, Foster City, Calif.).s

Example 2

In Vitro Inhibition of VEGF-Induced Endothelial Cell Proliferation

Studies were performed to assess VEGF-induction of human umbilical vein endothelial cell (HUVEC) proliferation and to determine whether VEGF-induced HUVEC proliferation would be inhibited by rAAV-mediated sFLT-1. The presence of sFLT-1 in transduced cells was first confirmed by Western blot analysis of conditioned media (FIG. 2, panel a). Conditioned medium from rAAV.sFlt-1-transduced and rAAV.gfp-transduced 293 cells were added to VEGF-treated HUVECs in increasing dilutions. A control starvation medium (normal HUVEC growth medium without bovine endothelial growth factor) only was also included. Heparin was added to each well at 100 μg/mL. The relative VEGF-induced proliferation of HUVECS treated with VEGF and the different conditioned media was assayed by addition 25 μL of 3-(4,5-dimethylthiazol-2-yl)-2,5-diphenyltetrozolium bromide (MTT, 5 mg/mL, Sigma) to each well for 4 hours at 37° C. The secreted sFLT-1 encoded by the rAAV vector in 40 μL of conditioned medium from rAAV.sFlt-1-transduced 293 cells was confirmed to inhibit VEGF-induced proliferation of HUVECS by 32%. Doubling the volume of conditioned medium resulted in complete inhibition with cell growth equivalent to basal levels similar to culture in starvation medium (FIG. 2, panel b).

In Vitro Assessment of rAAV.sFt-1 Vector Potency

Studies were performed to assess the potency of AAV vectors encoding the recombinant human sFlt-1 gene by quantifying human sFlt-1 protein expression of transduced human embryonic kidney 293 (HEK293) cells by ELISA. Human embryonic kidney 293 cells were obtained from the American Type Culture Collection (Rockville, Md., USA) and cultured in Dulbecco's Modified Eagle Medium (DMEM; Gibco, Grand Island, N.Y., USA) with 10% Fetal bovine serum (FBS, GIBCO) and 1× Penicillin-Streptomycin-Glutamine. All cultures were maintained at 37° C. and 5% CO2 in a humidified atmosphere.

The HEK293 cells were seeded at 8E4 or 1.5E5 cells/24 well and transduced at 60-90% confluency with the recombinant AAV vectors at a multiplicity of infection (MOI) ranging from 1×10³-1×10⁶ in DMEM medium supplemented with 2% FBS. After 72 hours, post-transduction, conditioned media were collected. Aliquots of the conditioned media were prepared for ELISA using reagents and according to standard instructions from the R&D Systems SVR100B Quantikine ELISA Human sVEGF R1/sFlt-1 kit. (R&D Systems, Minneapolis, Minn.). Samples, standards and controls were prepared according to the ELISA kit instructions with the R&D Systems ELISA reagents and then transferred to an ELISA plate pre-coated with an antibody to sVEGF R1/sFlt-1 and incubated for two hours at room temperature on a horizontal orbital microplate shaker. After incubation, anti-sVEGF R1 Conjugate (two hours), substrate solution (30 minutes) and stop solution were sequentially applied to each well with aspiration and wash steps between each according to standard ELISA assay procedures. The optical density (OD) of the samples, standards and controls was measured within 30 minutes of stopping the substrate reaction with an ELISA plate reader. The concentration of sFlt-1 in pg/mL was calculated using SoftmaxPro software using the OD measurements from the ELISA plate reader.

Figure 25A:
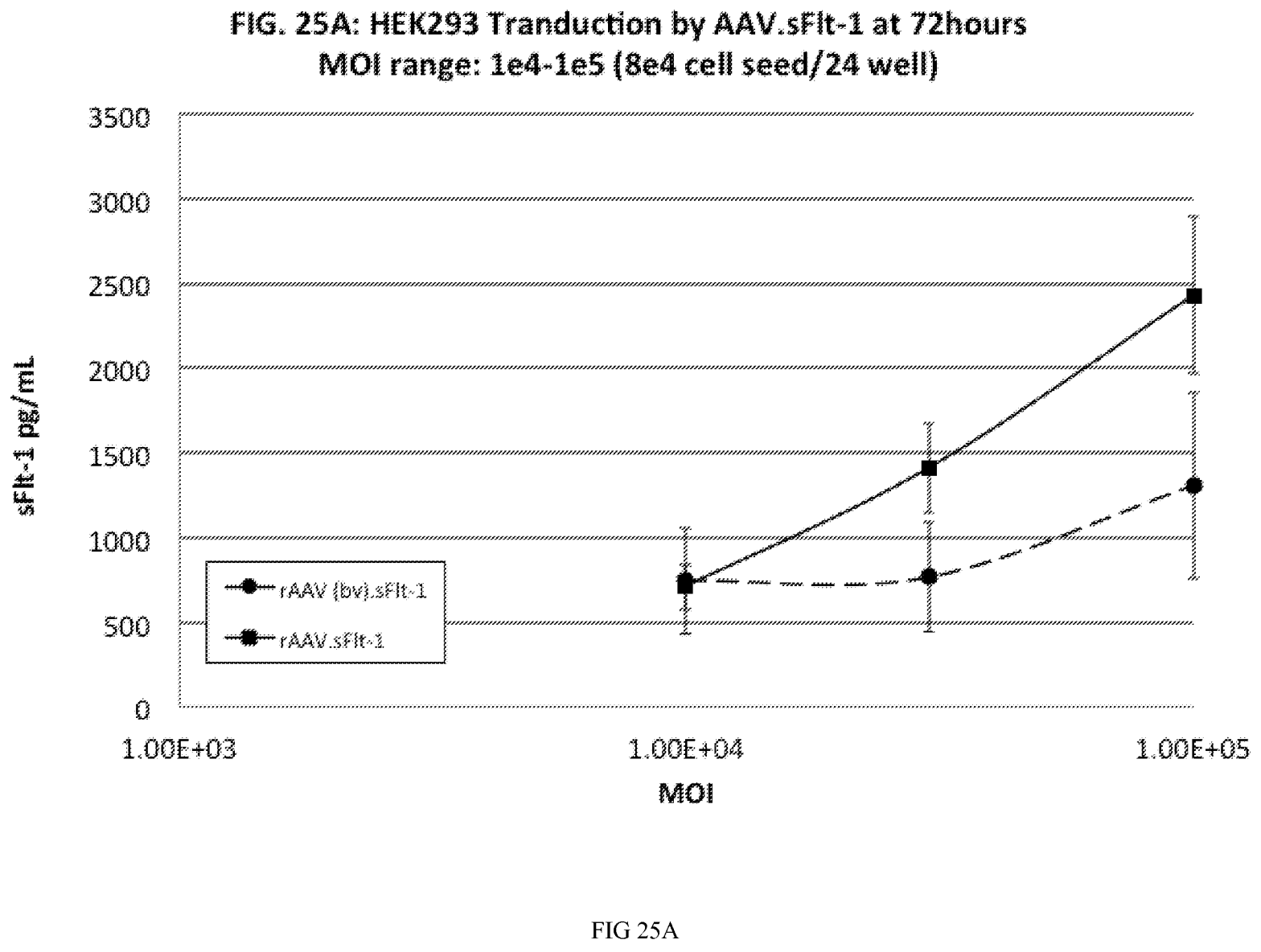
Figure 25B:
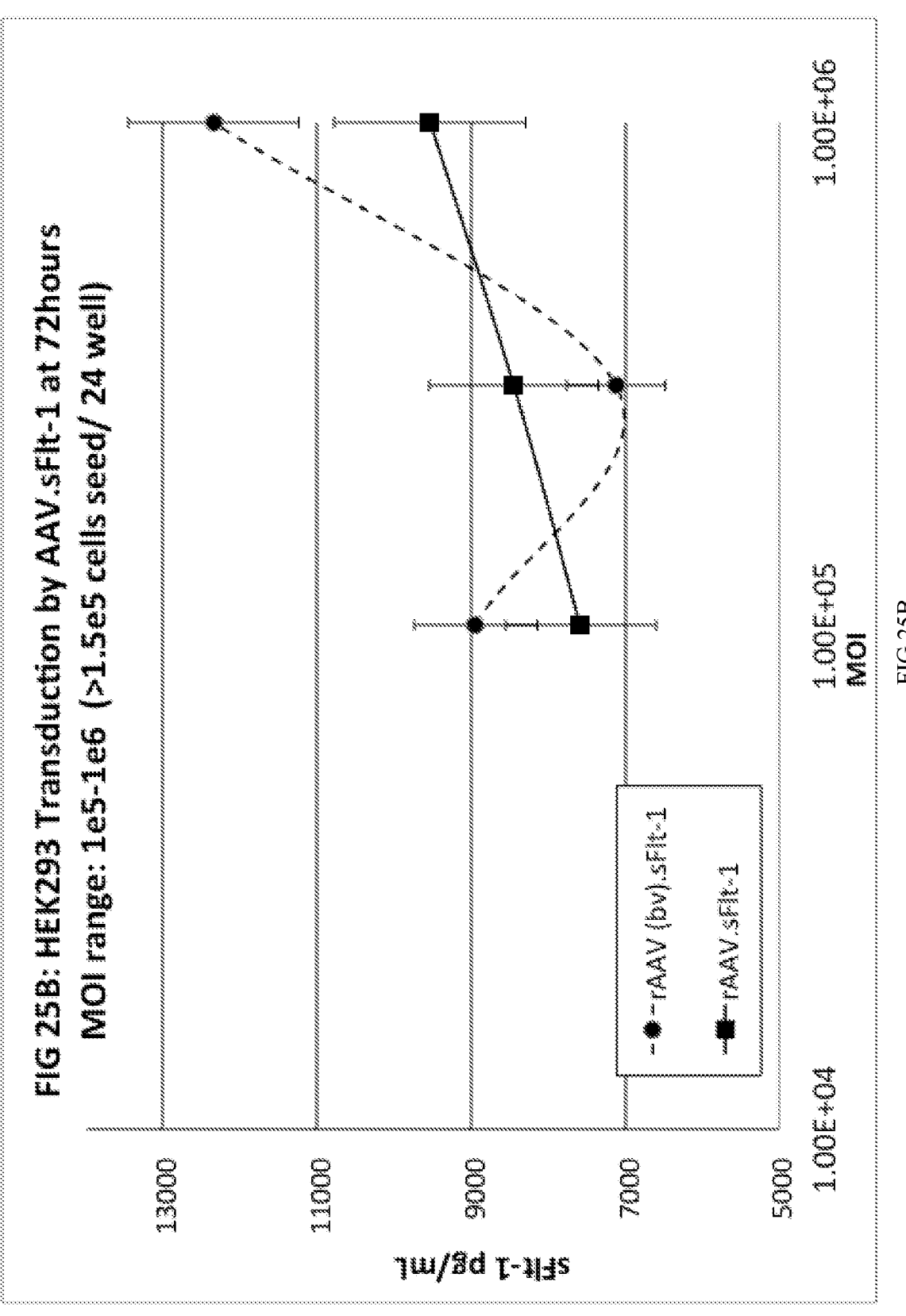

Results of the studies for rAAV.sFlt-1 and rAAV(bv) .sFlt-1 are presented in FIG. 25A and FIG. 25B. The concentration of sFlt-1 protein expressed by HEK293 cells 72 hours after transduction with rAAV.sFlt-1 and rAAV(bv) .sFlt-1 ranged from 100-1,000 pg/mL at an MOI of $1 \times 10^4$, 100-10,000 pg/mL at an MOI of $1 \times 10^5$ and 1,000-10,000 pg/mL at an MOI of $1 \times 10^6$.

Example 3 rAAV.sFlt-1 Studies in Mice

Transgenic mice (trVEGF029) with slow, but stable retinal neovascularization induced by transgenic expression of human VEGF from photoreceptor cells were used as a model for retinal neovascularization. Two separate studies with these mice have been conducted.

In the first mouse study, 13 transgenic mice were assessed for ocular neovascular changes before and after administration of the rAAV.sFlt-1 vector ($1 \times 10^{11}$ vector particles) in one eye and control vector in the contralateral eye. Eyes were assessed for neovascular changes using fluorescein angiography at one, three and eight months after injection. The extent, intensity and stage of neovascularization were graded (0-4) by three observers, masked to the treatment received in the eyes examined. There was a statistically significant overall reduction in the neovascular grading from a median grade of '3' (before injection) to a median grade of '1' at one month after injection (P=0.012). This reduction was maintained at three months (median=1; P=0.001) and at eight months (median=1; P=0.001) after injection with rAAV.sFlt-1. Injection of rAAV.sFlt-1 vector resulted in the long-term (at least eight months) regression of neovascular vessels in 85% (11 of 13) of treated eyes compared to 8% (1 of 13) in the control vector-treated eyes.

Histological examination of the eyes in this preclinical study revealed that disturbance or loss of photoreceptors was significantly (P<0.01) more pronounced in control vector-injected eyes compared to eyes injected with rAAV.sFlt-1. Expression of sFLT-1 was also confirmed by reverse transcriptase-polymerase chain reaction analysis of tissue samples; mRNA for sFLT-1 was detected in all four eyes tested. No rAAV.sFlt-1 vector-specific adverse effects were noted in the eye injected with rAAV.sFlt-1 when compared to the eye injected with the control (rAAV.gfp) vector.

In the second study, conducted in trVEGF02 transgenic mice, the aim of the study was to determine whether subretinal injection of rAAV.sFlt-1 resulted in any cell-mediated immune responses that could negatively impact on long-term expression of sFLT-1 or cause immune response-associated damage to the retina. In this study, 50 trVEGF02 transgenic mice were given subretinal injections of rAAV.sFlt-1 (8×109 viral particles) or phosphate-buffered saline (PBS) in one eye. The retinas of 30 mice from either the rAAV.sFlt-1 or control treatment groups were then assessed at one week and one month post-injection for the presence of immune cells (leucocytes, macrophages and B- and T-lymphocytes). Flow cytometric examination of the posterior eye cup showed that at one week post-injection there was a statistically significant increase in CD45+ leucocytes (6.6-fold increase compared to control; P<0.05) and CD11b+ macrophages (5.7-fold increase compared to control; P<0.036). However, there were no differences in CD19+, CD8+ and CD4+ (B- and T-lymphocytes) at this time point. At one month post-injection, there were no differences in cell numbers between leucocyte subsets (i.e. CD45+, CD19+, CD11b+, CD8+ or CD4+ cells) in the mouse eyes treated with rAAV.sFlt-1 or the PBS control, suggesting that the infiltration of leucocytes and macrophages was transient. Flow cytometric evaluation of lymphocyte subsets of the spleens from these mice at the one-week and one-month time points showed no significant differences in the numbers of lymphocytes. This finding suggests that there was no systemic immune response observed, albeit a transient, localized immune response had been shown in the retina.

In this second study, histological examination of the eyes from five of the mice injected with either rAAV.sFlt-1 or PBS revealed no observable immune-response associated destruction or sequelae in the retinas of any of the mice examined.

To assess the impact of rAAV.sFlt-1 on the level of neovascularization in this transgenic mouse model (trVEGF02) of retinal neovascularization, the retinas of the mice injected with either rAAV.sFlt-1 or PBS were also graded independently by two different assessors at two months after treatment. Overall, there was a significant reduction in mean neovascularization grades (before injection: 1.46±0.58; after injection: 0.81±0.57; P<0.00015) in the rAAV.sFlt-1-injected eyes whereas there was a significant increase in mean neovascularization grades (before injection: 1.08±0.56; after injection: 1.63±0.96; P<0.018) in the PBS control-injected eyes.

The findings from this second mouse study clearly indicate that treatment with rAAV.sFlt-1 appeared to reverse the progressive increase in neovascularization observed in this mouse model of retinal neovascularization and AMD. Furthermore, only a limited, localized, inflammatory response was observed one week after subretinal injection with rAAV.sFlt-1 and resolved at one month. This immune response did not appear to compromise the long-term therapeutic efficacy of rAAV.sFlt-1 in the retina.

The transgenic mice models described in this Example 3 demonstrate that the pharmaceutical compositions disclosed herein can be used for the treatment and/or prophylaxis of other retinal vascular diseases in which VEGF inhibition is implicated. These include diabetic macular edema, diabetic retina ischemia, diabetic retinal edema, proliferative diabetic retinopathy, retinal vein occlusion, central retinal vein occlusion and branched retinal vein occlusion. In clinical studies some VEGF inhibitors, such as Lucentis, have been shown to effectively treat certain of these diseases including diabetic macular edema and retinal vein occlusion. The efficacy of rAAV.sFlt-1 demonstrated in these mouse models indicates rAAV.sFlt-1 is also effective in treating these VEGF mediated diseases.

Example 4 rAAV.sFlt-1 Study in Rats

In the rat rAAV.sFlt-1 study, two models of ocular neovascularization were used: cautery-induced corneal neovascularization and laser photocoagulation-induced choroidal neovascularization (CNV). In the corneal neovascularization model, 22 rats were injected with rAAV.sFlt-1 vector ($8 \times 10^8$ viral particles) in the anterior chamber of one eye and with control vector (rAAV.gfp) in the contralateral eye, followed by cauterization of the cornea. The eyes were then examined for neovascularization four days after cautery, using slit-lamp photography. A significantly lower rate of corneal vascularization was found in the rAAV.sFlt-1-treated eyes compared to the control-treated eyes (27% and 63%, respectively; P=0.009). Histological examination of the eyes showed that no corneal blood vessels were observed in the majority of cauterized, rAAV.sFlt-1-treated eyes. Histological examination also revealed that cellular infiltration of the corneal stromal layer was more pronounced in the control vector-injected eyes compared to the rAAV.sFlt-1-treated eyes. In addition, there was obvious edema and corneal stroma swelling in the control vector-treated eyes whereas there was no evidence of significant tissue swelling in rAAV.sFlt-1-treated eyes.

In the laser photocoagulation-induced CNV model, 10 rats were injected subretinally with rAAV.sFlt-1 vector (8×108 viral particles) in one eye, and a control vector (rAAV.gfp) in the contralateral eye. Laser photocoagulation was used to induce CNV one month after injection. Five weeks after laser photocoagulation, eyes were examined for CNV using fluorescein angiography. Only 41% of the laser-treated areas showed leakage in the rAAV.sFlt-1 treated eyes compared to 60% in the control vector-treated eyes (P=0.002). Sixteen weeks after laser-induced CNV, the rAAV.sFlt-1-treated eyes still showed significantly lower neovascularization than control eyes. Histological examination of the eyes in the areas immediately adjacent to the injection sites revealed a normal retinal pigmented epithelium and normal outer segments and outer nuclear layer. These findings suggested there was no obvious toxicity associated with sFLT-1 expression. Electroretinograms also indicated normal functioning of rAAV.sFlt-1-treated eyes. Most of the rAAV.sFlt-1 and control vector-treated laser lesions developed subretinal cellular membranes. However, the lesions in eyes treated with rAAV.sFlt-1 generally had less proliferating endothelial cells, reflecting the fluorescein angiography findings, and indicating that the rate of angiogenesis (i.e. neovascularization) was reduced in rAAV.sFlt-1-treated eyes.

rAAV.sFlt-1 and rAAV(bv).sFlt-1 Study in Rat Model of Diabetes

To further assess the safety and efficacy of rAAV.sFlt-1 and rAAV(bv).sFlt-1 for the treatment of diabetic retinopathy (DR) and diabetic macular edema (DME), an experiment in a rat model of diabetes is conducted.

Vision loss in diabetic patients is mediated by inflammation, leading to the eventual breakdown of the blood-retinal-barrier and subsequent vascular leakage, resulting in macular edema. The streptozotocin (STZ)-diabetic rat model displays a well-characterized pattern of vascular leakage, in which VEGF is strongly upregulated as early as 2 weeks. (Miyamoto, K., et al. Proc Natl Acad Sci USA 96, 10836-10841 (1999). Current approaches to treating animal models of DR demonstrate only a partial resolution of vascular leakage.

Diabetes is induced in Brown Norway rats by intraperitoneal injection of streptozotocin (50 mg/kg). Diabetes is confirmed and monitored by blood glucose measurements. Rats with blood glucose >350 mg/dl are considered diabetic. Eight days following onset of diabetes, rats are treated by subretinal injection (n=12 eyes per group) with 5 μL containing either $1\times10^{10}$ or $5\times10^{10}$ vg of rAAV.sFlt-1 or rAAV (bv).sFlt-1 using established techniques as described in Chalberg, T. W. et al., Invest Ophthalmol Vis Sci 46, 2140-2146 (2005). AAV2.GFP ($5\times10^{10}$ vg) and vehicle are be injected as controls. Non-diabetic and diabetic no-treatment groups are also used as controls.

The effect of the rAAV(bv).sFlt-1 expressing sFLT-1 on vascular leakage is measure at 60 days. Retinal vascular leakage is measured by the FITC-albumin leakage method following the injection using the FITC-conjugated albumin as tracer. The FITC-albumin leakage method directly measures the leakage of FITC-albumin leaking into the retina from the circulation and is a commonly used method to measure retinal vascular permeability. Retinal vascular leakage in injected eyes will be compared to non-diabetic controls, untreated and vehicle-treated diabetic eyes, and wildtype AAV serotypes 2 and 8.

Results: rAAV(bv).sFlt-1 expressing sFLT-1 reduces vascular leakage in the STZ-diabetic rat whereas injection of AAV2.GFP and other controls does not.

Example 5 rAAV.sFlt-1 Study in Monkeys

The efficacy and safety of rAAV.sFlt-1 was also examined in a nonhuman primate (macaque) model of AMD using laser photocoagulation to induce CNV. One challenge in developing treatments for AMD in humans is that nonhuman primates do not develop AMD. Laser photocoagulation induced CNV simulates some symptoms of AMD, but the underlying biological process is healing of an acute injury rather than progression of a chronic disease and thus may not be predictive of the performance of any particular treatment for CNV in humans with AMD or other CNV based diseases. Nonetheless, because human eyes are anatomically more similar to nonhuman primate eyes than nonprimate eyes, nonhuman primates are frequently studied to assess toxicity and histological response to a potential treatment or other intervention.

In the first study on nonhuman primates, five macaque monkeys were injected subretinally with rAAV.sFlt-1 ($4\times10^{12}$ viral particles) in one eye, and a control vector (rAAV.gfp) in the contralateral eye. The eye health of the monkeys was periodically assessed after subretinal injection. There was no apparent complication related directly to subretinal injection of either the control or rAAVsFlt-1 vector. A transient conjunctival irritation and vitreous haze was noted in the week following injection, which cleared by the second week. Subretinal injection was unsuccessful in the right eye of one of the monkeys; therefore this animal was not subjected to further evaluation.

Subretinal injection of 40-100 μL of rAAV suspension lifted the retina, creating a bleb that housed the vector between the pigment epithelium and the photoreceptor layer in a localized manner. This bleb self-corrected within 24 to 48 hours. Except for a minor disturbance to the retinal pigment epithelium at the point of needle penetration, no other retinal abnormalities were observed for the duration of the follow-up (3 to 17 months post-injection). No other abnormalities or adverse events were observed; at no time was retinal detachment associated with the surgery.

To assess the long-term therapeutic efficacy of rAAVsFlt-1, the four injected monkeys were then subjected to intense laser photocoagulation 16 months after treatment with the vectors. Eight lesions were induced using laser in each eye, and the eyes then monitored for CNV at two and four weeks after laser treatment. After laser photocoagulation, only three of the four monkeys were analyzable, therefore, efficacy data was collected for three animals. None of three monkey eyes treated with rAAVsFlt-1 developed CNV-related lesions and only weak fluorescein staining was observed, indicating minimum leakage/neovascularization. All contralateral eyes treated with control vector developed CNV-related lesions.

In a follow-up study aimed at assessing the safety and toxicity of rAAV.sFlt-1 injected into the subretinal space, eight monkeys were used: five were injected in their left eyes with rAAV.sFlt-1, two injected in their left eyes with rAAV.gfp, one injected in both eyes with recombinant Flt-1 protein and one was kept as uninjected control. The monkeys were examined preinjection and post injection by color fundus photography, fluorescein angiography and electroretinography. Blood was collected routinely for assaying sFLT-1 levels and peripheral blood lymphocytes were isolated for flow cytometry to assess immune cell subset response. At time of sacrifice (3, 9 and 12 months post injection), tissues were collected for i) biodistribution studies on the rAAV.sFlt-1 vector using real-time polymerase chain reaction on extracted genomic DNA; ii) hsFlt-1 protein and AAV2 capsid protein level quantitation by ELISA; and iii) histology of the eyes.

Color fundus photography, fluorescein angiography and electroretinography did not detect any adverse effect on the eye following injection. Plasma sFLT-1 level did not show any rAAV.sFlt-1 injection-related rise in level in any of the male or female monkeys examines. Except for an optic nerve sample, the rAAV.sFlt-1 sequence was not detected in the genomic DNA of any of the other tissues sampled (lymph nodes, spleen, liver, brain, brain, heart, spleen, cornea). Haematoxylin and eosin stained paraffin-embedded sections of the eyes appeared normal.

While non-human primate anatomy is more similar to human anatomy than the anatomy of smaller mammals such as mice, limitations do exist which make studies in non-human primates intriguing, but not predictive of clinical results in humans. As noted above, the study in this example uses a laser injury model in which the animal has otherwise healthy retinal tissue. The retinal tissue was not degraded over time as in disease retinal tissue nor are the disease specific pathogenic factors present. Non-human primates frequently differ from humans with respect to biodistribution, pharmacokinetics and dose dependencies, antibody titer, immune response and inflammatory response in ways that are not predictable. Additional differences include the ILM (inner limiting membrane) and the volume of the vitreous chamber, which is approximately four times larger in humans than the nonhuman primates used in this study. The human inner limiting membrane, a barrier that acts to limit transport between the retina and the vitreous, is a more a more profound and effective barrier than the ILM of a monkey.

Example 6

Safety Studies

Figure 3A:
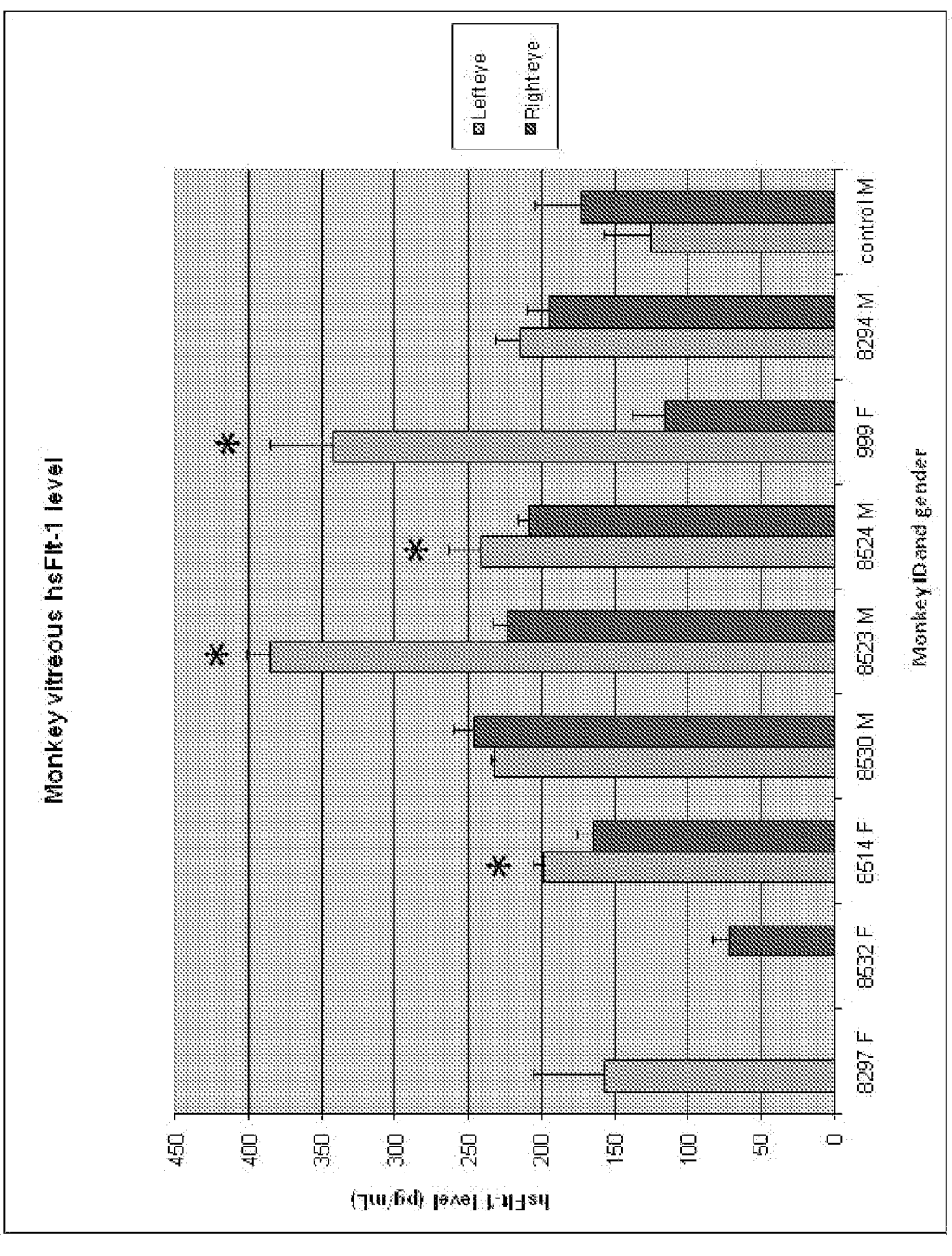
FIG. 3A depicts graph showing human sFlt-1 (hsFLT-1) expression in the vitreous of monkeys injected in the left eyes with rAAV.sFlt-1 (Monkey 8514, 8530, 8523, 8524 and 999), rAAV.gfp (Monkey 8297 and 8532), in both eyes with recombinant sFLT-1 protein (Monkey 8294) and control uninjected monkey (control). Control and monkeys 8294 and 999 were euthanized at 3 months post injection, Monkey 8524 was euthanized at 9 months post injection and monkeys 8297, 8532, 8514, 8530 and 8523 were euthanized at 12 months post injection. * denotes sFLT-1 protein levels that are significantly higher in the rAAV.sFlt-1 injected eyes (p<0.05).

In these studies, sFLT-1 protein was measured in the vitreous and plasma of animals using an enzyme linked immunosorbent assay kit for sFLT-1 protein detection. sFLT-1 protein level was upregulated in vitreous and eyes of animals injected with rAAV.sFlt-1. FIG. 3A shows the vitreous sFLT-1 protein level in monkey eyes injected with rAAV.sFlt-1 (left eye) and control eye injected with rAAV.gfp and uninjected eyes (right eye). sFLT-1 protein levels were significantly higher in four out of the five rAAV.sFlt-1 injected eyes. Table 5.3.1 shows the sFLT-1 protein level in the mouse eyes that were not injected and that were injected with rAAV.sFlt-1 and enucleated at one month post injection. Overexpression of sFLT-1 in the eyes of mice and vitreous of monkeys did not have any adverse effect on their overall well-being. In monkeys, sFLT-1 overexpression in the vitreous did not have any effect on their retinal function and did not have any clinically or histologically evident toxic effects on the eyes. The significantly higher sFLT-1 protein levels in the rAAV.sFlt-1 injected eyes suggests long-term rAAV-mediated hsFLT-1 expression and supports previous data on detection of viral mRNA sequence and presence of rAAV-mediated gfp expression in monkey retina 17 months post injection.

TABLE 1

Summarizing hsFLT-1 protein levels in rAAV.sFlt-1-injected mouse eyes and uninjected mouse eyes at 1 month post injection.

| Animal species and number of eyes | Treatment | Time post injection (week) | sFLT-1 protein level (pg/mL) |
|---|---|---|---|
| Mouse (n = 1) | uninjected | NA | 101.4 ± 4.8 |
| Mouse (n = 1) | uninjected | NA | 91.0 ± 10.9 |
| Mouse (n = 1) | uninjected | NA | 113.4 ± 6.3 |
| Mouse (n = 1) | uninjected | NA | 160.2 ± 8.9 |
| Mouse (n = 1) | rAAV.sFlt-1 injected | 4 | 1034.7 ± 44.3 |
| Mouse (n = 1) | rAAV.sFlt-1 injected | 4 | 610.3 ± 16.3 |
| Mouse (n = 1) | rAAV.sFlt-1 injected | 4 | 1417.2 ± 50 |
| Mouse (n = 1) | rAAV.sFlt-1 injected | 4 | >max |

Figure 3B:
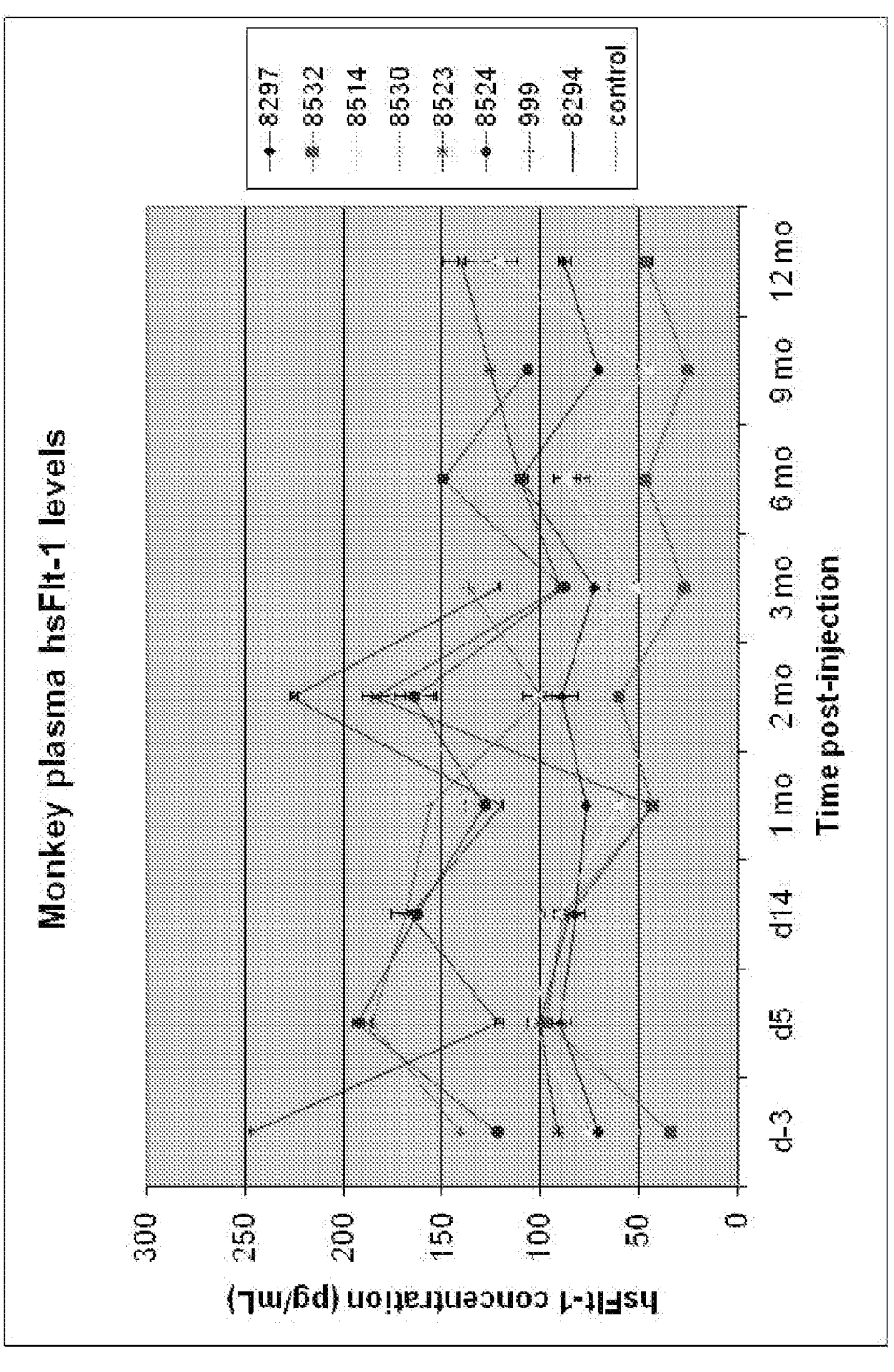
FIG. 3B depicts graphs showing hsFLT-1 levels in the rAAV.sFlt-1-injected (999, 8524, 8523, 8530 and 8514), rAAV.gfp-injected (8297 and 8532), recombinant sFlt-1 protein-injected (8294) and uninjected (control) monkeys at different times post injection.
Figure 15A:
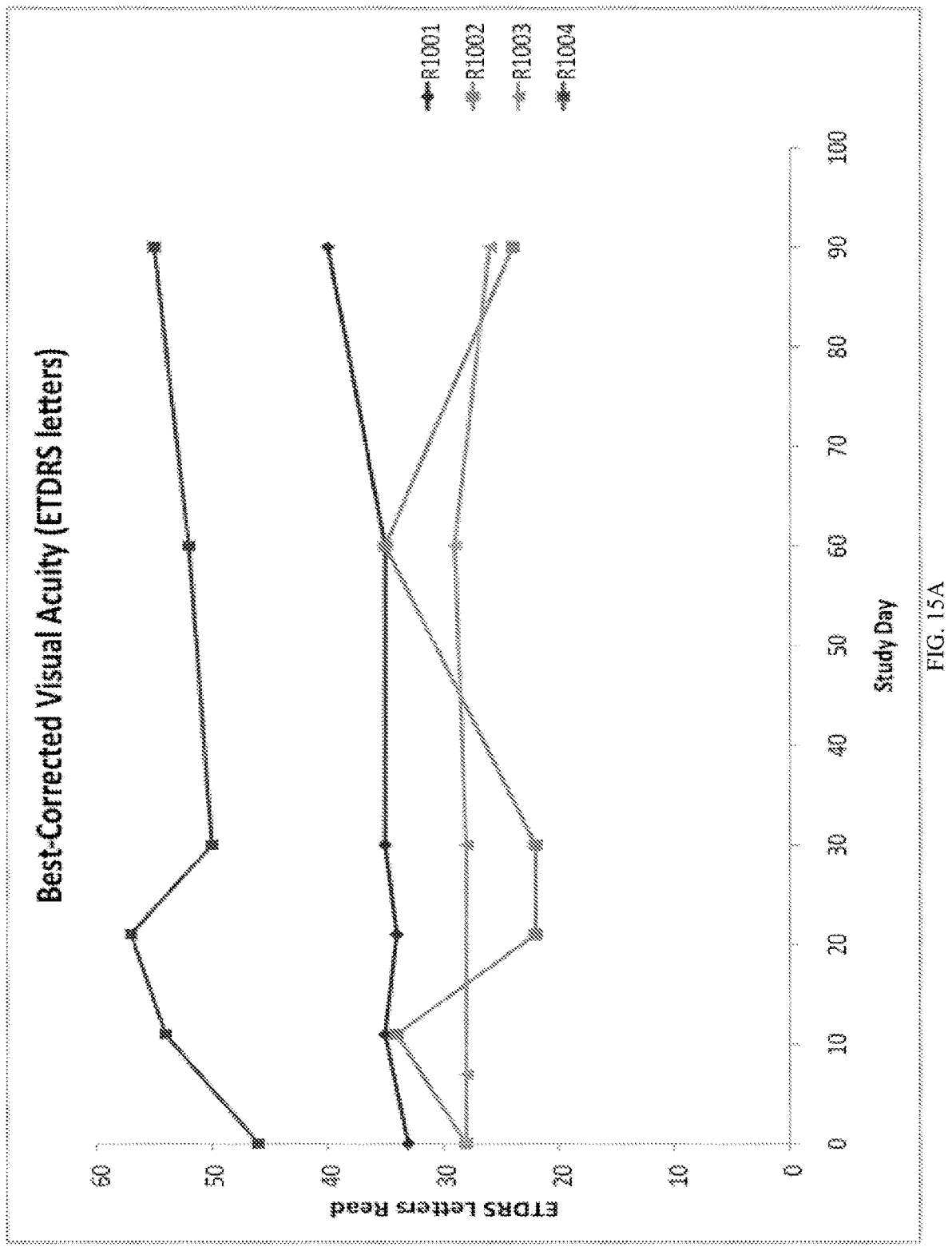
FIGS. 15A and 15B depict visual acuity results.
Figure 15B:
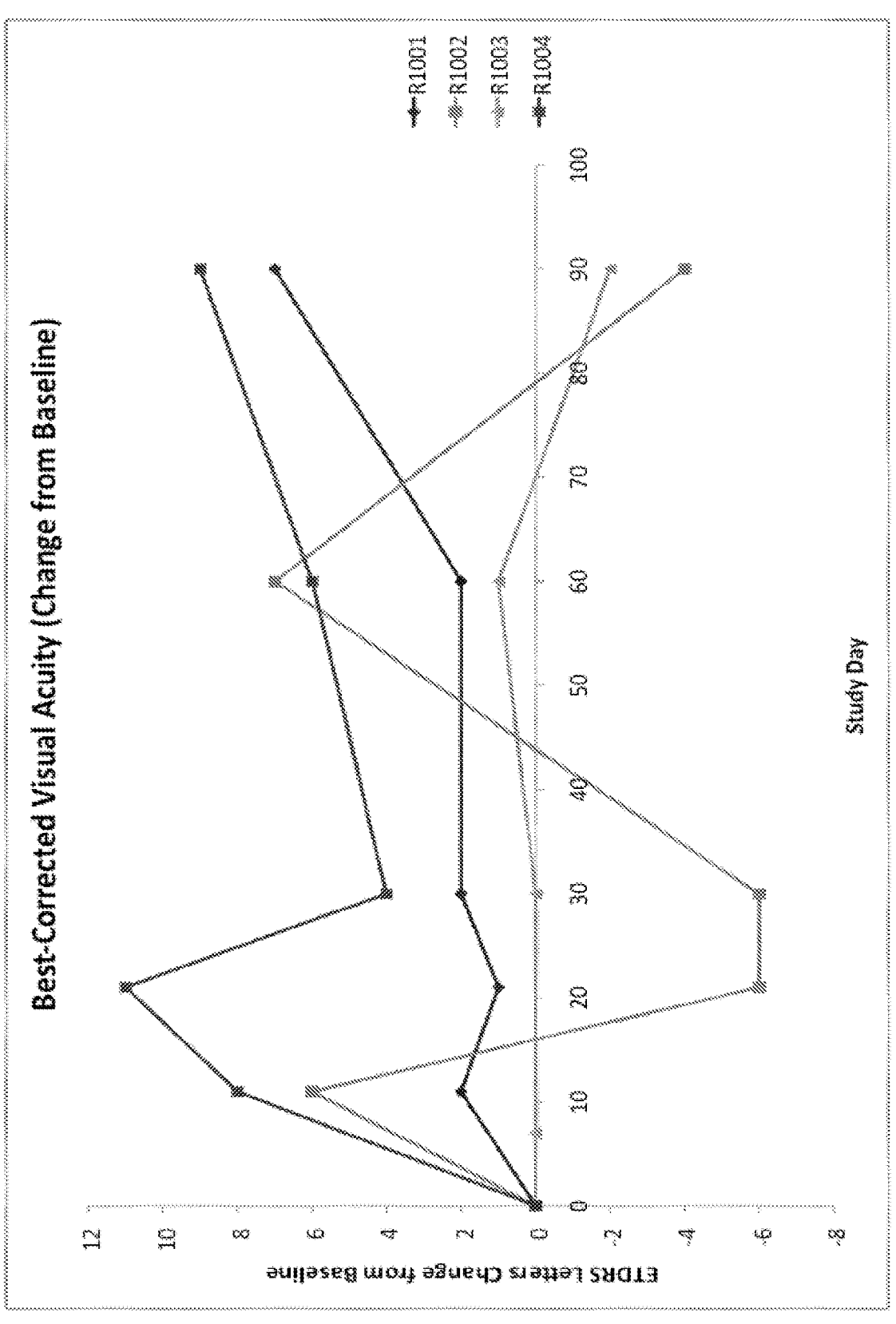
Figure 16:
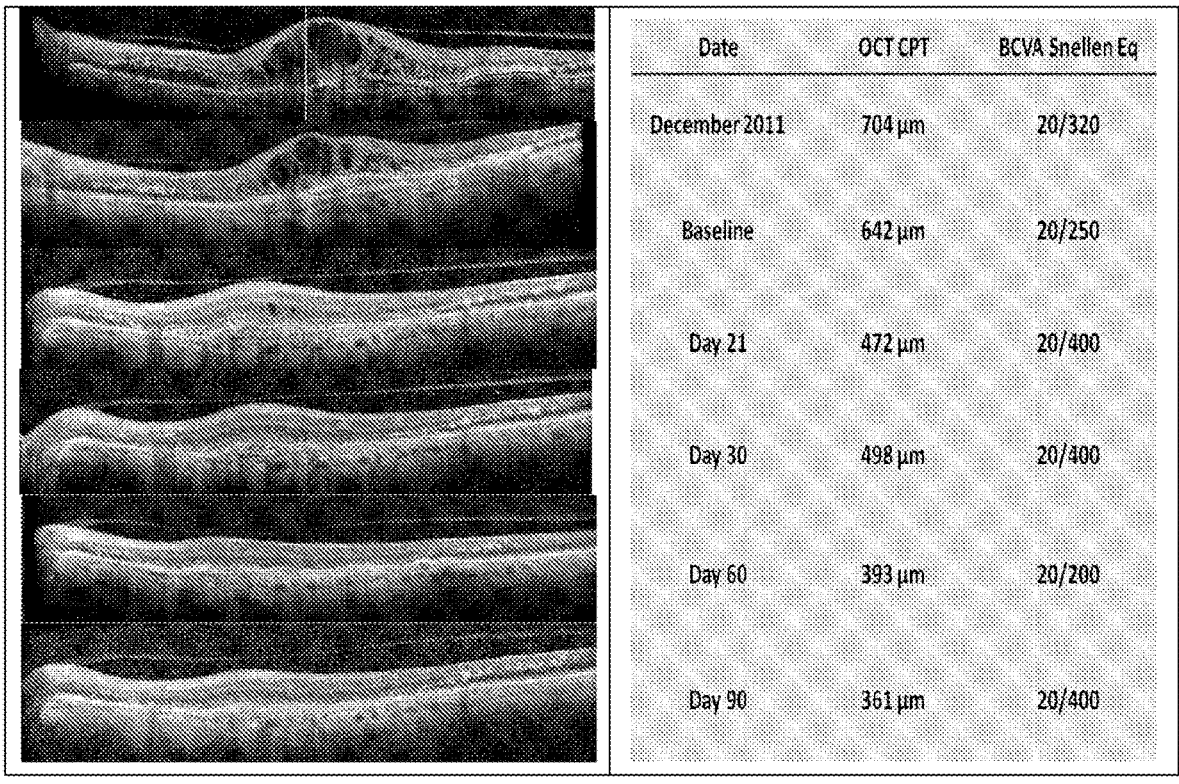
FIG. 16 depicts the measurement of retina thickness of a patient who was given 24 previous Lucentis injections.
Figure 20A:
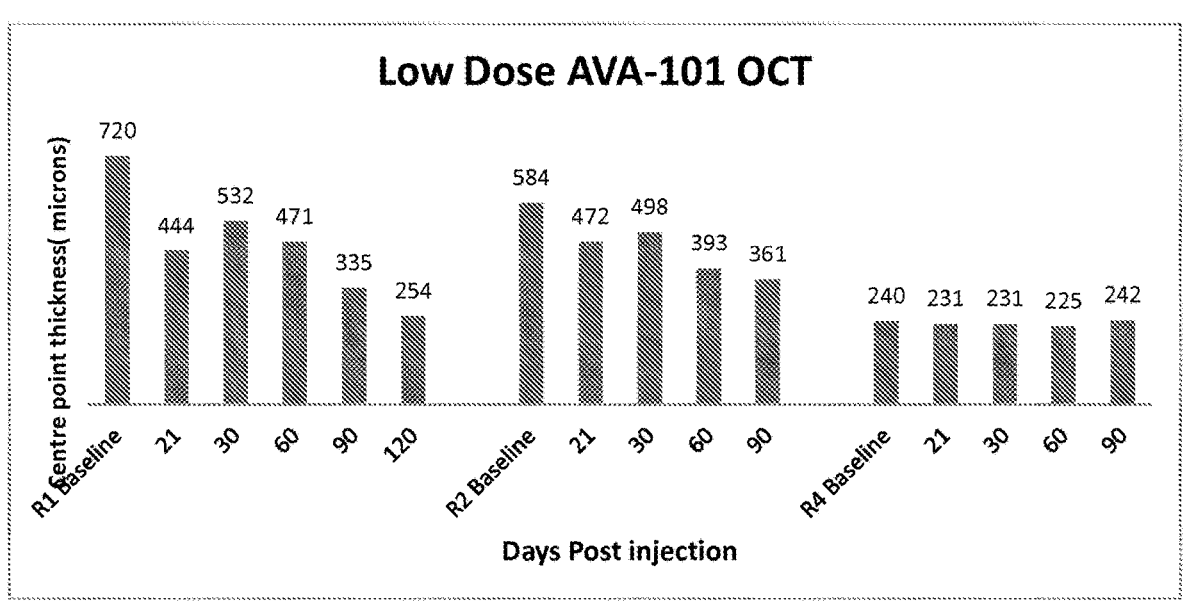
FIGS. 20A and 20B depict OCT assessments of patients administered with either low dose rAAV.sFlt-1 (R1, R2, R4) or high dose of rAAV.sFlt-1 (R5, R6 and R8).
Figure 20B:
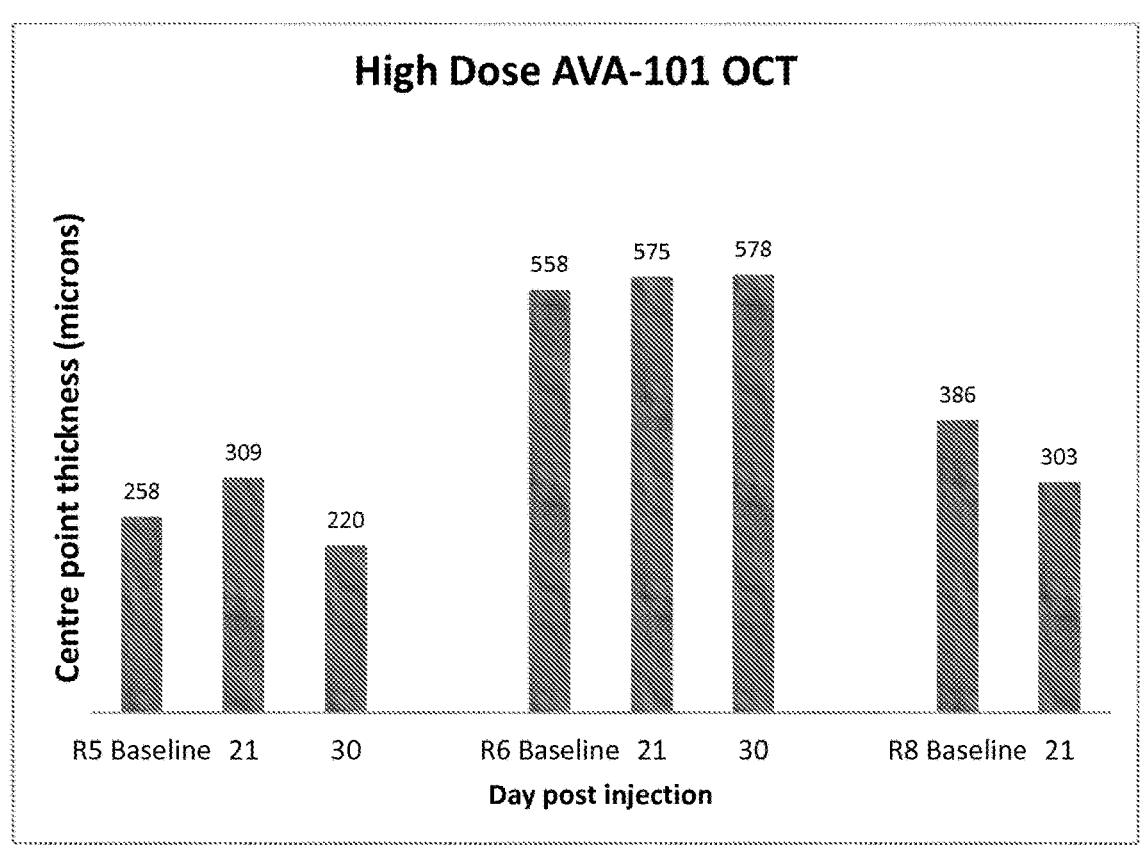
Figure 21A:
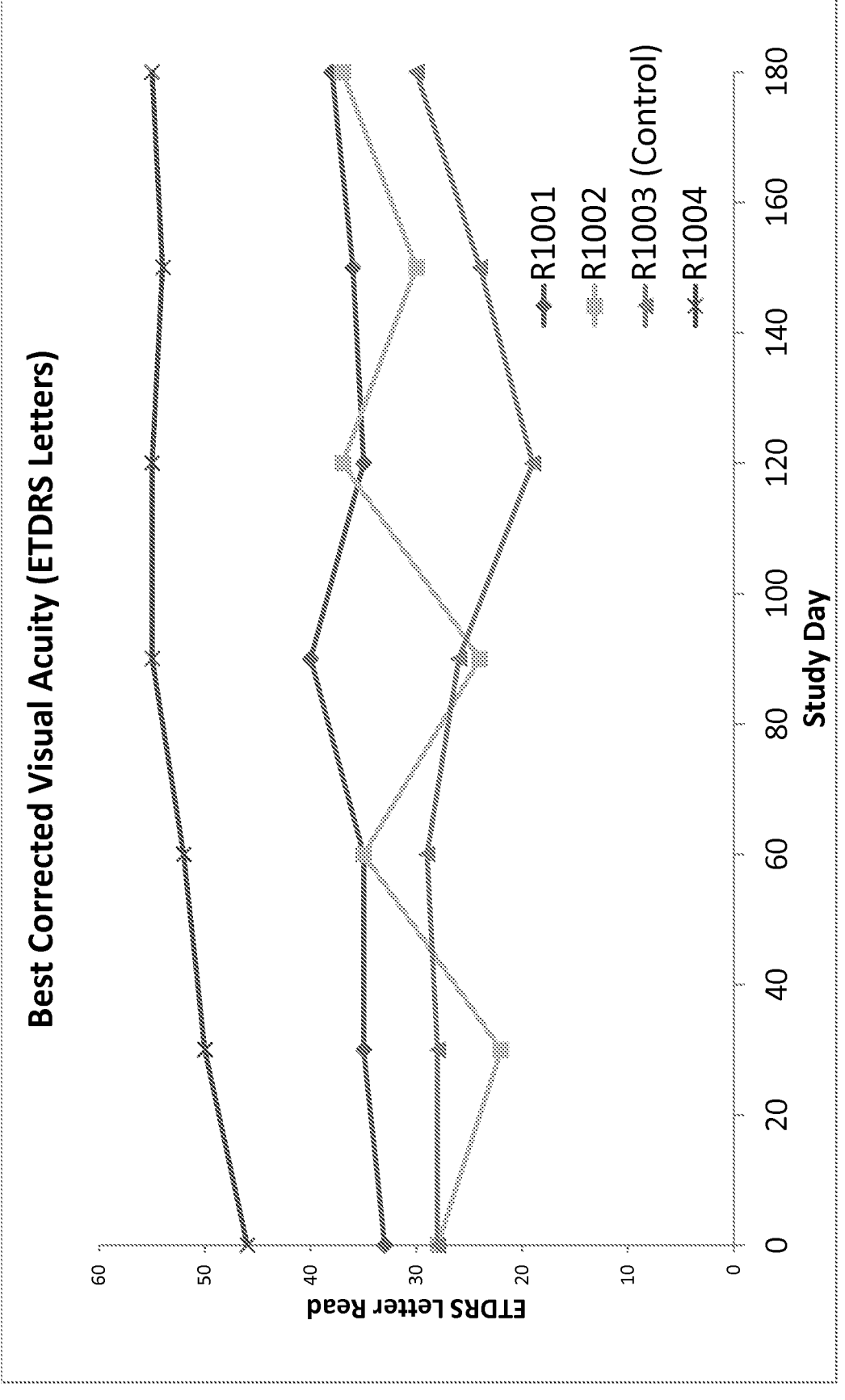
FIGS. 21A and 21B depict visual acuity results of human subjects treated with rAAV.sFlt-1 vs. untreated control patients at 180 days following treatment.
Figure 21B:
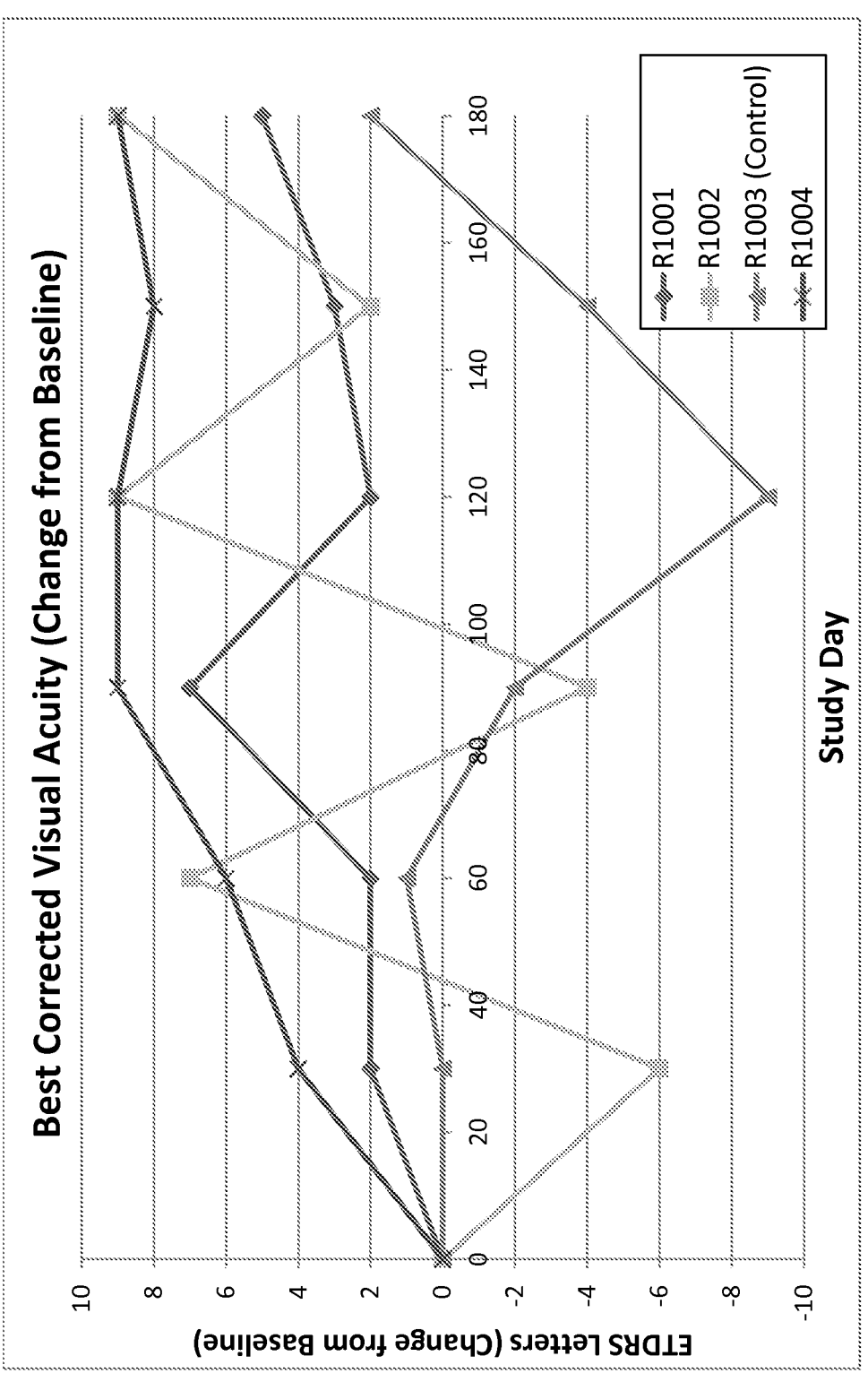
Figure 22A:
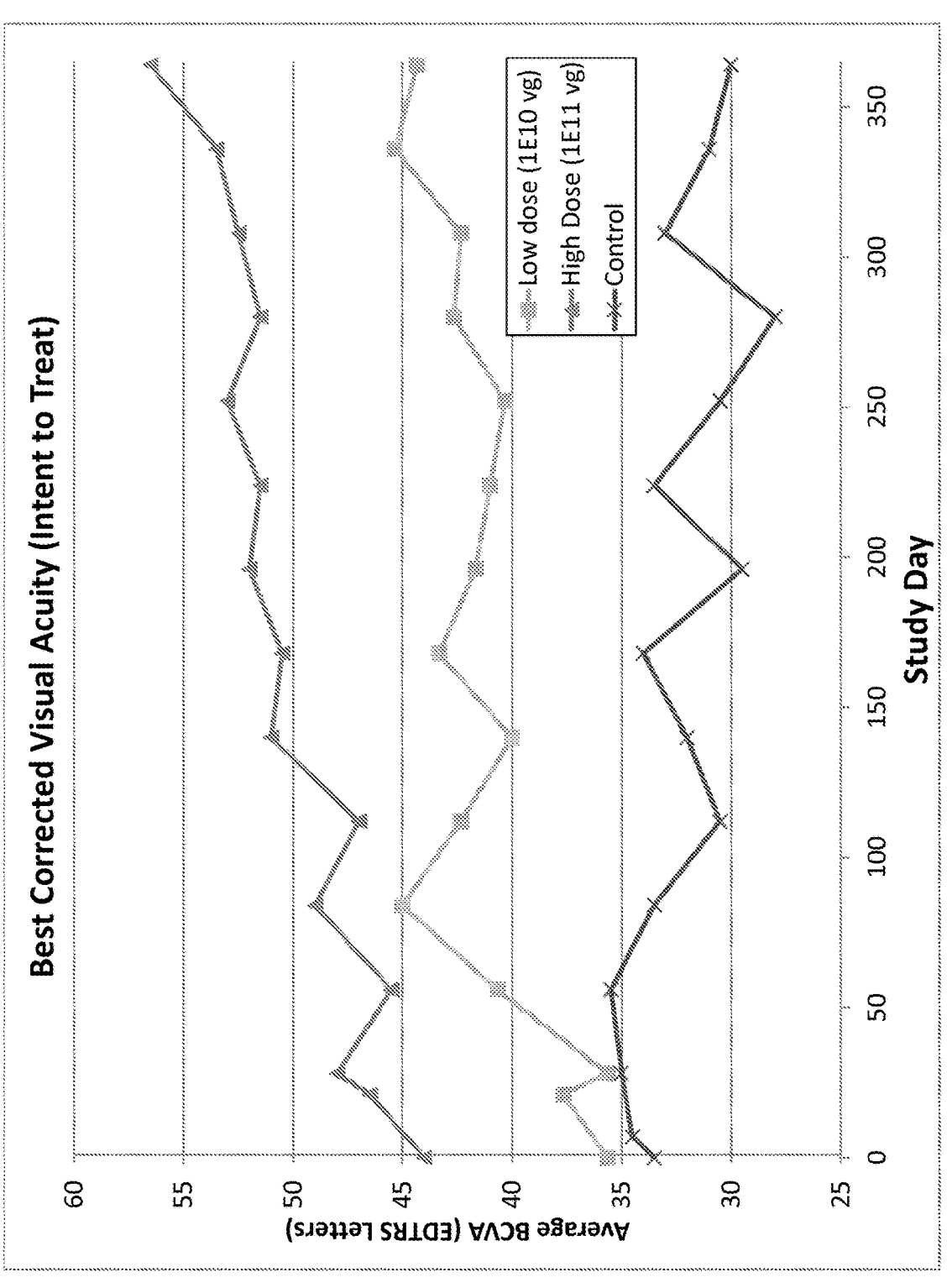
FIGS. 22A and 22B depict visual acuity results of human subjects treated with rAAV.sFlt-1 vs. untreated control patients at 1 year after treatment.
Figure 22B:
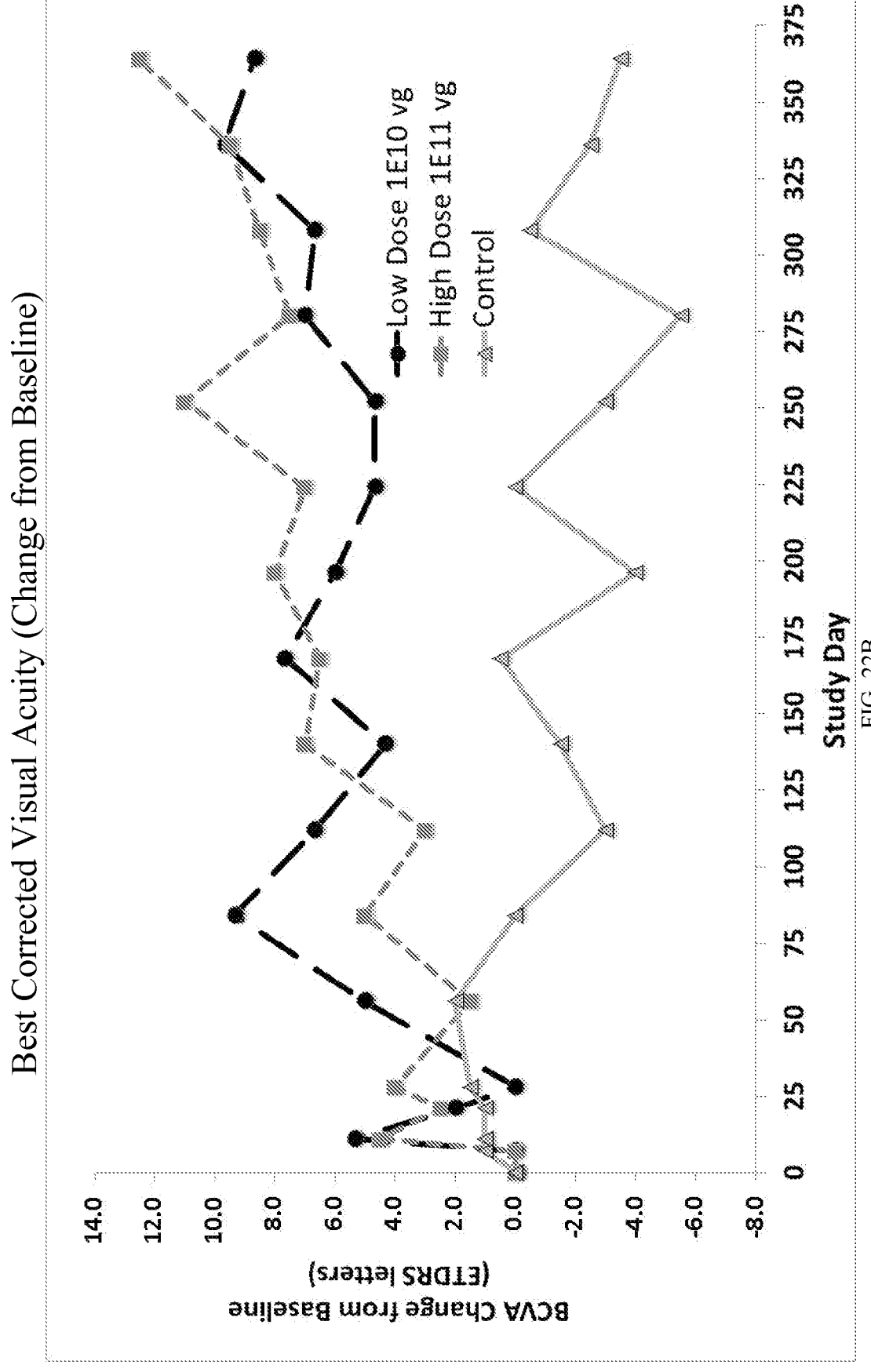

Plasma hsFLT-1 levels in the monkeys did not show any trend at the different sampling times (FIG. 3B). This suggests that the injection of rAAV.sFlt-1 did not have an obvious effect on the plasma hsFLT-1 level. The fluctuating levels did not have any effect on the well-being of the monkeys.

TABLE 2

Immunogenicity Studies

| Species/ Strain | Method of administration | Duration of dosing | Doses | GLP compliance |
|---|---|---|---|---|
| C57Bl/6 mice | subretinal | 1, 2 and 4 weeks | $8 \times 10^9$ vector genomes | No |
| Monkeys | subretinal | 12 months | $8 \times 10^{11}$ vector genomes | No |

Table 2: Summary of animal strain, injection route, duration and dose of rAAV.sFlt-1 used in immunogenicity studies

Example 7

Immunogenicity Studies on Mice

The cellular immune response to rAAV.sFlt-1 therapy was assessed in the mouse eye one, two and four weeks post injection using flow cytometry. Infiltrating leucocytes were identified on the basis of CD45 expression and classified as monocytes/granulocytes, B cells, CD4$^+$ T cells and CD8$^+$ T cells on the basis of CD11b, CD19, CD4 and CD8 expression, respectively. The posterior eye cup was collected from five mice in each group (rAAV.sFlt-1-injected, PBS-injected, uninjected control) and pooled for analysis. As shown in FIG. 4A, there was no difference in the number of cells recovered from each group of mice over the course of this experiment. However, there was a significant increase in the number of CD45$^+$ cells one and two weeks post injection that disappeared by four weeks (FIG. 4B). Almost all of the increase seen at one week could be attributed to an increase in CD11b$^+$ cells (FIG. 4C), since there was no difference in the number of CD4$^+$, CD8$^+$, and CD19$^+$ cells (FIGS. 4D-F). At two weeks though, there was no longer a significant difference in the number of CD11b$^+$ present in the eyes of AAV.sFlt-1 injected mice; instead, there was a significant increase in the number of CD4$^+$ and CD8$^+$ T cells and a possible trend towards an increase in B cells. The number of CD4$^+$ and CD8$^+$ cells fell sharply at four weeks yet remained significantly increased compared to the PBS-injected and uninjected mice. In contrast, there was no change in the number of CD11b$^+$, CD4$^+$, CD8$^+$ and CD19$^+$ cells in the spleen during the course of this experiment (FIGS. 5A-E).

The function of the T cells infiltrating the retina was examined more closely by stimulating them with PMA/ionomycin or anti-CD3 and measuring intracellular IFN-γ production by flow cytometry. FIG. 6 shows that compared to uninjected controls, a small proportion of both CD4$^+$ and CD8$^+$ T cells were primed to produce IFN-γ after the injection of rAAV.sFlt-1. The frequency of IFN-γ producing cells did not vary significantly over the course of the experiment despite an apparent increase amongst CD8$^+$ T cells on day 3 (FIG. 6B). Lower levels of IFN-γ were measured when the T cells were restimulated with a class I MHC-restricted epitope of rAAV capsid protein and some IFN-γ was also detected in the absence of any stimulation (data not shown). Taken together, these results indicate a small proportion of the T cells infiltrating the eyes of rAAV.sFlt-1-injected mice had been recently activated to produce IFN-γ, but this did not vary amongst either T cell subset during the course of this experiment.

The data presented for these experiments on the infiltration of immune cells into the eyes of AAV-sFLT-1 injected mice clearly show two waves of cell infiltration. There was an early wave of CD11b$^+$ cells at 1 week followed by a wave of CD4$^+$ and CD8$^+$ T cells at 2 weeks. Importantly, neither wave of infiltration was still present at 4 weeks, suggesting the infiltration had resolved itself. Importantly, sFLT-1 protein production was did not wane at this point, and indeed, continued to be expressed at very high levels.

The data on IFN-γ production indicated that around 5% of the CD4$^+$ and CD8$^+$ T were recently primed, and this frequency did not vary over the course of the experiment. Hu. et al first described the breakdown of the blood-retinal barrier by activated T cells, and the data presented here is consistent with the infiltration of activated CD4$^+$ and CD8$^+$ cells. However, there was no evidence of an increase in the number of capsid-specific T cells amongst this population since restimulation with specific peptide only revealed low and levels of IFN-γ production that did not change over the course of the experiment. Taken together, these observations suggest that the initial insult that occurred with injection of rAAV.sFlt-1 produced a short-lived wave of immune cell infiltration that resolved itself within four weeks, but failed to elicit an ongoing immune response that could harm the tissues of the eye or affect sFLT-1 expression.

Example 8

Immunogenicity Studies on Monkeys

Immune response following subretinal injection of rAAV.sFlt-1 or rAAV.gfp was analyzed using a panel of antibodies that would identify changes in immune cell subset populations. The results are summarized in FIG. 4. In some monkeys, very small changes in immune cell subset populations were observed but they were not statistically significant. Despite this, this was followed by a more in-depth study of circulating cells. Specifically, we assessed the possibility that either the vector (rAAV) or the inserted gene product (sFLT-1) may cause immune activation. Activation of B cells and T cells was investigated (FIG. 5 and FIG. 6). Other lymphocyte populations were also analyzed to determine whether the therapy caused any observable differences that may be indicative of direct activation or a response to activation. Analysis was conducted using a combination of classic markers (Pitcher, 2002 #129), as well as a novel phenotypic analysis described in a recently published report (Miller, 2008 #126). Using a small subset of phenotypic markers (HLA-DR, Ki-67, and Bcl-2) we investigated whether following administration of rAAV-sFLT-1 CD4+ or CD8+ T cells and/or B cells showed signs of activation. In the studies published by Miller and colleagues, activated T cells display an activated effector phenotype characterized by the expression of the differentiation marker HLA-DR and the cell cycle associated nuclear antigen Ki-67, which is used as a marker for proliferation. Resting T cells do not express Ki-67, whereas cycling or recently divided T cells upregulate Ki-67 expression. A level of Ki-67 expression is normally detected as part of homeostatic cell cycling.

Example 9

Biodistribution of rAAV.sFlt-1

Genomic DNA was extracted from tissues collected (optic nerve, lymph node, brain, heart, lungs, spleen, liver, cornea) immediately after euthanasia of monkeys. Real time polymerase chain reaction was performed on the genomic DNA to determine whether the rAAV.sFlt-1 vector construct injected in the subretinal space would be present elsewhere. Based on comparison of Ct values between known amounts of control plasmid pssv.C1.sflt-1 DNA, the rAAV.sFlt-1 construct was found at low gene copy number in the optic nerve of one injected eye and not in any of the other tissues samples. This suggests that rAAV.sFlt-1 injected into the subretinal space remains mainly within the eye. Table 4 is a summary of the Ct values from genomic DNA extracted from monkeys that were not injected or injected with rAAV.sFlt-1- and rAAV.gfp.

TABLE 3

Ct values and Ct standard deviation values for the different genomic DNA and control plasmid DNA samples analyzed.

| Sample ID | Ct Mean | Ct Std Dev |
|---|---|---|
| No DNA 0 copy | 40.83970125 | 0.08415232 |
| pssv.C1.hsFlt-1 (0.045 ng) 6000000 copies | 18.17500393 | 0.522299978 |
| pssv.C1.hsFLT-1 (0.009. ng) 1000000 copies | 22.5311632 | 0.318372962 |
| pssv.C1.hsFLT-1 (0.0009 ng) 100000 copies | 26.23701276 | 0.183232131 |
| pssv.C1.hsFLT-1 (0.00009 ng) 10000 copies | 25.2483849 | 0.164140658 |
| pssv.C1.hsFLT-1 (0.000009 ng) 1000copies | 29.4265616 | 0.415926721 |
| Control uninjected monkey | | |
| 1 LE Optic nerve | 42.11 | 0.573 |
| 2 RE Optic nerve | 43.58 | 0.323 |
| 3 axillary LN | 45.86 | 1.319 |
| 4 cervical LN | N/A | N/A |
| 5 spleen | 40.71 | 0.093 |
| 6 liver | 44.16 | 0.604 |
| Monkey 999: rAAV.sFlt-1 injected, euthanized 3 mo p.i. | | |
| 7 LE optic nerve | 39.13 | 0.137 |
| 8 RE optic nerve | 42.25 | 0.153 |
| 9 axillary LN | 40.87 | 0.728 |
| 10 submandibular LN | 40.54 | 0.453 |
| 11 spleen | N/A | N/A |
| 12 liver | 41.23 | 0.388 |

TABLE 3-continued

Ct values and Ct standard deviation values for the different
genomic DNA and control plasmid DNA samples analyzed.

| Sample ID | Ct Mean | Ct Std Dev |
|---|---|---|
| Monkey 8294: sFLT-1 protein injected, euthanized 3 mo p.i. | | |
| 13 LE optic nerve | 42.15 | 0.545 |
| 14 RE optic nerve | 42.67 | 0.411 |
| 15 axillary LN | 43.92 | 0.304 |
| 16 submandibular LN | N/A | N/A |
| 17 spleen | N/A | N/A |
| 18 liver | 40.45 | 0.981 |
| Monkey 8524: rAAV.sFlt-1 injected, euthanized 9 mo p.i. | | |
| 19 left cornea | 39.72 | 0.975 |
| 20 right cornea | N/A | N/A |
| 21 axillary LN | 44.12 | 0.216 |
| 22 cervical LN | N/A | N/A |
| 23 spleen | 37.91 | 0.668 |
| 24 liver | 41.8 | 0.648 |
| Monkey 8514: rAAV.sFlt-1 injected, euthanized 12 mo p.i. | | |
| 25 right optic nerve | 39.96 | 0.609 |
| 26 left optic nerve | 28.9 | 0.057 |
| 27 axillary LN | 40.08 | 0.221 |
| 28 cervical LN | 41.27 | 0.063 |
| 29 spleen | 39.22 | 0.196 |
| 30 liver | 40.79 | 0.367 |
| 31 brain | 41.14 | 0.798 |
| 32 heart | 42.19 | 0.265 |
| 33 lungs | 40.11 | 2.093 |
| Monkey 8523: rAAV.sFlt-1 injected, euthanized 12 mo p.i. | | |
| 34 left optic nerve | 37.27 | 0.838 |
| 35 right optic nerve | 37.92 | 1.181 |
| 36 axillary LN | 38.55 | 0.895 |
| 37 cervical LN | 39.68 | 0.583 |
| 39 spleen | 36.44 | 0.519 |
| 40 liver | 39.94 | 0.768 |
| 41 8523 brain | 40.29 | 0.397 |
| 42 8523 heart | 41.28 | 0.877 |
| 43 8523 lungs | 41.71 | 1.186 |
| Monkey 8530: rAAV.sFlt-1 injected, euthanized 12 mo p.i. | | |
| 44 left optic nerve | 38.52 | 0.777 |
| 45 right optic nerve | 40.67 | 1.354 |
| 46 axillary LN | 42.49 | 0.841 |
| 47 cervical LN | 38.55 | 0.895 |
| 48 spleen | 36.44 | 0.519 |

TABLE 3-continued

Ct values and Ct standard deviation values for the different
genomic DNA and control plasmid DNA samples analyzed.

| Sample ID | Ct Mean | Ct Std Dev |
|---|---|---|
| 49 liver | 39.94 | 0.768 |
| 50 brain | 40.29 | 0.397 |
| 51 heart | 41.67 | 1.787 |
| 52 lungs | 39.29 | 1.474 |
| Monkey 8532: rAAV.sFlt-1 injected, euthanized 12 mo p.i. | | |
| 53 left optic nerve | 35.07 | 1.06 |
| 54 right optic nerve | 38.14 | 0.665 |
| 55 axillary LN | 40.23 | 1.171 |
| 56 cervical LN | 40.82 | 0.496 |
| 57 spleen | 40.09 | 0.195 |
| 58 liver | 40.63 | 1.1052 |
| 59 brain | 38.68 | 0.295 |
| 60 heart | 40.04 | 0.685 |
| Monkey 8297: rAAV.sFlt-1 injected, euthanized 12 mo p.i. | | |
| 61 left optic nerve | 39.84 | 1.034 |
| 62 right optic nerve | 42.17 | 1.247 |
| 63 axillary LN | 41.19 | 2.174 |
| 64 cervical LN | 41.38 | 2.040 |
| 65 spleen | 39.09 | 1.273 |
| 66 liver | 41.36 | 0.683 |
| 67 brain | 37.84 | 1.243 |
| 68 heart | 40.74 | 0.868 |
| 69 lungs | 42.60 | 0.276 |

Example 10

Efficacy Studies on a Mouse Model of Retinal Neovascularization

Transgenic mice generated through VEGF upregulation in the photoreceptors cells were used in the study. One eye was injected with rAAV.sFlt-1 and the contralateral eye was injected with rAAV.gfp. The extent, intensity, and stage of neovascularization were graded by masked observers based on an agreed scale. The results shown that there was a statistically significant overall reduction in neovascularization grades from a median of 3 (severe) to a median of 1 (mild) at one month post injection (P=0.012). This low level of fluorescein leakage was maintained at three (median=1; P=0.001) and eight months (median 1; P=0.001) post-rAAV.sFlt-1 injection suggesting the long-term, sustained therapeutic effect of rAAV.sFlt-1.

TABLE 4

Grading of eyes before and after AAV.sFlt-1 and AAV.gfp injection
and photoreceptor numbers/rows at 8 months post-injection

| Animal ID | Grades at time (months) post injection | | | | Photo-receptor numbers | Rows of photo-receptors | Regression |
|---|---|---|---|---|---|---|---|
| | [a]0 | 1 | 3 | 8 | | | |
| 243 L | 1 | 0 | 0 | 0 | 68.8 ± 14.1 [b] | 4-8 | Moderate |
| 243 R | 1 | 3 | 3 | 3 | 0 | 0 | None |
| 244 L | 2 | 1 | 1 | 1 | 72.8 ± 18.8 [b] | 3-7 | Moderate |
| 244 R | 1 | 3 | 2 | 1 | 5.8 ± 3.1 | 0-1 | None |
| 247 L | 2 | 2 | 0 | 0 | 80.8 ± 31.0 [b] | 3-8 | Significant |
| 247 R | 1 | 1 | 1 | 1 | 28.3 ± 33.3 | 0-4 | None |
| 249 L | 3 | 1 | 1 | 1 | 0 | 0 | Significant |
| 249 R | 3 | 3 | 3 | 4 | 7.2 ± 13.1 | 0-1 | None |
| 250 L | 3 | 1 | 1 | 1 | 65.1 ± 24.4 [b] | 3-8 | Significant |
| 250 R | 3 | 3 | 3 | 3 | 0 | 0 | None |
| 251 L | 3 | 2 | 1 | 1 | 0 | 0 | Significant |
| 251 R | 3 | 3 | 3 | 4 | 0 | 0 | None |

TABLE 4-continued

Grading of eyes before and after AAV.sFlt-1 and AAV.gfp injection
and photoreceptor numbers/rows at 8 months post-injection

| Animal ID | Grades at time (months) post injection | | | | Photo-receptor numbers | Rows of photo-receptors | Regression |
|---|---|---|---|---|---|---|---|
| | [a]0 | 1 | 3 | 8 | | | |
| 253 L | 3 | 2 | 1 | 1 | 73.8 ± 20.39 [b] | 5-7 | Significant |
| 253 R | 3 | 2 | 3 | 2 | 20 ± 30.3 | 0-2 | Moderate |
| 254 L | 3 | 1 | 0 | 0 | 61.8 ± 14.3 [b] | 4-6 | Significant |
| 254 R | 2 | 2 | 2 | 2 | 8.8 ± 9.6 | 0-1 | None |
| 324 L | 1 | 1 | 1 | 1 | ND | ND | None |
| 324 R | 1 | 1 | 1 | 1 | ND | ND | None |
| 326 L | 2 | 1 | 1 | 1 | ND | ND | Moderate |
| 326 R | 2 | 2 | 2 | 2 | ND | ND | None |
| 327 L | 2 | 2 | 0 | 0 | ND | ND | Significant |
| 327 R | 2 | 3 | 2 | 2 | ND | ND | None |
| 329 L | 3 | 2 | 2 | 2 | ND | ND | Moderate |
| 329 R | 2 | 2 | 2 | 2 | ND | ND | None |
| 330 L | 3 | 3 | 2 | 3 | ND | ND | None |
| 330 R | 3 | 3 | 3 | 3 | ND | ND | None |

L = left eye injected with AAV.sFlt-1, R = right eye injected with AAV.GFP, ND = not done

[a]3 days prior to injection with AAV vectors.

[b] Statistically significant difference in photoreceptor numbers (p < 0.01)

Example 11

Efficacy Studies on a Monkey Model of Laser-Induced Choroidal Neovascularization Five monkeys were injected in one eye with rAAV.sFlt-1 and in the other with rAAV.gfp. Subretinal injection was unsuccessful in the right eye of one of the monkeys; therefore this animal was not subjected to further evaluation. Subretinal injection of 40-100 µl of rAAV suspension lifted the retina, creating a bleb that housed the vector between the pigment epithelium and the photoreceptor layer in a localized manner. This bleb self-corrected within 24 to 48 hours. Except for a minor disturbance to the retinal pigment epithelium at the point of needle penetration, no other retinal abnormalities were observed for the duration of the follow-up (3 to 17 months post-injection). No other abnormalities or adverse events were observed; at no time was retinal detachment associated with the surgery.

To assess the long-term therapeutic efficacy of rAAVsFlt-1, the four injected monkeys were then subjected to intense laser photocoagulation 16 months after treatment with the vectors. Eight lesions were induced using laser in each eye, and the eyes then monitored for choroidal neovascularization at two and four weeks after laser treatment. After laser photocoagulation, only three of the four monkeys were analyzable, therefore, efficacy data was collected for three animals. None of the three monkey eyes treated with rAAVsFlt-1 developed choroidal neovascularization-related lesions and only weak fluorescein staining was observed, indicating minimum leakage/neovascularization. All contralateral eyes treated with control vector developed choroidal neovascularization-related lesions. Efficacy data for the three animals are presented in Table 5.

TABLE 5

Effect of subretinal administration of rAAV.sFlt-1 or control (rAAV.gfp) vector on laser-induced CNV in macaque monkeys

| Monkey No. | Time of laser-induced CNV (months)* | CNV Lesions after Fluorescein Fundus Angiography[†] | | | |
|---|---|---|---|---|---|
| | | Right Eye (rAAV.sFlt-1) | | Left Eye (rAAV.gfp) | |
| | | 2 Weeks | 4 Weeks | 2 Weeks | 4 Weeks |
| 1 | 16 | 0/8 | 0/8 | 1/8 | 6/8 |
| 2 | 16 | 0/8 | 0/8 | 0/8 | 3/8 |
| 4 | 16 | 0/8 | 0/8 | 0/8 | 2/8 |

*CNV was induced at 16 months after subretinal injection of rAAVs.

[†]Number of macular lesions with neovascularization (fluorescein leakage) after laser photocoagulation. The retinal function of the monkeys was assessed by electroretinography. Amplitudes and implicit times from the responses of the injected eye and uninjected contralateral eye were calculated and compared pre-injection and at different times following injection. The results showed that injection of rAAV.sFlt-1, the recombinant sFLT-1 protein or rAAV.gfp did not have any adverse effect on the retinal function of the monkeys.

Example 12

The standard of care in treating wet AMD involves frequent intraocular injection of recombinant anti-VEGF proteins every 4-8 weeks. A rAAV construct has been developed for a potent (Kd ~10 pM), naturally occurring anti-VEGF protein, soluble Fms-related tyrosine kinase-1 (sFlt-1), for the treatment of wet AMD. rAAV.sFlt-1 was produced in accordance with FDA and ICH guidelines at the UNC Vector Core Human Application Laboratory. An eight patient controlled study on the safety and efficacy of rAAV.sFlt-1 was conducted. Eligibility, inclusion and exclusion criteria for the study were as follows:

Eligibility Criteria

Ages Eligible for Study: 65 Years and older
Genders Eligible for Study: Both
Accepts Healthy Volunteers: No Inclusion Criteria Age greater than or equal to 65 years;

Subfoveal CNV secondary to AMD and with best corrected visual acuity of 20/80-20/400 or better in the other eye;

Fluorescein angiogram of the study eye must show evidence of a leaking subfoveal choroidal neovascular lesion;

Must be a candidate for anti-VEGF intravitreal injections;

The entire dimension of the lesion must not exceed 12 Macular Photocoagulation Study disc areas;

No previous retinal treatment of photodynamic therapy or laser;

Able to provide informed consent;

Participant has clinically acceptable laboratory and ECG at the time of enrolment; and Able to comply with protocol requirements, including follow-up visits.

Exclusion Criteria

Liver enzymes >2× upper limit of normal;

Clinical evidence of active infection of any type, including adenovirus, hepatitis A, B, or C, or HIV virus;

Any prior treatment for AMD in the study/control eye, excluding anti-VEGF injections;

A tear in the retinal pigmented epithelium;

Extensive submacular scar tissue;

Significant retinal disease other than subfoveal CNV AMD, such as diabetic retinopathy or retinal vascular occlusion;

Significant non-retinal disease such as ocular atrophy or cataracts;

Known allergy to fluorescein;

Current use of prednisolone, other anti-inflammatory steroids or immune suppression drugs. Non-steroidal drugs such as aspirin are allowed;

Any other significant disease or disorder which, in the opinion of the Investigator, may either put the participants at risk because of participation in the study, or may influence the result of the study, or the participant's ability to participate in the study;

Participants who have participated in another research study involving an investigational product in the past 12 weeks; and Penicillin sensitivity.

Administration procedure: The pharmaceutical composition containing rAAV.sFlt-1 was administered to study subjects in a setting appropriate for subretinal injection according to the following procedure:

1. The subject's periocular skin and eyelid margins and eye lashes were cleaned with 5% povidone iodine prior to draping;

2. A sterile whole body drape was placed followed by an additional eye drape.

3. Inserted eyelid speculum, ensuring that it is well positioned underneath the eyelids to direct the eyelashes away from the field and protected by eye drape.

4. Inserted 3×23 G or 25 G vitrectomy ports;

5. Connected saline infusion to 1st port;

6. Inserted fiber optic into 2nd port;

7. A 36 G-41 G subretinal cannula was connected to drug syringe via microconnector in the 3rd port;

8. Under microscopic control, 100 microlitres is injected under the retina;

9. Following injection, instruments and ports were withdrawn;

10. Chloramphenicol ointment was applied;

11. Atropine 1% drop from sterile single use container was instilled; and

12. An eye pad and eye shield were applied.

The results of the rAAV.sFlt-1 study are summarized herein.

The eight enrolled subjects (mean age 77 years) all had active subfoveal choroidal neovascularization, with visual acuity of 20/40 to 20/400, and had previously received between 1 and 25 intravitreal injections of ranibizumab. The patients were randomly distributed into three groups, a control group and two experimental groups. All patients received intravitreal injections of ranibizumab on day 1 and day 30 of the study. On day 7, $1 \times 10^{10}$ vector genomes of rAAV.sFlt-1 in 100 ul volume was administered via subretinal injection to the first experimental group and $1 \times 10^{11}$ vector genomes of rAAV.sFlt-1 in 100 ul volume was administered via subretinal injection to the second experimental group. In all six cases for patients in the experimental groups, the bleb of sub-retinal fluid resolved within 4 hours. After 24 hours, most of the air in the vitreous had absorbed and only the retinal injection site remained visible. One patient developed a minor hemorrhage associated with the procedure that did not affect vision. As expected following vitrectomy, there was a transient increase in neutrophil counts that returned to normal by 14 days post injection. Vector sequence was found in the tears of one subject at one day post injection that cleared by day 30. Other than this single occurrence, AAV2 was not detected in any of the subjects' blood, saliva or urine samples either by qPCR or ELISA to date. Background levels of the naturally occurring sFLT-1 protein showed a high baseline variation in the urine, serum, and saliva with no increase following treatment. sFLT-1 levels in the vitreous also varied among subjects (975-2085 pg/ml). Blood biochemistry, complete blood count, and T-cell response, remained without any significant change compared to baseline. Subretinal injection of rAAV.sFlt-1 showed no clinically significant retinal toxicity as assessed by serial ophthalmic examinations over a two month period. No superficial, anterior segment or vitreous inflammatory signs were present in any of the subjects. There was no evidence of visual acuity loss, IOP elevation, retinal detachment, or any intraocular or systemic immune response in any of the patients. A summary of anti-VEGF treatments, both initial and rescue, are summarized for each patient in Table 6.

TABLE 6

| | | | | | | | | | | | | | | |
|---|---|---|---|---|---|---|---|---|---|---|---|---|---|---|
| | | | | | | Summary of Ranibizumab Injections by Patient | | | | | | | | |
| Subject | Day 0 | Day 30 | Day 60 | Day 90 | Day 120 | Day 150 | Day 180 | Day 210 | Day 224 | Day 252 | Day 280 | Day 308 | Day 336 | Day 364 |
| R1001 | X | X | 0 | 0 | 0 | 0 | 0 | No visit | No visit | 0 | 0 | 0 | 0 | 0 |
| R1002 | X | X | 0 | 0 | 0 | 0 | 0 | 0 | 0 | No visit | 0 | 0 | 0 | 0 |
| R1003 (control) | X | X | 0 | X | X | 0 | 0 | X | 0 | X | 0 | 0 | X | 0 |
| R1004 | X | X | 0 | 0 | 0 | 0 | 0 | 0 | 0 | 0 | 0 | 0 | 0 | X |
| R1005 | X | X | 0 | 0 | 0 | 0 | 0 | No visit | 0 | 0 | 0 | 0 | 0 | 0 |
| R1006 | X | X | 0 | X | No visit | 0 | 0 | 0 | 0 | 0 | 0 | 0 | 0 | 0 |
| R1007 (control) | X | X | 0 | 0 | 0 | X | 0 | 0 | 0 | 0 | 0 | 0 | 0 | 0 |
| R1008 | X | X | 0 | X | 0 | 0 | No visit | 0 | 0 | 0 | 0 | 0 | 0 | 0 |

Note:
Per protocol, injections at Day 0 and Day 30 were mandatory for all patients in the study\\

Notably, none of the patients in the experimental groups required rescue treatment at day 60 and most of the patients in the lower dose experimental group required 0 rescue treatments at day 90, day 120, day 150, day 180 or day 210 or day 270 or day 365 (1 year). The control patient required multiple rescue treatments. These results are unexpected and extend the promise of gene therapy for the large cohort of elderly patients suffering from wet AMD. Generally, patients treated with current anti-VEGF therapy, such as intravitreal injections of a VEGF inhibitor protein or other anti-VEGF agent will require additional injections in 30, 60 or 90 days.

Maximum expression levels of sFLT-1 in a study subject or a patient are reached six to eight weeks after subretinal administration of rAAV.sFLT-1. During this so called "ramp-up" period, at least one, two or three intravitreal injections of an anti-VEGF agent are injected at 15 to 45 day intervals, and preferably about 30 day intervals, to prevent disease progression. It is preferred to administer the first intravitreal injection of an anti-VEGF agent between 1 to 30 days, and preferably between 5 to 10 days, prior to administration of rAAV.sFlt-1 to allow for absorption of the intravitreally injected anti-VEGF agent (Lucentis or Avastin or Eylea or other non sFLT agents). If this first intravitreal injection is administered less than 24 hours prior to subretinal administration of rAAV.sFLT, it may be washed out of the vitreous during the subretinal injection procedure leading to a sub-therapeutic anti-VEGF agent concentration and disease progression.

After the completion of the ramp period, patients who express sufficient sFLT-1 to treat or prevent progression of their AMD may not need additional intravitreal anti-VEGF injections although it is expect that they will remain under the care of a physician. Patients are monitored and treated on an as-needed basis based on objective criteria, such as an increased center point retinal thickness measurement with an optical coherence tomography.

In this study, patients in the control and both experimental groups were evaluated for signs of active choroidal neovascularization on an approximately monthly basis and retreated with intravitreal ranibizumab if any of the following criteria was met:

>10 Early Treatment Diabetic Retinopathy Study (ET-DRS) letter loss from subject's previous visit (attributable to retinal causes), OR a decrease of >5 ETDRS letters from previous visit in conjunction with patient perception of functional loss;

Any increased, new, or persistent subsensory, sub-Retinal Pigment Epithelial (RPE), or intraretinal fluid on OCT;

Signs of increased CNV leakage via FA.

Example 13

Optical Coherence Tomography (OCT)

Spectral Domain Optical Coherence Tomography (SD-OCT) was performed using approved equipment (Heidelberg Spectralis® SD-OCT) and standard techniques to monitor center point retinal thickness and fluid leakage in the retina of patients.

Optical Coherence Tomography (OCT) is a non-contact medical imaging technology similar to ultrasound and MRI. With OCT, reflected light is used to produce detailed cross-sectional and 3D images of the eye. The SPECTRALIS® SD-OCT simultaneously measures multiple wavelengths of reflected light across a spectrum, hence the name spectral domain. The increased speed and number of scans translates into higher resolution and a better chance of observing disease. In patients with wet AMD, the detection of new retinal fluid or a clinically significant increase in retinal thickness may be detected by SD-OCT. (Adhi et al., Curr Opin Ophthalmol. 2013 May; 24(3):213-21; Malamos et al., Invest Ophthalmol Vis Sci. 2009 October; 50(10):4926-33). Detection of these symptoms in a patient with AMD indicates disease progression that warrants treatment with an anti-VEGF therapy such as Lucentis or Eylea.

The retinal health and symptoms of AMD progression of each subject in the study were monitored via SD-OCT. At least 6 radial scans through the macula, each approximately 6 mm in length, were taken; and OCT images/scans were collected at each specified visit. The SD-OCT images were evaluated for the presence of intraretinal fluid by a masked reader and the central retinal thickness was measured using Heidelberg Heyex SD-OCT software. The central retinal thickness results for each visit for 8 patients are presented below in Table 7.

TABLE 7

| Mean Change in Central Retinal Thickness from Baseline at Day 0 in microns by dosing group | | | | | | | | | | | | | |
| --- | --- | --- | --- | --- | --- | --- | --- | --- | --- | --- | --- | --- | --- |
| Study Day | 14 | 28 | 56 | 84 | 112 | 140 | 168 | 196 | 224 | 252 | 280 | 308 | 336 | 364 |
| Control | −101 | 24 | −194 | −178 | −176 | −199 | −131 | −124 | −186 | −190 | −198 | −172 | −157 | −138 |
| Low dose | −140 | −115 | −161 | −189 | −173 | −163 | −157 | −147 | −149 | −155 | −161 | −144 | −127 | −134 |
| High Dose | −254 | −245 | −266 | −254 | −245 | −239 | −235 | −209 | −219 | −225 | −215 | −239 | −246 | −245 |

As shown in table 7, the mean central retinal thickness of the subjects in all dosing cohorts decreased after administration of the intravitreal injections of the anti-VEGF protein (Lucentis) at the beginning of the study as required by protocol. As expected, the central retinal thickness of the patients in the control group starts to increase and fluid can be seen on SD-OCT images within 30-90 days of the administration of the anti-VEGF protein. Unexpectedly, the central retinal thickness of the subjects in the low and high dosing groups is generally well controlled by rAAV.sFlt-1 and does not increase over time. New intraretinal fluid does not occur in the retinas of the low dose group subjects or the high dose group subjects. This is shown by OCT, for example, in FIG. 24. At 12 months, the central retinal thickness of subjects treated with rAAV.sFlt-1 did not increase by more than 50 microns, or by more than 100 microns, or by more than 250 microns within 12 months of administration of a pharmaceutical composition comprising rAAV.sFlt-1. When compared against baseline, the central retinal thickness of human subjects treated with rAAV.sFlt-1 decreased by 50 microns or in some cases by 100 microns or in some cases, by 200 microns. This decrease was observed within 8 weeks of administering sFlt-1 and was maintained at 3 months, 6 months, 9 months and 12 months. This result is surprising and is unknown in in the clinical treatment of AMD and ocular neovascularization in human subjects. More generally, without additional administrations of an anti-VEGF protein or other VEGF inhibitor, intraretinal fluid and an increase in central retinal thickness will be observed with 30 days, 60 days, 90 days or 180 days of an initial anti-VEGF treatment.

Fluorescein Angiography (FA)

FA was performed using a standard technique. Transit images are taken of the study eye. Mid and late phase images are taken of the study and non-study eye; and FA is be obtained at each specified visit.

Biodistribution Studies

Dissemination of vector was investigated by polymerase chain reaction (PCR) amplification of vector genomes isolated from samples of tears, plasma, urine and saliva. Biodistribution of vector and sFLT-1 was investigated by ELISA for sFLT-1 and AAV2 capsids in plasma, tears and saliva.

Extraction of DNA

Samples (100-300 ul) were pipetted onto Sample Collection Cards (Qiagen, Valencia, Calif.) or sterile foam tip applicators. DNA was extracted from each sample as per manufacturer's protocol. Purified DNA was dissolved in 50 ul of elution buffer. The amount of DNA present was determined by spectrophotometry.

Detection of rAAV.sFlt-1 by Real Time PCR

Genomic DNA samples (0.5-1 µg) were screened for the presence of the AAV.sFlt-1 vector using the TaqMan® Gene Expression Assays (Applied Biosystems, U.S.A.). The assay consists of a pair of unlabeled PCR primers which amplifies a fragment between the AAV2 and the sFLT-1 sequences, and a TaqMan® probe with a FAM™ or VIC® dye label and minor groove binder moiety on the 5' end, and non-fluorescent quencher dye on the 3' end. The cycling conditions were 1 hold for 2 minutes at 50° C. and another hold at 95° C. for 20 seconds, followed by 45 cycles of 95° C. for 3 seconds and 60° C. for 30 seconds.

Samples positive for the rAAV.sFlt-1 fragment were further tested and the gene copy number of rAAV.sFlt-1 present were quantified by real time polymerase chain reaction (PCR). Between 0.5-1.0 ug of extracted DNA were amplified in 20-ul reaction mixes containing Platinum SYBR Green qPCR Supermix-UDG (Invitrogen, Carlsbad, Calif., USA) and 0.5 uM of each primer using the IQ5 Bio-Rad real-time PCR system (Bio-Rad, Hercules, Calif., USA). A similar set of samples spiked with plasmid DNA containing the target sequence was set up in parallel as the spiked samples. The primer pair used (forward: CACTAGTCCAGTGTGGTGGA; reverse: AGCCAGGA-GACAACCACTTC) was designed with the aid of Primer3 Output (Whitehead Institute, MA, USA) to amplify the region from the vector cDNA into the sFLT-1 gene using the Rotorgene (Corbett). The cycling conditions that were used were: 2 min 50.0° C., 2 min 95.0° C. and 60 three-step cycles of 95.0° C. 20 s, 60.0° C. for 20 s and 72.0° C. for 20 s. A standard curve was generated in each run from 10-fold dilutions of plasmid DNA (pSSV.sFlt-1) which had the same target vector sequence. Each sample was analyzed in triplicate.

Quantifying sFlt-1 Protein Concentration by ELISA

The concentration of sFLT-1 present in the plasma, tears and saliva were measured quantitatively by ELISA using a Quantikine ELISA kit (R&D Systems, Minneapolis, Minn.) which was based on the sandwich immunoassay technique. The samples (100 ul) were added to the 96-well plate coated with a monoclonal antibody specific for VEGF R1/sFLT-1 and allowed to incubate for 2 hours. Any unbound sFLT-1 was removed by washing with a buffer. Following incubation with an enzyme-linked polyclonal antibody specific for VEGF R1/sFLT-1, the excess of antibody-enzyme conjugate was washed off and the samples were then be incubated with a substrate solution. Enzyme-catalyzed chromogen formation was quantified by measuring the visible absorbance at 450 nm. The concentrations of sFLT-1 (in pg/ml) in the samples were calculated from the absorbance value using a calibration curve plotted with recombinant human sFLT-1.

Detection of AAV2 by ELISA

Presence of AAV2 capsid in the plasma, tears, urine and saliva was analyzed using the AAV2 Titration ELISA Kit (American Research Products, Inc., Belmont, Mass., USA). This kit is based on a sandwich ELISA technique and uses a mouse monoclonal antibody specific for a conformational epitope on assembled AAV particles. This monoclonal antibody is coated onto microplate strips and is used to capture AAV particles from the specimen. Captured AAV particles were detected in two steps. First a biotin-conjugated monoclonal antibody to AAV was bound to the immune complex. In the second step streptavidin peroxidase conjugate reacts with the biotin molecules. Addition of substrate solution results in a color reaction which was proportional to specifically bound virus particles. The absorbance was measured photometrically at 450 nm. The kit control provided contains an AAV particle preparation of empty capsids and it allowed the quantitative determination of samples of an unknown particle titer. Samples (100 ul) were added to the plates and the assay was to be carried out according to the manufacturer's protocol.

Detection of Neutralizing AAV-2 Antibody

Plasma was assayed for the ability to block the transduction of HEK293 cells with AAV2.gfp. Patient's plasma was serially diluted in normal mouse serum in multi-well plates. AAV2.gfp was added to each well and plates were incubated at 37° C. for 1 hour before addition to HEK293 cells in triplicate. The neutralizing antibody titer was expressed as the plasma dilution that resulted in 50% inhibition of transduction by AAV2-gfp. Maximum gfp activity was represented by vector diluted in normal mouse serum; maximum inhibition was represented by medium only in normal mouse serum. Baseline plasma from each subject was assayed alongside each post-op sample. Green cells from transduction of 293T cells with AAV2.gfp were counted in the test wells after 48 hours and compared with the number of green cells in the baseline serum sample.

Detection of Anti-AAV2 Antibodies

To detect plasma antibodies to AAV2 capsid, enhanced protein-binding ELISA plates were coated with $10^9$ vg/ml of AAV2 (Vector Core Facility, North Carolina) at 4° C. overnight. The plates were be blocked at 37° C. for 2 hours and then are incubated at 4° C. overnight with serially diluted anti-AAV2 monoclonal antibody (Industries International, Concord, Mass.) or 1:50, 1:100, 1:200, or 1:400 dilutions of patient plasma. The plates were incubated with horse radish peroxidase (HRP)-conjugated anti-human Ig at 37° C. for 2 hours, then with tetramethyl benzidine (TMP) substrate and hydrogen peroxide (H2O2). The reaction was stopped by phosphoric acid (H3PO4) and read at 450 nm on a plate reader. The titer of anti-AAV2 antibodies were calculated based on the standard curve of the commercial antibody determined in parallel. Each value was determined in triplicate.

Geographic Atrophy

The human study subjects were examined for signs of geographic atrophy in their treated and untreated eyes according to standard techniques. Increases geographic atrophy was not observed in patients treated with rAAV.sFlt-1 at 3 months, 6 months, 9 months, or 12 months. It is hypothesized that the treatment may stop progression of geographic atrophy in a treated eye for up to 15 months, 18 months, 24 months, 36 months, 5 years and 10 years.

Example 14

To further test the safety and efficacy of rAAV.sFlt-1 for the treatment of wet AMD and choroidal neovascularization, forty (40) additional subjects were enrolled in a controlled clinical study. As in Example 12, rAAV.sFlt-1 was produced in accordance with FDA and ICH guidelines at the UNC Vector Core Human Application Laboratory. Eligibility, inclusion and exclusion criteria for the study were as follows:

Eligibility

Ages Eligible for Study: 55 Years and older
Genders Eligible for Study: Both
Accepts Healthy Volunteers: No Inclusion Criteria Age greater than or equal to 55 years;
Subfoveal CNV secondary to AMD and with best corrected visual acuity in the study eye of 20/30-20/400 and 20/200 or better in the other eye;
Fluorescein angiogram of the study eye must show evidence of a leaking subfoveal choroidal neovascular lesion; or choroidal neovascularization currently under active management with anti-VEGF therapy;
Must be a candidate for anti-VEGF intravitreal injections;
The entire dimension of the lesion must not exceed 12 Macular Photocoagulation Study disc areas;
No previous retinal treatment of photodynamic therapy or laser;
Able to provide informed consent;
Participant has clinically acceptable laboratory parameters and ECG at the time of enrollment; and
Able to comply with protocol requirements, including follow-up visits.

Exclusion Criteria

Liver enzymes >2× upper limit of normal;
Clinical evidence of active infection of any type, including adenovirus, hepatitis A, B, or C, or HIV virus; or documented history of hepatitis B or hepatitis C;
Any prior treatment for AMD in the study/control eye, excluding anti-VEGF injections;
A tear in the retinal pigmented epithelium;
Extensive sub-fovial scarring, extensive geographic atrophy, or thick subretinal blood in the study eye as determined by the investigator;
Significant retinal disease other than subfoveal CNV AMD, such as diabetic retinopathy or retinal vascular occlusion, that could compromise vision in the study eye;
Significant non-retinal disease such as ocular atrophy or significant cataract in the study eye, including central corneal scarring that affects visual acuity, glaucoma with field defects, or any measurable uveitis;
Known allergy to fluorescein;
Current use of prednisolone, other anti-inflammatory steroids or immune suppression drugs. Inhaled steroids and non-steroidal drugs such as aspirin are allowed;
Any other significant disease or disorder which, in the opinion of the Investigator, may either put the participants at risk because of participation in the study, or may influence the result of the study, or the participant's ability to participate in the study;
Participants who have participated in another research study involving an investigational product in the past 12 weeks; and
Penicillin sensitivity confirmed by participant medical records.

Initial enrolled subjects had active subfoveal choroidal neovascularization, with visual acuity in the study eye of 20/30 to 20/400, and had previously received between 0 and 25 intravitreal injections of ranibizumab. The patients were randomly distributed into a control group or an experimental group until a total of 14 patients control patients and 26 experiments patients were enrolled. All patients received intravitreal injections of ranibizumab on day 1 and day 30 of the study. On day 7, $1\times10^{11}$ vector genomes of rAAV.sFlt-1 in 100 ul volume was administered via subretinal injection to the experimental group.

As in the study in Example 12, maximum expression levels of sFLT-1 in a study subject or a patient were reached six to eight weeks after subretinal administration of rAAV.sFLT-1. During this so called "ramp-up" period, at least one, two or three intravitreal injections of an anti-VEGF agent were injected at 15 to 45 day intervals, and preferably about 30 day intervals, to prevent disease progression. It is preferred to administer the first intravitreal injection of an anti-VEGF agent between 1 to 30 days, and preferably between 5 to 10 days, prior to administration of rAAV.sFLT-1 to allow for absorption of the intravitreally injected anti-VEGF agent (Lucentis or Avastin or Eylea or other non sFLT agents). If this first intravitreal injection is administered less than 24 hours prior to subretinal administration of rAAV.sFLT, it may be washed out of the vitreous during the subretinal injection procedure leading to a subtherapeutic anti-VEGF agent concentration and disease progression.

After the completion of the ramp period, patients who expressed sufficient sFLT-1 to treat or prevent progression of their AMD or other symptoms of choroidal neovascularization did not need additional intravitreal anti-VEGF injections although it is expected that they will remain under the care of a physician.

In this study recited in this example, patients in the control and experimental groups were evaluated for signs of active choroidal neovascularization on an approximately monthly basis and retreated with intravitreal ranibizumab if any of the following criteria was met:

>10 Early Treatment Diabetic Retinopathy Study (ET-DRS) letter loss from subject's previous visit (attributable to retinal causes), OR a decrease of >5 ETDRS letters from previous visit in conjunction with patient perception of functional loss;

Any increased, new, or persistent subsensory, sub-Retinal Pigment Epithelial (RPE), or intraretinal fluid on OCT;

Signs of increased CNV leakage via FA.

Example 15

To test the safety and efficacy of rAAV.sFlt-1 for the prevention or prophylaxis of the ocular neovascular disease Age Related Macular degeneration (AMD), an additional controlled clinical study with forty (150) patients is conducted. rAAV(bv).sFlt-1 is produced in accordance with FDA and ICH guidelines at Lonza Houston, Inc. (Houston, Tex.). Eligibility, inclusion and exclusion criteria for the study were as follows:

Eligibility

Ages Eligible for Study: 50 Years and older
Genders Eligible for Study: Both
Accepts Healthy Volunteers: Yes

Inclusion Criteria

Patients with nonexudative AMD (either categories 2, 3 or 4 according to the AREDS criteria; in group 4 the eyes with no-advanced AMD will be included); Patients with AMD classified as either "wet" or "dry" are included;
Age between 50 and 90 years;
Able to understand and comply with the requirements of the trial;
Visual acuity >0.4;

Exclusion Criteria

Currently enrolled in an ophthalmic clinical trial;
Eyes with concomitant macular or choroidal disorders other than AMD and with indefinite signs of AMD;
Eyes with a diagnosis of exudative AMD with active subretinal neovascularization (SRNV) or CNV lesions requiring laser photocoagulation in the study eye;
Subjects with significant ocular lens opacities causing vision decrease;
Subjects with amblyopia;
Subjects with optic nerve disease (neuropathy, atrophy, papilledema), unstable glaucoma as defined by intraocular pressures greater than 25 mm Hg, 3 or more glaucoma medications, C/D of 0.8 or greater and visual fields consistent with glaucoma; history of retina-vitreous surgery, degenerative myopia, active posterior intraocular inflammatory disease, chronic use of topical ocular steroid medications, vasoproliferative retinopathies (other than AMD), rhegmatogenous retinal detachment, and inherited macular dystrophies;
Subjects with demand type pacemakers or epilepsy;
Subjects with uncontrolled hypertension (defined as diastolic of 90 or greater and systolic of 150 or greater);
Subjects with recent history (within the previous year) of cerebral vascular disease;
manifested with transient ischemic attacks (TIA's) or cerebral vascular accidents (CVA's);
Subjects with a history of AIDS;
Subjects who have had intraocular surgery in trial eye within 3 months prior to enrolling in the trial;
Patients who are unwilling to adhere to visit examination schedules;

Primary Outcome Measures

MPOD and multifocal electroretinograms [Time Frame: 1 year] [Designated as safety issue: Yes]

Secondary Outcome Measures

The safety and efficacy of rAAV(bv).sFlt-1 in reducing the risk of the development of advanced AMD. [Time Frame: 1 year] [Designated as safety issue: Yes]

TABLE 9

| Experimental Design Arms | |
| --- | --- |
| Arms | Assigned Interventions |
| Active Comparator: Group I 1 × 10$^{10}$ vector genomes of rAAV(bv).sFlt-1 in 100 ul volume is administered via subretinal injection to the experimental group within 30-90 day intervals for 36 months | Drug: of rAAV(bv).sFlt-1 1 × 10$^{10}$ vector genomes of rAAV.sFlt-1 in 100 ul volume is administered via subretinal injection to the experimental group. |

TABLE 9-continued

| Experimental Design Arms | |
| --- | --- |
| Arms | Assigned Interventions |
| Active Comparator: Group II<br>1 × 10¹¹ vector genomes of rAAV(bv).sFlt-1 in 100 ul volume is administered via subretinal injection to the experimental group within 180-365 day intervals for 36 months | Drug: of rAAV(bv).sFlt-1<br>1 × 10¹¹ vector genomes of rAAV.sFlt-1 in 100 ul volume is administered via subretinal injection to the experimental group. |
| Placebo Comparator: Group Placebo<br>Drug Placebo: Saline solution | Drug Placebo: Saline solution<br>Drug Placebo: Saline solution, until one year. Patients on placebo showing early stages of AMD may receive rAAV(bv).sFlt-1 |
| Active Comparator: Ranibizumab 0.3 mg<br>Patients receive ranibizumab 0.3 mg monthly administered intravitreally for 36 months. | Drug: Ranibizumab<br>Sterile solution for intravitreal injection.<br>Other Name: Lucentis |

Example 16

To test the safety and efficacy of rAAV.sFlt-1 for the treatment of the ocular neovascular disease Diabetic Macular Edema (DME), an additional controlled clinical study with forty (40) patients is conducted. rAAV(bv).sFlt-1 is produced in accordance with FDA and ICH guidelines at Lonza Houston, Inc. (Houston, Tex.). Eligibility, inclusion and exclusion criteria for the study were as follows:

Eligibility

Ages Eligible for Study: 18 Years and older
Genders Eligible for Study: Both
Accepts Healthy Volunteers: No

General Inclusion Criteria

Subjects are eligible if the following criteria are met:
Willingness to provide written informed consent and, at U.S. sites, Health Insurance Portability and Accountability Act (HIPAA) authorization, and in other countries, as applicable according to national laws.
Diabetes mellitus (Type 1 or 2).
Retinal thickening secondary to diabetes mellitus (DME) involving the center of the fovea with central macular thickness ≥275 μm in the center subfield as assessed on optical coherence tomography (OCT).
Best corrected visual acuity (BCVA) score in the study eye of 20/40 to 20/320 approximate Snellen equivalent using the Early Treatment Diabetic Retinopathy Study (ETDRS) protocol at an initial testing distance of 4 meters.
Decrease in vision determined to be primarily the result of DME and not to other causes.
Ability (in the opinion of the investigator) and willingness to return for all scheduled visits and assessments.

Exclusion Criteria

History of vitreoretinal surgery in the study eye.
Panretinal photocoagulation (PRP) or macular laser photocoagulation in the study eye within 3 months of screening.
Proliferative diabetic retinopathy (PDR) in the study eye, with the exception of inactive, regressed PDR.
Iris neovascularization, vitreous hemorrhage, traction retinal detachment, or preretinal fibrosis involving the macula in the study eye.

Vitreomacular traction or epiretinal membrane in the study eye.
Ocular inflammation (including trace or above) in the study eye.
History of idiopathic or autoimmune uveitis in either eye.
Structural damage to the center of the macula in the study eye that is likely to preclude improvement in VA following the resolution of macular edema, including atrophy of the retinal pigment epithelium (RPE), subretinal fibrosis, or organized hard-exudate plaque.
Ocular disorders in the study eye that may confound interpretation of study results, including retinal vascular occlusion, retinal detachment, macular hole, or choroidal neovascularization (CNV) of any cause (eg, age-related macular degeneration (AMD), ocular histoplasmosis, or pathologic myopia).
Cataract surgery in the study eye within 3 months, yttrium-aluminum-garnet (YAG) laser capsulotomy within the past 2 months, or any other intraocular surgery within the 90 days preceding Day 0.
Uncontrolled glaucoma or previous filtration surgery in the study eye.
Uncontrolled blood pressure.
History of cerebral vascular accident or myocardial infarction within 3 months prior to Day 0.
Uncontrolled diabetes mellitus.
Renal failure requiring dialysis or renal transplant.
History of other disease, metabolic dysfunction, physical examination finding, or clinical laboratory finding giving reasonable suspicion of a disease or condition that contraindicates the use an investigational drug, might affect interpretation of the results of the study, or renders the subject at high risk from treatment complications.

Primary Outcome Measures

Percentage of Patients Who Gain ≥15 Letters in Their Best Corrected Visual Acuity (BCVA) Score From Baseline at Month 12 [Time Frame: Baseline to Month 12] [Designated as safety issue: No]

Secondary Outcome Measures

Mean Change From Baseline in Best Corrected Visual Acuity (BCVA) Score at Months 12, 24 and 36
Percentage of Patients With a Visual Acuity (VA) Snellen Equivalent of 20/40 or Better at Months 12, 24 and 36.

Mean Change From Baseline in Central Foveal Thickness as measured by SD-OCT at Months 12, 24 and 36.

Reduction in Frequency of concomitant anti-VEGF treatment ((e.g. Lucentis, Avastin, Macugen or Eyelea) [Designated as safety issue: No]

monthly basis and are retreated with intravitreal ranibizumab if any of the following criteria was met:

>10 Early Treatment Diabetic Retinopathy Study (ETDRS) letter loss from subject's previous visit (attributable to retinal causes), OR a decrease of >5 ETDRS

TABLE 10

Experimental Design Arms for DME Study

| Arms | Assigned Interventions |
|---|---|
| Experimental: I Low Dose<br>$1 \times 10^{10}$ vector genomes of rAAV(bv).sFlt-1 in 100 ul volume was administered via subretinal injection to the experimental group.<br>Follow-up phase: Participants on rAAV.sFlt-1 are monitored monthly and receive rescue treatments with intravitreal anti-VEGF therapy if they meet the study criteria for retreatment. | Drug: rAAV.sFlt-1 (AVA-01)<br>$1 \times 10^{10}$ vector genomes of rAAV.sFlt-1 in 100 ul volume was administered via subretinal injection to the experimental group. |
| Experimental: II High Dose<br>$1 \times 10^{11}$ vector genomes of rAAV.sFlt-1 in 100 ul volume was administered via subretinal injection to the experimental group.<br>Follow-up phase: Participants on rAAV.sFlt-1 are monitored monthly and receive rescue treatments with intravitreal anti-VEGF therapy if they meet the study criteria for retreatment. | Drug: rAAV.sFlt-1 (AVA-01)<br>$1 \times 10^{11}$ vector genomes of rAAV.sFlt-1 in 100 ul volume was administered via subretinal injection to the experimental group. |
| Active Comparator: Ranibizumab injection 0.3 mg.<br>Participants receive two initial injections of Ranibizumab at Day 0 and Day 30.<br>Follow-up phase: Participants are monitored monthly and receive rescue treatments with Ranibizumab if they meet the study criteria for retreatment. | Drug: Ranibizumab<br>Sterile solution for intravitreal injection.<br>Other Name: Lucentis |

Initial enrolled subjects have DME, with visual acuity in the study eye of 20/40 to 20/320, and will have previously received between 0 and 25 intravitreal injections of ranibizumab or aflibercept. The patients are randomly distributed into a control group or two experimental groups until a total of 14 patients control patients and 13 low dose experimental patients and 13 high dose experimental patients are enrolled. All patients received intravitreal injections of ranibizumab on day 1 and day 30 of the study. On day 7, $1 \times 10^{10}$ or $1 \times 10^{11}$ vector genomes of rAAV(bv).sFlt-1 in 100 ul volume are administered via subretinal injection to the experimental groups.

As in the study in Example 12, maximum expression levels of sFLT-1 in a study subject or a patient are reached are six to eight weeks after subretinal administration of rAAV(bv).sFLT-1. During this so called "ramp-up" period, at least one, two or three intravitreal injections of an anti-VEGF agent are injected at 15 to 45 day intervals, and preferably about 30 day intervals, to prevent disease progression. It is preferred to administer the first intravitreal injection of an anti-VEGF agent between 1 to 30 days, and preferably between 5 to 10 days, prior to administration of rAAV(bv).sFLT-1 to allow for absorption of the intravitreally injected anti-VEGF agent (Lucentis or Avastin or Eylea or other non sFLT agents). If this first intravitreal injection is administered less than 24 hours prior to subretinal administration of rAAV(bv).sFLT, it may be washed out of the vitreous during the subretinal injection procedure leading to a sub-therapeutic anti-VEGF agent concentration and disease progression.

After the completion of the ramp period, patients who express sufficient sFLT-1 to treat or prevent progression of their DME may not need additional intravitreal anti-VEGF injections although it is expect that they will remain under the care of a physician.

In this study recited in this example, patients in the control and experimental groups are evaluated for signs of active or new DME and neovascularization on an approximately letters from previous visit in conjunction with patient perception of functional loss;

Any increased, new, or persistent subsensory, sub-Retinal Pigment Epithelial (RPE), or intraretinal fluid on OCT;

Signs of increased CNV leakage via FA.

Example 17

To test the safety and efficacy of rAAV.sFlt-1 for the treatment of the ocular neovascular disease Retinal Vein Occlusion (RVO), an additional controlled clinical study with forty (40) patients is conducted. The clinical study is performed with patients of 2 cohorts, 1 cohort including patients with Central Retinal Vein Occlusion (CRVO) and 1 cohort including Branched Retinal Vein Occlusion (BRVO). As in Example 15, rAAV(bv).sFlt-1 is produced in accordance with FDA and ICH guidelines at Lonza Houston, Inc. (Houston, Tex.). Eligibility, inclusion and exclusion criteria for the study were as follows:

Inclusion Criteria

Center-involved macular edema secondary to central retinal vein occlusion (CRVO) or Branch-involved macular edema secondary to BRVO for no longer than 9 months with mean central subfield thickness ≥250 μm on optical coherence tomography (OCT);

Adults ≥18 years;

Early treatment diabetic retinopathy study (ETDRS) best corrected visual acuity (BCVA) of 20/40 to 20/320 (73 to 24 letters) in the study eye;

Exclusion Criteria

Any prior treatment with anti-VEGF agents in the study eye (Pegaptanib sodium, anecortave acetate, bevacizumab, ranibizumab, etc.) or previous administration of systemic anti-angiogenic medications;

Prior panretinal laser photocoagulation or macular laser photocoagulation in the study eye CRVO disease duration >9 months from date of diagnosis; BRVO disease duration >9 months from date of diagnosis;

Previous use of intraocular corticosteroids in the study eye or use of periocular corticosteroids in the study eye within the 3 months prior to Day 1;

Iris neovascularization, vitreous hemorrhage, traction retinal detachment, or preretinal fibrosis involving the macula in either the study eye or fellow eye;

Primary Outcome Measures

Mean Change From Baseline in Best Corrected Visual Acuity (BCVA) Score at 6 Months. [Time Frame: Baseline and 6 months] [Designated as safety issue: No].

Defined study baseline range of Early Treatment Diabetic Retinopathy Study (ETDRS) Best Corrected Visual Acuity (BCVA) letter score of 73 to 24 (=Acuity of 20/40 to 20/320) in the study eye; a higher score represents better functioning. Nominator=(Number of participants who maintained vision*100); Denominator=Number of participants analyzed.

Secondary Outcome Measures

Percentage of Participants Who Gained ≥15 Letters in BCVA Score at Month 6 Compared With Baseline.

Mean Change From Baseline in Central Retinal Thickness (CRT) at 6 months [Time Frame: Baseline and 6 months] [Designated as safety issue: No]

Reduction in frequency of concomitant anti-VEGF treatment ((e.g. Lucentis, Avastin, Macugen or Eyelea) [Designated as safety issue: No]

Initial enrolled subjects have CRVO or BRVO, with visual acuity in the study eye of 20/40 to 20/320, and will have previously received between 0 and 25 intravitreal injections of ranibizumab or aflibercept. The patients are randomly distributed into a control group or two experimental groups until a total of 14 patients control patients and 13 low dose experimental patients and 13 high dose experimental patients are enrolled. All patients received intravitreal injections of ranibizumab on day 1 and day 30 of the study. On day 7, $1 \times 10^{10}$ or $1 \times 10^{11}$ vector genomes of rAAV(bv).sFlt-1 in 100 ul volume are administered via subretinal injection to the experimental groups.

As in the study in Example 14, maximum expression levels of sFLT-1 in a study subject or a patient are reached are six to eight weeks after subretinal administration of rAAV(bv).sFLT-1. After the completion of the ramp period, as described in Example 14, patients who express sufficient sFLT-1 to treat or prevent progression of their BRVO or CRVO may not need additional intravitreal anti-VEGF injections although it is expect that they will remain under the care of a physician.

In this study recited in this example, patients in the control and experimental groups are evaluated for signs of active or new retinal vein occlusion and neovascularization on an approximately monthly basis and are retreated with intravitreal ranibizumab if any of the following criteria was met:

>10 Early Treatment Diabetic Retinopathy Study (ETDRS) letter loss from subject's previous visit (attributable to retinal causes), OR a decrease of >5 ETDRS letters from previous visit in conjunction with patient perception of functional loss;

Any increased, new, or persistent subsensory, sub-Retinal Pigment Epithelial (RPE), or intraretinal fluid on OCT;

Signs of increased CNV leakage via FA.

TABLE 11

| Experimental Design Arms for BRVO/CRVO Study | |
|---|---|
| Arms | Assigned Interventions |
| Experimental: $1 \times 10^{10}$ vector genomes of rAAV.sFlt-1 in 100 ul volume is administered via subretinal injection to the experimental group, on Day 7. Follow-up phase: Participants on rAAV.sFlt-1 are monitored monthly and receive rescue treatments with intravitreal anti-VEGF therapy if they meet the study criteria for retreatment. | Biological: $1 \times 10^{10}$ vector genomes of rAAV.sFlt-1. Subretinal injection. Drug: Ranibizumab injection 0.3 mg if meet reinjection criteria. |
| Experimental: $1 \times 10^{11}$ vector genomes of rAAV.sFlt-1 in 100 ul volume is administered via subretinal injection to the experimental group, on Day 7. Follow-up phase: Participants on rAAV.sFlt-1 are monitored monthly and receive rescue treatments with intravitreal anti-VEGF therapy if they meet the study criteria for retreatment. | Biological: $1 \times 10^{11}$ vector genomes of rAAV.sFlt-1. Subretinal injection. Drug: Ranibizumab injection 0.3 mg if meet reinjection criteria. |
| Active Comparator: Ranibizumab injection 0.3 mg. Participants receive two initial injections of Ranibizumab at Day 0 and Day 30. Follow-up phase: Participants are monitored monthly and receive rescue treatments with Ranibizumab if they meet the study criteria for retreatment. | Drug: Ranibizumab injection 0.3 mg Ranibizumab injection 0.3 mg in a single-dose regimen given at Day 0 and Day 30. Other Name: Lucentis |

What is claimed is:

1. A method for the treatment of ocular neovascularization in a human subject suffering from ocular neovascularization, the method comprising:

i) administering a first dose of an anti-Vascular Endothelial Growth Factor (anti-VEGF) agent to the human subject;

ii) within 90 days of administering the anti-VEGF agent to the eye according to step (i), administering to the eye of the human subject a single unit dose of a pharmaceutical composition comprising a recombinant adeno-associated virus (rAAV) comprising a nucleic acid sequence encoding an anti-VEGF protein, wherein the anti-VEGF protein comprises a polypeptide selected from the group consisting of (a) a polypeptide having at least 90% identity to SEQ ID NO: 121 and (b) a polypeptide having at least 90% identity to SEQ ID NO: 121 plus a domain 3, wherein the domain 3 is selected from domain 3 of sFLT and domain 3 of KDR, wherein the single unit dose comprises at least $1\times10^6$ and at most $1\times10^{15}$ vector genomes of the rAAV; and iii) administering a second dose of an anti-VEGF agent within 30 days post administration of the rAAV.

2. The method of claim 1, wherein the human subject has or is suspected of having one or more conditions selected from the group consisting of: age-related macular degeneration (AMD), wet-AMD, dry-AMD, retinal neovascularization, choroidal neovascularization and diabetic retinopathy.

3. The method of claim 1, wherein the human subject has or is suspected of having one or more conditions selected from the group consisting of: proliferative diabetic retinopathy, retinal vein occlusion, central retinal vein occlusion, branched retinal vein occlusion, diabetic macular edema, diabetic retinal ischemia, ischemic retinopathy and diabetic retinal edema.

4. The method of claim 1, wherein the rAAV is selected from AAV2 and AAV8.

5. The method of claim 4, wherein no increased anti-AAV cytotoxic T cell response is measured following the administering step.

6. The method of claim 4, wherein no virus is detected in the human subject's blood, saliva or urine samples, 3, 7, 14, 21 or 30 days after administering the pharmaceutical composition.

7. The method of claim 1, wherein the anti-VEGF protein consists of a polypeptide having at least 95% identity to SEQ ID NO: 121.

8. The method of claim 1, wherein the anti-VEGF protein consists of a polypeptide having at least 90% identity to SEQ ID NO:121 and a domain 3, wherein said domain 3 is selected from domain 3 of sFLT and domain 3 of KDR.

9. The method of claim 1, wherein the single unit dose comprises at least $1\times10^9$ and at most $3\times10^{13}$ vector genomes of the rAAV.

10. The method of claim 9, wherein the eye of the subject receives the first dose of the anti-VEGF agent in i) between about 1 to 30 days prior to the administration of the pharmaceutical composition.

11. The method of claim 10, wherein the anti-VEGF agent is aflibercept or ranibizumab.

12. The method of claim 1, wherein the administering is performed outside the fovea.

13. The method of claim 1, wherein a best corrected visual acuity (BCVA) of the human subject improves by at least 1, 2, 3, 4 or 5 lines as measured by ETD RS (Early Treatment Diabetic Retinopathy Study) letters following the administering of the pharmaceutical composition.

14. The method of claim 1, wherein a best corrected visual acuity (BCVA) of the human subject decreases by fewer than 15 letters as measured by ETDRS (Early Treatment Diabetic Retinopathy Study) following the administering of the pharmaceutical composition.

15. The method of claim 1, wherein administering the pharmaceutical composition is performed under conditions selected from the group consisting of: administering the pharmaceutical composition in one eye, administering the pharmaceutical composition sequentially in two eyes, and administering the pharmaceutical composition simultaneously in two eyes.

16. The method of claim 1, wherein a reduction in neovascularization, as observed by a Fluorescein Angiography (FA), follows the administering of the pharmaceutical composition.

17. The method of claim 1, wherein no superficial, anterior segment or vitreous inflammatory signs are present in the human subject at least 1 week after administration of the single unit dose of ii.

18. The method of claim 1, wherein the human subject has sensitivity or allergy to penicillin.

19. The method of claim 1, wherein the administration of the single unit dose of ii) does not increase systemic levels of sFlt-1 in the human subject.

20. The method of claim 1, wherein the administering of the pharmaceutical composition is performed at a frequency less than 3 times a year in the human subject.

21. The method of claim 1, wherein the administering of the pharmaceutical composition reduces the frequency of administration of additional VEGF inhibitor treatments in the human subject.

22. The method of claim 1, wherein the method comprises administering to the eye of the human subject the single unit dose of the pharmaceutical composition within 60 days of administering the anti-VEGF agent to the eye according to step (i).

23. The method of claim 22, wherein the method comprises administering to the eye of the human subject the single unit dose of the pharmaceutical composition within 30 days of administering the anti-VEGF agent to the eye according to step (i).

24. A unit dose of a pharmaceutical composition for use in a method for the treatment of an ocular neovascular disease in a human subject having ocular neovascularization, the unit dose comprising recombinant adeno-associated viruses (rAAVs) of 1×1010 to 3×1012 vector genomes of the rAAV, wherein the recombinant viruses comprise a promoter operatively linked to a nucleic acid sequence encoding an anti-VEGF protein, wherein the anti-VEGF protein comprises a polypeptide selected from the group consisting of (a) a polypeptide having at least 90% identity to SEQ ID NO: 121 and (b) a polypeptide having at least 90% identity to SEO ID NO: 121 plus a domain 3, wherein domain 3 is selected from domain 3 of sFLT and domain 3 of KDR, wherein the human subject has previously received a first intravitreal injection of an anti-Vascular Endothelial Growth Factor (VEGF) agent in an amount such that the anti-VEGF agent is present in the eye of the subject at a concentration sufficient to prevent progression of the neovascularization at the time of administration of the unit dose.

* * * * *